(12) United States Patent
Ellingboe et al.

(10) Patent No.: US 9,393,357 B2
(45) Date of Patent: Jul. 19, 2016

(54) BLOOD PERFUSION SYSTEM

(71) Applicant: Sorin Group USA, Inc., Arvada, CO (US)

(72) Inventors: Bruce S. Ellingboe, Littleton, CO (US); William D. Dalke, Aurora, CO (US); J. Steven Ingebrigtsen, Lakewood, CO (US); John J. Kappus, Denver, CO (US); Bruce E. Lawrence, Evergreen, CO (US); Mike E. Schwab, Golden, CO (US); Gary A. Carson, Golden, CO (US); Kevin J. Kollar, Ada, MI (US)

(73) Assignee: Sorin Group USA, Inc., Arvada, CO (US)

( * ) Notice: Subject to any disclaimer, the term of this patent is extended or adjusted under 35 U.S.C. 154(b) by 159 days.

(21) Appl. No.: 14/105,286

(22) Filed: Dec. 13, 2013

(65) Prior Publication Data

US 2014/0099235 A1 Apr. 10, 2014

Related U.S. Application Data

(63) Continuation of application No. 13/285,642, filed on Oct. 31, 2011, now abandoned, which is a continuation of application No. 11/333,671, filed on Jan. 17, 2006, now Pat. No. 8,057,419, which is a continuation of (Continued)

(51) Int. Cl.
*A61M 37/00* (2006.01)
*A61M 1/32* (2006.01)
*A61M 1/36* (2006.01)

(52) U.S. Cl.
CPC .............. *A61M 1/32* (2013.01); *A61M 1/3621* (2013.01); *A61M 1/3626* (2013.01);

(Continued)

(58) Field of Classification Search
CPC ............ A61M 1/3632; A61M 1/3621; A61M 1/3643; A61M 1/3639; A61M 1/3663; A61M 1/3626; A61M 1/3666
USPC ....................... 604/6.09, 6.13, 6.14
See application file for complete search history.

(56) References Cited

U.S. PATENT DOCUMENTS 4,003,892 A 1/1977 Lohr et al.
4,479,762 A 10/1984 Bilstad et al.
(Continued)

FOREIGN PATENT DOCUMENTS

DE 19534502 A1 3/1997
EP 0893603 B1 10/2002
(Continued)

OTHER PUBLICATIONS

Communication issued in European Application No. 01985677, May 8, 2009, 3 pages.
(Continued)

*Primary Examiner* — Leslie Deak
(74) *Attorney, Agent, or Firm* — Faegre Baker Daniels LLP

(57) ABSTRACT

An extracorporeal blood perfusion system includes a disposable assembly and a control unit having a control interface region. The interface region includes pump assemblies for selective pumping of venous blood, arterial blood, cardioplegia solution, suctioned blood and blood removed from the left ventricle. Valve assemblies control the flow of fluids through the assembly and to/from the patient and sensors monitor various fluid parameters including temperature and pressure within the various fluid circuits. The user interface is a functional screen interface for effecting the operation of the control unit and valve assemblies. The screen interface may be a touch screen having objects that corresponds to the component interface region. The display may be selectively controlled to provide graphic depictions of disposable assembly components with corresponding narrative instructions.

13 Claims, 60 Drawing Sheets

Related U.S. Application Data application No. 09/963,878, filed on Sep. 26, 2001, now abandoned.

(60) Provisional application No. 60/235,837, filed on Sep. 27, 2000.

(52) U.S. Cl.
CPC .......... *A61M 1/3632* (2014.02); *A61M 1/3639* (2013.01); *A61M 1/3643* (2013.01); *A61M 1/3663* (2013.01); *A61M 1/3624* (2013.01); *A61M 1/3664* (2013.01); *A61M 1/3666* (2013.01); *A61M 2205/123* (2013.01); *A61M 2205/128* (2013.01); *A61M 2205/3389* (2013.01); *A61M 2205/505* (2013.01); *A61M 2205/705* (2013.01); *A61M 2205/707* (2013.01); *A61M 2209/082* (2013.01)

(56) References Cited

U.S. PATENT DOCUMENTS

| | | | |
|---|---|---|---|
| 4,619,639 A | 10/1986 | Nose et al. | |
| 4,756,705 A | 7/1988 | Beijbom et al. | |
| 4,824,339 A | 4/1989 | Bainbridge et al. | |
| 4,911,549 A | 3/1990 | Karkar | |
| 5,215,450 A | 6/1993 | Tamari | |
| 5,273,517 A | 12/1993 | Barone et al. | |
| 5,356,593 A | 10/1994 | Heiberger et al. | |
| 5,385,540 A * | 1/1995 | Abbott | A61M 1/3664 128/DIG. 3 |
| 5,423,749 A | 6/1995 | Merte et al. | |
| 5,462,416 A | 10/1995 | Dennehey et al. | |
| 5,482,440 A | 1/1996 | Dennehey et al. | |
| 5,573,502 A | 11/1996 | LeCoca et al. | |
| 5,581,687 A | 12/1996 | Lyle et al. | |
| 5,588,816 A | 12/1996 | Abbott et al. | |
| 5,628,908 A | 5/1997 | Kamen et al. | |
| 5,645,531 A | 7/1997 | Thompson et al. | |
| 5,676,644 A | 10/1997 | Toavs et al. | |
| 5,702,358 A | 12/1997 | Witherspoon et al. | |
| 5,752,931 A | 5/1998 | Nazarian et al. | |
| 5,769,811 A | 6/1998 | Stacey et al. | |
| 5,813,972 A | 9/1998 | Nazarian et al. | |
| 5,820,579 A * | 10/1998 | Plotkin | A61M 1/3621 128/DIG. 3 |
| 5,823,986 A | 10/1998 | Peterson | |
| 5,830,134 A | 11/1998 | Caputo et al. | |
| 5,837,905 A | 11/1998 | Strauss et al. | |
| 5,863,421 A | 1/1999 | Peter, Jr. et al. | |
| 5,899,873 A | 5/1999 | Jones et al. | |
| 5,902,476 A | 5/1999 | Twardowski | |
| 5,906,598 A * | 5/1999 | Giesler | A61M 5/1411 206/564 |
| 5,941,842 A | 8/1999 | Steele et al. | |
| 6,071,258 A * | 6/2000 | Dalke | A61M 1/3621 422/44 |
| 6,180,058 B1 | 1/2001 | Lindsay | |
| 6,251,284 B1 | 6/2001 | Bischof et al. | |
| 6,302,860 B1 | 10/2001 | Gremel et al. | |
| 6,315,751 B1 | 11/2001 | Cosgrove et al. | |
| 6,630,989 B1 | 10/2003 | Caputo et al. | |
| 6,632,189 B1 | 10/2003 | Fallen et al. | |
| 6,731,379 B2 | 5/2004 | Caputo et al. | |
| 6,783,328 B2 | 8/2004 | Lucke et al. | |
| 6,960,322 B2 * | 11/2005 | Stringer | A61M 1/3626 210/645 |
| 7,278,981 B2 | 10/2007 | Ellingboe et al. | |
| 8,057,419 B2 | 11/2011 | Ellingboe et al. | |
| 2002/0085952 A1 | 7/2002 | Ellingboe et al. | |
| 2003/0135152 A1 | 7/2003 | Kollar et al. | |
| 2003/0163078 A1 * | 8/2003 | Fallen | A61M 1/3664 604/6.01 |
| 2004/0027557 A1 | 2/2004 | Caputo et al. | |
| 2006/0015056 A1 | 1/2006 | Ellingboe et al. | |
| 2006/0167400 A1 | 7/2006 | Ellingboe et al. | |
| 2008/0027368 A1 | 1/2008 | Kollar et al. | |
| 2012/0109037 A1 | 5/2012 | Ellingboe et al. | |

FOREIGN PATENT DOCUMENTS

| | | |
|---|---|---|
| GB | 2110564 A | 6/1983 |
| WO | WO9913926 A2 | 3/1999 |

OTHER PUBLICATIONS

International Preliminary Examination Report issued in PCT/US01/30301, completed Apr. 2, 2004, 4 pages.

International Preliminary Examination Report issued in PCT/US01/42355, completed Nov. 17, 2003, 3 pages.

International Search Report issued in PCT/US01/30301, mailed Jul. 3, 2002, 1 page.

International Search Report issued in PCT/US01/42355, mailed May 29, 2002, 2 pages.

Lewis, Richard J., Sr., ed., Hawley's Condensed Chemical Dictionary, Thirteenth Edition, John Wiley & Sons, Inc., New York, 1997, p. 687.

Supplemental European Search Report issued in EP Application No. 01979904, completed May 7, 2010, mailed May 18, 2010, 3 pages.

Supplemental European Search Report issued in European Application No. 01985677.2, completed Jun. 20, 2007, 2 pages.

Tas, J., "Polyacrylamide Films as a Tool for Investigating Qualitative and Quantitative Aspects of the Staining of Glycosaminoglycans with Basic Dyes," Histochemical Journal, 9:267-276 (1977).

Templeton, Douglas M., "General Occurrence of Isosbestic Points in the Metachromatic Dye Complexes of Sulfated Glycosaminoglycans," International Journal of Biological Macromolecules, 10:131-136 (1988).

* cited by examiner

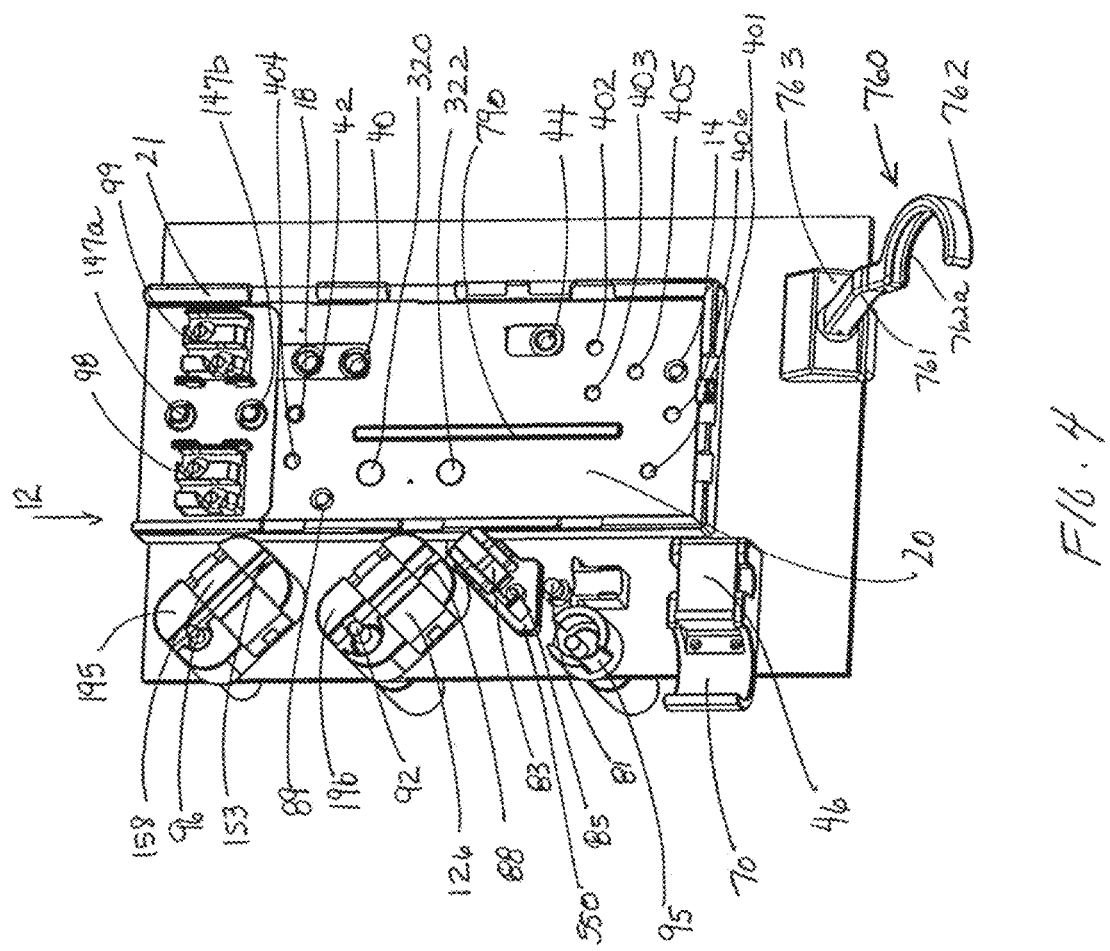

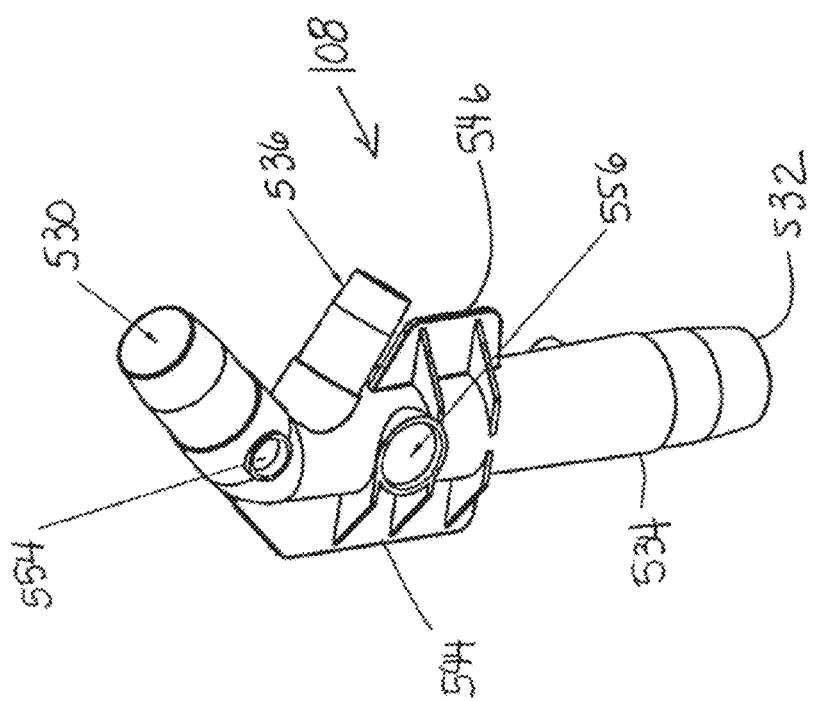
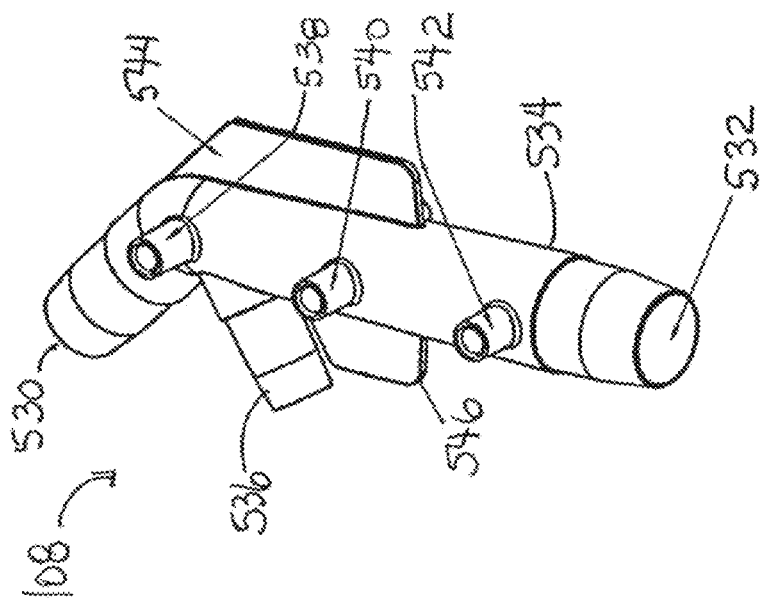

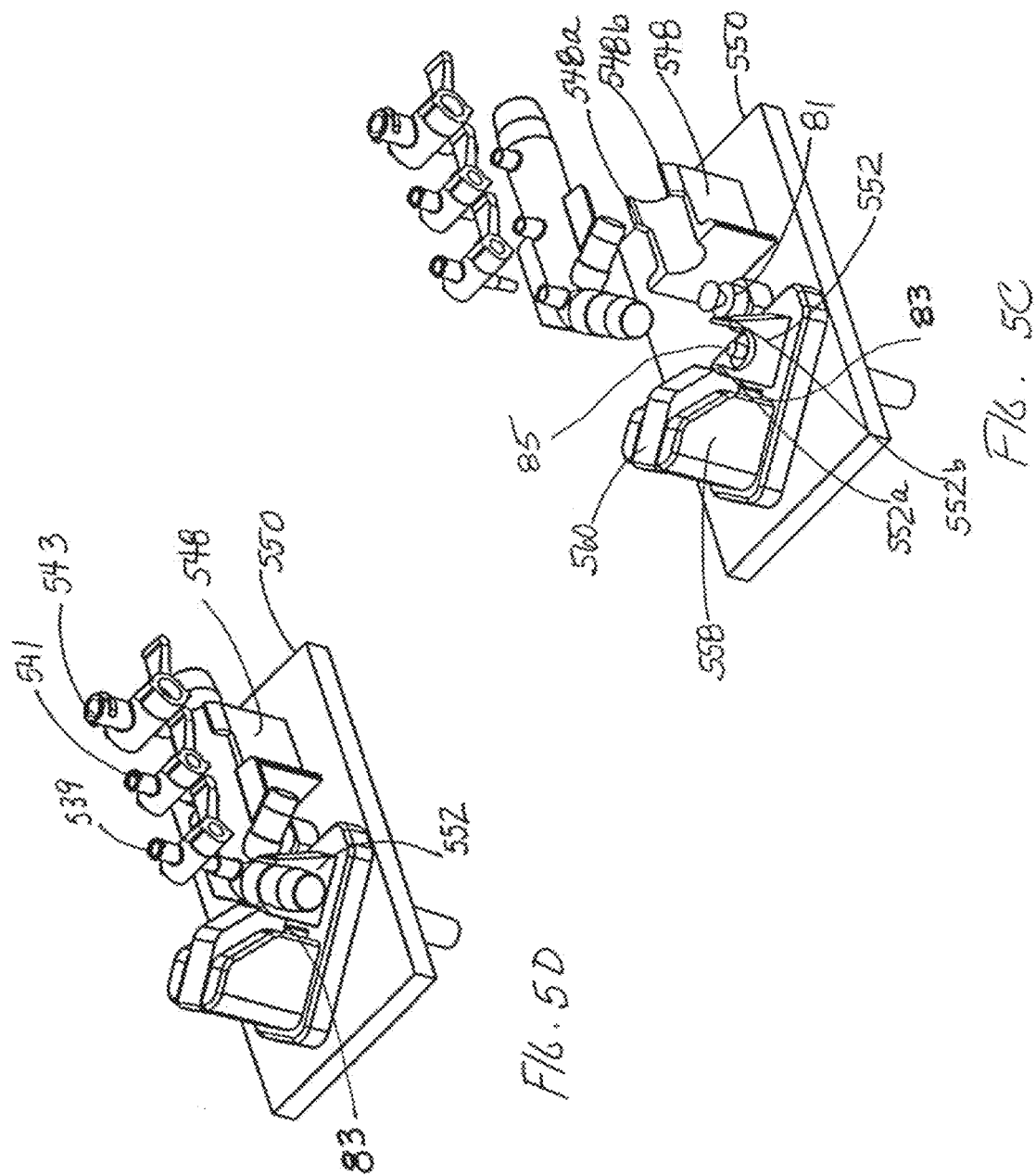

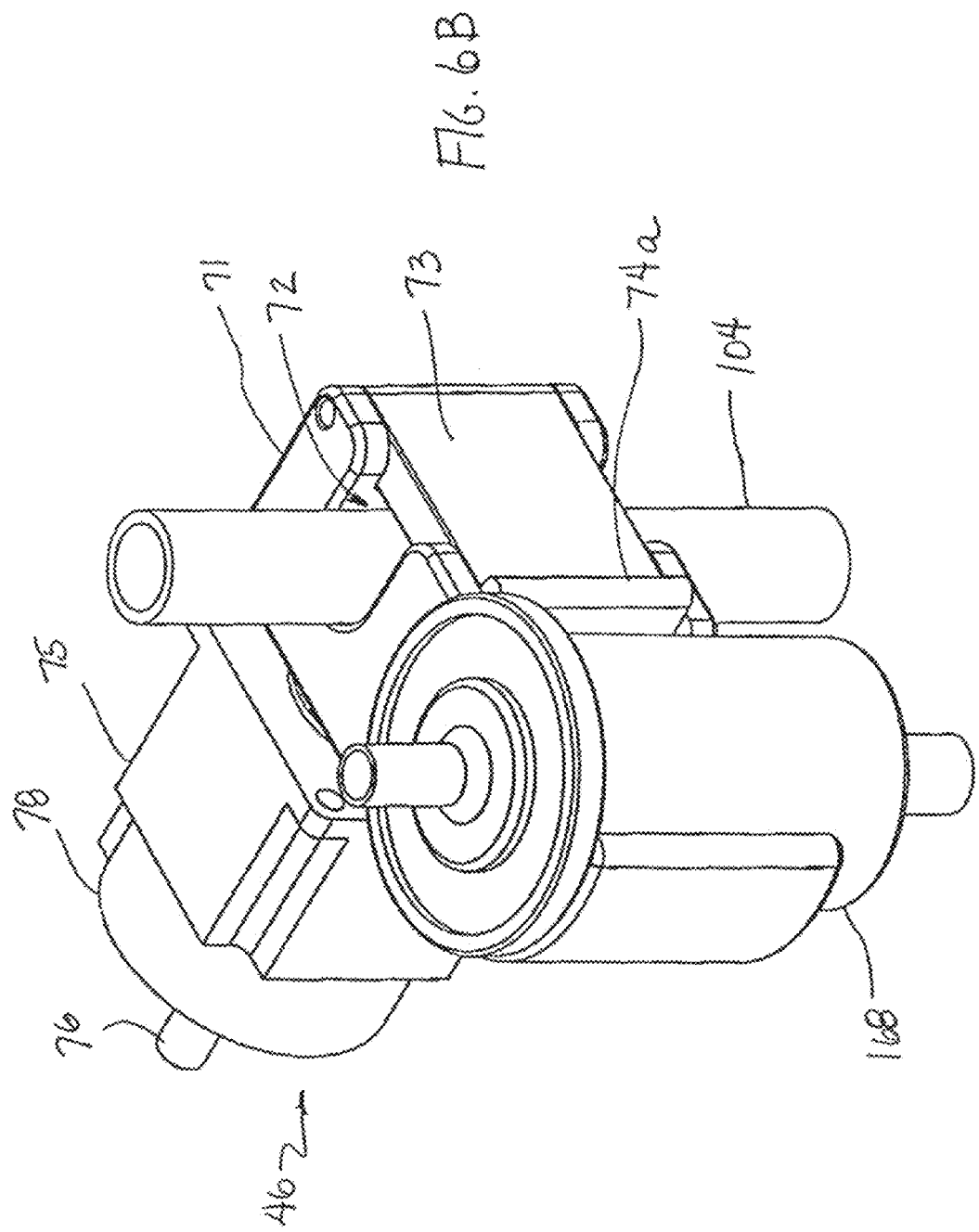

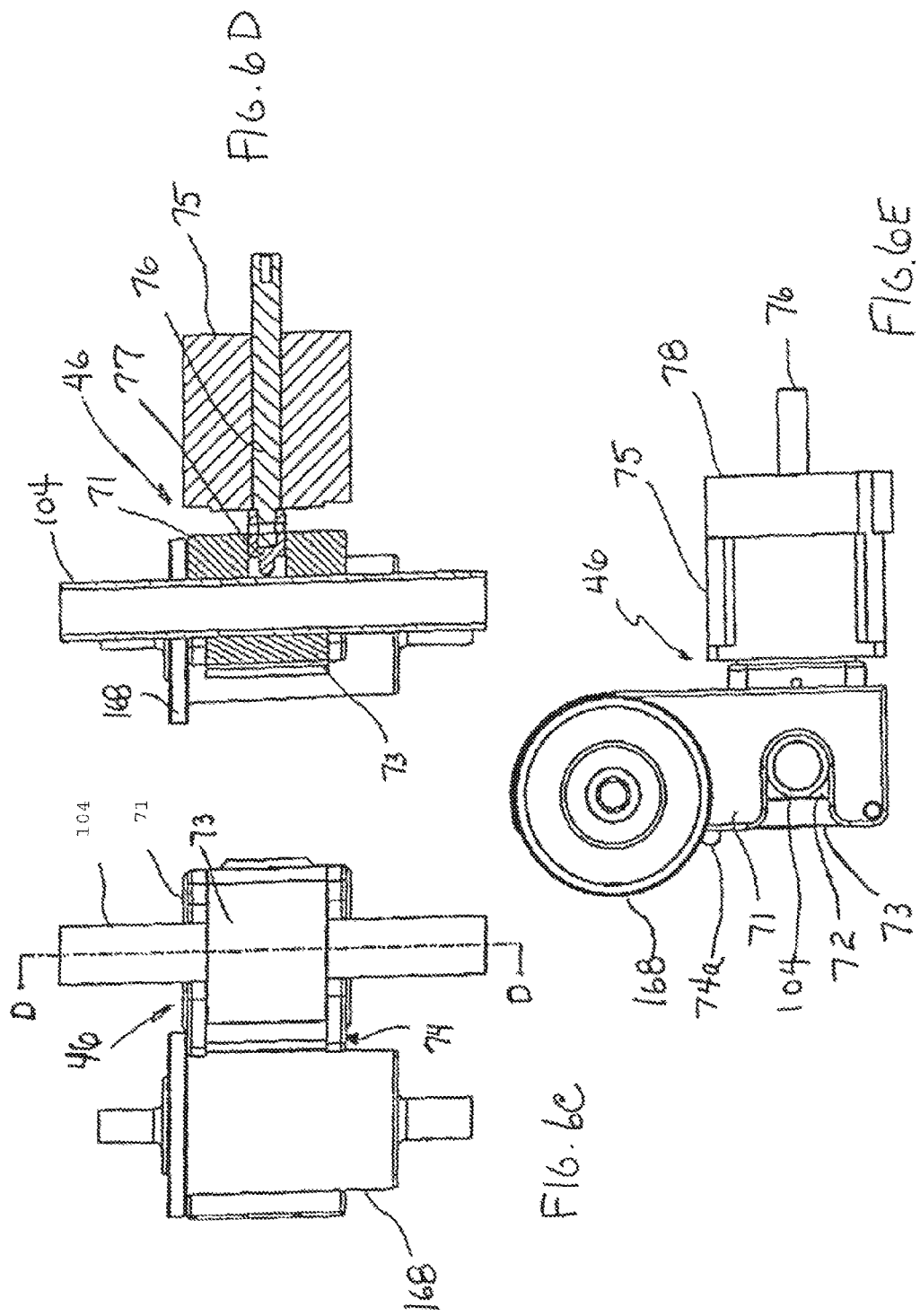

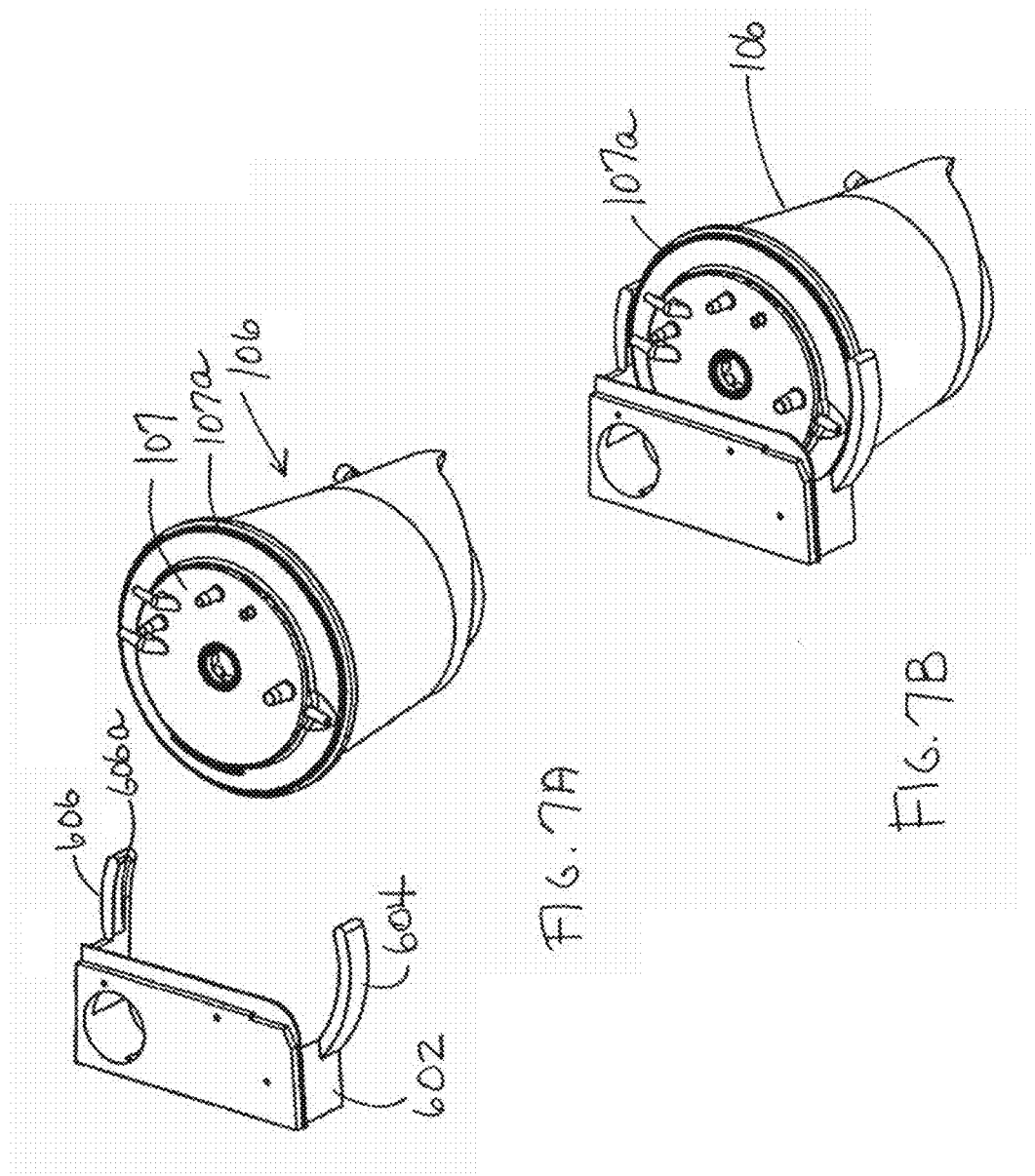

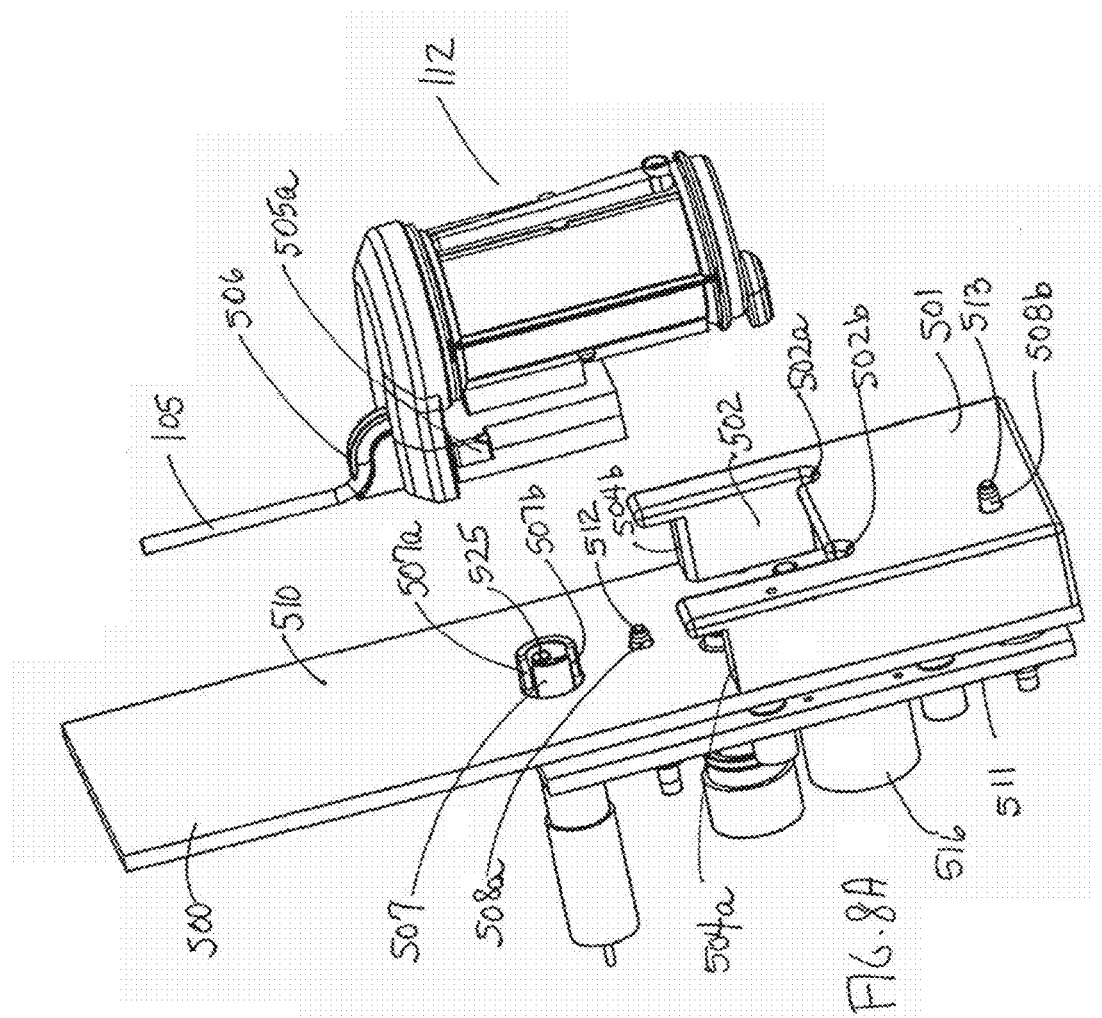

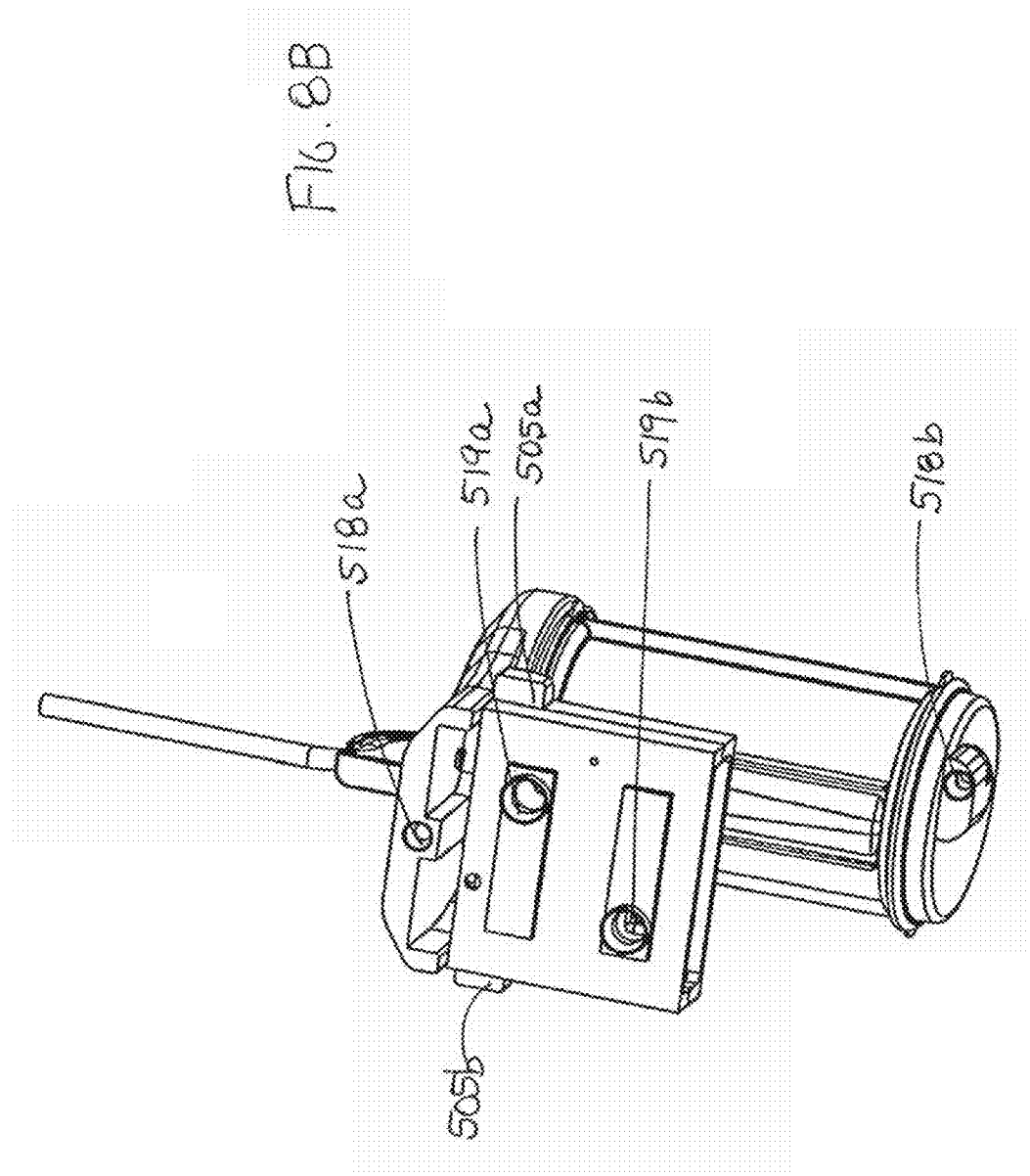

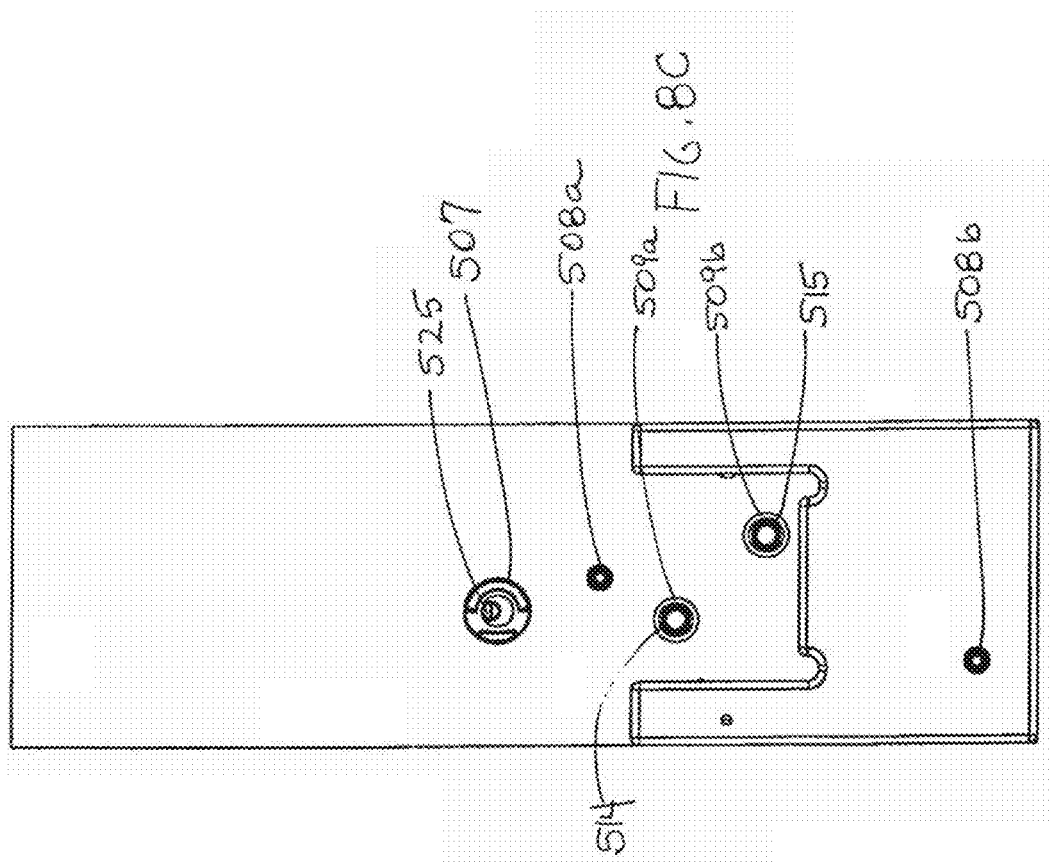

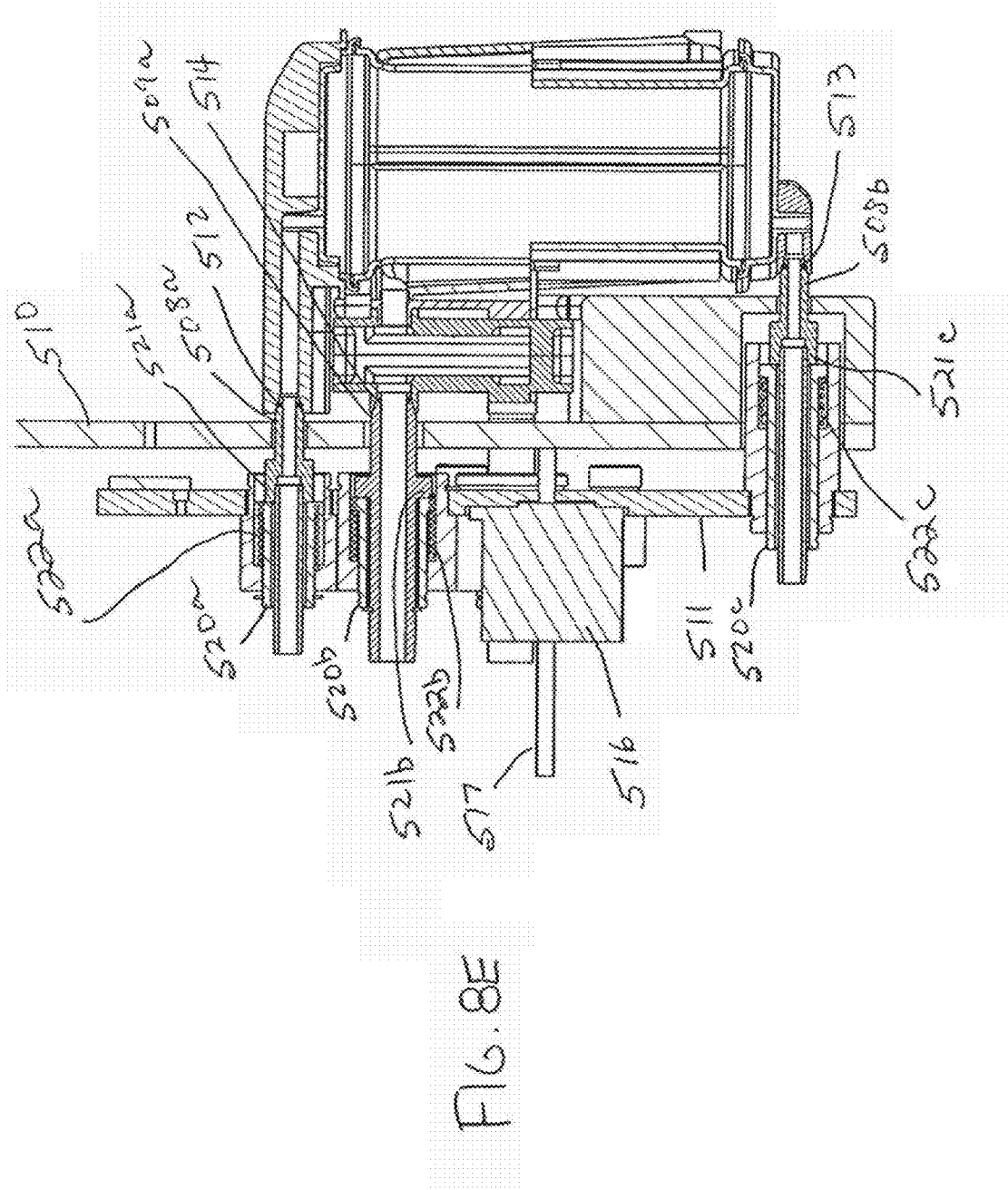

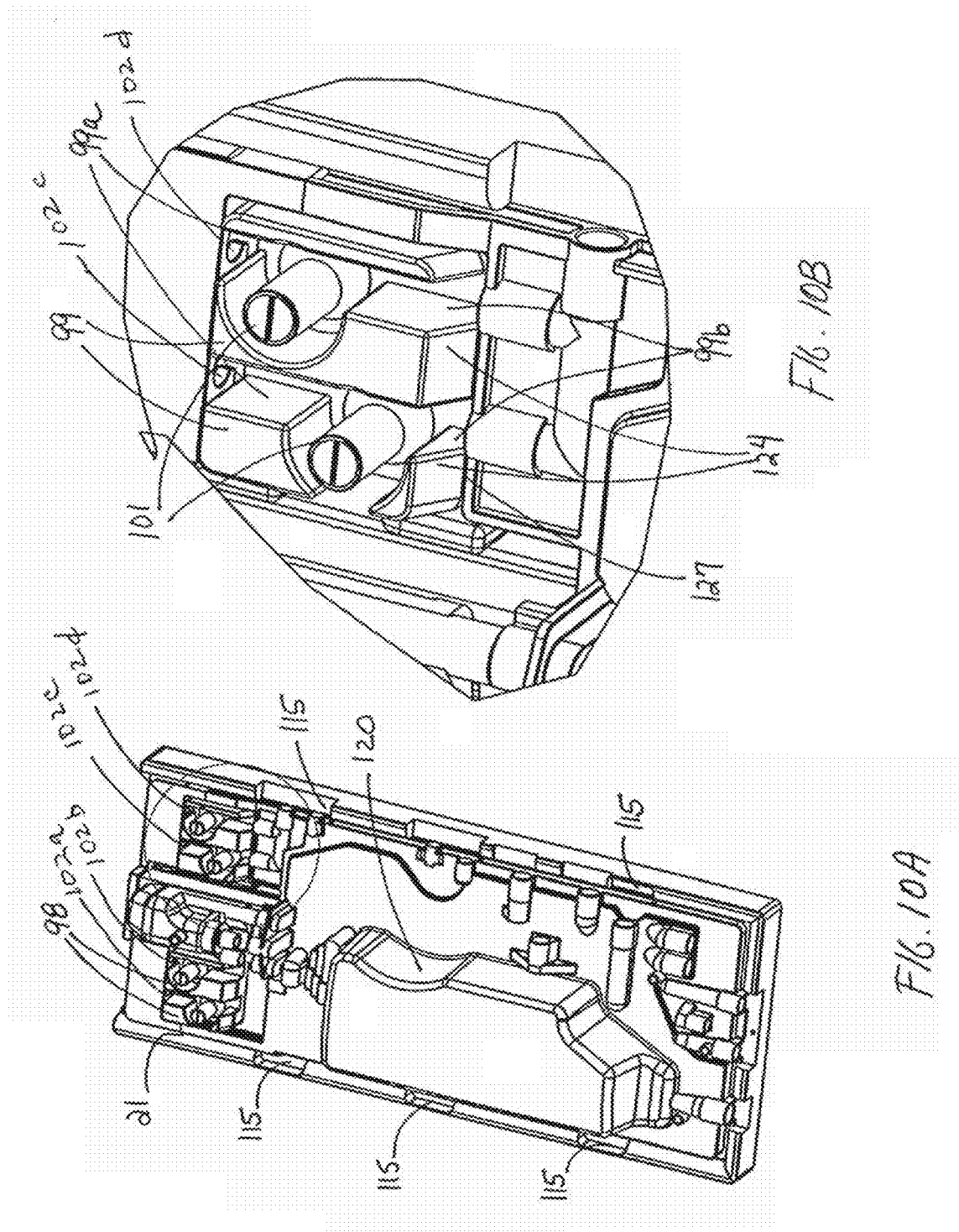

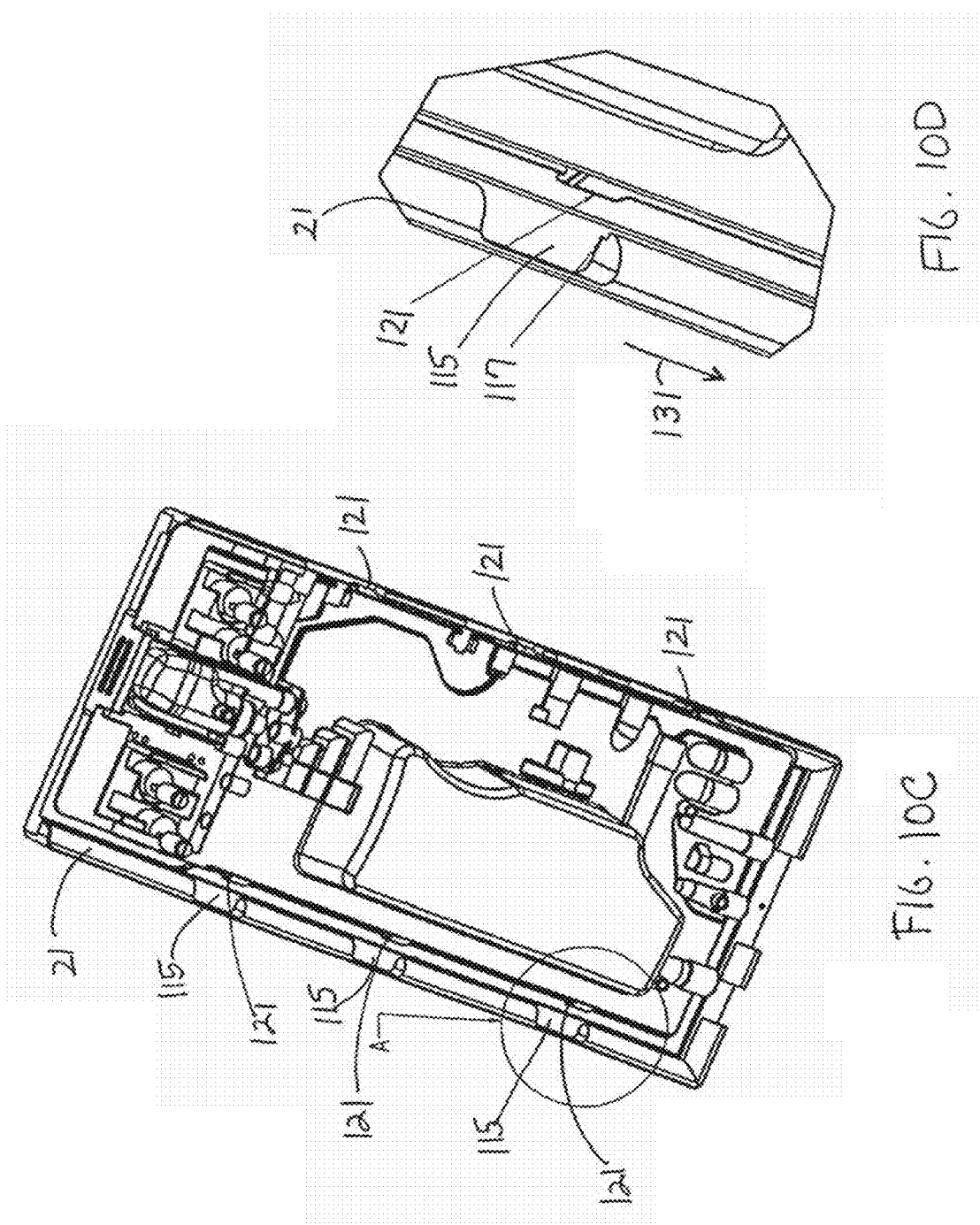

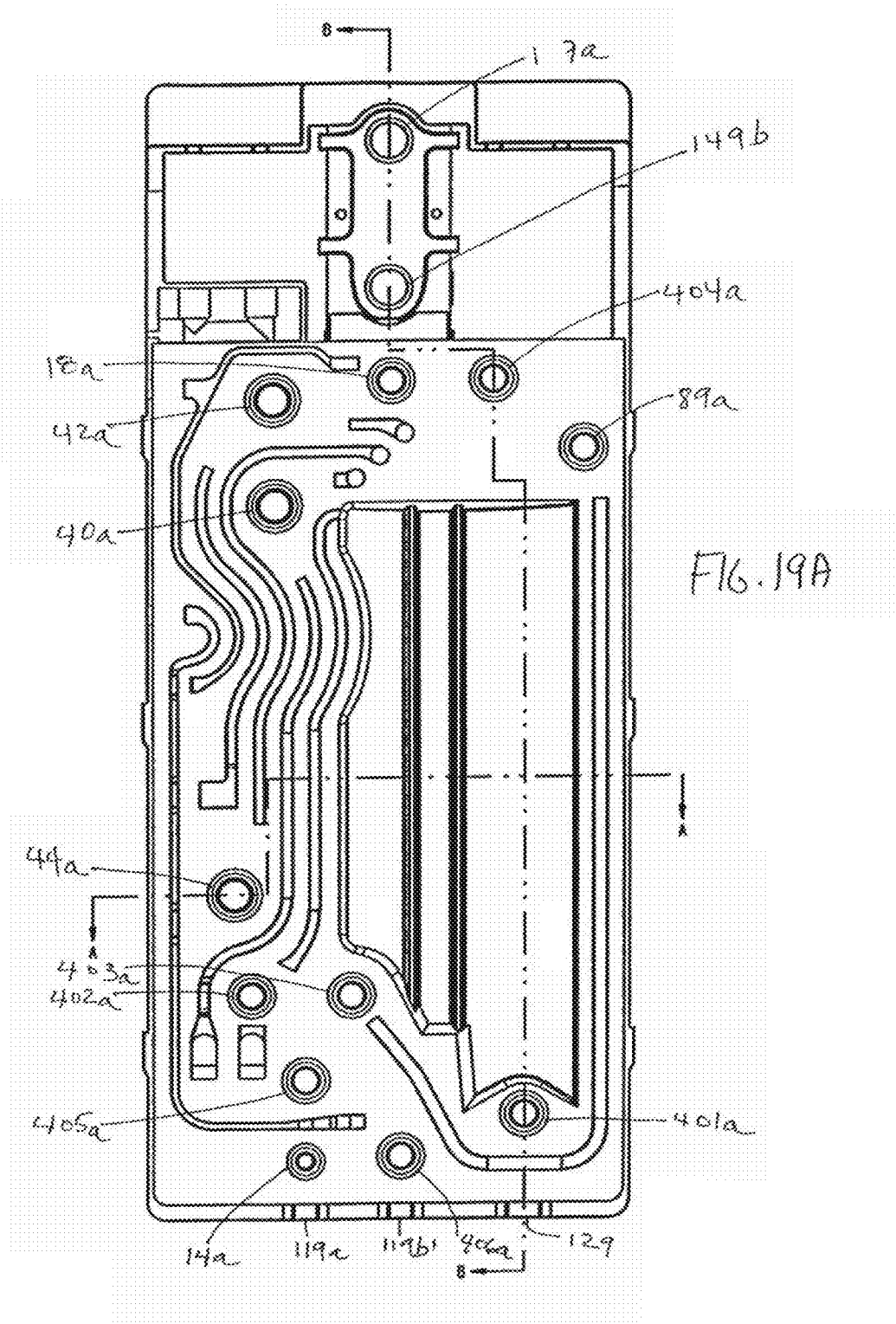

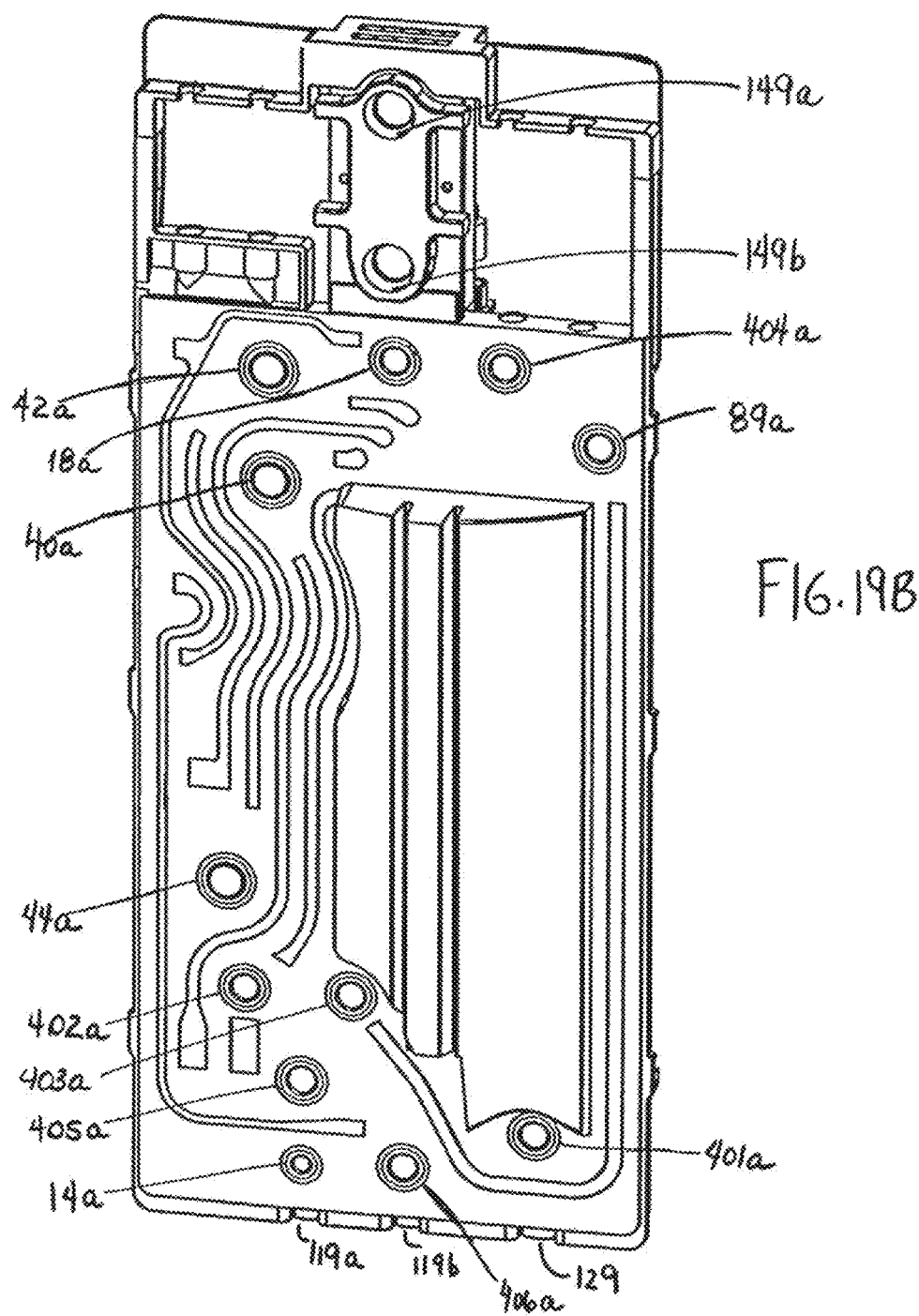

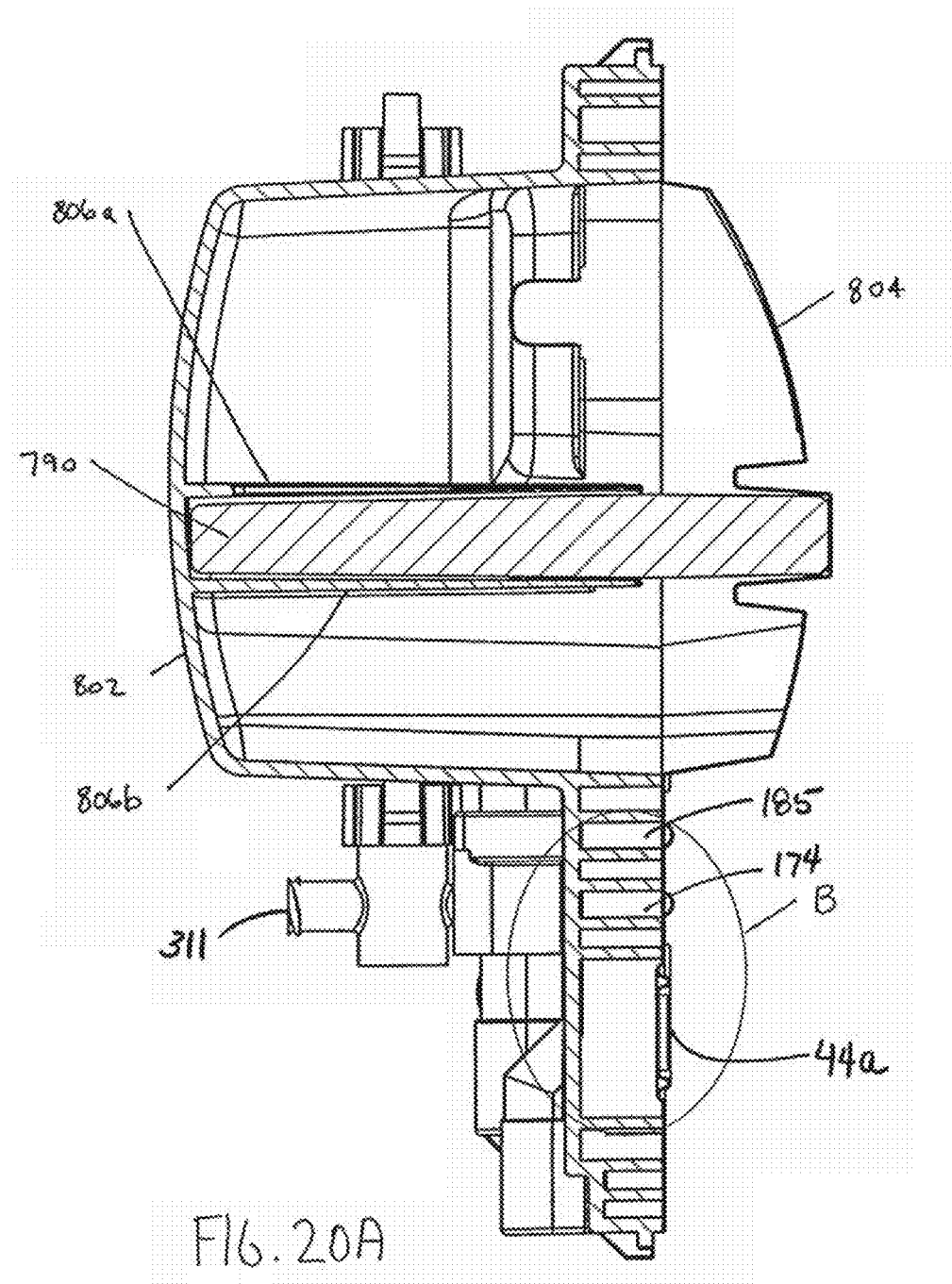

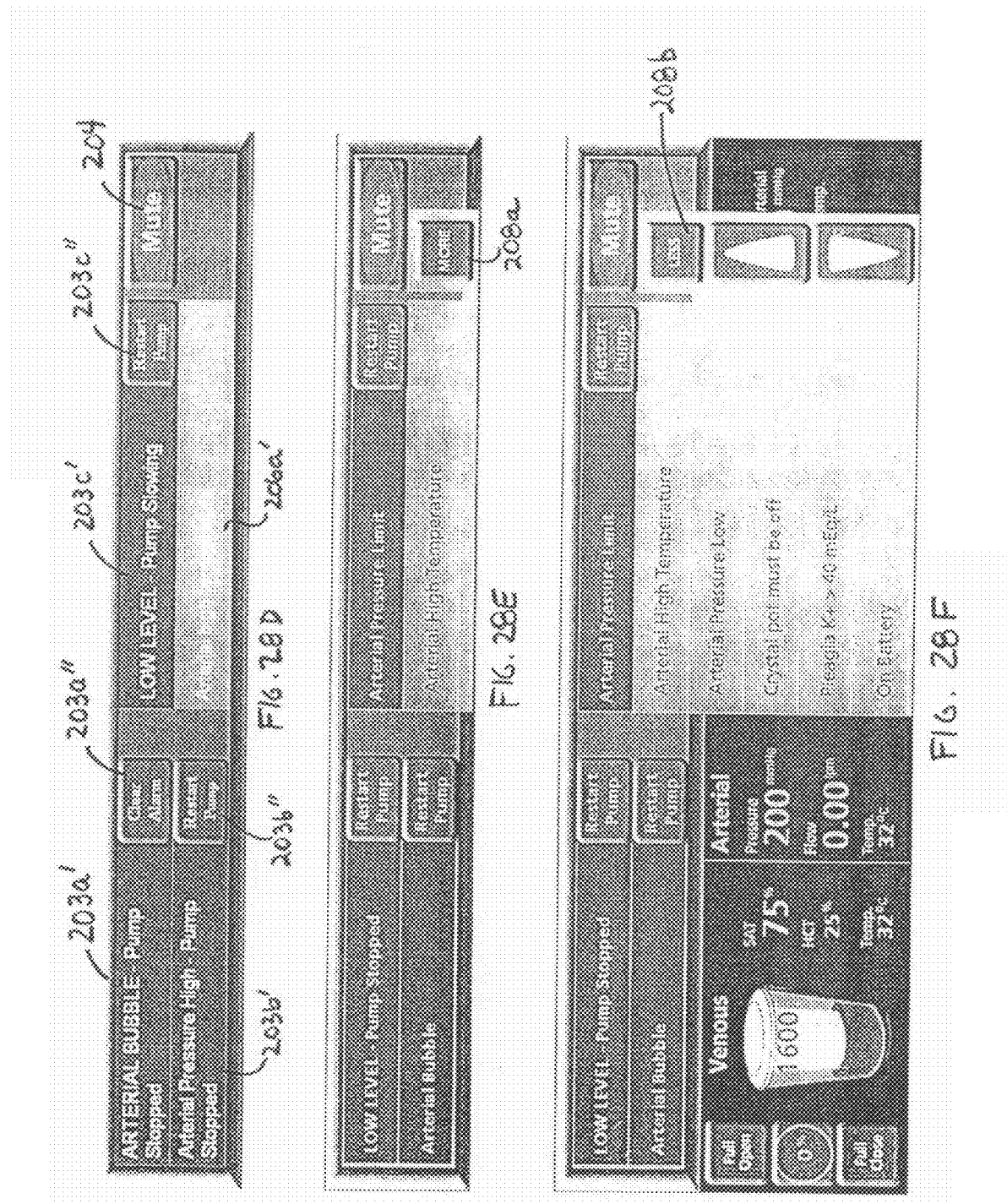

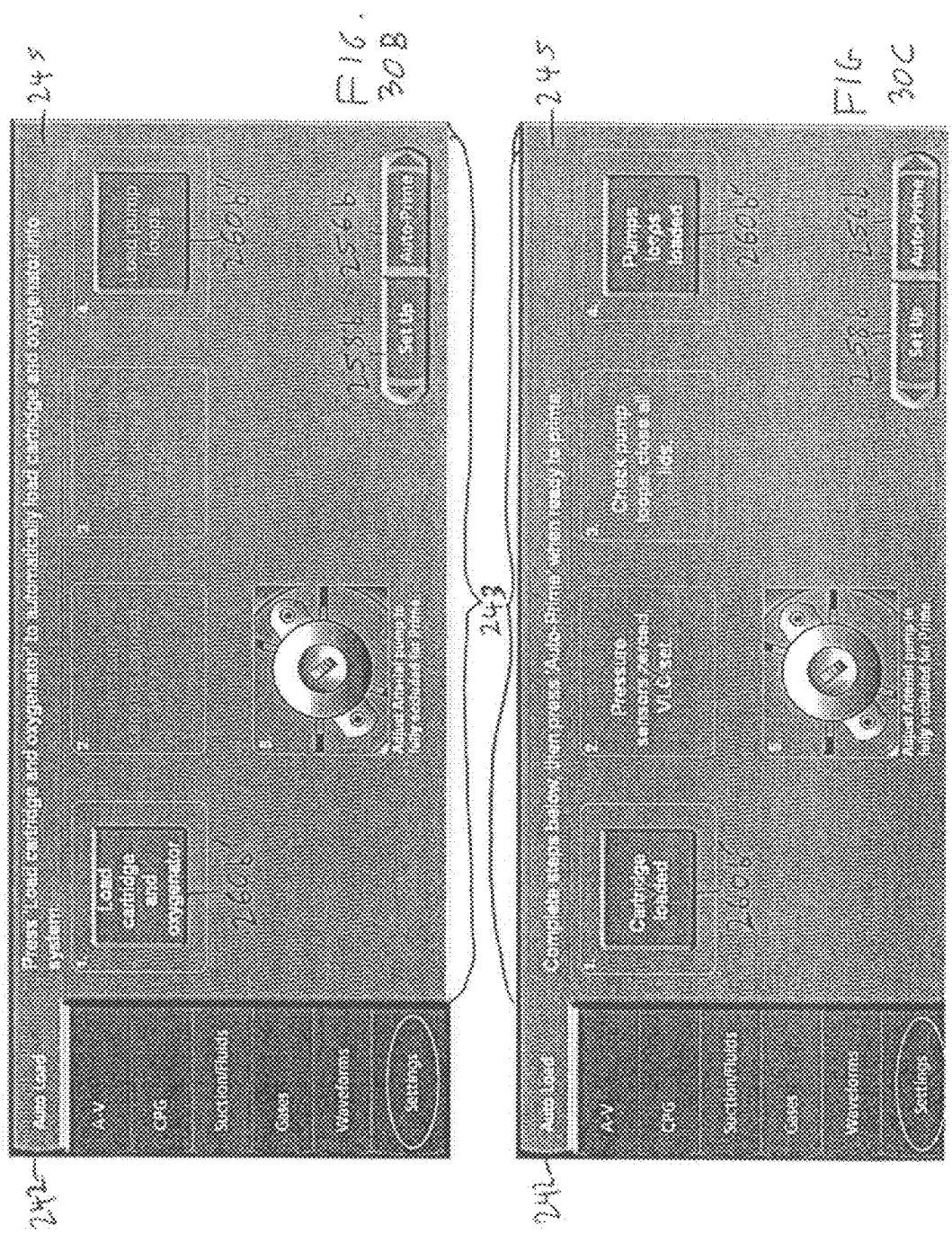

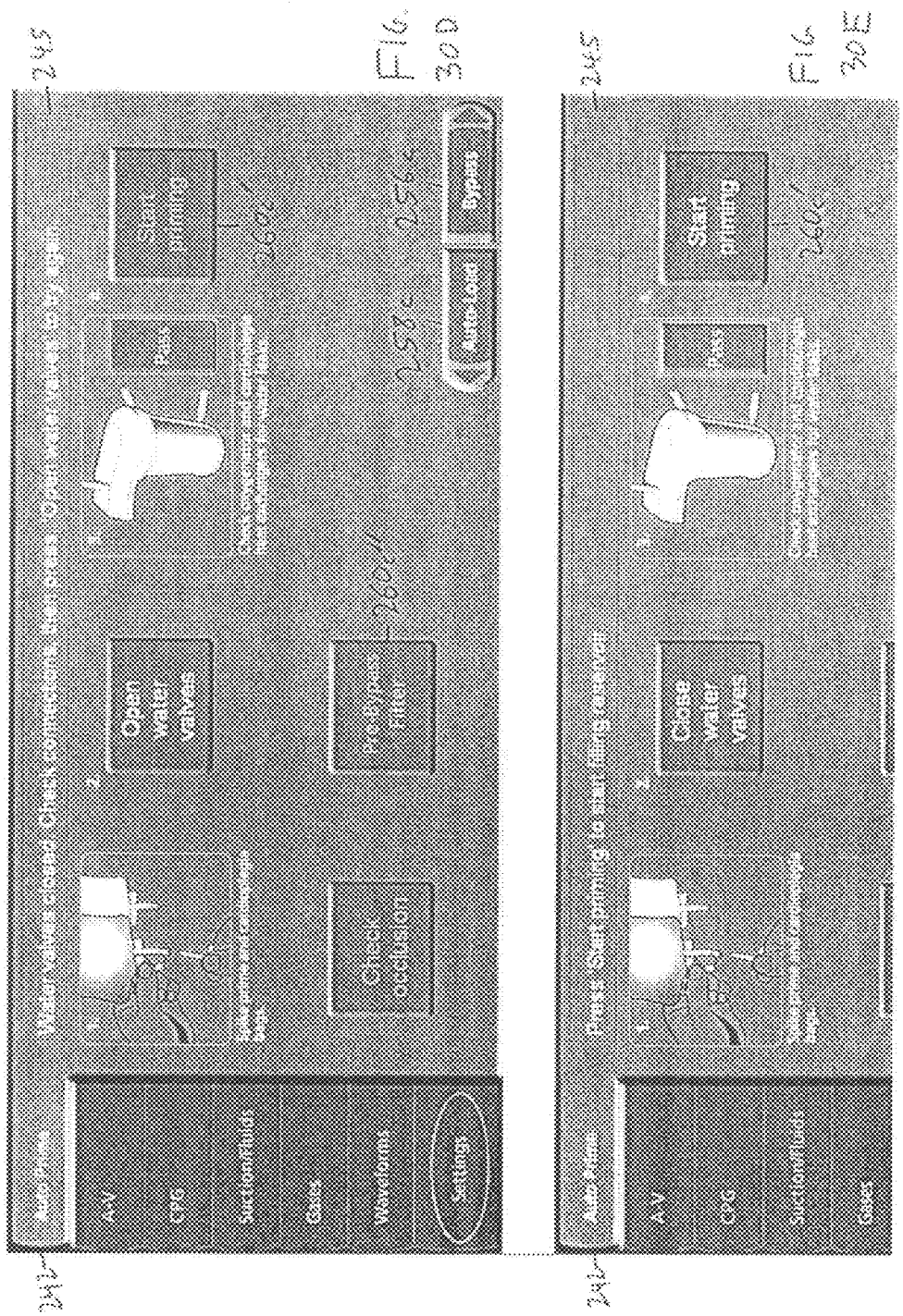

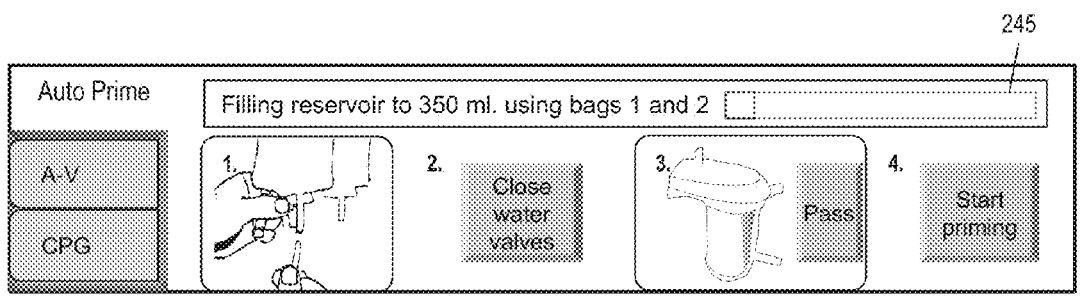
FIG. 30F
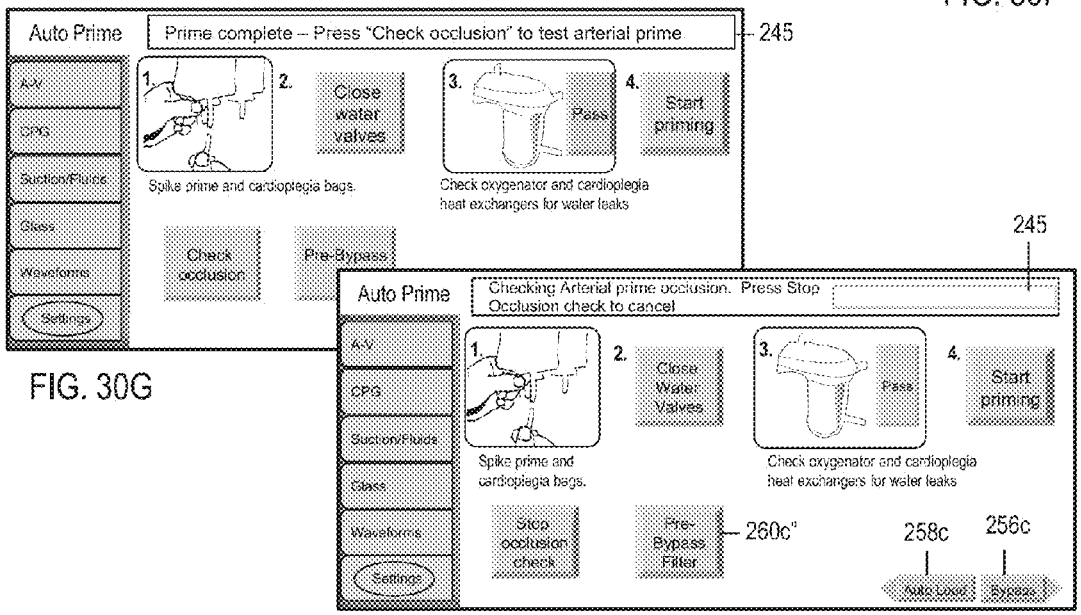
FIG. 30G
FIG. 30H

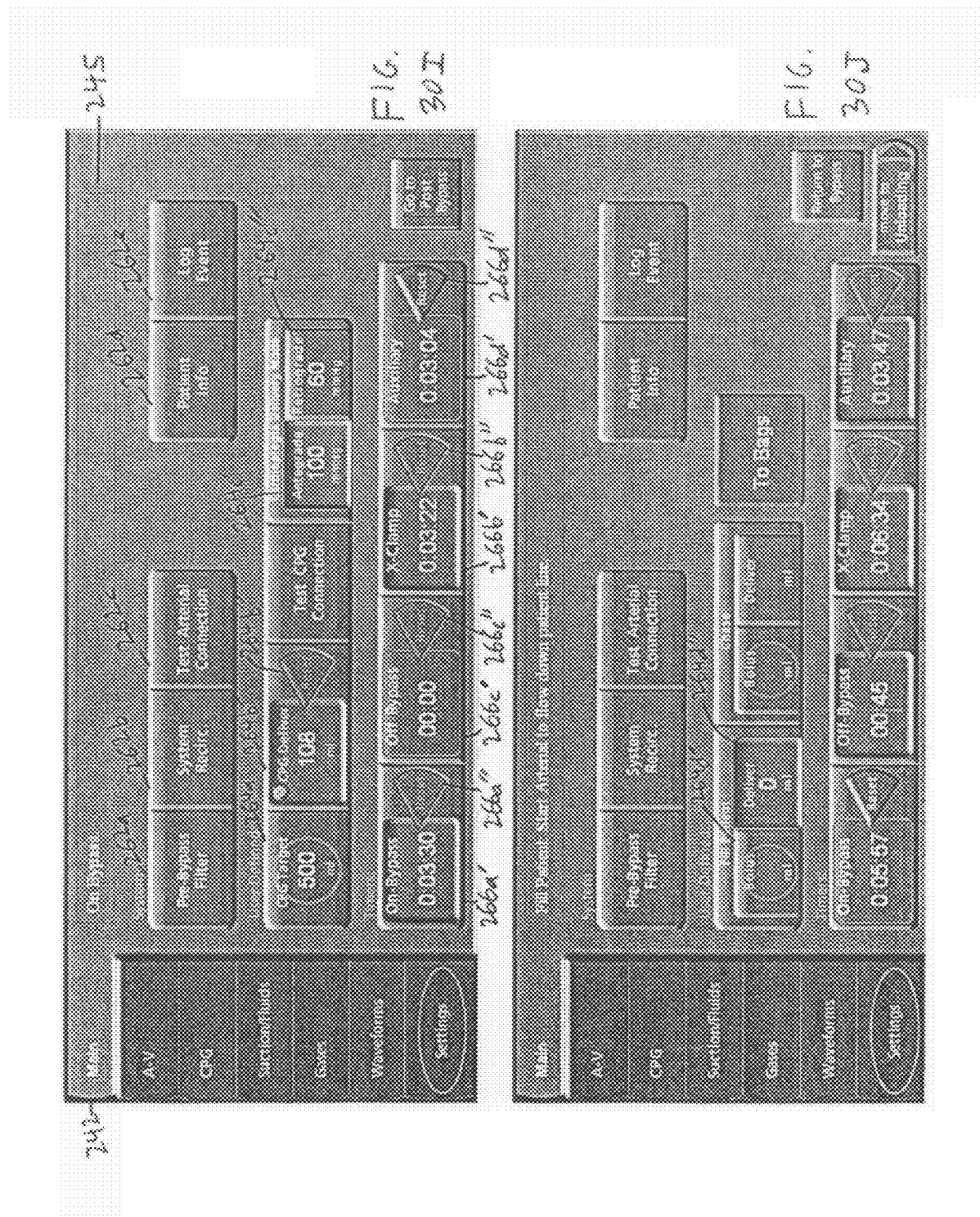

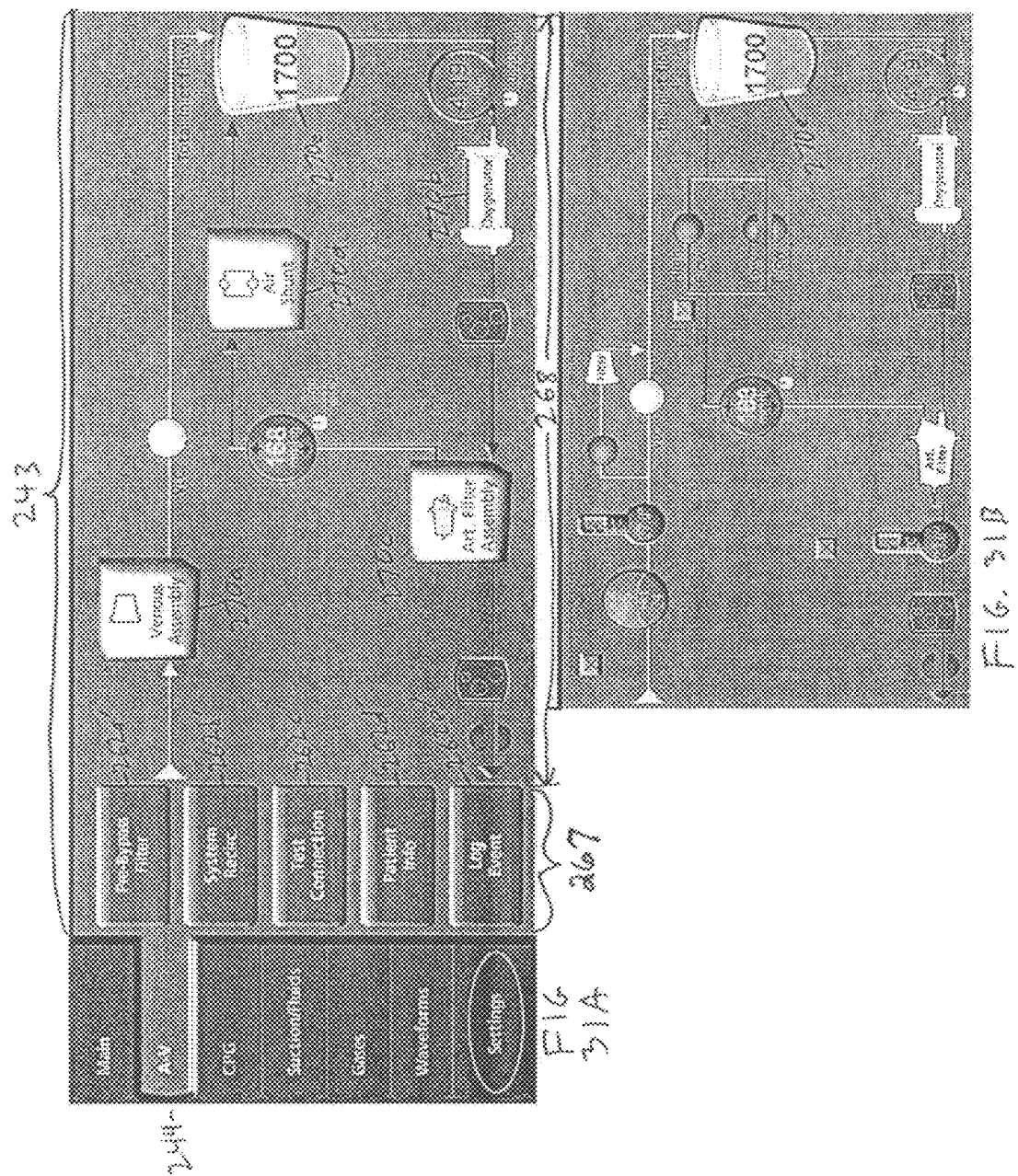

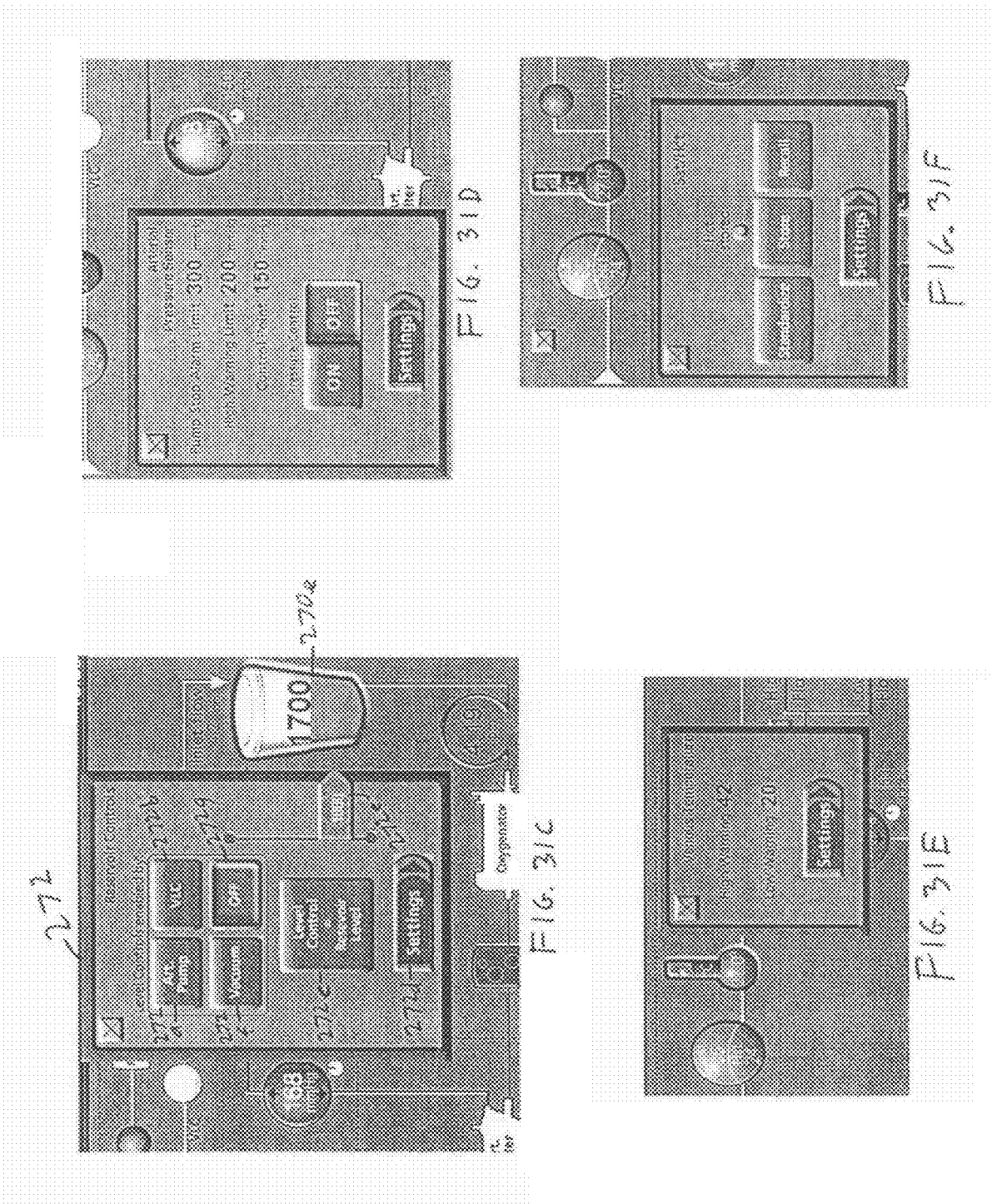

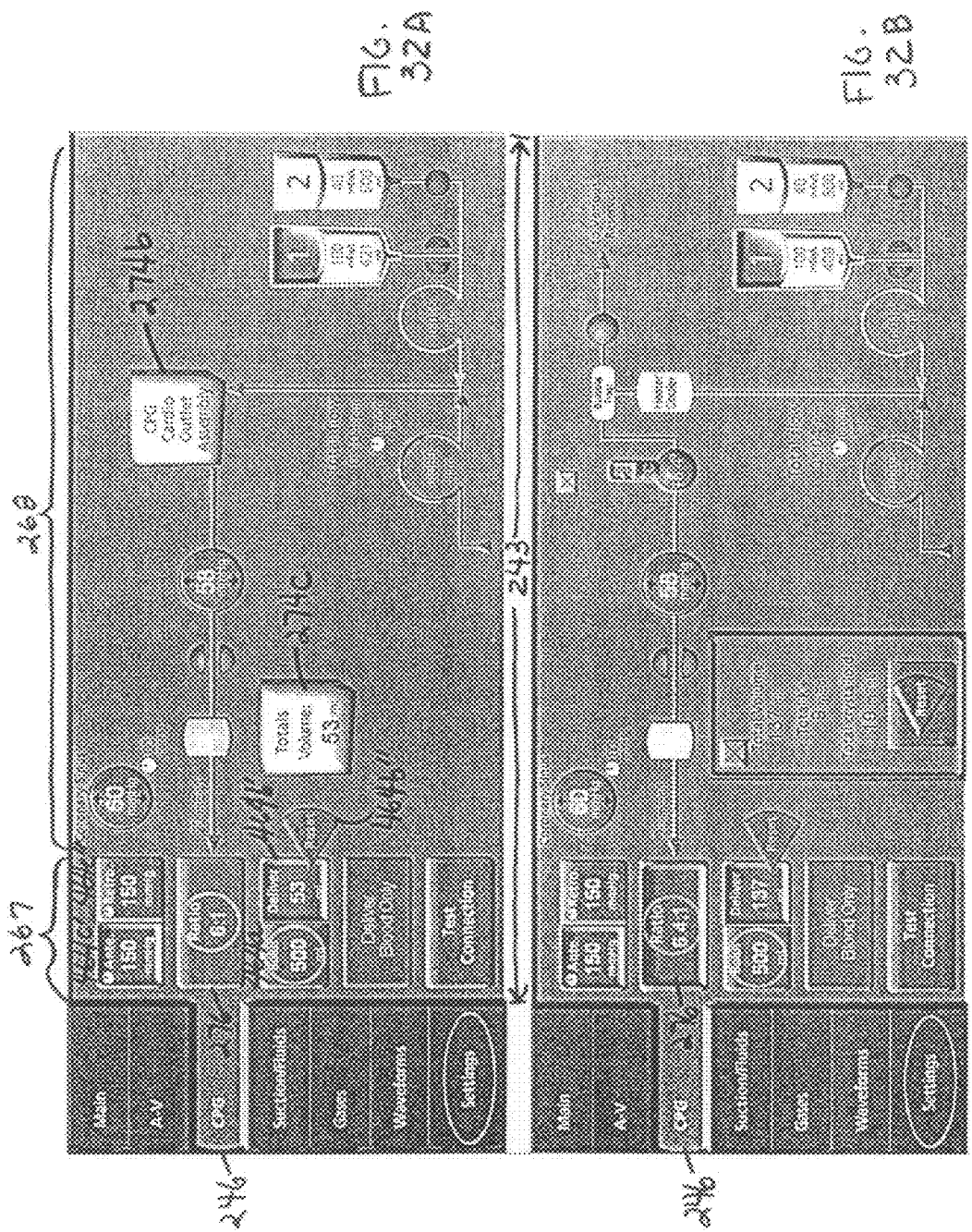

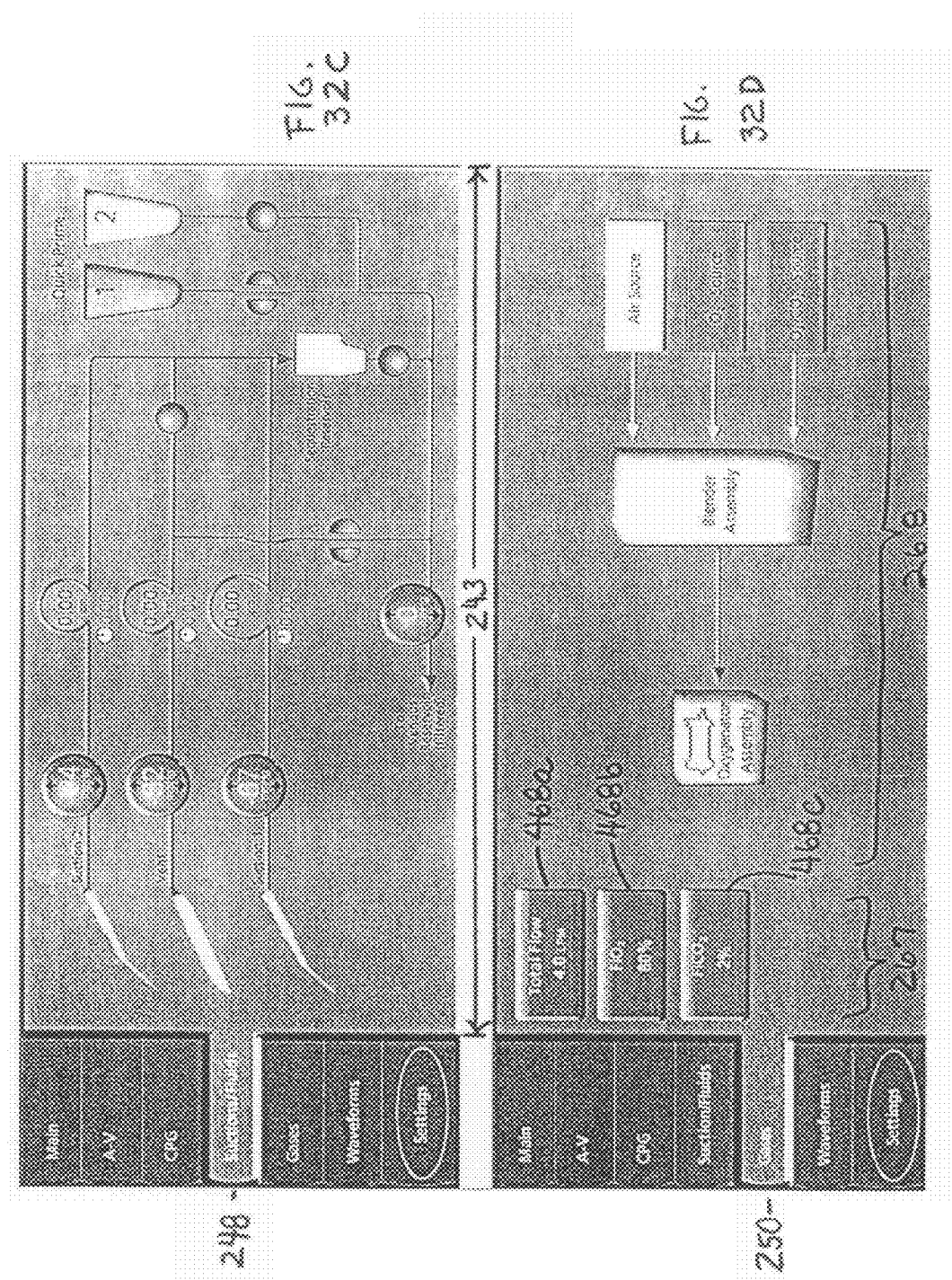

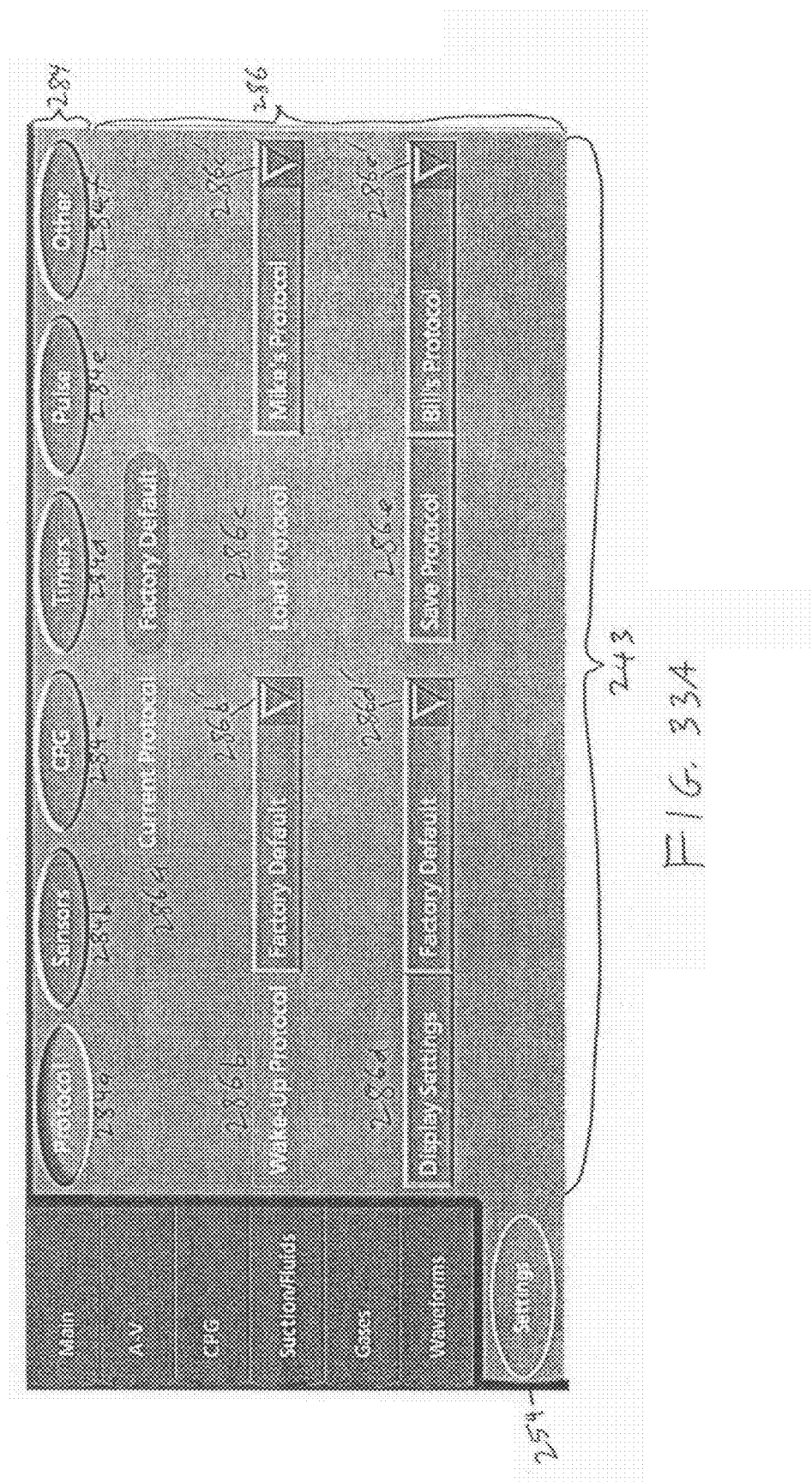

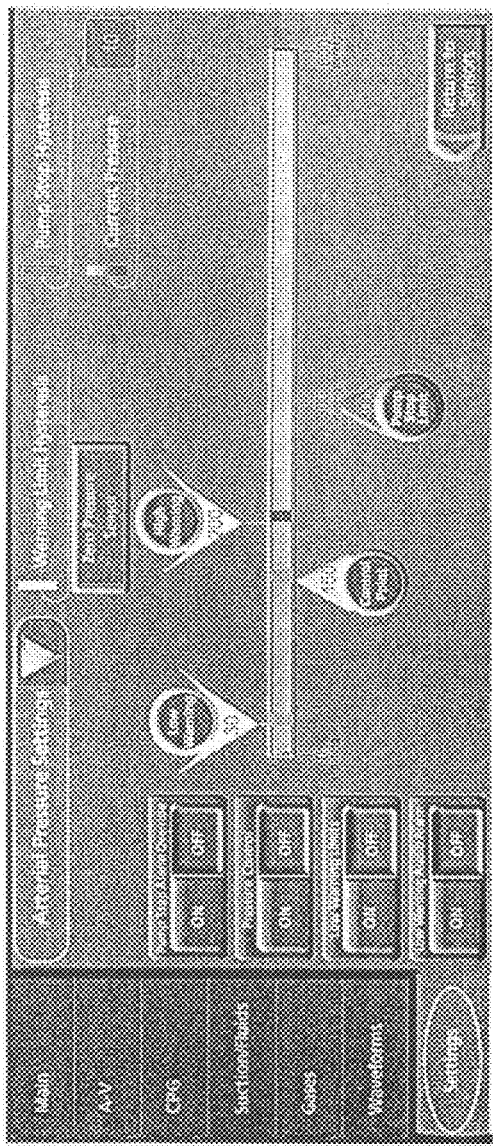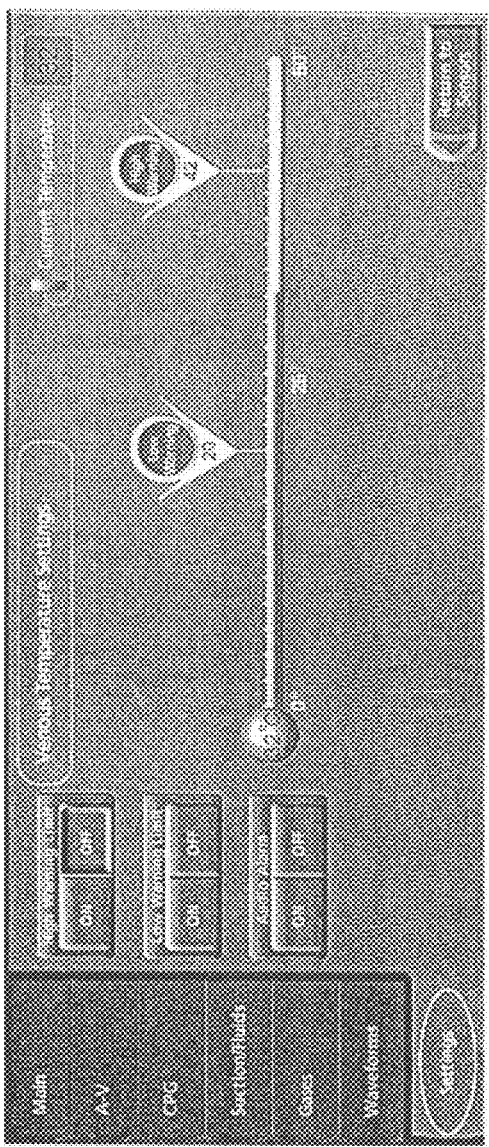

BLOOD PERFUSION SYSTEM

CROSS-REFERENCE TO RELATED APPLICATION

This application is a continuation of U.S. application Ser. No. 13/285,642, filed Oct. 31, 2011, which is a continuation of U.S. application Ser. No. 11/333,671, filed Jan. 17, 2006, now U.S. Pat. No. 8,057,419, which is a continuation of U.S. application Ser. No. 09/963,878, filed Sep. 26, 2001, which claims the benefit under 35 U.S.C. 119(e) of U.S. Provisional Application No. 60/235,837, filed on Sep. 27, 2000, the contents of which are hereby incorporated herein by reference in their entirety.

TECHNICAL FIELD

The present invention relates to blood perfusion systems. In one embodiment, the present invention can be used in cardiopulmonary bypass procedures.

BACKGROUND

In general, blood perfusion entails forcing blood through the vessels of a bodily organ. For such purposes, blood perfusion systems typically entail the use of one or more pumps in an extracorporeal circuit that is interconnected with the vascular system of a patient.

Of particular interest, cardiopulmonary bypass surgery requires a perfusion system that provides for the temporary cessation of the heart to create a still operating field by replacing the function of the heart and lungs. Such isolation allows for the surgical correction of vascular stenosis, valvular disorders, and congenital heart defects. In perfusion systems used for cardiopulmonary bypass surgery, an extracorporeal blood circuit is established that includes at least one pump and an oxygenation device to replace the functions of the heart and lungs.

More specifically, in cardiopulmonary bypass procedures oxygen-poor blood, i.e., venous blood, is gravity-drained or suctioned from a large vein entering the heart or other veins in the body (e.g., femoral) and is transferred through a venous line in the extracorporeal circuit. The venous blood is pumped to an oxygenator that provides for oxygen transfer to the blood. Oxygen may be introduced into the blood by transfer across a membrane or, less frequently, by bubbling oxygen through the blood. Concurrently, $CO_2$ is removed across the membrane. The oxygenated blood is then returned through an arterial line to the aorta, femoral, or other artery.

In addition to the above-noted components, extracorporeal fluid circuits used for cardiopulmonary bypass procedures also typically provide for the flow of a cardioplegia mixture through a cardioplegia line into the root of the aorta, coronaries and/or coronary sinus in order to nourish, arrest, and maintain the arrest of the heart. The cardioplegia mixture is typically circulated through a heat exchanger prior to patient delivery. Additional devices that can be employed include a reservoir to hold the venous blood, a heat exchanger to cool or heat the returned blood, and various filters to keep particles greater than a predetermined size from passage into the patient.

Further, extracorporeal fluid circuits utilized during cardiopulmonary bypass procedures may also include various suction lines. Such lines are employed to remove blood that collects in the thoracic cavity during surgery. Such blood may contain debris such as skin, air, bone chips, etc. and may be salvaged via filtering and routed to a reservoir for subsequent washing and/or oxygenation and return to the patient. A vent line may also be utilized to remove blood that accumulates in the heart or vasculature (e.g., aortic root, pulmonary artery, etc.) during the bypass procedure. Removal of such accumulated blood may be important to avoid heart distention. The vented blood may be routed to a reservoir for subsequent oxygenation and return to the patient or washing. In addition to the above-noted components, extracorporeal fluid circuits utilized in connection with cardiopulmonary bypass procedures may include components for the introduction into the blood of various nutrients and pharmaceuticals.

The various fluid circuitry and components of an extracorporeal circuit are set up by medical personnel prior to the bypass procedure. This can be a time consuming process since many of the connections are made by hand. As will be appreciated, this set-up procedure is also the source of potential error. Any incorrect or leaky connection can jeopardize both the success of the surgical procedure and the safety of the patient. Further, such an approach has entailed the separate setup and monitoring of each circuit by medical personnel during the course of a cardiopulmonary bypass procedure. Further, establishment of the operative interrelationships between the various circuits has been left to the attention and coordination of medical personnel. In view of the foregoing it would be desirable to have an integrated perfusion system which is easy to set-up, use and monitor during the bypass procedure. Such a system should eliminate many of the sources of error in the set-up, monitoring and use of conventional extracorporeal perfusion circuits as well as improve system monitoring and safety. The present invention comprises an integrated perfusion system which overcomes many of the disadvantages of present perfusion systems.

SUMMARY

In view of the foregoing, one objective of the present invention is to provide a blood perfusion system that provides for simplified set-up and interconnection/disconnection of various disposable components with monitoring/control components.

Relatedly, another objective of the present invention is to provide a blood perfusion system that provides for both enhanced/simplified monitoring and control over various operating parameters during a medical procedure, and that concomitantly yields system performance advantages.

Yet another objective of the present invention is to provide a blood perfusion system that readily provides medical personnel with information to facilitate setup and/or to facilitate operation, parameter monitoring and alarm response during perfusion procedures.

An additional objective of the present invention is to provide a blood perfusion system that maintains a wide range of configurability for customized use by medical personnel on a patient-specific basis. While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

One or more of the above-noted objectives and additional advantages are provided by the blood perfusion system disclosed herein. The system integrates one or more fluid lines and flow-through components in a disposable assembly that operatively interfaces with integrated fluid monitoring/flow control components of a control unit. Additional objectives and advantages may also be realized in the present invention via the provision of a multifunctional, graphic user interface that is operatively interconnected with fluid monitoring/flow control componentry in the disclosed system.

Figure 1:
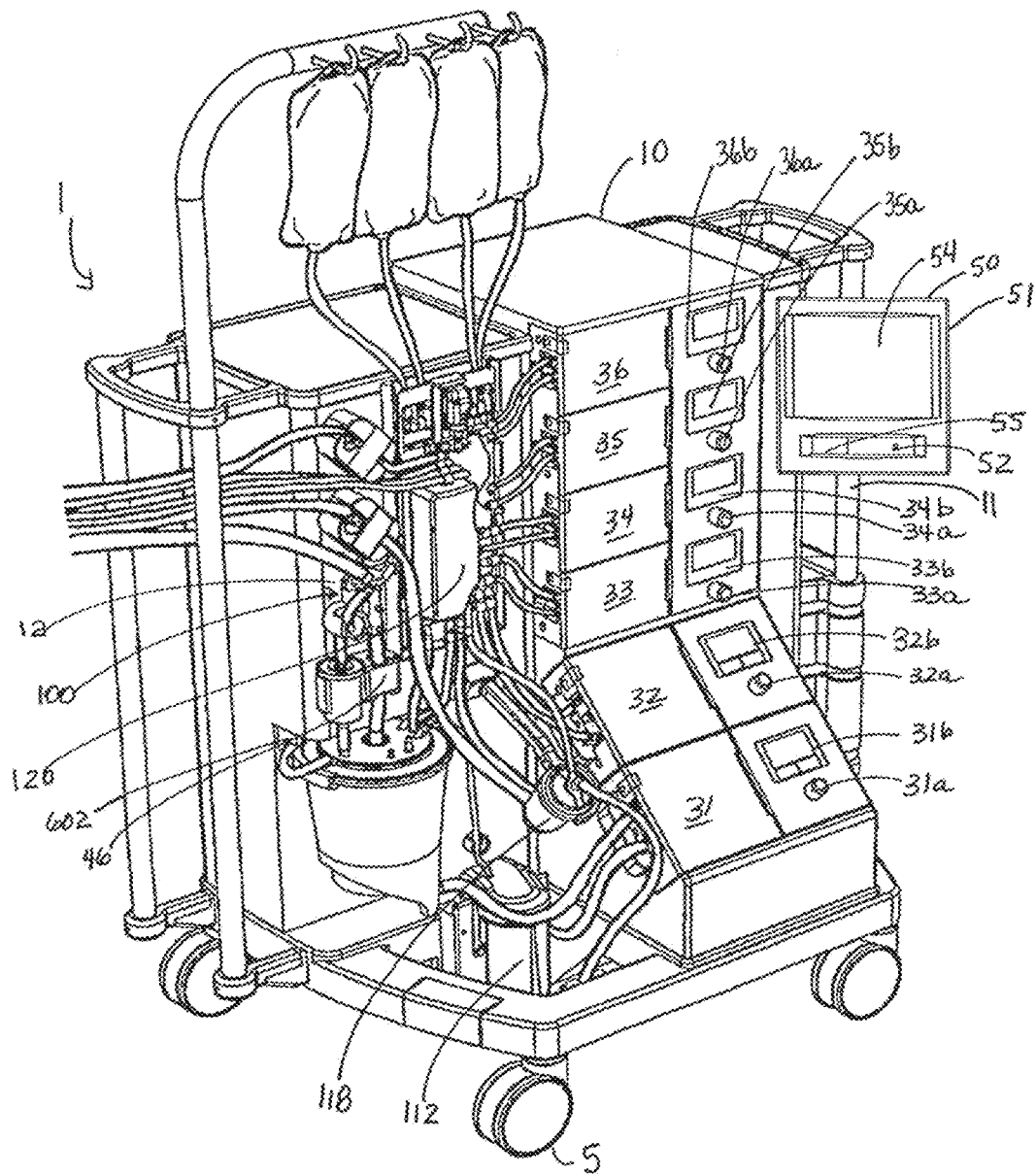

In one aspect, this invention is an extracorporeal blood perfusion system for receiving venous blood from a patient and for returning oxygenated blood to the patient in a cardiopulmonary bypass procedure, comprising a disposable assembly including a cartridge and a plurality of interconnected tubing lines, the cartridge having a plurality of internal fluid passageways, wherein a first of the tubing lines is fluidly interconnected with at least one of the plurality of fluid passageways and wherein the disposable assembly defines a blood circuit for receiving venous blood from the patient and transferring oxygenated blood to the patient in a cardiopulmonary bypass procedure; and a control unit having a component interface region, the component interface region including a cartridge interface region for operatively interfacing with the cartridge, and a first pump for operatively interfacing with a the blood circuit, wherein the venous blood is pumped through the blood circuit by the first pump.

The disposable assembly may further comprise a reservoir for accumulating the venous blood from the patient, and the component interface region may further comprise a flow control clamp for controlling the flow of venous blood through a second tubing line to the reservoir. The flow control clamp may be controllable to maintain at least one of a predetermined relative flow percentage through the second tubing line to the reservoir and a predetermined fluid volume within the reservoir. The disposable assembly may further comprise an oxygenator connected in the blood circuit downstream from the reservoir, and the first pump may be configured to pump accumulated venous blood from the reservoir through the oxygenator to provide for the transfer of the oxygenated blood to the patient. The disposable assembly of the perfusion system may also include a reservoir for accumulating the venous blood from the patient, and the component interface region may further comprises a sensor for detecting the presence of gaseous bubbles within the oxygenated blood and at least one valve assembly configured for diverting the flow of the oxygenated blood to the reservoir upon detection of gaseous bubbles in the oxygenated blood by the sensor.

The disposable assembly further defines a cardioplegia circuit for supplying a cardioplegia solution to the patient, the cardioplegia circuit including a fluid interconnection with the blood circuit for flowing at least a portion of the oxygenated blood to one of the plurality of fluid passageways for mixture with a cardioplegia solution. The component interface region may include a plurality of sensors positioned for monitoring an oxygen saturation, hematocrit and temperature of the venous blood received in the blood circuit and may include a pressure sensor positioned for monitoring a fluid pressure of the oxygenated blood in the blood circuit. The control unit of the system is operable to automatically suspend operation of the first pump when the pressure sensor detects a fluid pressure greater or less than a predetermined level and the cartridge comprises a housing including a first rigid portion connected to a second flexible portion. The cartridge interface region may further include a pressure sensor configured to sense fluid pressure in an internal passageway of the cartridge through the second flexible portion of the housing. The cartridge interface region optionally includes a valve actuator and the cartridge optionally includes a valve station, the valve station being in fluid communication with at least two of the internal passageways, the valve station having a flexible member configured to be moveable from a first position allowing fluid flow between the at least two internal passageways and a second position preventing fluid flow between the at least two internal passageways, the valve actuator being configured to interface with the flexible member to cause movement of the flexible member between the first and second positions.

In a second aspect, this invention is an extracorporeal blood perfusion system for use in receiving venous blood from a patient and for returning oxygenated blood to the patient, comprising a disposable assembly including a cartridge and a plurality of interconnected tubing lines, the disposable assembly defining a blood circuit for receiving venous blood from the patient and transferring oxygenated blood to the patient and a cardioplegia circuit for transferring a cardioplegia solution to the patient; a control unit having a component interface region including a cartridge interface region for operatively interfacing with the cartridge; and a first pump for controlling the flow of venous blood through a first tubing loop comprising the blood circuit, and a second pump for controlling the flow of cardioplegia solution through a second tubing loop comprising the cardioplegia circuit, wherein the second tubing loop is fluidly interconnected at each end thereof to the cartridge.

Preferably, the first and second pumps are substantially vertically aligned in relative fixed relation, and wherein the first pump is located below the second pump. The component interface region may further include a third pump for controlling the flow of blood through a third tubing loop comprising the cardioplegia circuit, wherein the third tubing loop is fluidly interconnected at each end thereof to the cartridge, and wherein the second pump and the third pump combinatively control the flow of cardioplegia solution to the patient. The second and third pumps may be substantially vertically aligned in relative fixed relation. The system's disposable assembly further defines a blood recovery circuit for receiving vented blood from a left ventricle of the patient and the component interface region further comprises a fourth pump for controlling the flow of the vented blood through a fourth tubing loop comprising the blood recovery circuit. The first, second, third and fourth pumps may be in substantial vertical alignment in relative fixed relation.

The disposable assembly further defines a first autologous blood circuit for receiving autologous blood from the patient, and the component interface region further comprises a fifth pump for controlling the flow of the autologous blood through a fifth tubing loop comprising the first blood recovery circuit, the fifth pump being positioned to create during operation a suction at a free end of the first blood recovery circuit. The first, second, third, fourth and fifth pumps preferably are in substantial vertical alignment in relative fixed relation.

In a third aspect, this invention is an extracorporeal blood perfusion system for use in receiving venous blood from a patient's heart and for transferring oxygenated blood back to the patient, comprising a disposable assembly including a reservoir, an oxygenator and a plurality of tubing lines, wherein a first tubing line is connected for transferring venous blood from the patient to the reservoir, and a second tubing line is connected for transferring oxygenated blood to the patient; and a control unit having a component interface panel including a clamp assembly for controlling the rate of transfer of the venous blood through the first tubing line to the reservoir.

The component interface panel may further include a first pump connected for pumping the venous blood from the reservoir through the oxygenator and for pumping the oxygenated blood through the second tubing line to the patient. The clamp assembly may include a plunger and a lid configured for clamping the first tubing line therebetween. The control unit is configured to selectively control advancement and retraction of the plunger relative to the lid, wherein a predetermined degree of occlusion of the first tubing line by the clamp assembly is selectable by a user.

In a fourth aspect, this invention is an extracorporeal blood perfusion system for use in receiving venous blood from a patient and returning oxygenated blood to the patient, comprising a disposable assembly including a cartridge and a plurality of tubing lines, the disposable assembly defining at least a blood circuit for receiving venous blood from the patient and returning oxygenated blood to the patient and a cardioplegia circuit for transferring a cardioplegia solution to the patient; and a control unit having a component interface panel comprising a cartridge interface region operatively interfacing with the cartridge, and including a first pressure sensor for monitoring a fluid pressure within the blood circuit, and a second pressure sensor for monitoring a fluid pressure within the cardioplegia circuit; and first and second pumps, the first pump being configured to control a flow rate of the oxygenated blood in the blood circuit, and the second pump being configured to at least partially control a flow rate of the cardioplegia solution in the cardioplegia circuit.

The disposable assembly further defines at least a first blood recovery circuit for receiving vented blood from a left ventricle of the patient, and the cartridge interface region comprises a third pressure sensor configured for monitoring a fluid pressure within the blood recovery circuit. The disposable assembly also further defines at least a first autologous blood circuit configured for suctioning autologous blood from the patient, and the cartridge interface region comprises a fourth pressure sensor configured for monitoring a fluid pressure within the first autologous blood circuit.

In a fifth aspect, this invention is an extracorporeal blood perfusion system for use in receiving blood from a patient's heart and for transferring the blood back to the patient comprising a disposable assembly including a cartridge and a plurality of tubing lines, the disposable assembly defining a blood circuit for receiving blood from the patient and for transferring the blood back to the patient, the cartridge including a plurality of internal passageways and at least one reservoir containing a cardioplegia solution, the at least one reservoir being configured to be interconnectable to the cartridge to flow the cardioplegia solution into at least one of the plurality of fluid passageways of the cartridge; and a control unit having a cartridge interface region for operatively interfacing with the cartridge, the cartridge interface region having at least one sensor configured for sensing one of a pressure and temperature of a fluid flowing through the at least one fluid passageway of the cartridge. The at least one sensor may comprise a first sensor for sensing fluid pressure and a second sensor for sensing fluid temperature within the at least one fluid passageway of the cartridge. The cartridge may further comprise a filter configured for filtering the cardioplegia solution. The cartridge may also comprise a trap configured to remove gaseous bubbles from the fluid flowing through the at least one fluid passageway of the cartridge. The disposable assembly may include a cardioplegia tubing line fluidly interconnected to the at least one internal passageway of the cartridge for transferring the cardioplegia solution to the patient.

In a sixth aspect, this invention is an extracorporeal blood perfusion system for use in receiving venous blood from a patient and returning oxygenated blood to the patient, comprising a disposable assembly including a plurality of fluid channels, the disposable assembly defining a blood circuit for receiving venous blood from the patient and returning oxygenated blood to the patient, the plurality of fluid channels including a first fluid channel fluidly interconnected to the blood circuit, the first fluid channel being at least partially defined by a first tubing line, and a second fluid channel being at least partially defined by a second tubing line, the first and second fluid channels being fluidly interconnected to a third fluid channel; and a control unit including a component interface region comprising a first pump connected for operatively interfacing with the first tubing line, wherein oxygenated blood is pumped through the first tubing line by the first pump, and a second pump connected for operatively interfacing with the second tubing line, the second pump being configured to pump a cardioplegia solution through the second tubing line, the control unit being configured such that a volumetric ratio of the cardioplegia solution and the oxygenated blood is selectively established in the third fluid channel by control of the first and second pumps.

The disposable assembly comprises a cartridge having a first internal passageway interconnected with the first tubing line, a second internal passageway interconnected with the second tubing line, and a third internal passageway at least partially defining the third fluid channel, wherein the first, second and third internal passageways adjoin within the cartridge. The cartridge may further comprise a bubble trap configured for removing gaseous bubbles from fluid passing through the third internal passageway. The component interface region may comprise a cartridge interface region for operatively interfacing with the cartridge, the cartridge interface region including a pressure sensor configured for monitoring a fluid pressure within the third internal passageway.

In a seventh aspect, this invention is an extracorporeal blood perfusion system for receiving venous blood from a patient and transferring oxygenated blood to the patient, comprising a disposable assembly including a cartridge and a plurality of tubing lines, the disposable assembly defining a blood circuit for receiving venous blood from the patient and transferring oxygenated blood to the patient, and a blood recovery circuit for receiving at least one of autologous blood from the patient and vented blood from a left ventricle of the patient; and a control unit having a component interface region configured for controlling the flow of fluids in each of the blood and blood recovery circuits.

The cartridge includes a sequestration reservoir configured for accumulating the at least one of autologous blood and vented blood. The blood circuit includes a venous reservoir connected for accumulating the venous blood, and the component interface region includes a valve positioned for selectively controlling the flow of fluid from the sequestration reservoir to the venous reservoir. The blood recovery circuit may be connected to receive the vented or suctioned blood, and the component interface region may include a valve assembly, the control unit being configured to selectively operate the valve assembly in a manner that controls the flow of the vented blood directly from the blood recovery circuit into the blood circuit.

In an eighth aspect, this invention is an extracorporeal blood perfusion system for use in receiving venous blood from a patient and transferring oxygenated blood to the patient, comprising a disposable assembly defining a plurality of fluid circuits, including a blood circuit for receiving venous blood from the patient and transferring oxygenated blood to the patient; a control unit having a component interface region for operatively interfacing with the disposable assembly, the component interface region including a flow controller to control the rate of flow of fluids through a first of the plurality of fluid circuits; and a user interface, operatively interconnected with the flow controller, including a display configured to be selectively controllable to display an object that provides a functional interface for user control over the operation of the flow controller.

The plurality of fluid circuits further includes a cardioplegia circuit for supplying a cardioplegia solution to the patient, and wherein the display is configured to be selectively controllable to display graphic depictions of each of the blood and cardioplegia circuits. The flow controller may comprise a first valve operatively interfacing with the blood circuit, and a second valve operatively interfacing with the cardioplegia circuit. The graphic depiction of the blood circuit comprises a first object corresponding with the first valve, the display being configured such that the first object provides a functional interface for user control over the operation of the first valve, and the graphic depiction of the cardioplegia circuit comprises a second object corresponding with the second valve, the display being configured such that the second object provides a functional interface for user control over the second valve. The display may be configured such that the first object provides a visual indication of whether the first valve is open or closed, and the second object provides a visual indication of whether the second valve is open or closed. The functional interface corresponding with the first object and the functional interface corresponding with the second object preferably are defined by a touch-screen attribute of the display. The flow controller may comprise a first pump configured to operatively interface with the blood circuit, and a second pump configured to operatively interface with the cardioplegia circuit. The display may be configured such that the graphic depiction of the blood circuit comprises a first flow rate indicator corresponding with the first pump to indicate a current fluid flow rate established by the first pump, and the graphic depiction of the cardioplegia circuit comprises a second flow rate indicator corresponding with the second pump to indicate a current fluid flow rate established by the second pump. The component interface region may also include at least a first sensor configured to operatively interface with one of the plurality of fluid circuits to monitor a first fluid parameter corresponding with fluid flowing through the one fluid circuit, and the user interface may be operatively interconnected with the first sensor to display a value corresponding with the monitored first fluid parameter and to provide a user alert when the monitored first fluid parameter is outside of a predetermined range. The display is configured to be selectively controllable to display an object selectable by a user for setting the predetermined range.

In a ninth aspect, this invention is an extracorporeal blood perfusion system for use in receiving venous blood from a patient and transferring oxygenated blood to the patient, comprising a disposable assembly defining a plurality of fluid circuits, including a blood circuit for receiving venous blood from the patient and transferring oxygenated blood to the patient; a control unit including a component interface region for operatively interfacing with the disposable assembly, the component interface region including at least one sensor configured to operatively interface with one of the plurality of fluid circuits to monitor a first fluid parameter corresponding with a fluid flowing through the one fluid circuit; and a user interface operatively interconnected with the component interface region and configured to display a value corresponding with the monitored first parameter and to provide a user alert when the monitored first parameter is outside of a predetermined range.

The user interface is configured to be selectively controllable by a user to display an object corresponding with the at least one sensor, the interface being configured such that the object provides a functional interface for setting the predetermined range by a user. The functional interface may be provided by the object via a touch-screen attribute of the user interface. The user interface may further comprise a control knob configured such that upon functional interface by a user with the object, the control knob may be manipulated by a user to set the predetermined range, and the user interface may be configured to be selectively controllable by a user to display a graphic depiction corresponding with the blood circuit, the graphic depiction including a plurality of objects corresponding with a plurality of sensors comprising the component interface region to monitor a corresponding plurality of fluid parameters corresponding with fluid flowing through the blood circuit. The user interface also may be configured such that the plurality of monitored fluid parameters includes oxygen saturation, hematocrit and temperature of the venous blood. The component interface region may further comprise a flow controller to control the flow of fluid through the one fluid circuit, and the control unit comprises a processor, operatively interconnected with the flow controller and the first sensor, wherein the processor is operable to automatically provide a control signal to the flow controller when the monitored first parameter is outside of the predetermined range.

In a tenth aspect, this invention is an extra corporeal blood perfusion system, comprising a disposable assembly defining a plurality of fluid circuits; a control unit having a component interface region for operatively interfacing with the disposable assembly, the component interface region being configured to monitor a plurality of fluid parameters corresponding with fluid flowing through the plurality of fluid circuits; and a user interface, operatively interconnected with the component interface region, including a display having at least two display regions selected from a group of (1) a first display region for continuously displaying at least a first set of values corresponding with each of a first set of the plurality of monitored parameters; (2) a second display region for selectively displaying one of a plurality of graphic depictions, each graphic depiction corresponding with a given one of the plurality of fluid circuits; and (3) a third display region for displaying user alert indications when a given one of the plurality of monitored parameters is outside of a corresponding predetermined range. The disposable assembly defines a blood circuit configured to receive venous blood from a patient and to return oxygenated blood to the patient, and the first set of values may comprise an oxygen saturation value, blood hematocrit value and temperature value for the venous blood. The first display region may be configured to continuously display a second set of values corresponding with each of a second set of the plurality of monitored parameters, and the second set of values may comprise a pressure value, a flow rate value and a temperature value for the oxygenated blood. The disposable assembly defines a cardioplegia circuit for supplying a cardioplegia solution to a patient, and the first set of values may comprise a fluid pressure value, a flow rate value and a temperature value of the cardioplegia solution. The disposable assembly also defines a blood circuit for receiving venous blood from a patient and transferring oxygenated blood to the patient, and a cardioplegia circuit for supplying a cardioplegia solution to the patient; the first display region may be configured to continuously display a second set of values corresponding with each of a second set of the plurality of monitored parameters, and the first set of values may comprise a fluid pressure value, flow rate value and temperature value of the cardioplegia solution, and the second set of values may comprise at least one of a first subset of values comprising an oxygen saturation value, blood hematocrit value and temperature value for the venous blood, and a second subset of values comprising a fluid pressure value, flow rate value and temperature value for the oxygenated blood.

The first display region preferably is configured to continuously display at least a second set of values corresponding with each of a second set of the plurality of monitored parameters, wherein the second set of values comprises at least one of a bolus volume value corresponding with an amount of the cardioplegia solution to be supplied to the patient and an ischemic time value corresponding with an elapsed amount of time between successive periods during which the cardioplegia solution is supplied to a patient. The disposable assembly defines a blood circuit for receiving venous blood from a patient and transferring oxygenated blood to the patient and includes a blood reservoir, and the first display region may be configured to continuously display a graphic representation of the volumetric fluid content of the reservoir on a real-time basis. The first display region may further comprise a numeric display of the volumetric amount of fluid contained by the reservoir on a real-time monitored basis. The disposable assembly may comprise a blood circuit for receiving venous blood from a patient and transferring oxygenated blood to a patient, wherein the blood circuit includes a venous reservoir for receiving the venous blood; the component interface region may comprise a clamp configured to control the rate of flow of the venous blood to the reservoir; and the first display region may include an object providing a functional interface for a user to establish a degree to which the clamp is open for passage of the venous blood to the reservoir. Preferably, the user interface further comprises a control knob, the user interface being configured such that upon functional interface with the object by a user, the control knob is manipulatable by a user to establish the degree to which the clamp is open.

In an eleventh aspect, this invention is an extracorporeal blood perfusion system, comprising a disposable assembly including a cartridge and a plurality of tubing lines, the disposable assembly defining a blood circuit for receiving venous blood from a patient and transferring oxygenated blood to the patient, and a cardioplegia circuit for transferring a cardioplegia solution to the patient; a control unit including a component interface region for operatively interfacing with the disposable assembly; and a user interface, operably interconnected with the component interface region, including a display, the display being configured for displaying narrative instructions and corresponding graphic depictions for loading the disposable assembly on the component interface region. The display preferably is configured such that the narrative instructions and corresponding graphic depictions are presented in a plurality of sequentially presented display boxes.

In a twelfth aspect, this invention is an extracorporeal blood perfusion system, comprising a disposable assembly defining a plurality of fluid circuits; a control unit having a component interface region including a flow controller configured to control the flow of fluids through at least a first of the plurality of fluid circuits, and at least a first sensor for monitoring a first fluid parameter corresponding with fluid flowing through the first fluid circuit, wherein the flow controller is configured to be controllable to automatically adjust the flow of fluid through the first fluid circuit when the first sensor detects that the first parameter is outside of a predetermined range; and a user interface, operatively interconnected with the component interface region, including a display configured for selectively displaying functional objects, at least one of the objects being employable by a user to set the predetermined range.

The disposable assembly defines a blood circuit for transferring venous blood from a patient and returning oxygenated blood to the patient, the flow controller comprises a first pump for controlling the flow rate of the oxygenated blood, and the first sensor is configured to monitor a fluid pressure of the oxygenated blood, wherein the first pump is controllable to automatically stop when the first sensor detects that the fluid pressure is outside of a predetermined pressure range. The disposable assembly optionally may define a blood circuit for receiving venous blood from a patient and returning oxygenated blood to the patient, the blood circuit including a reservoir for accumulating the venous blood and an oxygenator, wherein the flow controller comprises a first pump for controlling a flow rate of the venous blood from the reservoir through the oxygenator to provide the oxygenated blood, and wherein the first sensor monitors a volumetric content of the reservoir, wherein the first pump is configured to be controllable to automatically stop the flow of the oxygenated blood when the first sensor detects that the volumetric fluid content of the reservoir is outside of a predetermined range. The disposable assembly may also define a cardioplegia circuit for supplying a cardioplegia solution to a patient, the flow controller may comprise at least a first pump connected for controlling a flow rate of the cardioplegia solution, and the first sensor may monitor a fluid pressure of the cardioplegia solution, the first pump being configured to be controllable to automatically stop the flow of the cardioplegia solution when the first sensor detects a fluid pressure outside of a predetermined pressure range.

The disposable assembly may also define a blood circuit for receiving venous blood from a patient and returning oxygenated blood to the patient, the blood circuit including a reservoir for accumulating the venous blood and providing the accumulated venous blood for oxygenation, and the flow controller may include a flow control clamp configured for controlling the flow of venous blood to the reservoir and a first pump configured for controlling the flow rate of the oxygenated blood, and the first sensor may be configured to monitor a fluid level within the reservoir, such that one of the flow control clamp and the first pump is automatically controllable to maintain a predetermined fluid level in the reservoir based upon an output provided by the first sensor.

In a thirteenth aspect, this invention is extracorporeal blood perfusion system, comprising a disposable assembly defining a plurality of fluid circuits; a control unit including a component interface region for operatively interfacing with the disposable assembly; a user interface, operatively interconnected with the component interface region, including a display configured to provide a context-driven display region, the context-driven display region displaying a plurality of tabs provided for functional interface with a user, and any one of a plurality of information sets, each information set corresponding with a given one of the tabs, wherein separate first and second tabs are provided in corresponding relation to at least a first fluid circuit and a second fluid circuit comprising the plurality of fluid circuits.

The first circuit may be a blood circuit for receiving venous blood from a patient and returning oxygenated blood to the patient, and the second fluid circuit may be a cardioplegia circuit for supplying cardioplegia to the patient, such that the information sets corresponding with the first and second tabs comprise graphic depictions of the blood circuit and the cardioplegia circuit, respectively. The component interface region may comprise a first sensor for monitoring a parameter of fluid flowing in the blood circuit and a first pump for controlling the flow rate of the oxygenated blood in the blood circuit, and a second sensor for monitoring a parameter of the cardioplegia solution flowing in the cardioplegia circuit and a second pump for controlling the flow rate of the cardioplegia solution.

In a fourteenth aspect, this invention is an extracorporeal blood perfusion system for receiving venous blood from a patient and for returning oxygenated blood to the patient in a cardiopulmonary bypass procedure comprising a cardiopulmonary circuit configured to receive venous blood from the patient and to return oxygenated blood to the patient; a cardioplegia circuit configured for delivering a cardioplegia solution to the patient; a cardiotomy circuit configured for withdrawing fluids from the patient; and a cartridge having a housing defining a plurality of internal passageways connected to the cardiopulmonary circuit, the cardioplegia circuit, and the cardiotomy circuit.

The system further comprises a ventricular vent circuit configured for draining blood from the patient's left ventricle and wherein the housing of the cartridge defines a plurality of internal passageways connected to the cardiopulmonary circuit, the cardioplegia circuit, the cardiotomy circuit, and the ventricular vent circuit. The housing of the cartridge may comprise a first rigid portion connected to a second flexible portion in a manner defining at least in part the plurality of internal passageways. The first rigid portion may comprise a translucent material configured to allow viewing of fluid in an internal passageway and/or a bubble detector connected for detecting bubbles in the cardiopulmonary circuit. The bubble detector is positioned for detecting bubbles in at least one of the internal passageways. The system may include a filter positioned for filtering at least one of blood, cardioplegia solution, and fluid flowing in an internal passageway. The first portion of the cartridge may define a plurality of inlet and exit ports in fluid communication with the plurality of internal passageways.

In a fifteenth aspect, this invention is an extracorporeal blood perfusion system comprising a disposable assembly comprising a plurality of components interconnected by a plurality of tubing lines, the plurality of components including a cartridge and at least one of an oxygenator, a heat exchanger, a blood reservoir and an arterial filter, the cartridge having a housing defining a plurality of internal fluid passageways, the tubing lines interconnecting the components to define a blood circuit for receiving venous blood from a patient and returning oxygenated blood to the patient; and a control unit having an interface region for operatively interfacing with the disposable assembly, the interface region including a plurality of sensors for sensing at least one fluid characteristic including pressure, temperature, level and air bubbles, and for generating a signal indicative of each fluid characteristic sensed, at least one of the sensors being positioned to sense a characteristic of fluid in an internal passageway of the cartridge, the control unit further including at least one flow control element configured to control the rate of flow of blood in the blood circuit in response to at least one of the sensed fluid characteristics.

The flow control element may be a roller pump attached to a tubing line in the blood circuit.

In a sixteenth aspect, this invention is for maintaining the level of blood in a venous reservoir at a predetermined level when the reservoir is used in an extracorporeal blood perfusion system which includes a cardiopulmonary blood circuit for receiving venous blood from a patient through a venous line, oxygenating the blood in an oxygenator, and returning the oxygenated blood to the patient through an arterial line, the venous reservoir having an inlet connected to the venous line and an outlet connected to the oxygenator, the method comprising providing a level control element operatively connected to the venous reservoir for controlling at least one of the rate of flow of venous blood out of the venous reservoir and the rate of flow of venous blood into the venous reservoir through the venous line; providing a level sensor configured to continuously monitor the level of blood in the venous reservoir and to provide level signals indicative of the blood level; and providing a control unit connected to received the level signals, the control unit being connected to the level control element and being configured to functionally control operation of the level control element such that when the level signals are indicative of a level below the predetermined level the flow control element is caused to increase venous blood level in the venous reservoir by at least one of increasing venous blood flow into the venous reservoir and decreasing venous blood flow out of the venous reservoir, and when the level signals are indicative of a level which is above the predetermined level the flow control element is caused to decrease venous blood level in the venous reservoir by at least one of decreasing venous blood flow into the venous reservoir and increasing venous blood flow out of the venous reservoir.

The step of providing a level control element may comprise providing a pump connected to the outlet of the venous reservoir and the step of providing a control unit may comprise providing a control unit which is configured such that when the level signals are indicative of a level below the predetermined level the pump is caused to slow the flow of blood out of the venous reservoir and when the level signals are indicative of a level above the predetermined level the pump is caused to increase the flow of blood out of the venous reservoir. The step of providing a level control element may comprise providing a flow control member operatively connected to the venous line for controlling the rate of blood flow through the venous line into the venous reservoir and the step of providing a control unit may comprise providing a control unit which is configured such that when the level signals are indicative of a level below the predetermined level the flow control member is caused to increase the flow of blood into the venous reservoir and when the level signals are indicative of a level above the predetermined level the flow control member is caused to decrease the flow of venous blood into the reservoir. The step of providing a level control element comprises providing a venous line clamp attached to the venous line. The venous reservoir may be a sealed reservoir, and the step of providing a level control element may comprise connecting a vacuum source to the venous reservoir and the step of providing a control unit may comprise providing a control unit which is configured such that when the level signals are indicative of a level below the predetermined level the amount of vacuum applied to the venous reservoir is increased and when the level signals are indicative of a level which is above the predetermined level the amount of vacuum applied to the venous reservoir is decreased.

In a seventeenth aspect, in an extracorporeal blood perfusion system for receiving blood from a patient through a venous line, oxygenating the blood, and returning the oxygenated blood to the patient through an arterial line, a method of preventing the return of oxygenated blood containing gaseous bubbles to the patient, the extracorporeal blood perfusion system including a cardiopulmonary blood circuit having a plurality of tubing lines interconnecting a venous reservoir, a blood oxygenator and an arterial blood filter, this invention is a method comprising connecting the blood perfusion system for receiving venous blood from the patient and returning oxygenated blood to the patient; providing an air purge line including a purge valve having an open position for opening the purge line and a closed position for closing the purge line; fluidly connecting a first end of the purge line with an outlet of the oxygenator and a second end of the purge line with an inlet of the venous reservoir; and providing a control unit having a sensor for determining the presence of gaseous bubbles in a tubing line connected to an outlet of the oxygenator, the control unit being connected to the first pump for controlling the speed of the first pump and being connected to the purge valve for automatically opening the purge valve when gaseous bubbles are sensed by the sensor such that at least a portion of the oxygenated blood is diverted from the patient through the air purge line back to the venous reservoir.

The step of fluidly connecting the first and second ends of the purge line may include connecting the first end of the purge line to a purge port on the arterial blood filter. The method also may include providing an arterial valve in the arterial line, the arterial valve having an open position for opening the arterial line and a closed position for closing the arterial line and the step of providing a control unit may include providing a control unit connected to the arterial valve for automatically closing the arterial valve when gaseous bubbles are sensed by the sensor. The step of providing a control unit may include providing a control unit connected to the first pump for automatically slowing the speed of the first pump when gaseous bubbles are sensed by the sensor.

In an eighteenth aspect, this invention is a method of automatically priming an extracorporeal blood perfusion system which includes a cardiopulmonary blood circuit for receiving venous blood from a patient, oxygenating the blood and returning the oxygenated blood to the patient, the blood circuit being defined by a plurality of tubing lines interconnecting a plurality of components including a venous reservoir and an oxygenator, the blood perfusion system further including a first pump for causing fluid to flow in the blood circuit, the method comprising providing a source of priming fluid; providing a priming fluid valve; connecting the source of priming fluid to the blood circuit through the priming fluid valve in a manner such that the flow of priming fluid to the blood circuit is controllable by the priming fluid valve; providing a control unit having a component interface region for functionally interfacing with and controlling the first pump and the priming fluid valve, the control unit having a plurality of selectable operational modes including an automatic priming mode whereby upon selection of the automatic priming mode the control unit opens the priming fluid valve and controls the speed of the first pump to prime the blood circuit; and selecting the automatic priming mode on the control unit to prime the blood circuit including the venous reservoir, oxygenator and interconnecting tubing.

The plurality of components may include a heat exchanger and an arterial blood filter and wherein the step of selecting the automatic priming mode comprises priming of the blood circuit including the venous reservoir, oxygenator, heat exchanger, arterial blood filter and interconnecting tubing. The blood perfusion system may include a cardioplegia circuit for providing a cardioplegia solution to the patient, the cardioplegia circuit including a second pump for causing fluid to flow in the cardioplegia circuit and wherein the step of providing a control unit includes providing a control unit having a component interface region for functionally interfacing with and controlling the first and second pumps and the priming fluid valve, the control unit having a plurality of selectable operational modes including an automatic priming mode whereby the control unit opens the priming fluid valve and controls the speed of the first and second pumps to prime the blood circuit and the cardioplegia circuit, and wherein the step of selecting the automatic priming mode causes the blood circuit and the cardioplegia circuit to be automatically primed.

In a nineteenth aspect, in an extracorporeal blood perfusion system for receiving venous blood from a patient through an end of a venous line, oxygenating the blood and returning the oxygenated blood to the patient through an end of an arterial line, the perfusion system including a cardiopulmonary blood circuit defined by a plurality of tubing lines interconnecting a plurality of components including a venous reservoir and oxygenator, the perfusion system also including a first roller pump attached to a tubing line of the cardiopulmonary blood circuit, this invention is a method of testing for leaks and pump loading and occlusion in the cardiopulmonary blood circuit comprising sealing the ends of the venous and arterial lines; providing a control unit having a pressure sensor for measuring pressure in the cardiopulmonary blood circuit, the control unit being connected for controlling the operation of the first roller pump, the control unit having a cardiopulmonary blood circuit test mode, selection of which causes the control unit to automatically operate the first roller pump until a first predetermined pressure is measured by the sensor, and to monitor the pressure over a predetermined period of time to determine whether the decay of pressure is within a predetermined acceptable range; and selecting the cardiopulmonary blood circuit test mode of the control unit.

In a twentieth aspect, in an extracorporeal blood perfusion system for receiving venous blood from a patient through an end of a venous line, oxygenating the blood and returning the oxygenated blood to the patient through an end of an arterial line, the perfusion system including a cardiopulmonary blood circuit defined by a plurality of tubing lines interconnecting a plurality of components including a venous reservoir and oxygenator, a cardioplegia circuit for delivering a cardioplegia solution to the patient through an end of a cardioplegia line, and a suction circuit for removing blood and other fluids from the patient through an end of a suction line, a method of testing for leaks and for proper pump loading and occlusion in the cardiopulmonary blood circuit, the cardioplegia circuit, and the suction circuit, this invention is a method comprising sealing the ends of the venous, arterial, cardioplegia and suction lines; providing a control unit having at least one pressure sensor for measuring fluid pressure in the cardiopulmonary blood circuit, the cardioplegia circuit and the suction circuit, the control unit being connected for controlling the operation of the first, second and third roller pumps, the control unit having a cardiopulmonary blood circuit test mode, selection of which causes the control unit to automatically operate the first roller pump until a first predetermined pressure is measured by the sensor and to monitor the pressure over a first predetermined period of time to determine whether the decay of pressure is within a first predetermined acceptable range, the control unit further having a cardioplegia circuit test mode, selection of which causes the control unit to automatically operate the second roller pump until a second predetermined pressure is measured by the sensor and to monitor the pressure over a second predetermined period of time to determine whether the decay of pressure is within a second predetermined acceptable range, the control unit further having a suction circuit test mode, selection of which causes the control unit to automatically operate the third roller pump until a third predetermined pressure is measured by the sensor and to monitor the pressure over a third predetermined period of time to determine whether the decay of pressure is within a third predetermined acceptable range; selecting the cardiopulmonary blood circuit test mode of the control unit to test for leaks in the cardiopulmonary blood circuit and proper pump loading and occlusion of the first pump; selecting the cardioplegia circuit test mode of the control unit to test for leaks in the cardioplegia blood circuit and proper pump loading and occlusion of the second pump; and selecting the suction circuit test mode of the control unit to test for leaks in the suction circuit and proper pump loading and occlusion of the third pump.

DETAILED DESCRIPTION

FIG. 1 illustrates a cardiopulmonary bypass system embodiment of the present invention.

Figure 2A:
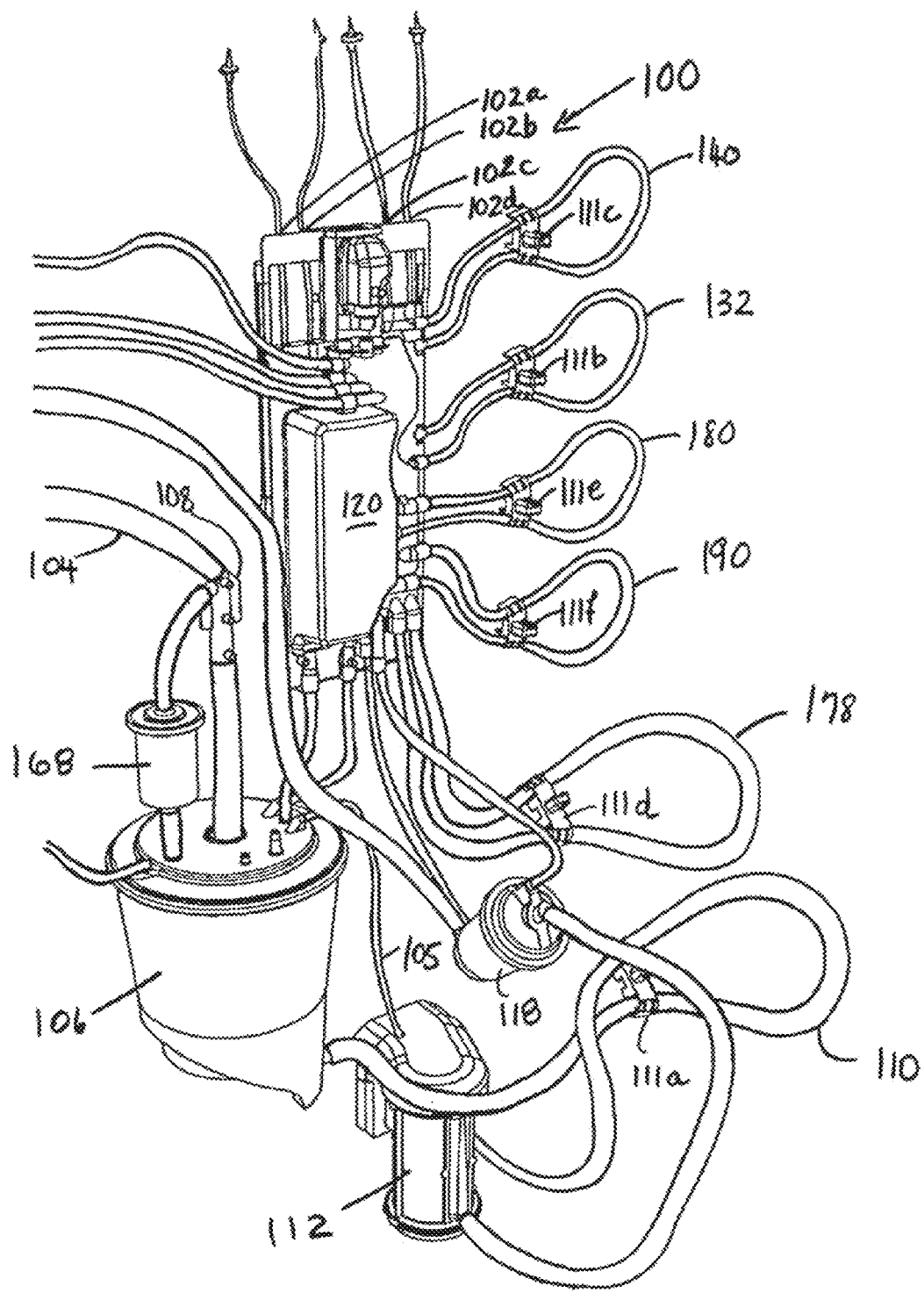

FIG. 2A illustrates one embodiment of a disposable assembly for use in the system embodiment of FIG. 1.

Figure 2B:
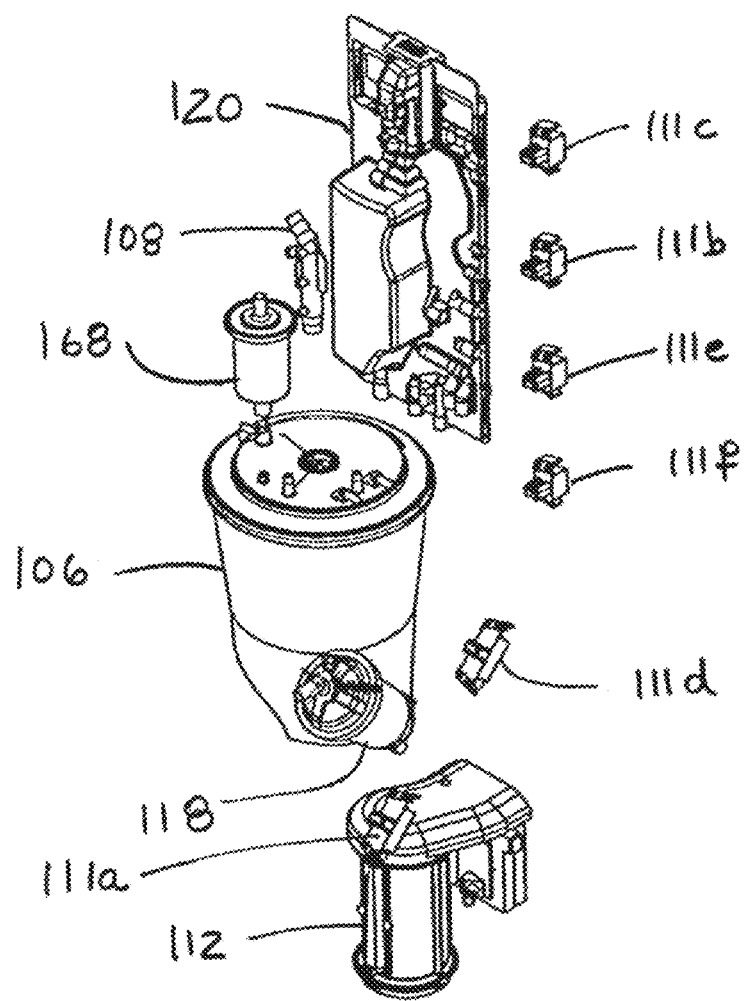

FIG. 2B illustrates the disposable assembly of FIG. 2A

Figure 3A:
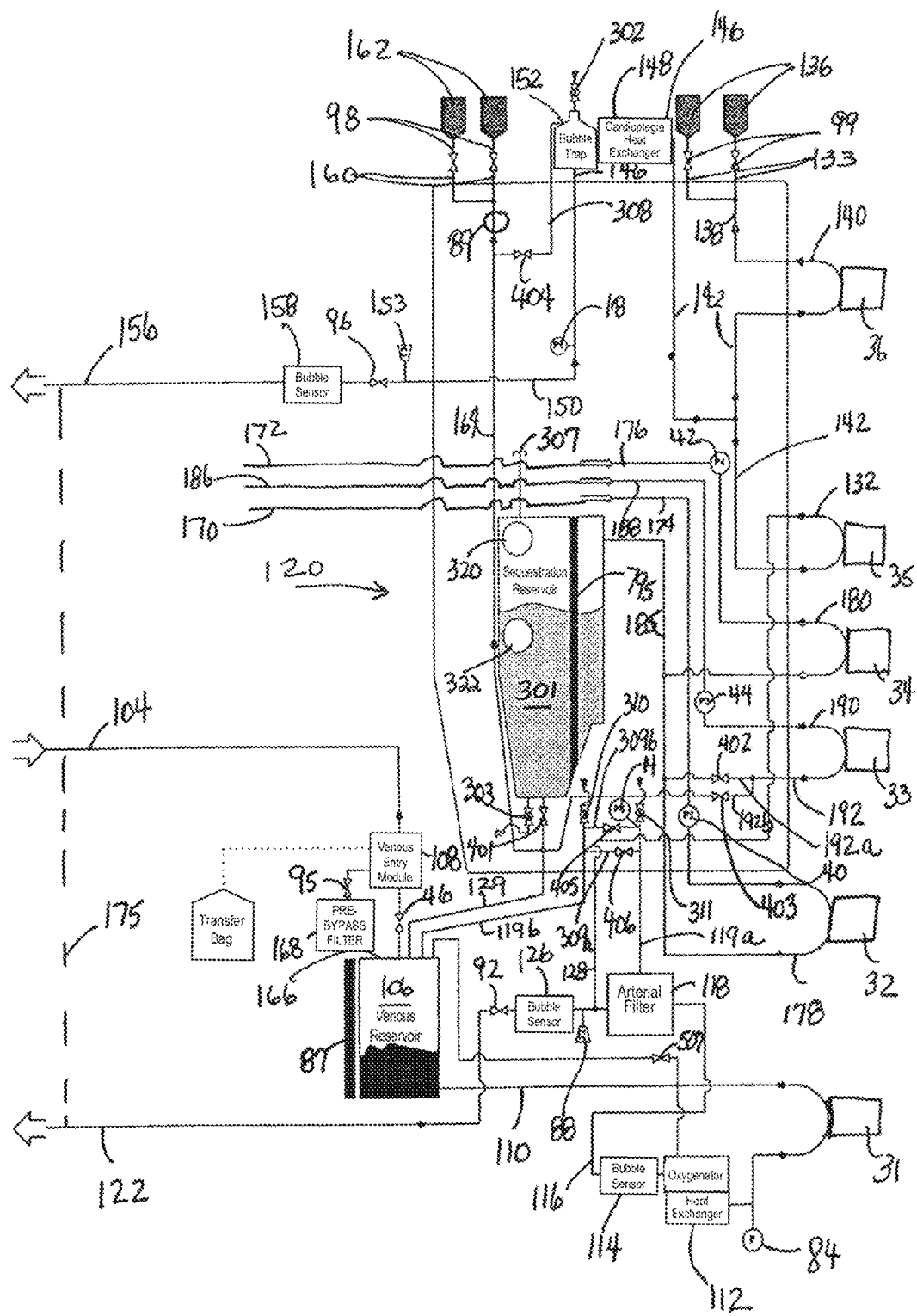

FIG. 3A is a schematic diagram illustrating the interface between components of the disposable assembly and component interface region embodiments of FIGS. 2A and 2B, respectively.

Figure 3B:
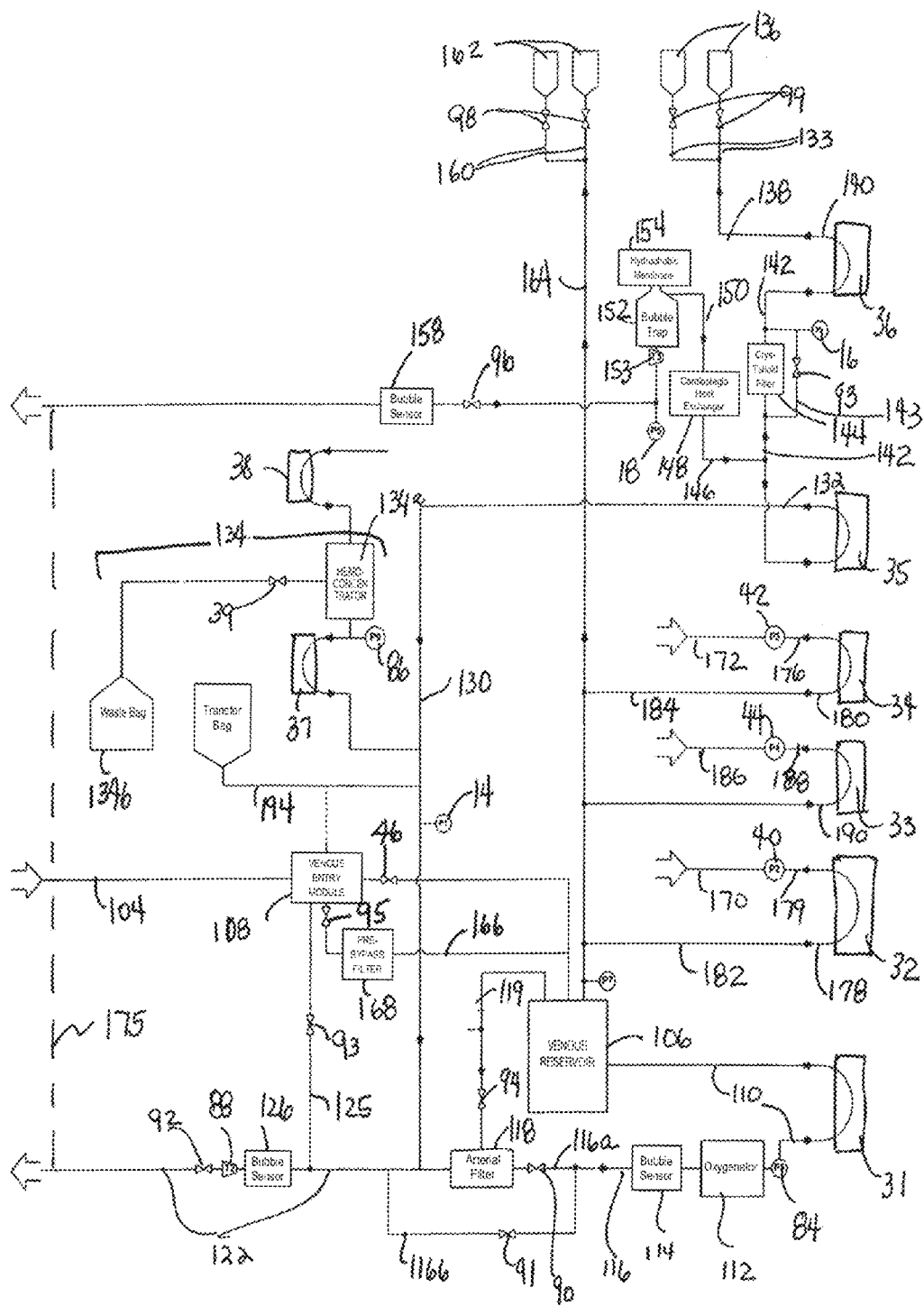

FIG. 3B is a schematic diagram illustrating the interface between components of an alternate embodiment of a disposable assembly and a corresponding alternate embodiment of a component interface region.

FIG. 4 is a perspective view of the component interface region of the embodiment of FIG. 3A showing the cartridge, valve, arterial filter, and sensor interfaces.

Figure 5F:
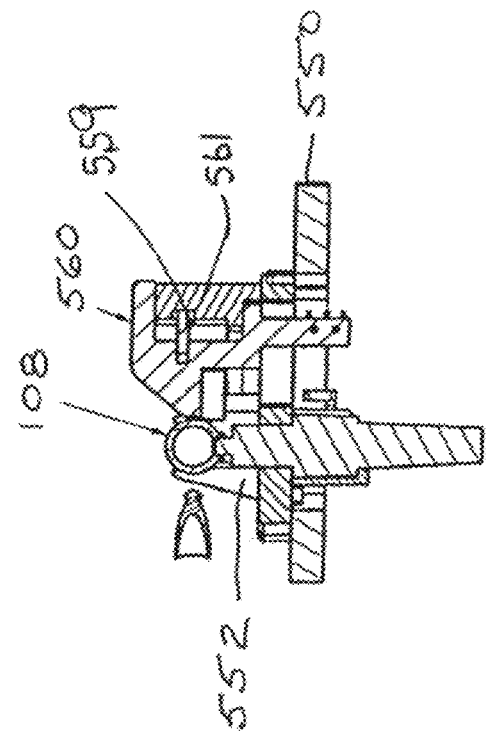
Figure 5E:
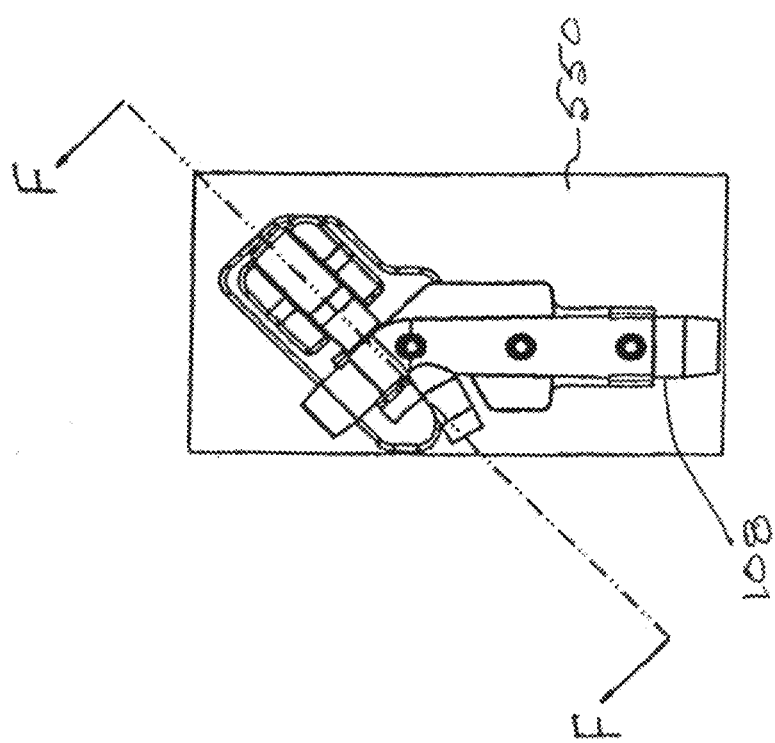
Figure 6A:
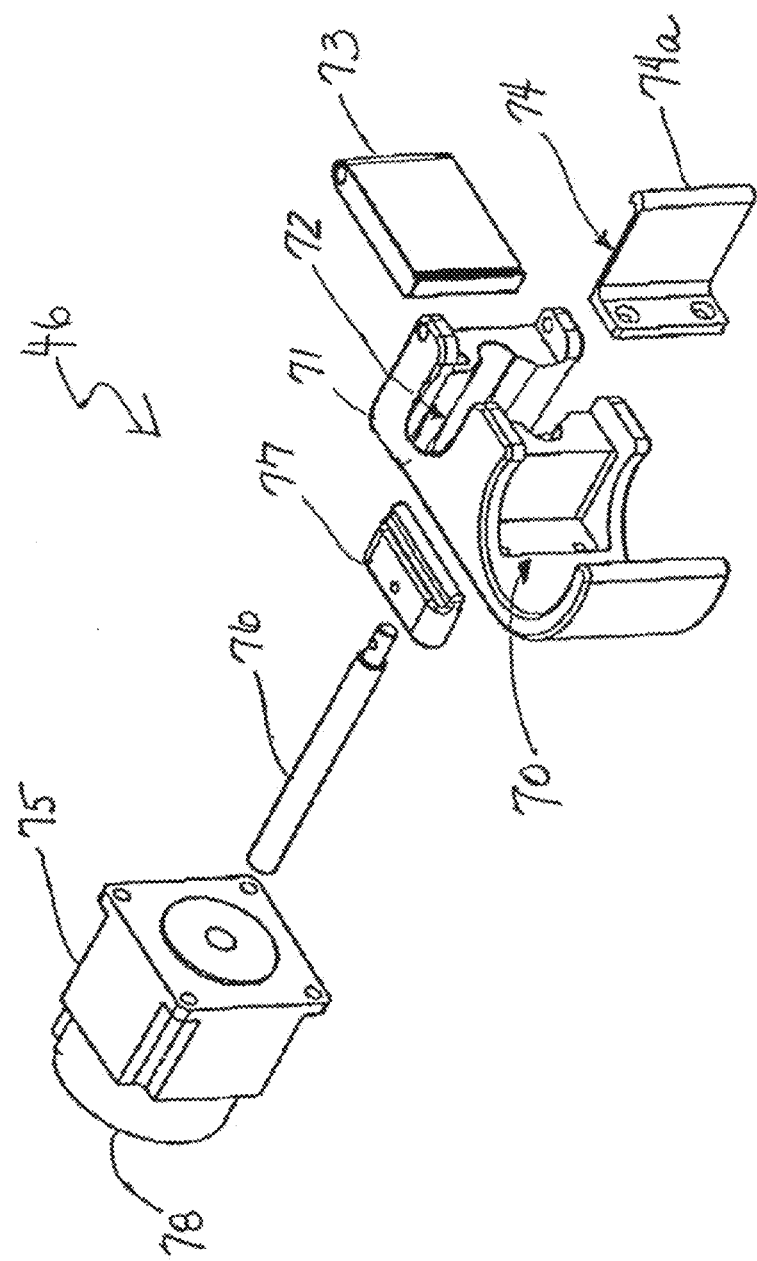

FIGS. 5A and 5B are perspective views of the venous entry module of FIGS. 3A and 3B; FIGS. 5C and 5D perspective views of the mounting bracket for the module of FIGS. 5A and 5B; FIG. 5E is a sectional view of the module of FIGS. 5A and 5B; and FIG. 5F is a cross-sectional view along line F-F of the view of FIG. 5E.

FIGS. 6A to 6E are views of the venous line clamp.

FIGS. 7A and 7B are views of the venous reservoir bracket/mount.

FIGS. 8A to 8E are views of the oxygenator mount/interface.

FIGS. 9A to 9F are views of the tubing clips.

FIGS. 10A to 10D are views of the cartridge cam locks and tabs.

Figure 11:
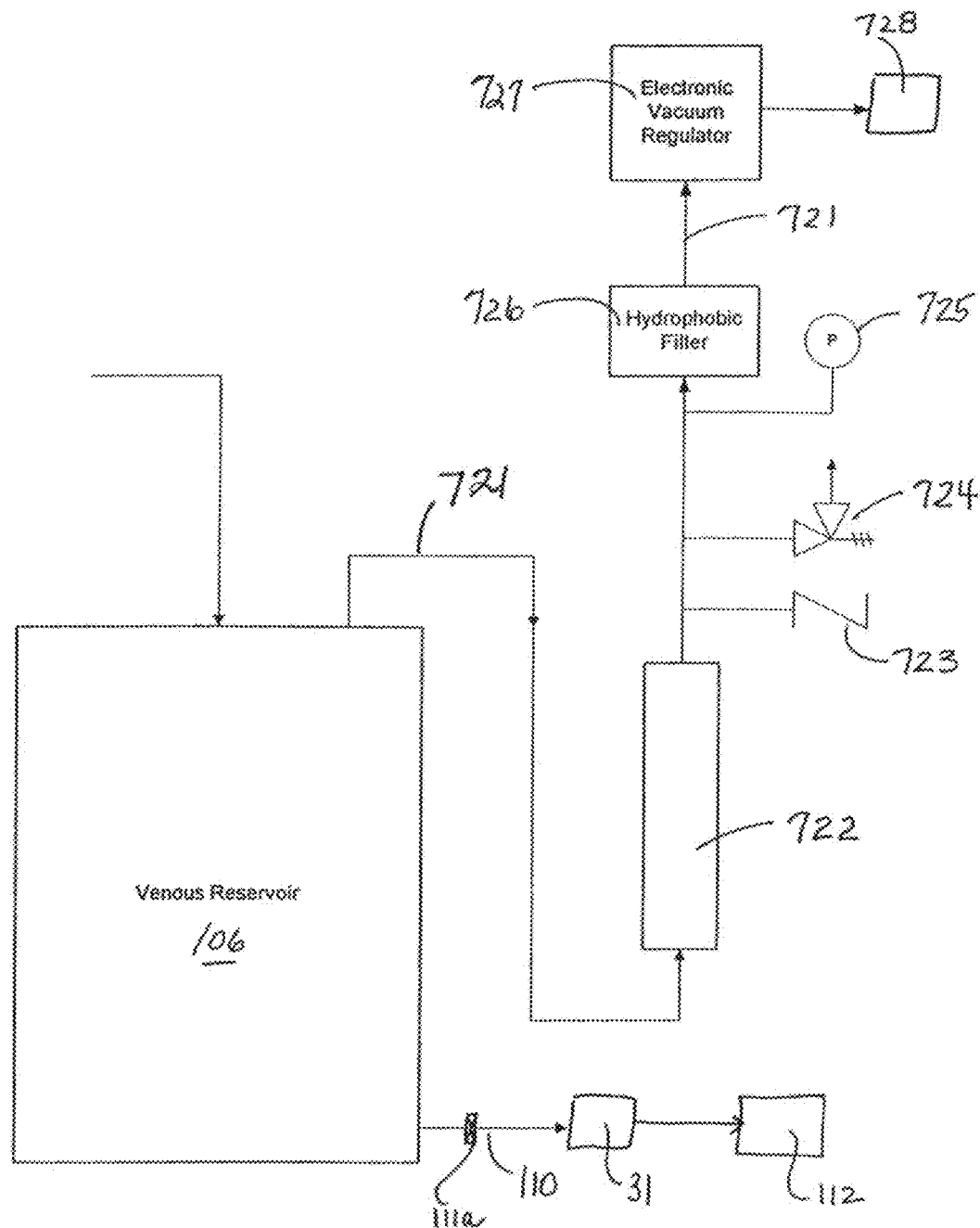

FIG. 11 is a block diagram of an alternative embodiment wherein the venous reservoir is connected to a vacuum source for use in vacuum assisted drainage procedures.

Figure 12:
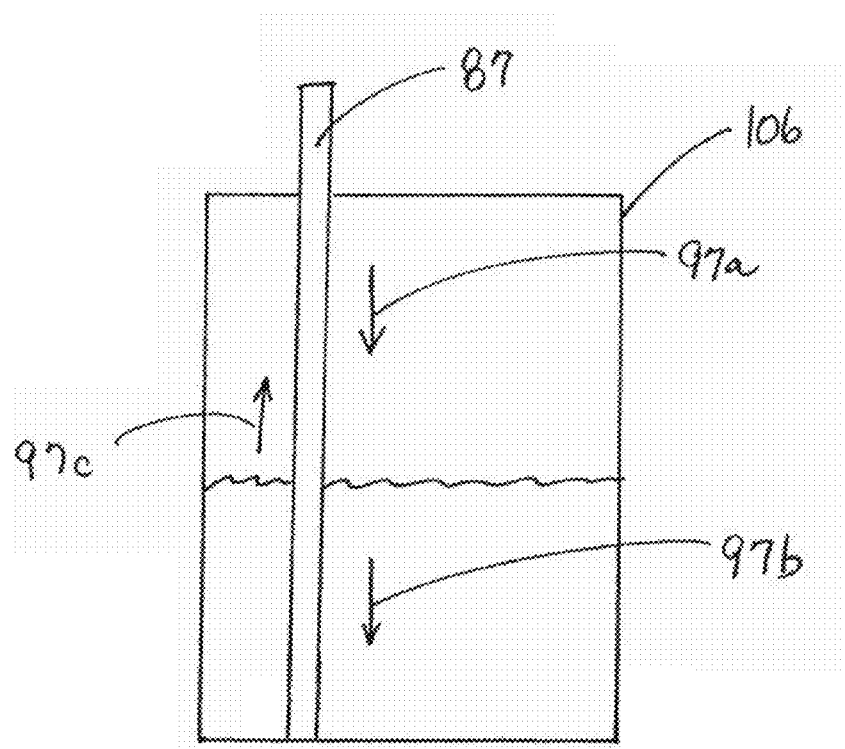

FIG. 12 is a functional diagram of the continuous level sensor used to measure fluid level in the venous reservoir.

Figure 13:
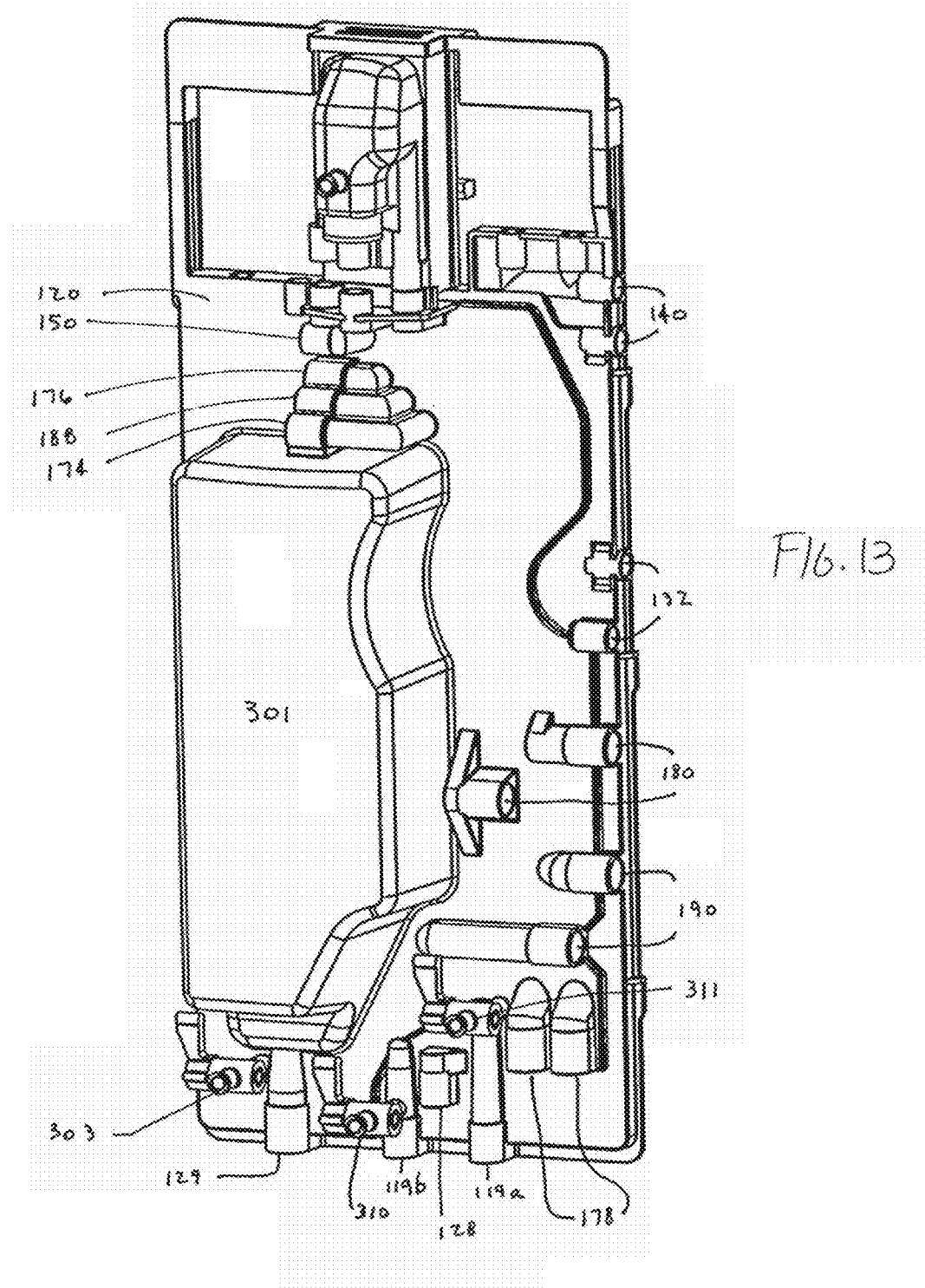

FIG. 13 is a front perspective view of cartridge 120.

Figure 14:
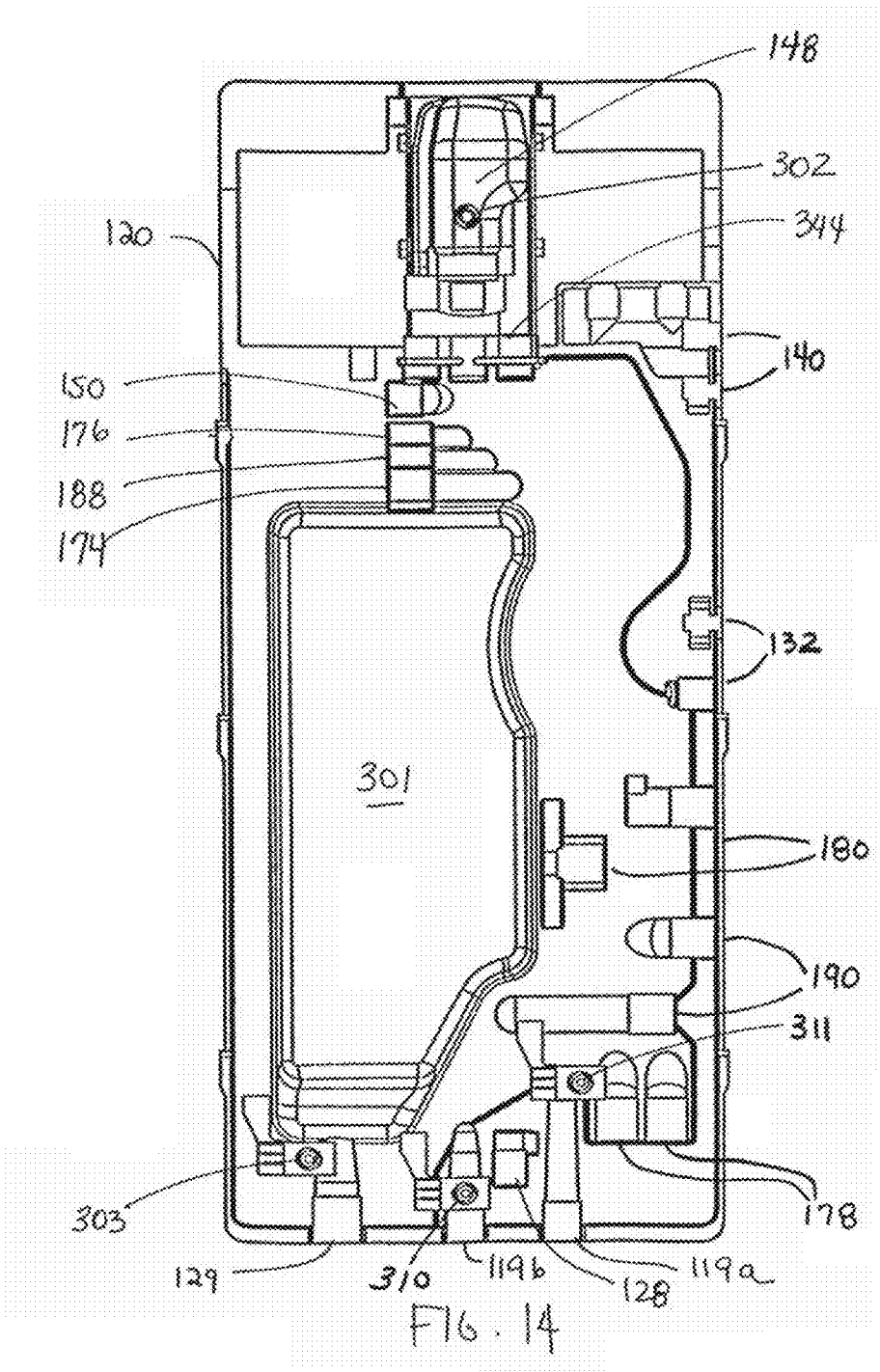

FIG. 14 is a front plan view of cartridge 120.

Figure 15:
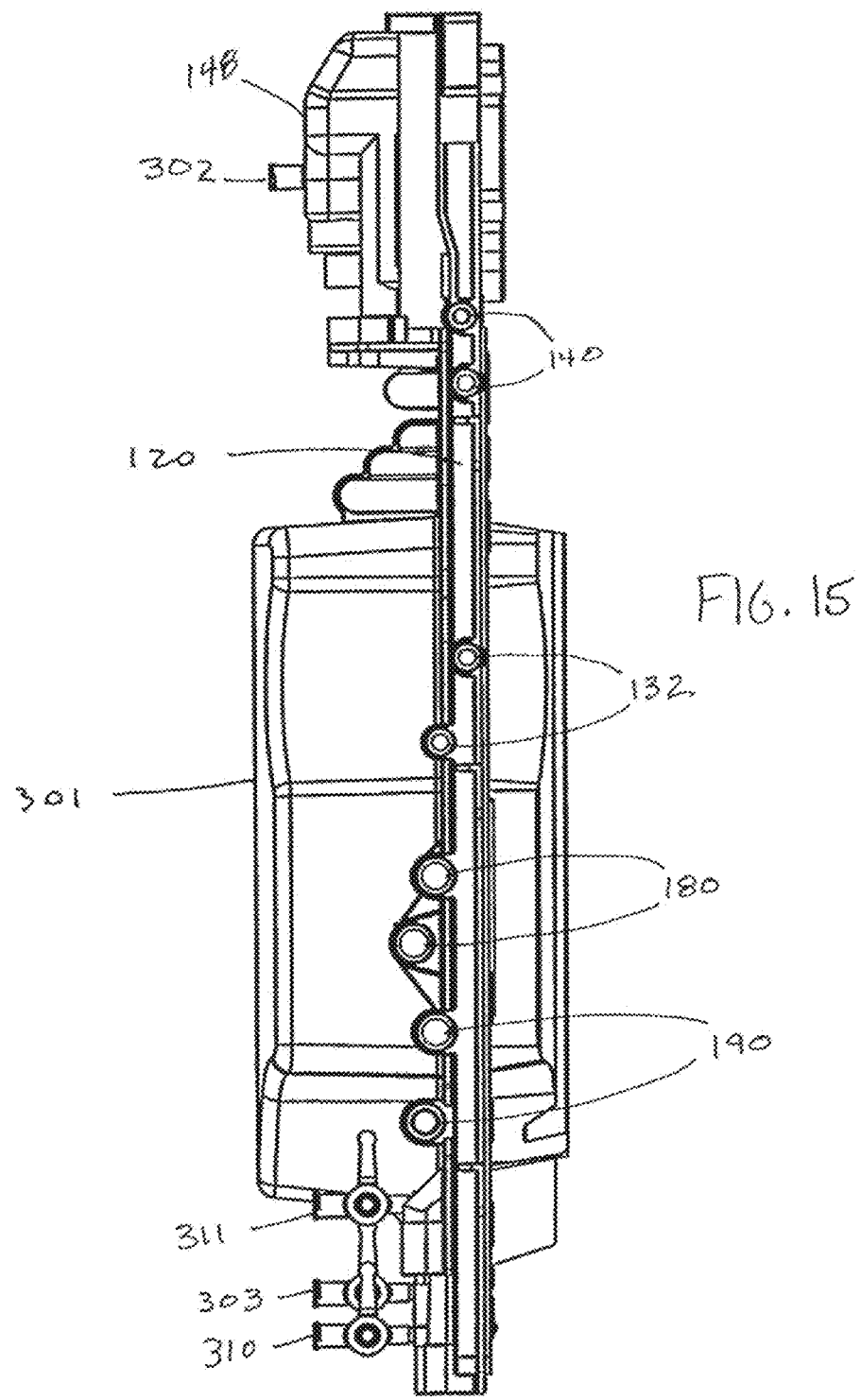
Figure 16:
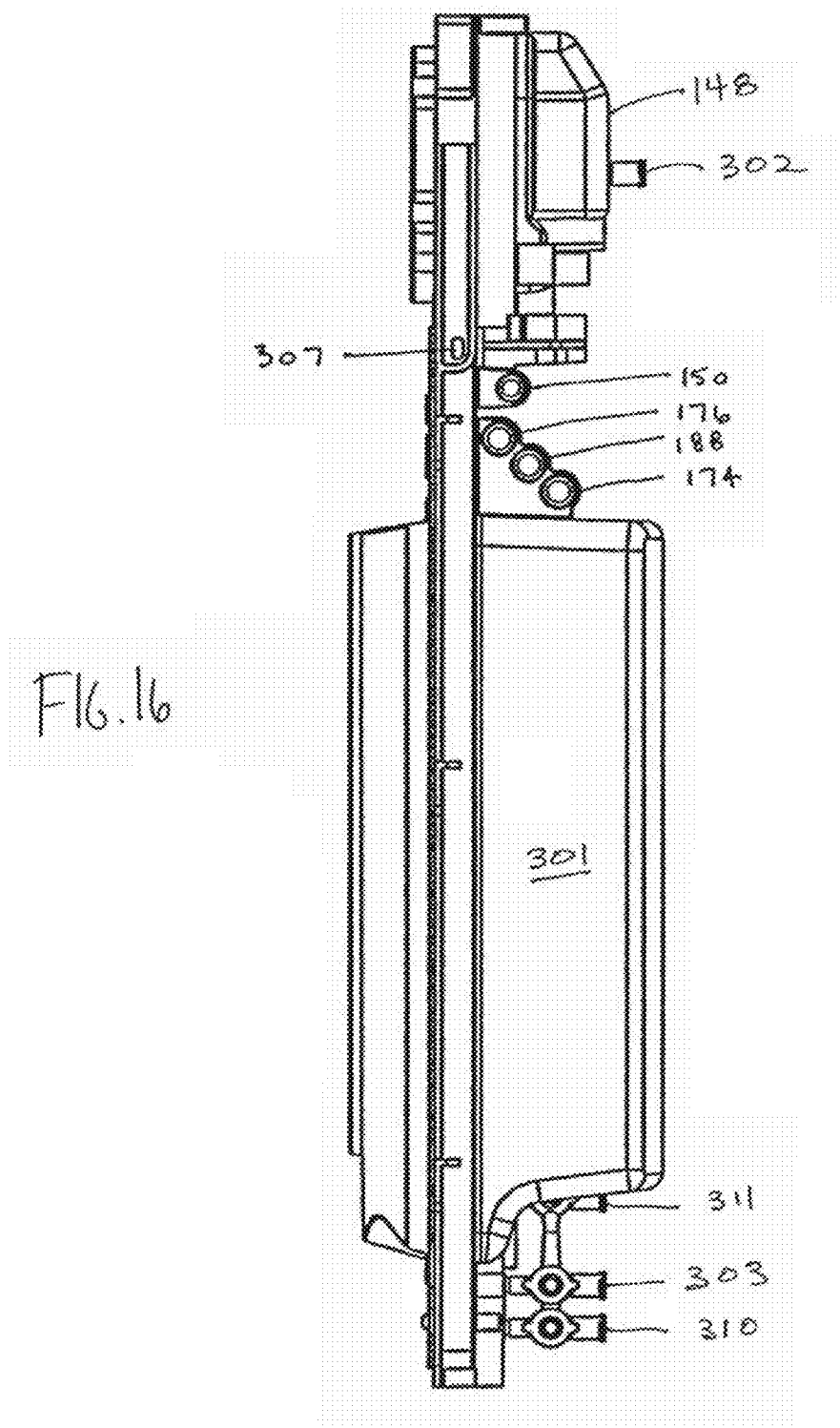

FIGS. 15 and 16 are right and left side views, respectively, of cartridge 120.

Figure 17:
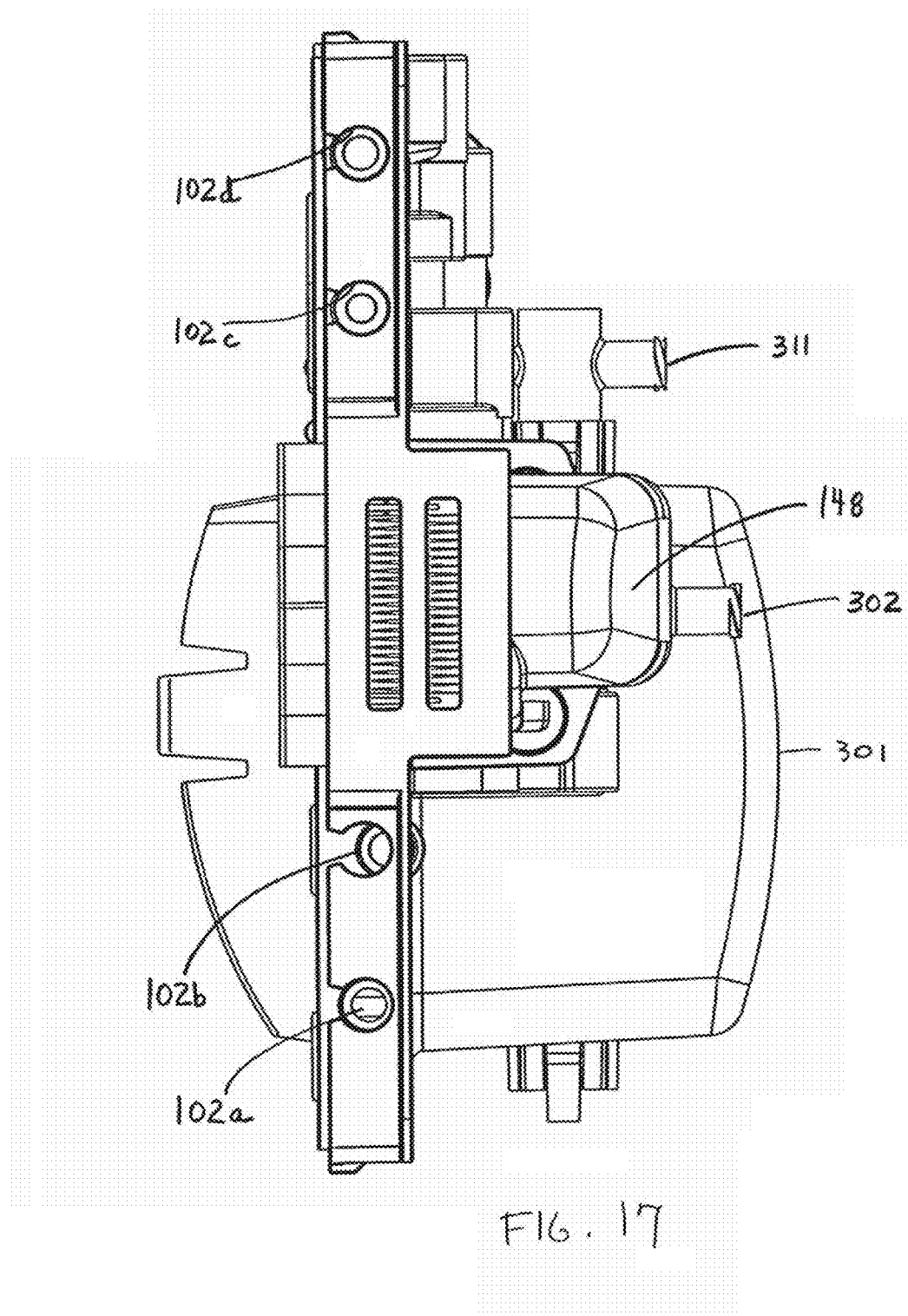
Figure 18:
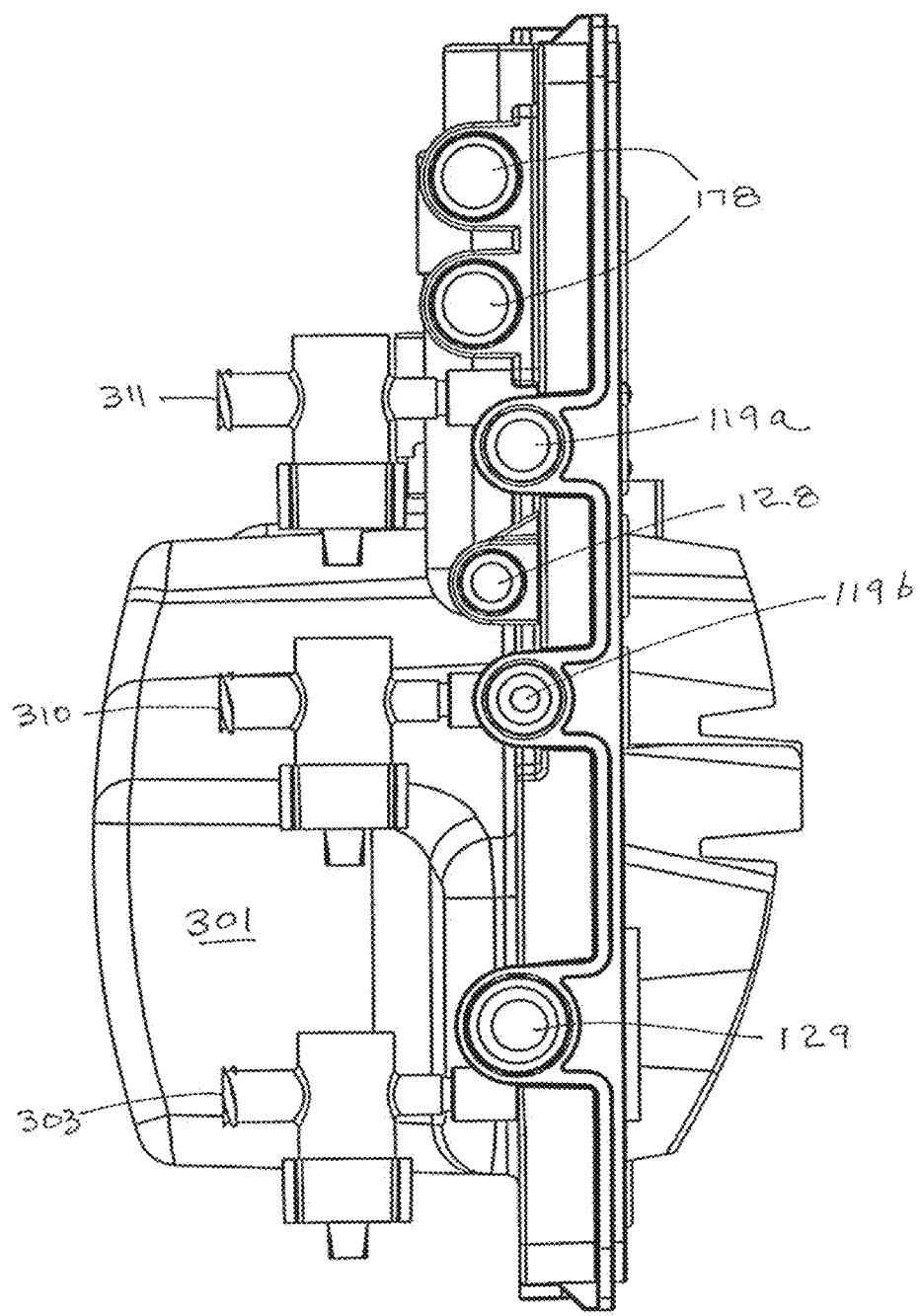

FIGS. 17 and 18 are top and bottom views, respectively, of cartridge 120.

FIGS. 19A and 19B are back plan and back perspective views, respectively, of cartridge 120.

FIG. 20A is a cross-sectional view of cartridge 120 taken along line A-A of FIG. 19A.

Figure 20B:
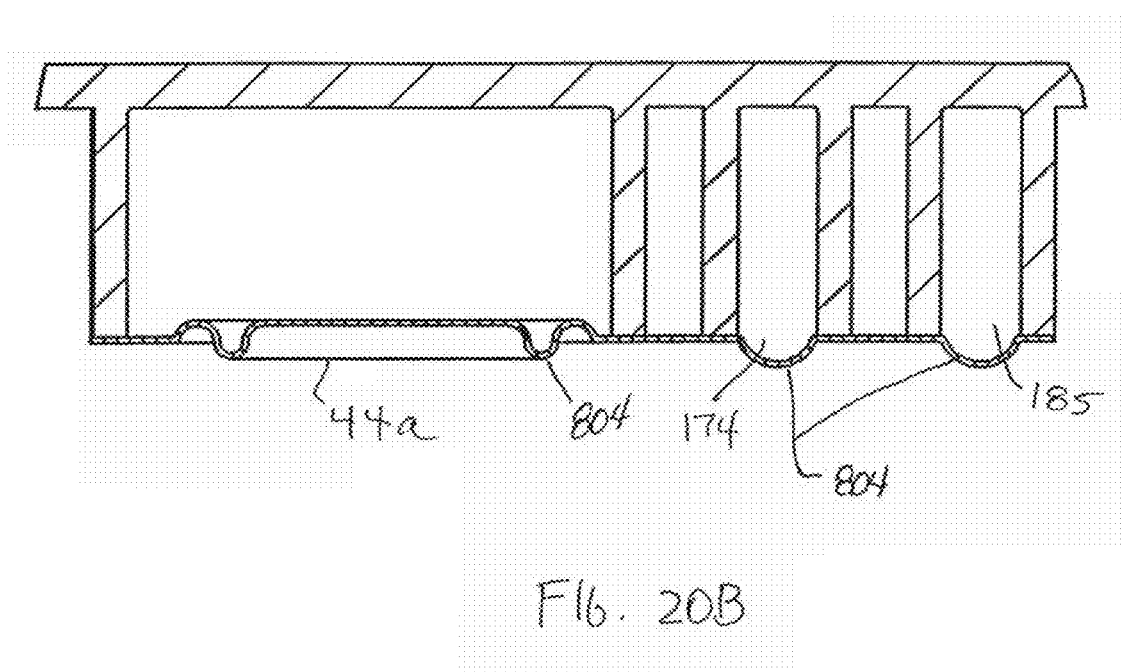

FIG. 20B is an enlarged view of detail B of FIG. 20A.

Figure 21:
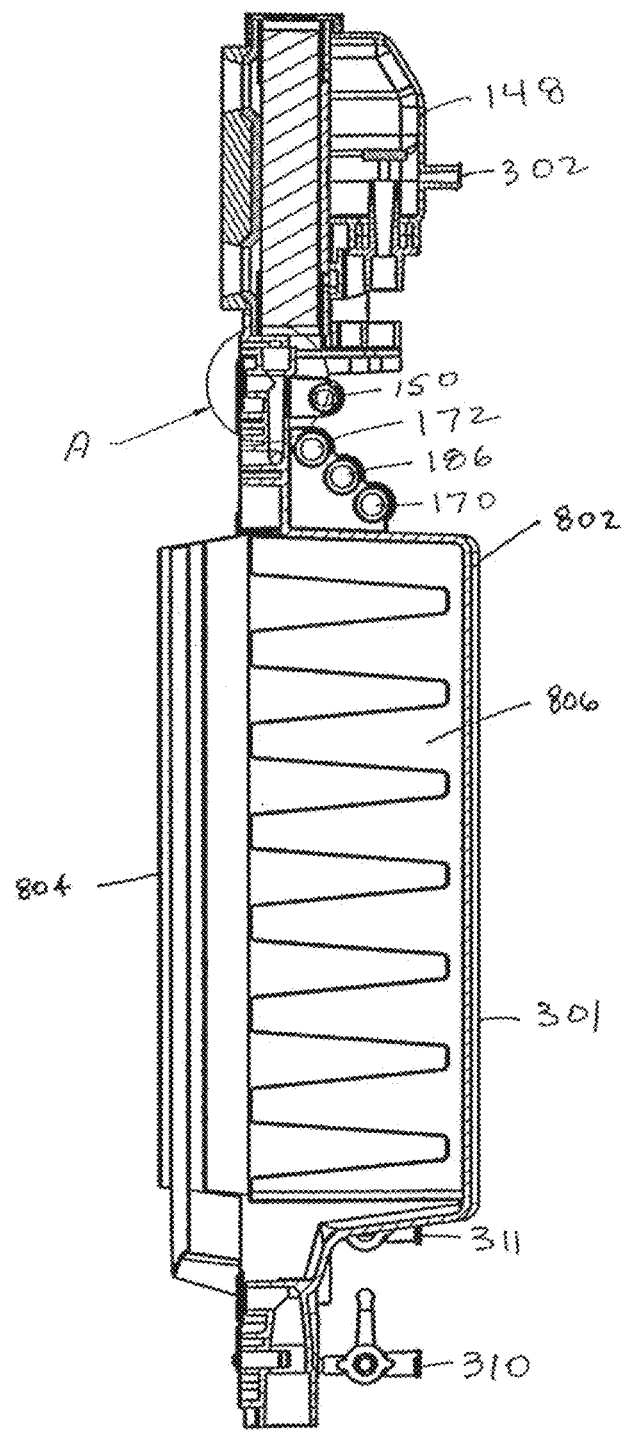

FIG. 21 is a cross-sectional view of cartridge 120 taken along line BB of FIG. 19A.

Figure 22:
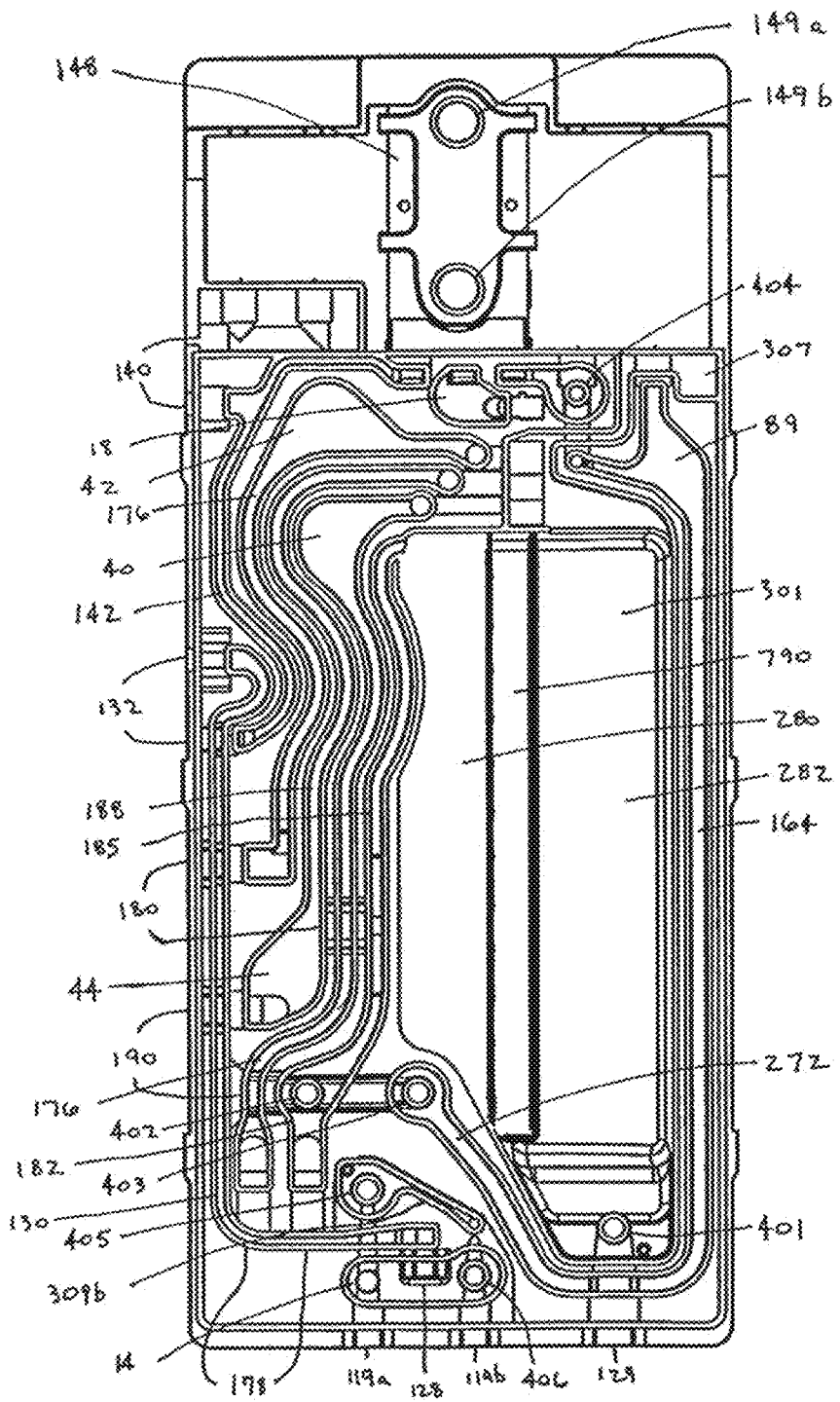
Figure 23A:
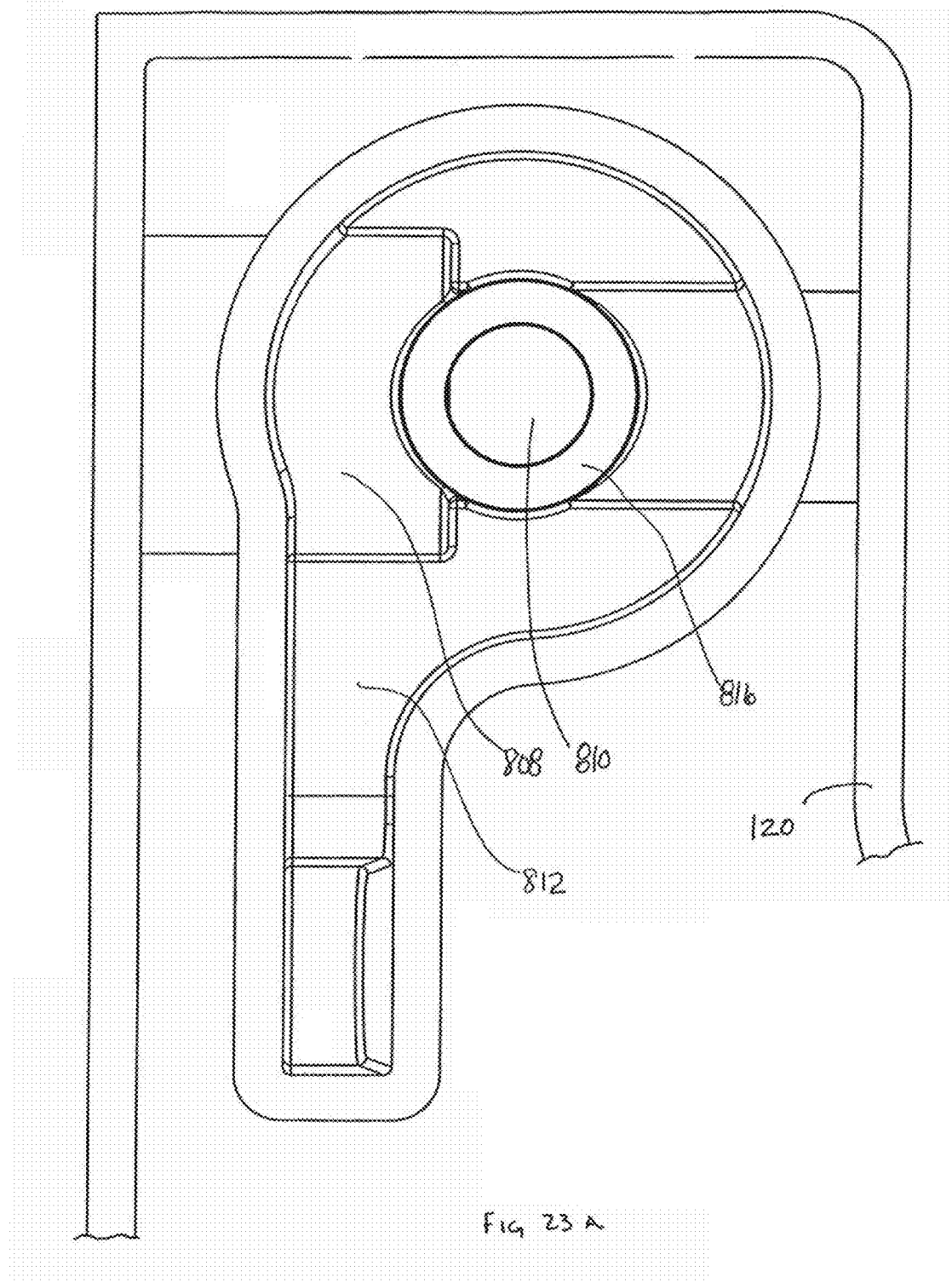
Figure 23B:
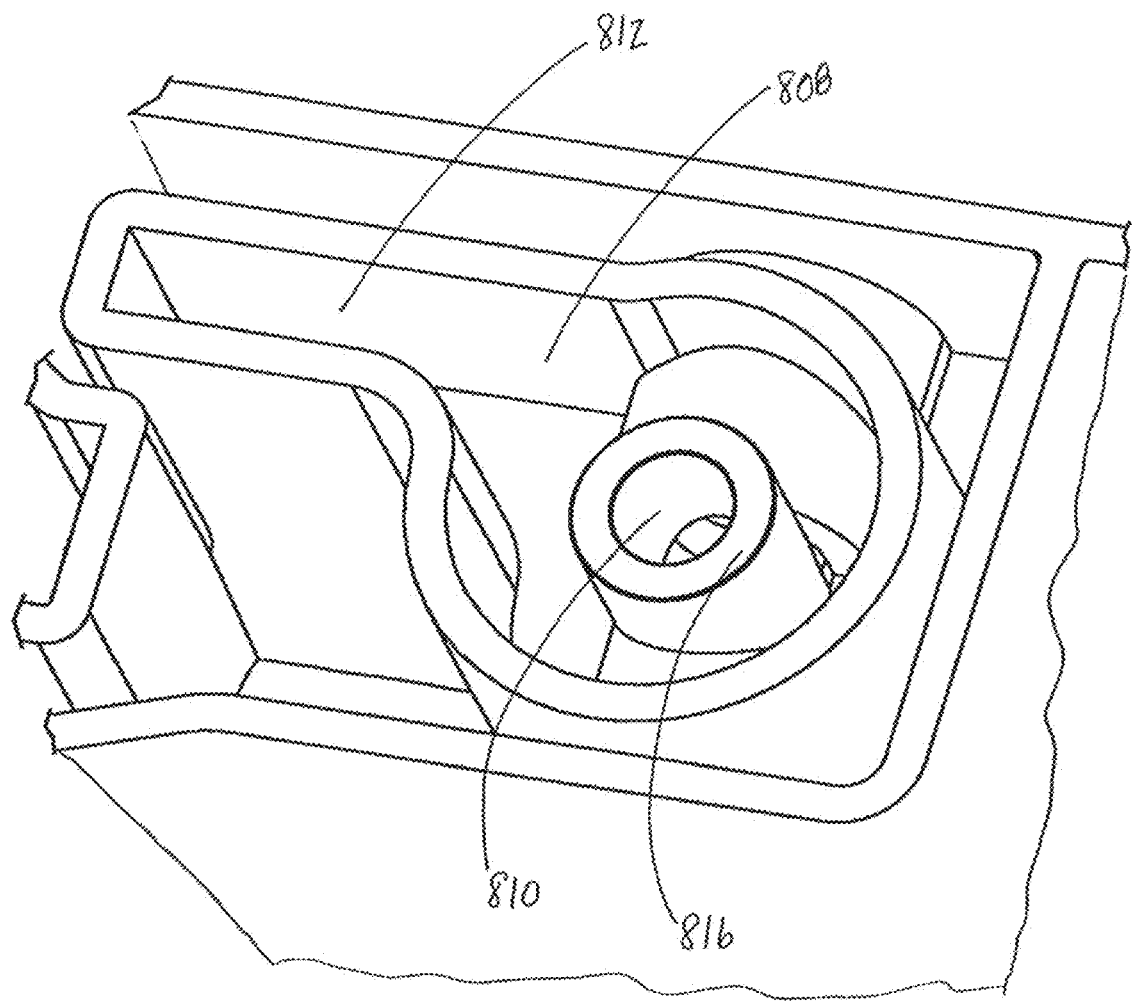
Figure 24A:
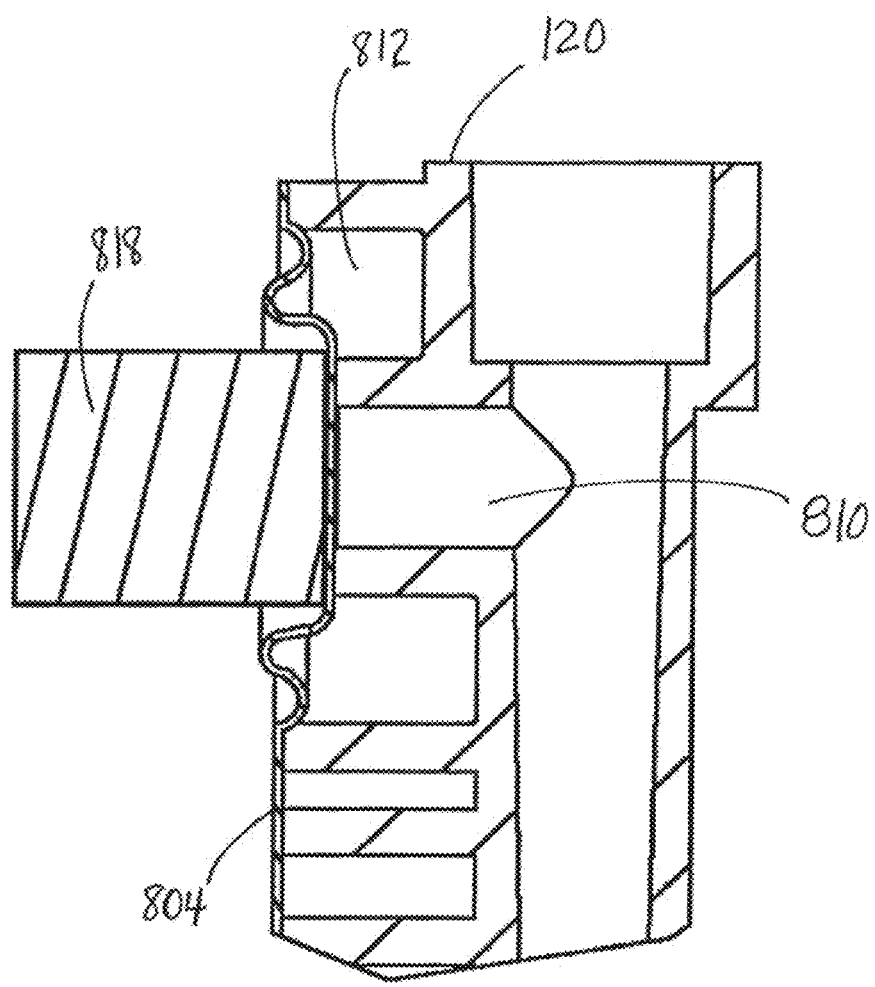
Figure 24B:
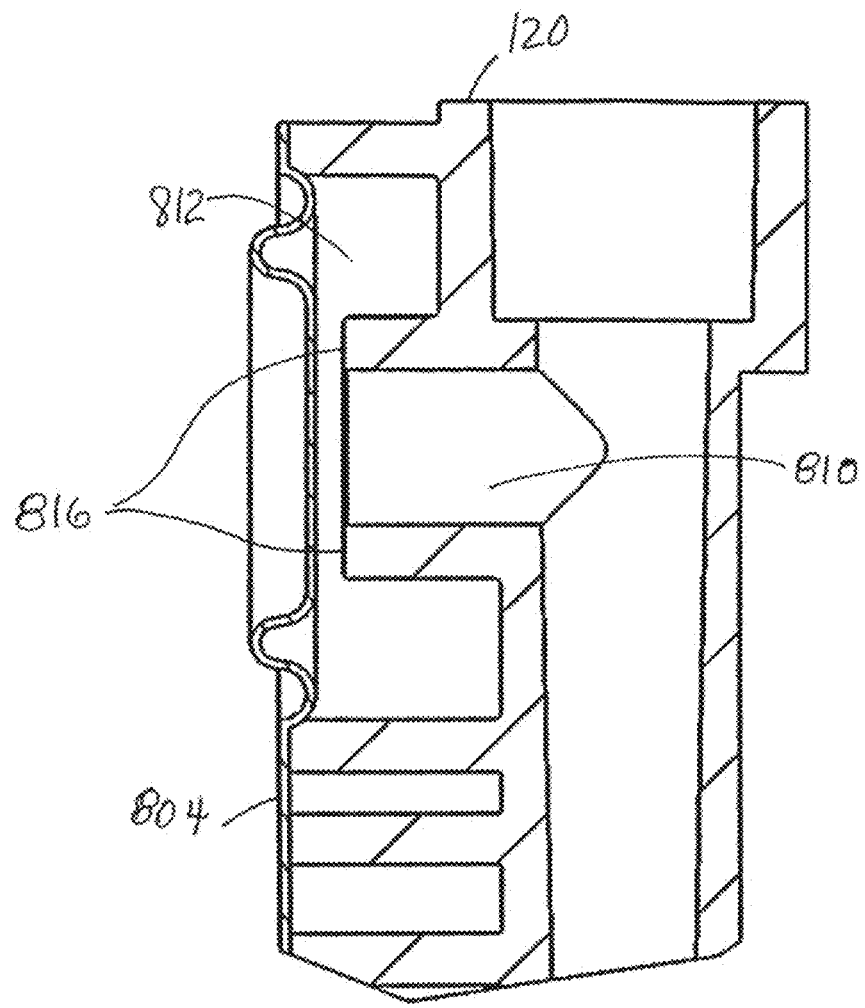

FIG. 22 is a back plan view of cartridge 120 with the flexible back layer removed.

FIGS. 23A, 23B, 24A and 24B are partial views of a valve station in cartridge 120.

Figure 25:
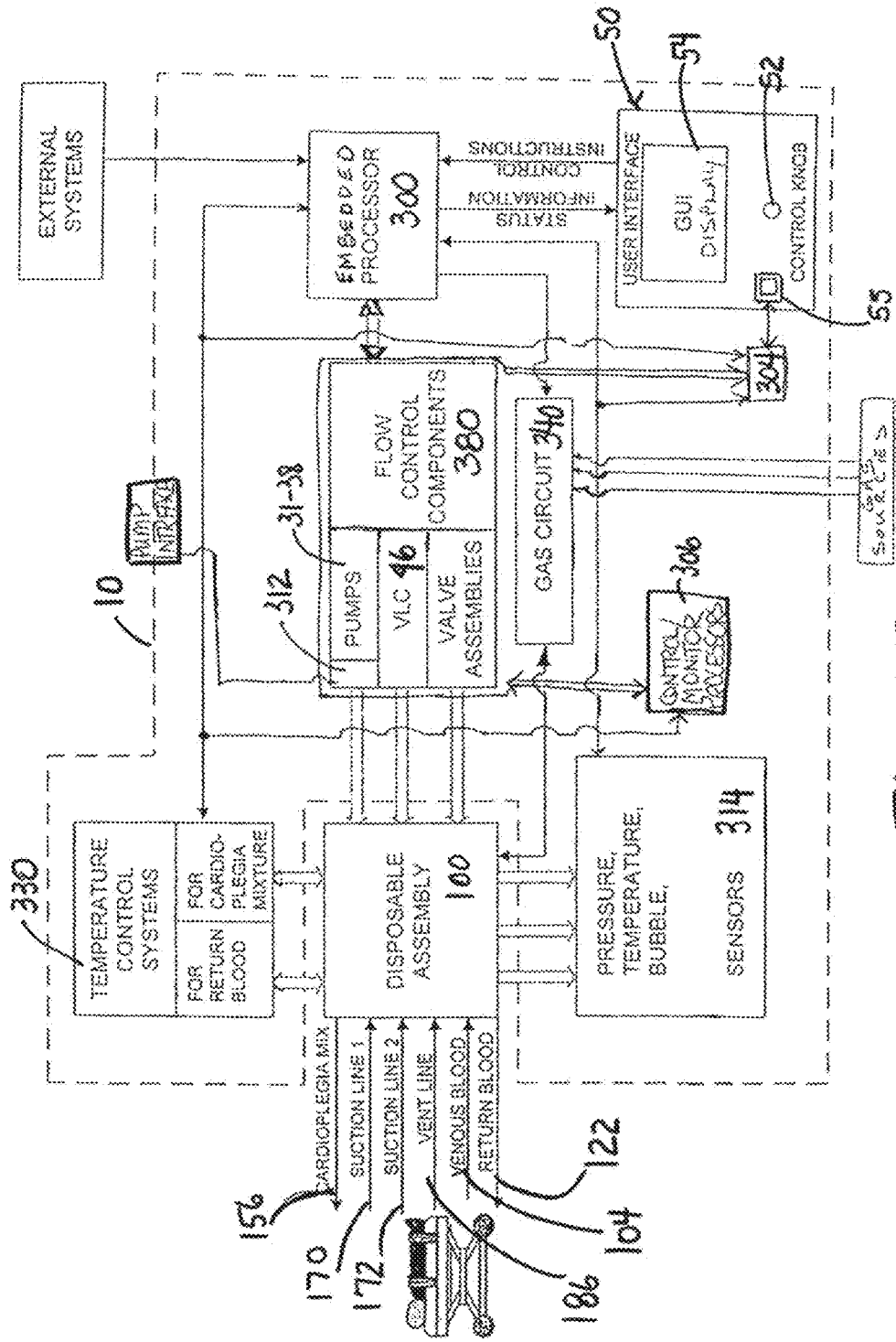

FIG. 25 is a block diagram of the system architecture of the blood perfusion system of the present invention.

Figure 26:
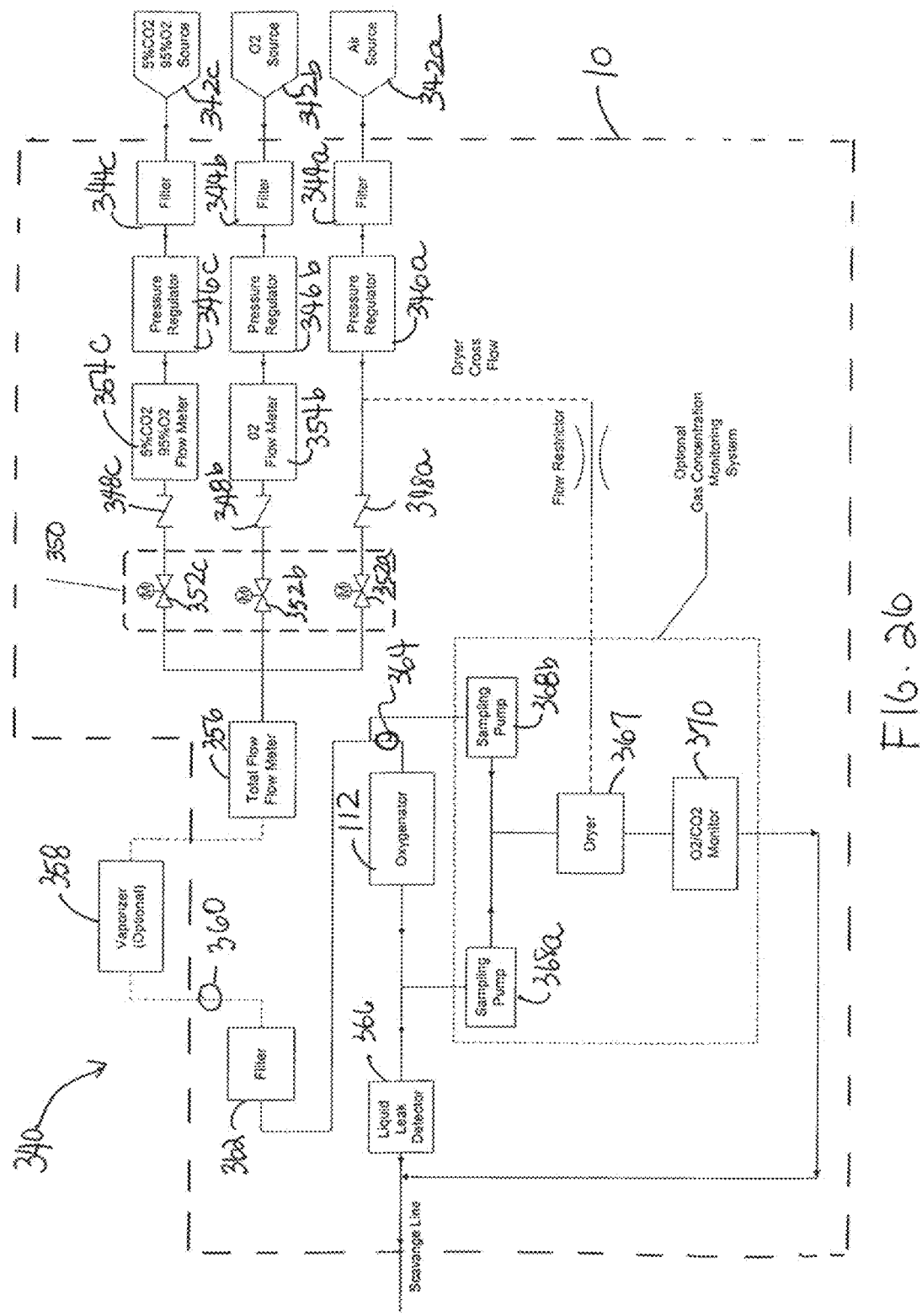

FIG. 26 illustrates a schematic block diagram for the gas circuit shown in FIG. 25.

Figure 27:
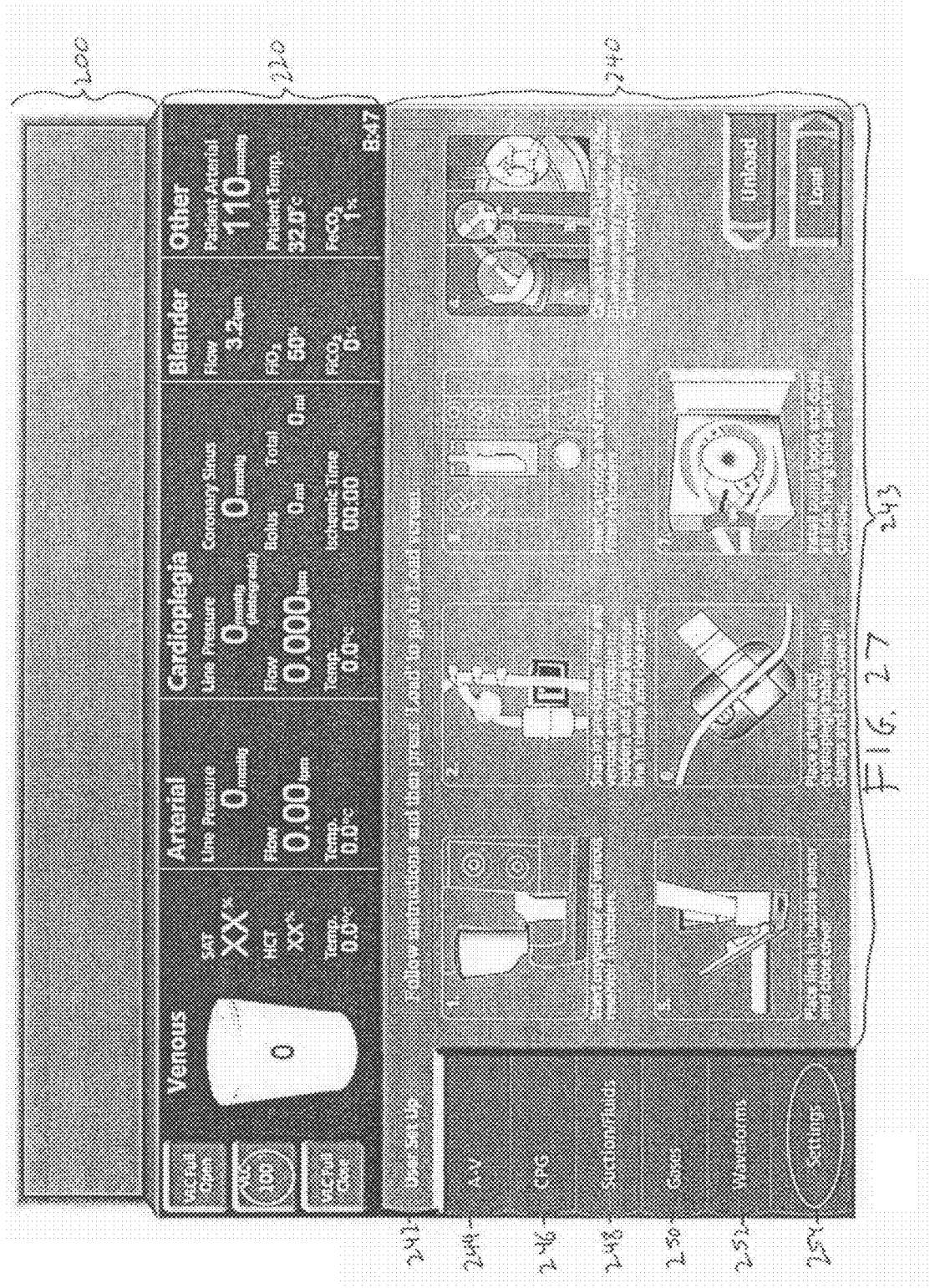

FIGS. 27 to 33 illustrate various operational examples of one embodiment of the system user interface 50. In particular, FIG. 27 illustrates the three display regions of display 54 of the user interface.

FIGS. 28A-28F illustrate a variety of alarm and status messages displayed in the first region of display 54.

Figure 29:
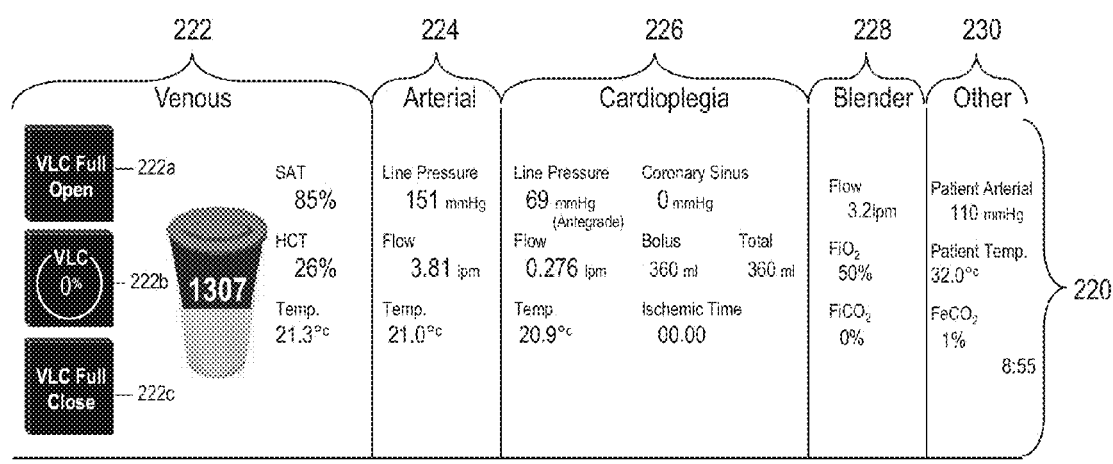

FIG. 29 illustrates information sets displayed in the second region of display 54.

FIGS. 30A-30L illustrate various context-driven information sets and corresponding context-driven user control options displayed in the third region of display FIGS. 31A-31F, FIGS. 32A-32E and FIGS. 33A-33F illustrate various features of context-driven portion 243.

DETAILED DESCRIPTION OF THE PREFERRED EMBODIMENTS

The present invention is an integrated vertical perfusion system. The main components of the system are a console which houses the various pumps, control circuitry, sensors and other nondisposable hardware, and a disposable assembly which connects to and interfaces with the console. The disposable assembly includes all of the disposable components used in the extracorporeal blood circuit including, for example, a venous reservoir, a blood oxygenator, a heat exchanger and an arterial blood filter, as well as the tubing which connects the various components and which forms the extracorporeal blood flow path. The disposable assembly also includes a dedicated disposable cartridge which provides a primary interface between the disposable assembly and the console. The cartridge is provided with multiple fluid flow paths through which the various fluid circuits of the system flow. Sensors which interface with the fluid flow paths monitor certain characteristics of the system such as pressure, temperature, fluid level and the presence of bubbles in various locations in the system. These characteristics provide an indication of whether the system is operating within acceptable ranges. Should these monitored characteristics deviate from acceptable ranges the system is provided with feedback control features which cause the system to automatically return pressure, flow, and fluid levels back to safe and acceptable ranges. After any deviation, the system will alert the user and go into a safe mode if necessary/appropriate. The system will facilitate any required intervention by the user to return to safe and acceptable ranges.

The perfusion system of the present invention will now be described. For purposes of clarity an overview of the system will first be provided. Then the various components and features of the system will be described including the disposable assembly and component interface, the system control, the user interface and an operational summary of the perfusion system.

I. Perfusion System Overview

FIG. 1 illustrates a perfusion system 1 for use during cardiopulmonary bypass surgery. The system comprises one embodiment of various aspects of the present invention. Other applications and embodiments of the inventive aspects will be apparent to those skilled in the art.

The system 1 comprises a console or control unit 10 and a disposable assembly 100. Disposable assembly 100 is best seen in FIG. 2A which shows the disposable assembly prior to attachment to control unit 10. In the illustrated embodiment, control unit 10 is "left-handed," thereby permitting placement in an operating room so that it allows a user (e.g., perfusionist) to visually monitor the disposable assembly 100 when interfaced with control unit 10 during operations, and to readily maintain a direct line-of-sight with a head surgeon who is located in a sterile surgical field surrounding a patient table (not shown). In this regard, and by way of example only, control unit 10 is provided with wheels 5 and may be oriented at an angle relative to the patient table, as desired. As will be appreciated, control unit 10 may also be designed to be "right-handed" or universal.

Control unit 10 includes various sensors and mounting hardware for supportably receiving and/or operatively interfacing with disposable assembly 100. More particularly, an upper component interface plate 12 shown in FIG. 4 includes a cartridge interface region 20 for receiving a cartridge 120 which forms a part of disposable assembly 100. The cartridge interface region 20 includes various sensors for monitoring parameters of fluid flowing through the cartridge 120 during use as will be explained in more detail hereafter. Further, control unit 10 includes additional sensors for monitoring fluid parameters and various valves for controlling the flow of fluid through disposable assembly 100.

Control unit 10 includes a plurality of vertically "stacked" roller pump assemblies 31-36. Each pump assembly comprises a rotatable control knob 31a-36a and a pump information display 31b-36b, respectively.

The control unit 10 further includes one or more embedded processor(s) and a user interface 50 having a main display 54, user control knob 52, and a back up display 55. User interface 50 may be incorporated into the main housing of control unit 10 or may be provided in a separate housing 51 that it can be selectively interconnected at a desired height and angular orientation relative to an outboard pole 11 or other pole or mounting bracket located in a desired position on control unit 10 such as shown in FIG. 1. As will be further described, main display 54 and backup display 55 of user interface 50 may be provided with various graphic user interface (GUI) features, including touch-screen capabilities, which together with user control knob 52 may be selectively employed with the embedded processor(s) to establish/modify various settings for monitoring and controlling various parameters in a cardiopulmonary bypass procedure.

In general, set-up of the system 1 entails removal of disposable assembly 100 from sterile packaging, e.g., a disposable tray, and positioning of the various components of the disposable assembly 100 relative to corresponding interfacing components of control unit 10 as will be discussed in more detail hereafter. In general, three primary fluid flow circuits are defined by the disposable assembly 100: a venous circuit (i.e., for receiving venous blood from a patient), an arterial circuit (i.e., for returning oxygenated blood to a patient) and a cardioplegia circuit (i.e., for delivery of cardioplegia to a patient). The arterial and venous circuits may be combinatively referred to as the arterial-venous, or "AV" circuit. Secondary circuits defined by disposable assembly 100 include two suction circuits (i.e., for selective suctioning of fluids from a patient by medical personnel), and a vent circuit (i.e., for venting accumulated blood or fluid from a patient's heart or vasculature). Another circuit comprising a fluid management or priming circuit is used prior to bypass to prime disposable assembly 100. As will be further described, for flow control purposes through the fluid circuits, positioning of the disposable assembly 100 on control unit 10 includes the placement of various looped tubing lines within pump assemblies 31-36 and positioning of various tubing lines into various valve assemblies on control unit 10.

Additionally, for monitoring various parameters within the fluid circuits, the cartridge 120 and various tubing lines and other components of disposable assembly 100 are positioned in operative relationship to various pressure, temperature, bubble, fluid level, hematocrit, oxygen saturation and other sensors included in control unit 10. Further, an oxygenation device and one or more heat exchangers included within disposable assembly 100 are connected to gas and/or fluid inlet/outlet ports on control unit 10. After initial connections are made between the disposable assemblies and control unit 10, the various fluid circuits defined by the disposable assembly 100 are primed (i.e., filled with liquid to remove air), according to predetermined protocols. Thereafter, various tubing lines may be interconnected to a patient to provide for the flow of fluids to/from the patient and disposable assembly 100.

II. Disposable Assembly

One embodiment of the disposable assembly 100 is shown in FIGS. 2A and 2B. Disposable assembly 100 comprises various extracorporeal blood circuit components interconnected by tubing to create a blood flow path. FIG. 2A is a view of disposable assembly 100 before it is interfaced with control unit 10. FIG. 2B is similar to FIG. 2A except that the tubing has been removed to more clearly show the disposable components of the assembly. These disposable components include disposable cartridge 120, venous entry module 108, pre-bypass filter 168, venous blood reservoir 106, a combined oxygenator and heat exchanger 112, an arterial blood filter 118 and tubing clips 111a-111f. Note that although the oxygenator and heat exchanger are shown as an integrated unit, separate devices could be used as is known in the art. The venous entry module 108, cartridge 120 and tubing clips 111 are unique to the perfusion system of the present invention and are discussed in more detail hereafter.

III. Hardware Interface and Mounting Assemblies

Control unit 10 is provided with various structural elements including line clamps, sensors and mounting brackets for interfacing with components of disposable assembly 100. Many of those sensors and interfacing structures are located on upper component interface plate 12 as seen in FIG. 4. Interface plate 12 includes a cardioplegia-valve tubing block 195. Tubing block 195 includes a cardioplegia air bubble sensor 158, a cardioplegia temperature sensor 153 and a motorized cardioplegia line valve 96. Arterial valve tubing block 196 includes an arterial line air bubble sensor 126, arterial temperature sensor 88, and a motorized arterial patient line valve 92. Venous entry module mounting bracket 550 includes oxygen saturation-hematocrit standardization surface 83, oxygen saturation-hematocrit optical sensor 85 and a venous temperature sensor 81. Interface plate 12 includes a motorized pre-bypass filter valve 95 positioned above venous line clamp 46 and pre-bypass filter mount 70. Located at the bottom portion of plate 12 is an arterial filter mounting arm 760.

Upper component interface plate 12 includes a disposable cartridge interface region 20. Interface region 20 includes those components of control unit 10 which interface directly with cartridge 120. Cartridge mounting assembly 21 is used to secure the cartridge to region 20 in a manner discussed hereafter with regards to FIGS. 10A-10D. Region 20 includes numerous pressure sensors for sensing line pressure in various circuit locations. These sensors include venous reservoir pressure sensor 89, first suction pump pressure sensor 40, second suction pump pressure sensor 42, vent pump pressure sensor 44, arterial line pressure sensor 14, and cardioplegia line pressure sensor 18. Each of these pressure sensors function in the same manner except that the sensors in the suction circuits sense negative pressure. Each sensor includes a load cell in control unit 10 and a load cell stem or cylinder magnetically coupled thereto (not shown). The load cell stem is aligned with the cartridge at the location pressure that is to be sensed. Pressure affects the vinyl backing of the cartridge causing a force to be exerted against the load cell stem. This force is converted to an electrical signal by the load cell. This electrical signal is then converted to a pressure by a microprocessor. An example of such a pressure sensor is described in U.S. Pat. No. 5,676,644 (Toays et al.) which is incorporated herein by reference.

A plurality of solenoid valve plungers are also included within region 20. These valve plungers interface with complimentary valve structures within cartridge 120 to open and close valves in various fluid circuits within cartridge 120. These valve assemblies include cardioplegia bubble trap purge valve 404, vent pump to sequestration reservoir valve 402, vent pump to venous reservoir valve 403, low flow purge valve 405, high flow purge valve 406 and sequestration reservoir drain valve 401. Additional valve assemblies could be included. For example, valve assemblies could be included from the suction pump to sequestration reservoir and/or suction pump to venous reservoir (not shown).

Cartridge interface region 20 includes several components which interface directly with a sequestration reservoir located within cartridge 120. First and second sequestration level sensors 320 and 322 are used to monitor the fluid level in the sequestration reservoir. A defoamer push bar 790 is used to apply pressure to a defoamer within the sequestration reservoir to ensure that fluid which enters the sequestration reservoir is caused to pass through the defoamer. Means is provided in control unit 10 for bringing the cartridge 120 into automatic operative engagement with the various components in interface region 20 by advancing such components through plate 12 into contact with the cartridge.

At the upper portion of cartridge interface region 20 are motorized priming solution (or other solution) bag line valves 98 and cardioplegia crystalloid bag line valves 99. Water connections 147a and 147b are provided for connecting to a cardioplegia heat exchanger. Water connections 147a and 147b are designed to mate with ports 149a and 149b on cardioplegia heat exchanger 148 in a manner similar to that which will be described hereafter with respect to the water connections made to heat exchanger 505 shown in FIGS. 8A-8E

Control unit 10 includes additional structural elements for interfacing with disposable assembly 100. For example, the structure of the venous entry module 108 and the mounting bracket with which it is attached to control unit 10 are shown in FIGS. 5A-5F. The structure and operation of the venous line clamps 46 and the mounting bracket for the pre-bypass filter 168 are shown in FIGS. 6A-6E. The mounting bracket for the venous reservoir is shown in FIGS. 7A-7B. The mounting hardware for the combined oxygenator/heat exchanger 112 is shown in FIGS. 8A-8E. The mounting hardware for the arterial filter 118 is shown in FIGS. 1 and 4. The manner in which cartridge 120 is mounted and interfaced with control unit 10 is shown in FIGS. 10A-10D. Finally, the structure of tubing clamps 111a-111f is shown in FIGS. 9A-9F. A discussion of these components and their mounting and interface with control unit 10 follows.

Although certain sensors, valves, etc., are packaged together in blocks in this embodiment, they could be provided as individual components or combined together in any variety of integrated assemblies or in one common assembly.

1. Venous Entry Module

The venous entry module 108 is a unique component which allows multiple functions to be accomplished within a single circuit component. The structure and features of the venous entry module can best be understood with reference to FIGS. 5A and 5B. The manner in which the venous entry module is mounted and interfaced with control unit 10 is shown in FIGS. 5C-5F.

With particular reference to FIGS. 5A and 5B which are perspective views of the top and bottom portions of the venous entry module it can be seen that the venous entry module has inlet and outlet ports 530 and 532, respectively, which may be barbed. Housing 534 defines a lumen or conduit between the inlet and outlet ports which comprises the primary flow passage for venous blood entering reservoir 106. A secondary flow port 536 is provided allowing the flow through the venous entry module to be diverted through the pre-bypass filter during priming of the disposable assembly 100 as described more fully hereafter. Housing 534 is also provided with sampling/infusion fluid addition/removal ports 538, 540 and 542. These ports are connected to stopcock valves 539, 541 and 543, respectively. These valves allow access to the venous line for the addition of medication or fluids or removal of blood. For example, these valves allow a venous blood sample to be taken, allow fluids or drugs to be infused during the bypass procedure, allow blood to be removed for pre-donation sequestration prior to the procedure, and allow fluid to be added at some later point in the procedure. Mounting tabs 544 and 546 on the side portions of housing 534 are located and sized to provide a handhold for easy loading and to ensure proper positioning of the venous entry module in upper and lower mounting clips 548 and 552 of mounting bracket 550 as shown in FIGS. 5C and 5D.

As shown in FIGS. 5B and 5C, housing 534 includes an oxygen saturation-hematocrit sensing window 554 and a temperature sensing window 556. Window 554 is aligned with optical sensor 85 on mounting bracket 550 so that hematocrit and oxygen saturation of the venous blood flowing through the venous entry module can be measured. The manner of sensing oxygen saturation-hematocrit is described in detail in U.S. Pat. No. 5,356,593 (Heiberger et al.), the entirety of which is incorporated herein by reference. Window 556 is aligned with infrared temperature sensor 81 to allow the temperature of the venous blood to be monitored. This temperature sensor is of conventional design and need not be described in detail herein.

As best seen in FIGS. 5C and 5D the venous entry module is held in place in clips 548 and 552 by arms 548a, 548b, 552a and 552b. FIG. 5E is a front view of venous entry module 108 in bracket 550. FIG. 5F is a sectional view taken along line F—F of FIG. 5E. The distance between the adjacent arms is slightly less than the outer dimension of the portion of the venous entry module positioned between the arms. Therefore, the venous entry module is snap fit into bracket 550 and held by the adjacent arms. Bracket 550 includes a block 558 having a sliding portion 560. Sliding portion 560 is spring loaded by virtue of spring 559 acting on stationary surface 561. Portion 560 includes a lower surface to which is mounted standardization surface 83. During power up prior to insertion of the venous entry module standardization surface 83 is positioned over sensor 85 to allow the sensor to automatically standardize at power up. The light reflects off the standardization surface which allows the device to standardize. As the venous entry module is installed, the sliding portion moves out of the way so that window 554 is positioned over sensor 85.

2. Pre-Bypass Filter and Venous Line Clamp

As noted above, the component interface region includes a venous line clamp assembly (VLC) 46 for receiving tubing line 104 therewithin and a bracket for mounting the pre-bypass filter to control unit 10. The tubing size of the portion of line 104 between VLC 46 and venous reservoir 108 is preferably larger in diameter than the portion from the patient to VLC 46. For example, the portion from the patient to VLC 46 may be a one-half inch line while the portion from the VLC to the venous reservoir may be five-eighth inch. In general, VLC 46 is provided to control the passage of venous blood from a patient to the venous reservoir 106 during bypass procedures. FIGS. 6A-6E illustrate one embodiment of a VLC 46, which comprises a housing 71 for receiving venous tubing line 104 through a slot 72 provided in the housing 71. A lid 73 may be hingedly interconnected to housing 71. Housing 71 includes a bracket 70 into which pre-bypass filter 168 may be secured. Bracket 70 is substantially cylindrically shaped and forms slightly more than 180° of the circumference of a cylinder. The dimensions of this cylindrical configuration are chosen so that the pre-bypass filter can be snap fit into the bracket and held without further attachment. A lid latch 74 may be interconnected to housing 71, wherein a lip portion 74a is adapted for selectively retaining lid 73 in a closed condition relative to housing 71. As will be appreciated, when lid 73 is in such a closed condition, a venous tubing line 104 may be retained within the slot 72 of the housing 71.

The VLC 46 further includes a stepper motor 75. One end of a lead screw 76 may be positioned in the stepper motor 75 and the other end of lead screw 76 may be interconnected to a plunger 77, wherein the stepper motor 75 may be selectively operated for advancement/retraction of plunger 77. The plunger 77 is sized and oriented to pass through an opening in the back of the housing 71, wherein selective operation of the stepper motor 75 allows the plunger 77 to be advanced across/retracted from the slot 72 passing through housing 71. By virtue of such selective ability to position plunger 77, the VLC 46 provides for the selective occlusion of a tubing line 104 positioned within the slot 72 housing 71. More particularly, when tubing line 104 is positioned through slot 72 and lid 73 is secured in a closed position by the latch 74, actual advancement of plunger 77 by stepper motor 75 will cause the tubing line 104 to be pinched between plunger 77 and lid 73 so as to occlude the tubing line 104 to a desired, selective extent. The lid 73 can be opened at anytime, anywhere from the venous line clamp being fully open or closed. This allows removal of the venous line in the event of a failure so it can be manually clamped. The lid 73 is also clear so the user can verify venous line clamp actuation and open/closed status. In order to facilitate calibration at VLC 46 (e.g., to accommodate varying wall thickness in tubing line 104), VLC 46 may further include an optical encoder 78, wherein a calibration procedure may be carried out to determine the desired positioning of lead screw 76 for a given procedure.

3. Venous Reservoir

The mounting assembly of venous reservoir 106 is shown in FIGS. 7A and 7B. FIG. 7A is a perspective view of reservoir mounting bracket 602 spaced from reservoir 106 prior to reservoir 106 being inserted into bracket 602. FIG. 7B is a perspective view of reservoir 106 attached to mounting bracket 602. For purposes of illustrating clearly the mounting structure mounting bracket 602 is shown detached from control unit 10. During use it will be understood that bracket 602 is affixed to control unit 10 in the position shown in FIG. 1.

As shown in FIGS. 7A and 7B mounting bracket 602 includes flexible arms 604 and 606. The arms are provided with grooves 606a and 604a which are shaped to receive the circumferential edge 107a of a lid 107 at the top of reservoir 106. Reservoir 106 is mounted by sliding edge 107a into grooves 604a and 606a. Flexible arms 604 and 606 are slightly curved and extend more than 180° around edge 107a so that reservoir 106 is held in a snap fit configuration by arms 604 and 606.

4. Oxygenator/Heat Exchanger

Figure 8D:
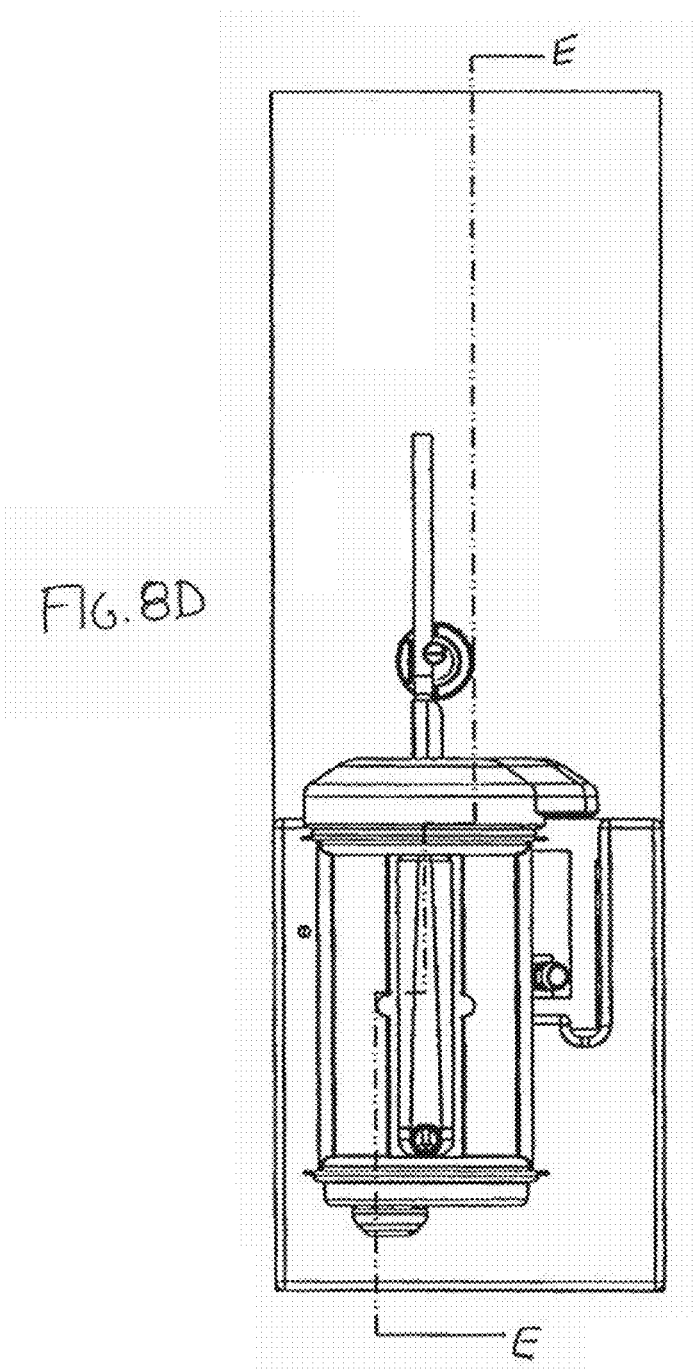
Figure 9A:
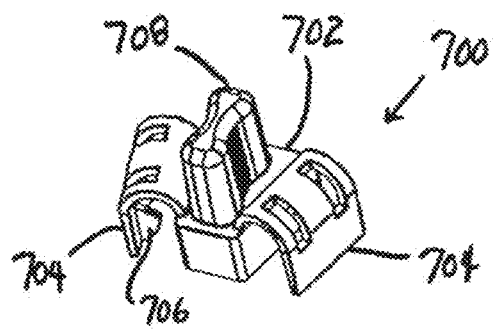
Figure 9B:
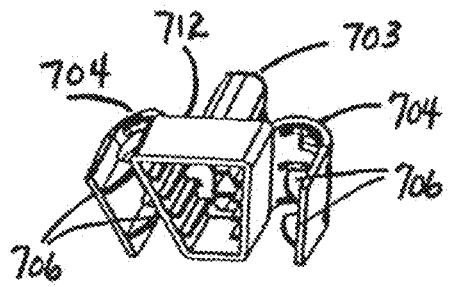
Figure 9C:
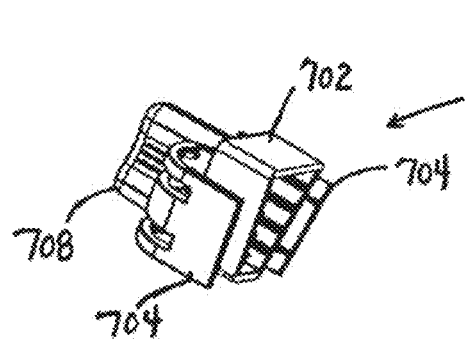
Figure 9D:
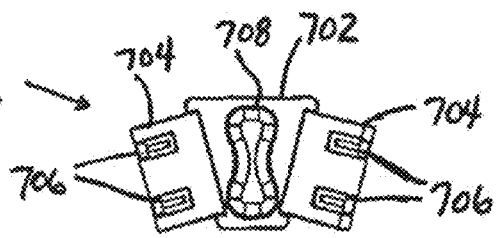
Figure 9E:
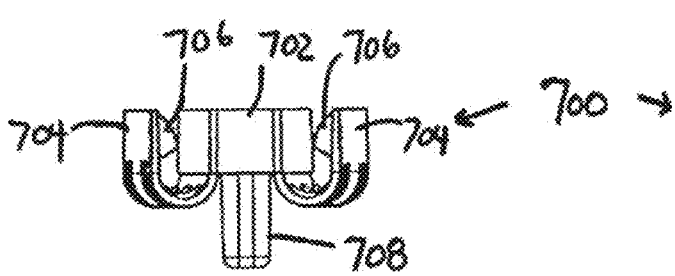
Figure 9F:
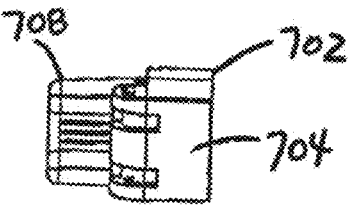

The mounting assembly for the combined oxygenator/heat exchanger is shown in FIGS. 8A-8E. FIG. 8A is a perspective view of oxygenator/heat exchanger 112 separated from mounting bracket 500. FIG. 8B is a back perspective view of oxygenator/heat exchanger 112 showing the location of the various gas and water inlet and outlet ports. FIG. 8C is a front view of mounting bracket 500 showing the location of gas and water connections. FIG. 8D is a front view of the oxygenator/heat exchanger 112 mounted on bracket 500 and FIG. 8E is a cross-sectional view taken along line E-E of FIG. 8D.

In the embodiment shown in FIGS. 8A and 8B mounting assembly 500 includes a lower portion 501 which is configured to receive the heat exchanger. Portion 501 has a heat exchanger receiving slot 502 with lower grooves 502a and 502b. Between grooves 502a and 502b is a ledge 503 for retaining the heat exchanger. Slotted side portions 504a and 504b are configured to receive heat exchanger mounting tabs 505a and 505b. Thus, to mount oxygenator/heat exchanger 112 on lower portion 501 the heat exchanger 505 is inserted in slot 502 with heat exchangers tabs 505a and 505b above slotted side portions 504a and 504b. The heat exchanger is then moved in a downward direction so that the heat exchanger tabs mounting 505a and 505b are received in slots 504a and 504b, respectively, and so that retaining ledge 503 is positioned between the heat exchanger and the oxygenator.

As best seen in FIG. 8C mounting assembly 500 includes gas fittings 508a and 508b for providing oxygen-containing gas to the oxygenator and removing carbon dioxide therefrom. Additionally fittings 509a and 509b are provided for circulating heating/cooling fluid through the heat exchanger. Motorized oxygenator vent line valve 507 is provided to receive vent line 105 connected between the oxygenator and venous reservoir. Loading of the vent line into the vent line valve is facilitated by vent line loading element 506 which is slotted to receive and route the vent line through slots 507a and 507b of valve 507. Valve 507 includes a roller 525 eccentrically mounted on a rotating member (not shown) that, when rotated, causes the roller to pinch the tubing to occlude or partially occlude flow.

Fittings 508a, 508b, 509a and 509b are tapered at their end portions and have O-rings 512, 513, 514 and 515 disposed thereabout. The tapered ends of fittings 508a and 508b are designed to sealingly engage gas inlet and outlet ports 518a and 518b on the oxygenator while tapered fittings 509a and 509b are designed to sealingly engage water inlet and outlet ports 519a and 519b of the heat exchanger. Mounting assembly 500 is designed to automatically engage the tapered fittings with the corresponding ports of the oxygenator and heat exchanger. Mounting assembly 500 includes a stationary face plate 510 and a moveable carriage member 511. The carriage member may be advanced or retracted with respect to face plate 510 by operation of a stepper motor 516 acting on a lead screw 517 as shown in FIGS. 8A and 8E.

The carriage member rides on guide rods (not shown) which are pressed into the face plate. Forward and reverse limit switches (not shown) are used to indicate when the carriage member is forward or fully retracted. The carriage member must be retracted to load an oxygenator into the bracket.

As best seen in FIG. 8E, the water and gas fittings are spring loaded along the fitting axes and able to move freely perpendicular to the axes. All of the fitting axes are parallel to allow them all to engage the oxygenator or heat exchanger in a single motion. Each fitting is mounted in a flanged bushing, such as 520*a*, 520*b*, and 520*c*. The inside diameter of the bushing is larger than the outside diameter of the fitting at the inserted section, so that the fitting can move freely inside the bushing.

Axial motion of the fitting relative to the bushing is prevented in one direction by a flange on the fitting (i.e., 521*a*, 521*b*, 521*c*) which mates with a flange on the bushing. Motion in the opposite direction is limited by a retaining ring (not shown) attached to the fitting which collides with the back surface of the bushing.

The fitting assembly is spring loaded towards the mating port with a compression spring (i.e., 522*a*, 522*b*, 522*c*). The compression spring exerts a force on the back side of the bushing flange. The opposite end of the spring pushes against a surface of the fitting base which is fixedly attached to the carriage member.

The heat exchanger water fittings are machined from a single piece of material. However, the gas supply fitting and scavenge line fitting are made from an assembly of a machined fitting piece and a standard pipe nipple. The pipe nipple rides inside the flanged bushing. The back portion of the gas fitting rides against the flange face of the flanged bushing.

The gas and water fittings are connected to the carriage member so that they are caused to advance or retract by movement of the carriage member. Thus, once the heat exchanger has been mounted on lower portion 501 the connections for water and gas may be automatically made by advancing the carriage so that the fittings are caused to engage with the corresponding ports on the oxygenator and heat exchanger.

5. Arterial Blood Filter

The manner in which the arterial blood filter 118 is mounted and interfaced with control unit 10 can best be understood with reference to FIGS. 1 and 4. Blood filter 118 held by mounting arm 760. Arm 760 extends from a lower portion of upper component mounting plate 12. Arm 760 includes a first straight portion 761 and a second flexible curved portion 762. Curved portion 762 is provided with a groove 762*a* which is sized to accommodate an outwardly extending lip on the cover of filter 118. Curved portion 762 is substantially semicircular and extends slightly past 180°. Therefore, the outwardly extending lip may be snapped into place in groove 762*a* so that the arterial filter is held securely by arm 760.

A rotating assembly means 763 is activated during the priming of disposable assembly 100 to cause arm 760 along with arterial filter 118 to rotate 180°. This facilitates removal of air bubbles from filter 118. By flipping the filter 180° during an automated priming procedure, even though priming fluid follows an antegrade path through the filter from the inlet to the outlet the direction is from bottom to top. In conventional priming techniques retrograde flow of priming fluid from outlet to inlet is required in order to get bottom to top flow. In conventional systems, this requires extra set up for priming of the filter and a bypass line with extra ports.

In order to enhance the efficiency of bubble removal during priming portion 761 is angled about 22½° from the horizontal and portion 762 is angled about 45° from the horizontal to allow air to rise to the arterial filter purge outlet. This results in filter 118 being held at an angle during bypass as shown in FIG. 1. However, during the priming procedure discussed in more detail hereafter, when arm 760 is rotated 180° the angled portions 761 and 762 cause filter 118 to be held such that its longitudinal axis is perpendicular to an intersecting horizontal plane. This allows priming fluid (and bubbles) to flow vertically and upwardly through the filter from the inlet to the outlet which lessens the chance of bubbles being trapped within the filter during priming.

6. Tubing Clips

As indicated hereinabove, clips 111*a-f* may be provided to define predetermined U-shaped configurations for tubing loops 110, 132, 140, 178, 180, and 190, respectively. One embodiment that may be employed for tubing clips 111*a-f* is illustrated in FIGS. 9A-9F. As shown, the exemplary tubing clip 700 may include a central body member 702 having two tubing connector wings 704 extending from opposing sides of the central body member 702. Each of the tubing connector wings 704 may define a longitudinally-extending J-shaped channel for receiving a tubing length therethrough. One or more wedge-shaped members 706 may be disposed within each of the J-shaped channels of the tubing connector wings 704 for retaining tubing positioned through the channels. Alternatively, the tubing may be glued within the channels to prevent movement. The tubing connector wings 704 may be oriented at an angle relative to the main body member 702 so that the center axis of each of the channels are angled. This allows the tubing entering the pump to conform to the pump raceway. This allows a desired tubing loop configuration to be formed when the clip is applied to the tubing thus facilitating the loading of the tubing loop into one of the pump assemblies 31-36. The central body member 702 may include a projecting grip tab 708 contoured in an hourglass configuration to facilitate handling and placement of the clip 700 in a pump assembly. In the latter regard, the central body member may include a hollow bottom portion to matingly fit over a projection provided on a pump assembly. The clip 700 may be integrally formed (e.g., via molding, etc.). The tubing clips may be color coded to match corresponding color coding on control unit 10 to ensure correct placement of the pump loops.

7. Cartridge

The perfusion cartridge 120 allows for automation of the perfusion system because the compact and standardized format of the positioning of the passageways in the cartridge 120 allows computer controlled sensors and actuators to interact with the cartridge 120. It is important that the interface between cartridge 120 and control unit 10 be precise and secure. The manner in which cartridge 120 is mounted on control unit 10 is shown in FIGS. 10A and 10D. In this regard, cartridge mounting assembly 21 secures the perfusion cartridge 120, as shown in FIG. 10A, to cartridge interface region 20. Interface region 20 contains temperature and/or pressure sensors located to interface mount with sensor stations on the cartridge 120. Region 20 also contains valve plungers positioned to interface with valve stations on the cartridge.

FIG. 10A shows cartridge 120 contained within mounting assembly 21. Although interface region 20 and mounting assembly 21 are part of upper component interface plate 12 for purposes of illustration and to facilitate an understanding of the mounting of cartridge 120 only mounting assembly 21, interface region 20 and cartridge 120 are shown in FIGS. 10A-10-D.

FIG. 10C shows cartridge 120 spaced apart from mounting assembly 21. To facilitate mounting cartridge 120 is provided with mounting tabs 121. Assembly 21 has openings 115 which expose slots 117 which are sized to securely accept tabs 121 of cartridge 120. To load cartridge 120 into mounting assembly 21 tabs 121 are aligned with openings 115. The cartridge is then moved in the direction of interface region 20 until the tabs 121 align with slots 117. Once so aligned the cartridge is moved downward in the direction of arrow 131 (FIG. 10D). This secures each of the tabs in corresponding slots and holds cartridge 120 against interface region 20.

To insure that cartridge 120 is properly positioned with respect to interface region 20 and that it maintains the proper position during the bypass procedure a positioning mechanism is provided. As shown in FIG. 10B, which is an enlarged portion of FIG. 10A, motorized cardioplegia crystalloid valves 99 include an angled bottom surface 124. When cartridge 120 is loaded into mounting assembly 21 valves 99 are retracted so that they do not extend beyond the surface of interface region 20. Once cartridge 120 has been loaded into mounting assembly 21 the continuing set up of the system results in valves 99 being advanced past the surface of interface region 20 until they reach the position shown in FIG. 10B. As the valves advance angled surface 124 abuts against surface 127 on cartridge 120 resulting in a downward pressure being exerted on cartridge 120. This ensures that cartridge 120 is in its proper position and that it does not move during the bypass procedure.

Valves 99 are roller valves similar in structure to valve 507 and include rollers 101 and slots 99a and 99b. Valves 98 are roller valves similar to valves 99 although the specific structure is not shown in FIG. 10B. The cartridge includes tubing retainers 102a-d which hold the crystalloid solution and priming lines in the proper alignment for loading to valves 98 and 99.

IV. Functional Integration of Disposable Assembly and Control Unit

FIGS. 3A and 3B are schematic diagrams of different embodiments of the functional interface between disposable assembly 100 and control unit 10. The embodiment of FIG. 3A relates to the functional interface of a system using the cartridge 120 as disclosed in the drawing figures herein. The embodiment of FIG. 3B relates to a version of the perfusion system using a cartridge modified in a manner disclosed herein.

As shown in FIG. 3A, disposable assembly 100 includes a number of tubing lines that either alone or in combination with the integral passageways of cartridge 120 define a number of fluid circuits. In particular, tubing line 104 extends from a cannula assembly at a distal end (not shown) to a venous reservoir 106 via a venous entry module 108. As previously described the venous entry module includes sensing windows 554 and 556 which interface with oxygen saturation-hematocrit sensor 85 and temperature sensor 81 located in cartridge interface region 20. These sensors can provide feedback for use in various control circuits. For example, a user can set alarm limits which provide an alarm if a low oxygen saturation and/or hematocrit condition exists. Further, if oxygen saturation is low the system can be set to automatically increase the speed of the arterial blood pump 31 an incremental amount and/or automatically adjust the gas blender to increase gas flow or $F_iO_2$ concentration through the oxygenator, until the condition is corrected. Additionally, when blood is detected as flowing through the venous entry module by sensor 85 all pre-bypass activity is automatically inhibited (i.e., pre-bypass filter valve 95 is closed so that flow through the pre-bypass filter is discontinued). The venous entry module also allows pre-donation blood to be collected for reinfusion to the patient at the end of the procedure through a large bore stopcock 543 on the front of the venous entry module. Pre-donation is the collection of a portion of the patient's blood, usually about one liter but is based on calculating what the patient can give up without lowering the hematocrit below some predetermined value, as the blood first comes down the venous line. This blood is sequestered and usually reinfused back into the patient at the end of the procedure.

For purposes hereof, all components upstream of oxygenator 112 collectively comprise the "venous circuit". During a cardiopulmonary bypass procedure, tubing line 104 will transfer venous blood from one or more of the large veins entering the heart (e.g., the venae cava) or other veins of a patient to venous reservoir 106. As described with respect to FIGS. 6A-6E, the flow of venous blood though line 104 may be selectively regulated by a venous line clamp (VLC) 46. Flow may also be regulated by using a vacuum system interconnected to the venous reservoir 106 as discussed hereafter with respect to FIG. 11, or a pump (not shown) that regulates venous blood flow through line 104 upstream of the venous reservoir 106. The VLC is an integral part in the automatic control of the perfusion system. Once the bypass has been initiated the VLC is automatically kept open when arterial pump 31 is running. If pump 31 shuts down for any reason the VLC may automatically be closed by the system control. The VLC may be closed when the level sensor in the venous reservoir senses that the reservoir is full. Additionally, the rate of flow of blood to the venous reservoir can be controlled by the extent to which line 104 is occluded by the VLC. The control can be automatic such as a system initiated response due to a high blood level condition being sensed in the venous reservoir, or can be manual through user settings at the user interface.

Tubing line 104 may be constructed from a clear, flexible tubing to allow for selective occlusion by the VLC 46 and to otherwise allow for visual inspection of fluid passage therethrough by a user. In this regard, the VLC 46 may include a transparent lid 73.

Reservoir 106 may be of a hard shell or soft, plastic construction, and may be partially transparent with volumetric markings to facilitate visual monitoring of volume content by a user during a bypass procedure. The reservoir 106 may include a gas vent at a top end thereof to allow for the venting of any accumulated gas. Alternatively, the reservoir may be sealed, and may further include a top port for interconnection with a vacuum source for optional use in vacuum assisted venous drainage procedures. The vacuum source may comprise a vacuum pump (e.g., within control unit 10) or a regulator that may be selectively interconnected with a facility vacuum line.

FIG. 11 shows an alternative embodiment where reservoir 106 is connected to a vacuum source for use in vacuum assisted drainage procedures. In FIG. 11, vacuum line 721 is attached to the vacuum port of venous reservoir 106, connecting the venous reservoir to the vacuum system. The system comprises vacuum line 721 interconnected to float valve 722, hydrophobic filter 726, electronic vacuum regulator 727, and to an external vacuum source 728. The float valve 722 automatically closes to prevent fluid from entering the vacuum system in the event of a venous reservoir overflow. The hydrophobic filter 726 also prevents fluid from passing further into the vacuum system. The electronic vacuum regulator 727 provides continuously adjustable control of the vacuum level in the venous reservoir as measured by vacuum sensor 725, and as discussed hereafter, can be activated to provide level control within the venous reservoir. Also incorporated in the vacuum circuit are positive pressure relief valve 723 and excess vacuum relief valve 724. These valves will automatically open if required to provide additional control to prevent vacuum from exceeding a predetermined upper or lower limit.

The venous reservoir can be provided with a level sensor 87 as will be described in more detail hereafter with respect to FIG. 12. The sensed level can be used to activate alarms at the user interface indicative of, for example, full reservoir, empty reservoir, and low level. The sensed level can also be used in the closed loop feedback control of other parts of the perfusion system which affect the level of blood in the reservoir. For example, the sensed level can be used to control the fluid level in the reservoir by controlling VLC occlusion, arterial pump speed or the amount of vacuum if the reservoir is vacuum assisted in order to maintain, increase or decrease the reservoir volume or level as needed to transfer fluid back and forth to the patient or maintain a safe reservoir level to prevent emptying.

A reservoir filter pressure sensor 89 is included in integral passageway 164 in the embodiment of FIG. 3A. During bypass if suctioned cardiotomy blood is routed to the venous reservoir the reservoir filter can clog. This cardiotomy blood is gravity drained from the sequestration reservoir and if the venous reservoir filter becomes clogged, pressure can build. Sensor 89 senses the increased pressure from a clogged filter and provides an alarm on user interface 50. In the event of any alarm, the suction and vent pumps may be stopped and/or valve 401 may be automatically closed, and/or valve 98 may be automatically closed.

Connected to the bottom end of reservoir 106 is an interconnect tubing line 110 which carries blood from venous reservoir 106 to an oxygenator 112. Although referred to herein as oxygenator 112 it should be understood that the oxygenator may include an integral heat exchanger. As will be further described, the flow of blood through the interconnect tubing line 110 is selectively regulated by arterial pump 31. Tubing line 110 may include a clip 111a as described with respect to FIGS. 9A-9F for retaining a predetermined tubing length in a predetermined u-shaped configuration for ready interface with the arterial pump assembly 31. Further, such clip may be color-coded (e.g., red for arterial) and configured to facilitate ready pump interface identification and clip placement during loading procedures.

Pressure sensor 84 may be provided to sense the pressure in tubing loop 110 downstream of the arterial pump 31 and upstream of the oxygenator device 112. In this regard, the monitored pressure may be compared to predetermined minimum and maximum values. A monitored pressure below the predetermined minimum value indicates that pump 31 may not be occluding tubing loop 110 as desired or may not otherwise be operating at a rate set by use of control 31a, resulting in an alarm/indication at interface 50. A monitored pressure that exceeds the predetermined maximum value indicates that the arterial circuit downstream of sensor 84 may be undesirably occluded (e.g., partially or fully), and may effect automated stoppage or slow down of pump 31 and result in an alarm/indication at interface 50.

Oxygenation device 112 is fluidly interconnected at its outlet port to outlet tubing line 116 which is connected to the inlet of arterial filter 118. Outlet tubing line 116 may be retainably positioned relative to a bubble sensor 114 located on control unit 10. Bubble sensor 114 serves several functions. First, if bubbles are detected an alarm may be activated at user interface 50. Second, detected bubbles may cause an auto air shunt feature to be activated as described in more detail hereafter.

The embodiment of FIG. 3A includes an oxygenator vent tubing line 105 from the oxygenator to the venous reservoir. Tubing line 105 passes through oxygenator vent valve 507. Vent valve 507 has several functions. First, it is automatically opened during priming to remove air from the oxygenator and is closed after a predetermined time. Second, it can be manually opened by the user during bypass if, for example, the venous reservoir emptied causing air to enter the system necessitating that the system be reprimed or, repriming the oxygenator after oxygenator replacement.

Arterial filter 118 is designed to filter particles greater than a predetermined size (e.g., having a maximum cross-sectional thickness greater than 50 microns), and is fluidly interconnected to outlet tubing lines 122, 128, and 119a. Outlet tubing line 122 is provided for the return of oxygenated blood to a patient via a cannula assembly at a distal end (not shown). Tubing line 122 may be retainably positioned in a bubble sensor 126 located on control unit 10. If bubbles are sensed by sensor 126 an alarm at user interface 50 will be activated. Additionally, a signal will be fed to the control unit 10 which will cause the arterial pump 31 to stop. The system is designed so that anytime the arterial pump is stopped, purge valves 405 and 406 and the arterial patient valve 92 may be closed. It should be noted that anytime a detected alarm condition causes the system to automatically stop a pump or close a valve that action can be overridden by the user at the user interface.

In the event a user would like to draw a sample of the blood passing through arterial filter 118, a user may open a stopcock valve 310 or 311 provided on cartridge 120. If the sample is to be taken from valve 310, either valves 405 or 406 must be open. For purposes of hemoconcentration, a user may also manually open valve 310 or 311 provided on cartridge 120 to provide for the flow of arterial blood therethrough. In this regard, the user may provide a separate hemoconcentrator unit (not shown) having inlet tubing connected to stopcock valve 310 or 311 and outlet tubing interconnected to a transfer bag (not shown) or interconnected to an inlet port provided at venous entry module 108 or venous reservoir 106.

For purposes hereof, the noted components downstream from oxygenator 112 through outlet tubing line 122 collectively, comprise the "arterial circuit". To facilitate priming procedures, tubing lines 104 and 122 may be initially fluidly connected via a connector 175 which is removed after priming and prior to cannula placement.

In order to monitor the temperature of the oxygenated blood returned to a patient, the upper component interface plate 12 may also include temperature sensor 88 located in tubing line 122. Alternatively, the sensor 88 may be positioned for sensing temperatures at arterial filter 118. The monitored temperature of returned blood is compared to predetermined minimum/maximum range values, wherein an alarm or other indication (e.g., an indication of potential responsive action) can be provided at user interface 50 upon the detection of out-of-range conditions. Similarly, valve assembly 92 may be included to receive tubing line 122 downstream of the bubble sensor 126, and may be selectively and automatically opened/closed to control the flow of oxygenated blood through tubing line 122, including for example, closure both during pre- or post-bypass procedures and when bubble sensor 126 detects gaseous bubbles in the oxygenated blood during bypass procedures.

Tubing lines 119a and 119b are provided for fluid flow from arterial filter 118 to cartridge 120, and from cartridge 120 to reservoir 106, respectively. Adjoining integral passageways 309a and 309b are provided in cartridge 120 to selectively receive fluid flowing through tubing line 119a. In order to control the flow of fluid through passageways 309a and 309b, cartridge interface region 20 includes interface valve assemblies 405 and 406. When opened, valve 405 provides for a relatively low flow rate through passageway 309b. Valve 406 provides for a relatively high flow rate through passageway 309a when valve 406 is open. During bypass procedures, valves 405 and 406 typically remain open and closed, respectively; provided pressure sensor 14 senses a pressure greater than a predetermined minimum value. If a pressure lower than the minimum value is sensed both valves 405 and 406 automatically close in order to prevent air from being sucked from the venous reservoir into the arterial filter. A user may selectively change these states via user interface 50, as will be further described. In order to purge air from tubing line 116 and arterial filter 118 (e.g., upon bubble sensing by bubble sensor 114), valve 92 may be closed (e.g., automatically), and valves 405 and 406 may be opened (e.g., automatically), wherein blood will flow through tubing line 119a, integrated passageway spurs 309a and 309b, and tubing line 119b into venous reservoir 106 via an inlet port. Additionally, in the event that air is detected in tubing line 122, valves 92 and 96 may be closed and valve 404 opened so as to cause blood to flow retrograde from the patient through tubing line 122 through filter 118, flow tubing line 128, integral passageway 130 and ultimately through integral passageways 164 and 308 for return to venous reservoir 106 through line 129. It should be noted that valve 406 may be selectively opened for recirculation purposes or otherwise by a user.

As noted, arterial filter 118 is also interconnected to outlet tubing line 128, which in turn is interconnected with one end of an integral passageway 130 defined within the cartridge 120 to provide the blood supply for the cardioplegia system.

Pressure sensor 14 is provided in cartridge interface region 20 for monitoring the fluid pressure within fluid passageway 130 and tubing lines 128 and 122 fluidly interconnected thereto. During cardioplegia blood delivery via tubing line 128 and pump 35, the monitored pressure may be compared to a predetermined value to insure that an adequate blood delivery pressure is provided. If the pressure falls below a predetermined minimum value, pump 35 may be stopped and/or an alarm/indication may be provided at user interface 50. Additionally, if the arterial blood circuit has become occluded, automated stoppage of pump 31 may be provided and an alarm/indication may be provided at user interface 50 if the pressure exceeds a predetermined maximum value.

Tubing line 128, cartridge passageway 130 and tubing loop 132 are provided for the flow of blood therethrough for selective downstream mixture with a heart-arresting solution (e.g., a cardioplegic crystalloid solution) and/or a substrate enhancing solution (e.g., nutritional solution) in an integral passageway 142 of cartridge 120. As will be further described, tubing loop 132 interfaces with a cardioplegia blood pump assembly 35 of component interface region 12 to control mixture ratios. Tubing loop 132 may include a clip 111b to establish the desired u-shaped configuration for the pump interface, and the clip may be color-coded (e.g., red) to facilitate ready loading.

Disposable assembly 100 further includes one or more spiked tubing lengths 133 for interconnection between one or more corresponding bags 136 of a heart-arresting solution (e.g., crystalloid solution) and a fluid passageway 138 integrally defined within cartridge 120. One or more substrate enhancing solutions (not shown) may also be fluidly interconnected by spiked tubing lengths 133 to the integral passageway 138 of cartridge 120. When multiple bags 136 are provided they may contain solutions of different concentration and/or ingredients. The user is able to select the desired solution concentration by selecting at the user interface which one of valves 99 is opened. The user is able to select a volume or time bolus of solution and the opened valve 99 automatically closes when delivery is completed or interrupted such as when one or more of pumps 31, 35 or 36 is stopped. The user is also able to manually select and deliver the cardioplegia solution.

Passageway 138 is interconnected to a tubing loop 140 that flows heart-arresting or substrate enhancing solution out of and back into the cartridge 120 and interfaces therebetween with a pump assembly 36 on control unit 10 that regulates the flow rate through the tubing loop 140. Tubing loop 140 may include a clip 111c to establish the desired u-shaped configuration for pump interface, and the clip 111c may be color-coded to facilitate loading.

Integral passageway 142 is also interconnected to the above-mentioned tubing loop 132 for establishing a desired mixture between the cardioplegic crystalloid solution and blood pumped into the integral passageway 142. In this regard, it should be appreciated that cardioplegia provided to a patient may comprise predetermined (or dynamically adjusted) relative amounts of a heart-arresting solution (crystalloid) and blood, and may alternatively comprise only a heart-arresting solution (crystalloid), or alternatively comprise only oxygenated blood.

In this regard, a tubing line 146 is provided for the passage of a cardioplegia solution out of the cartridge 120, through a cardioplegia heat exchanger 148 and a bubble trap 152, and back into the cartridge 120. In an alternate arrangement, heat exchanger 148 and/or bubble trap 152 may be integrated into cartridge 120.

Of additional note, the embodiment of FIG. 3A includes a stopcock valve 302 in fluid communication with the bubble trap 152 through which the cardioplegia mixture flows during operations. The inclusion of stopcock valve 302 allows a user to selectively infuse drugs into the cardioplegia mixture. Further, stopcock valve 302 may be selectively employed by a user for interconnection of an auxiliary pressure sensor (i.e., monitor the cardioplegia pressure) or it can be used to sample the cardioplegia solution or can be connected to a hemoconcentrator (not shown). Relatedly, it is noted that the cartridge 120 in the FIG. 3A embodiment also includes an added integral passageway 308 that interfaces with a corresponding valve assembly 404 provided in the cartridge interface region 20. More particularly, valve 404 can be selectively opened/closed in opposing or same relation to valve 96 in a number of situations. For example, valve 96 may be closed and valve 404 opened during priming so as to cause fluid flowing through integral passageway 150 to flow through integral passageway 308 and into integral passageway 164. Additionally, during cardioplegia delivery, if a user observes a build-up of gas in bubble trap 152, a user may open valve 404, thereby causing at least some fluid to be diverted through integral passageway 308 into integral passage 164, thereby purging the air from bubble trap 152. If the fluid pressure is too low to effect purging, valve 404 may be automatically closed to prevent the introduction of air into the circuit.

At its downstream end, tubing line 146 is connected from bubble trap 152 to another integral passageway 150 of cartridge 120. In the embodiment disclosed the bubble trap 152 and cardioplegia heat exchanger 148 are combined in a single unit which is separate from cartridge 120 but that fits into the cartridge and interfaces directly with control unit 10 at cartridge interface region 20. Bubble trap 152 may be equipped with a bubble sensor (not shown) that, upon sensing bubbles would cause cardioplegia purge valve 404 to open and cardioplegia patient valve 96 to close thus routing the cardioplegia solution to the venous reservoir through line 164. Air bubbles may be manually purged from bubble trap 152 by activation of a button (not shown) on user interface 50. Bubble trap 152 may include a filter screen (e.g., a 200 micron screen) to trap particulates and air and may include a vent (e.g., a one-way valve) having a hydrophobic membrane.

Pressure sensor 18 is provided in cartridge interface region 20 to sense the pressure within passageway 150. During cardioplegia delivery the monitored pressure may be compared with a predetermined maximum value to identify if the cardioplegia circuit has become occluded (e.g., wherein automated stoppage of pumps 36 and/or 35 may be effected and an alarm/indication may be provided at interface 50). Additionally, the pressure may be monitored during cardioplegia delivery to insure an adequate cardioplegia delivery pressure. In the event the monitored pressure falls outside of user set limits an alarm/indication may be provided at interface 50 and/or the speed of one or both of pumps 35 and 36 is either increased or decreased in order to maintain the desired pressure. For example, the user may set at the user interface a high pressure limit of 150 mmHg, a low pressure limit of 20 mmHg and a control point of 100 mmHg. By utilizing the monitored pressure as a feedback control parameter the system will automatically adjust the speed of the pumps to maintain pressure at the control point. If the pressure exceeds for any reason the upper or lower limit an alarm is activated at the user interface.

A temperature sensor 153 is provided in cardioplegia valve block 195 to monitor the temperature of the fluid in line 156. High and low temperature alarm limits may be set by the user at the user interface and if those limits are exceeded an alarm is activated at user interface 50.

Additionally, if the pressure sensed by cardioplegia line sensor 18 is below the minimum limit the system automatically causes either or both the cardioplegia patient valve 96 and cardioplegia purge valve 404 to close. This prevents retrograde air from being introduced into the cardioplegia circuit through patient tube line 156, cardioplegia sample/infusion valve 302 or cardioplegia purge line 308. Integral passageway 150 is interconnected to tubing line 156 having a catheter assembly (not shown) at its distal end for the delivery of the cardioplegia mixture to a patient.

Tubing line 156 may be fluidly interconnected via tubing connector 175 to tubing line 104 and 122 for priming purposes, wherein tubing line 156 is disconnected from tubing connector 175 after priming. Tubing line 156 may be retainably positioned in cardioplegia valve block 195 containing a cardioplegia patient valve 96, a temperature sensor 153, and a bubble sensor 158 provided in the upper component interface plate 12, as described. If bubbles greater than an acceptable size are detected at sensor 158 the system automatically stops one or both of pumps 35 and 36 and provides an alarm at user interface 50. For purposes hereof, the above-described components that provide for the flow of blood from tubing line 128 and crystalloid solution from bags 136, through tubing line 156, collectively comprise the "cardioplegia circuit".

For priming purposes and/or adding blood or other solutions, disposable assembly 100 further includes one or more spiked tubing line lengths 160 for interconnection between one or more bags 162 of priming fluid or other solutions and a fluid passageway 164 integrally defined within cartridge 120. An outlet of fluid passageway 164 is interconnected to a filtered inlet of reservoir 106. Relatedly, it is also noted that the disposable assembly 100 includes a tubing spur 166 interconnected with the venous entry module 108 of the component interface region for the selective passage of priming fluid therethrough during priming operations. Further in this regard, tubing spur 166 includes a pre-bypass filter 168 for filtering the priming solution to ensure that particles having a size greater than a predetermined value (e.g., greater than 5 microns) are filtered from the system prior to the initiation of bypass procedures. During priming flow is automatically directed through pre-bypass filter 168 by closing VLC 46 and opening pre-bypass filter valve 95. Since the pores of the pre-bypass filter are very fine and would be clogged by blood, as soon as the presence of blood is sensed at sensor 85 of the venous entry module valve 95 is closed and the VLC 46 is opened thus routing the blood directly to the venous reservoir 106.

For purposes of priming and for filtering in conjunction with priming, valve assembly 95 is provided to receive tubing line 166 for selective and automatic closure/opening. Similarly, valve assembly 96 is provided to receive cardioplegia tubing line 156 and is selectively and automatically operable for opening/closure, including for example, automatic closure upon detection of gaseous bubbles in the cardioplegia mixture by bubble sensor 158. One or more valve assemblies 98 are also provided in component interface region 12 for automatically and selectively controlling the flow of priming solution from one or more priming solution bags 162 through tubing line(s) 160. Similarly, one or more valve assemblies 99 are provided for selectively and automatically controlling the flow of crystalloid solution from the one or more crystalloid solution bags 136 through tubing line(s) 133.

The disposable assembly 100 also includes first and second tubing suction lines 170 and 172, respectively, each of which are interconnectable at their distal ends to corresponding suctioning devices (not shown) for removing fluid from a patient surgical site. The first and second tubing lines 170, 172 are initially plugged at the end to allow leak testing, occlusion testing of the suction pumps 32 and 34 and testing to ensure that the pump loops are loaded in the pumps in the correct direction. Each of such tubing lines 170 and 172 are interconnected to corresponding integral passageways 174 and 176, respectively, within the cartridge 120, which passageways are in turn interconnected with tubing loops 178 and 180, respectively.

Pressure sensors 40 and 42 are provided in cartridge interface region 20 to monitor the pressures within suction tubing lines 170 and 172, respectively, which are interconnected with passageways 174 and 176, respectively. In this regard, the monitored pressures may be compared with a predetermined negative pressure value (e.g., corresponding with a risk of blood trauma or tissue damage or indicating that a suction wand is occluded against tissue), wherein automated stoppage of pump 32 or 34, respectively, may be effected upon detection of a pressure that is below the predetermined negative pressure value and an alarm/indicator may be otherwise provided at interface 50. A positive pressure may indicate that a pump is operating in reverse wherein automated stoppage of pumps 32 and 34 may be effected upon detection of that positive pressure and an alarm indicator may be otherwise provided at user interface 50. Further, the user may set at the user interface a high pressure limit and a low pressure limit and a desired control point therebetween. The monitored pressure is used as a feedback control parameter to automatically adjust pump speed (32 or 34) to maintain pressure at the control point.

Tubing loops 178 and 180 interface with suction pumps 32 and 34 in the component interface region 12 to provide for the desired suction. The tubing loops 178 and 180 may be provided with clips 111*d* and 111*e* that define the desired u-shaped configuration for the pump interface. Each of such clips 111*d*, 111*e*, may be color-coded (e.g., yellow for suction) and otherwise configured to facilitate loading of the tubing loops 178 and 180. The downstream ends of tubing loops 178 and 180 are interconnected to integral passageways 182 and 184 of cartridge 120, which passageways 182, 184 are in turn each fluidly interconnected with the integral passageway 185 for the passage of suctioned blood to sequestration reservoir 301.

Disposable assembly 100 may also include a third suction tubing line 186 having a cannula assembly for interconnection with the left ventricle or vasculature of a patient's heart so as to provide for the venting of blood or fluid that may accumulate therewithin. The third suction tubing line 186 may initially be plugged at the end to allow leak testing, occlusion testing of the suction pump 33, and testing to ensure that the pump loop 140 is loading in pump 33 in the correct direction. Tubing line 186 is interconnected to an internal passageway 188 of cartridge 120 which in turn is interconnected to tubing loop 190. Pressure sensor 44 is provided to monitor the pressure within the suction line 186 which is interconnected with the passageway 188. Again, the monitored pressure may be compared to predetermined negative and positive pressure values, as previously described with respect to suction lines 170 and 172, wherein automated stoppage of pump 33 may be effected upon detection of a pressure that is below the predetermined negative pressure value or above the positive pressure value and an alarm/indication may be provided at interface 50 upon detection of an out-of-range condition (e.g., either above the positive pressure value or below the negative pressure value).

It should be noted that pressure sensors 40, 42 and 44 function in a manner similar to sensors 14 and 18 except that they measure both negative and positive pressure values. Tubing loop 190 interfaces with the vent pump 33 provided in component interface region 12 to provide the desired suction in tubing line 186, as will be further described. Tubing loop 190 may be provided with a clip 111f to define a predetermined u-shaped configuration for pump interface. The clip 111f may be color-coded (e.g., green) and otherwise configured to facilitate loading. The downstream end of tubing line 190 is interconnected to an internal passageway 192 which, in turn, splits into two passageways 192a and 192b. Flow through these passageways is controlled with valves 402 and 403, respectively, to route the fluid either to the sequestration reservoir 301 or the filtered inlet of the venous reservoir 106, at the user's option.

The cartridge 120 in the embodiment illustrated in FIG. 3A comprises an integral sequestration reservoir 301 for receiving fluids removed from a patient through first and second tubing suction lines 170 and 172, respectively, as well as through left ventricle tubing line 186. In this regard, it can be seen that integral passageways 182, 184 and 192 are fluidly interconnected to the sequestration reservoir 301.

The inclusion of sequestration reservoir 301 in the embodiment of FIG. 3A allows for selective, discretionary use of fluids collected therein. For example, such fluids may be processed to wash and separate red blood cells and other desired components for later reinfusion. More particularly, it can be seen that stopcock valve 303 may be provided on cartridge 120, in fluid connection with sequestration reservoir 301, to provide for the selective flow of accumulated fluids from sequestration reservoir 301 to a transfer bag (not shown) for subsequent autologous blood salvage procedures and return of the desired components to the patient; or for flow directly to an autologous blood salvage system.

Alternatively, the embodiment illustrated in FIG. 3A allows for the return of fluids collected in sequestration reservoir 301 directly to venous reservoir 106 via the inclusion of a valve assembly 401 in cartridge interface region 20 that interfaces with an added integral passageway 305 in cartridge 120. Valve 401 may be selectively opened/closed by a user or maybe automatically opened when the sequestration reservoir is full. When valve 401 is open, fluids collected in sequestration reservoir 301 will flow through the integral passageway 305 within cartridge 120, and then through tubing line 129 to a filtered inlet port at venous reservoir 106.

A vent 307 is provided at the top of sequestration reservoir 301 to vent gas that may accumulate in the reservoir 301. Additionally, the cartridge interface region 20 may be provided with one or more level sensors for monitoring the fluid level within sequestration reservoir 301. In this regard, a first level sensor 320 may be disposed adjacent to the top end of sequestration reservoir 301, wherein upon sensing of fluid at a predetermined level within reservoir 301, control unit 10 will operate so as to automatically open valve 401 so as to flow fluid from sequestration reservoir 301 to venous reservoir 106. The system may be set up by the user so that, upon sensing fluid at the upper level sensor, the control unit 10 may stop the suction and vent pumps and provide an alarm so that the user can empty the sequestration reservoir. Alternatively, instead of stopping the vent pump 33, the control unit 10 may automatically close valve 402 and open valve 403 to re-route the vent pump outlet from the sequestration reservoir to the venous reservoir. A second level sensor 322 may also be provided and disposed downward from the first sensor, wherein upon the detection of fluid, an alarm/indication may be provided at user interface 50. Alternatively, sequestration reservoir 301 may be provided with a continuous level sensor such as that described in connection with FIG. 12. Alternatively, the level in the sequestration reservoir 301 could be sensed continuously by measuring the pressure at the bottom of the reservoir through the membrane with a pressure sensor.

Sequestration reservoir 301 includes a defoamer element 795 which may be vertically disposed to facilitate in the removal of gas from fluid accumulating in venous reservoir 301. After cartridge 120 is loaded into its mounting assembly 21, defoamer push bar 790 is advanced to a position where it applies pressure through the vinyl backing of cartridge 120 against the side of defoamer 795. This pressure ensures that there are no flow paths between defoamer 795 and the vinyl backing and that any fluid which enters sequestration reservoir 301 is caused to flow through the defoamer.

It should also be noted that, since in many potential applications, the blood collected through left ventricle tubing line 186 may be of a high quality nature, the embodiment illustrated in FIG. 3A comprises further features that allow for the selective, direct flow of such blood from the cartridge 120 to venous reservoir 106. In particular, FIG. 3A illustrates the inclusion of integral passageway spurs 192a and 192b, each of which interface with a corresponding valve assembly 402 and 403, respectively, provided in the cartridge interface region 20. In the event that a user would like blood collected from the left ventricle to be collected in sequestration reservoir 301, the user may selectively control valve 403 to be closed and valve 402 to be open whereupon the collected blood will flow through integral passageway spur 192a into integral passageway 185 to sequestration reservoir 301. Alternatively, a user may selectively cause valve 402 to close and valve 403 to open whereupon the collected blood will flow through integral passageway spur 192b, adjoining integral passageway 164, and out of cartridge 120 through tubing line 129 to a filtered inlet port of venous reservoir 106.

The component interface region may comprise a level sensing assembly 87 positioned in immediate, predetermined relation to the region in which venous reservoir 106 is mounted. In this regard, the level sensing assembly 87 is operable to monitor the level of fluid within the venous reservoir 106 on an ongoing basis during procedures. Such monitored fluid level may be presented both graphically and in volumetric measure terms at user interface 50. Additionally, the fluid level value may be monitored in relation to predetermined minimum and maximum values, wherein automated slowage or stoppage of pump 31 may be effected when the fluid level drops below corresponding predetermined minimum values and wherein an alarm/indicator may be otherwise provided at user interface 50 upon detection of an out-of-range condition.

One embodiment of such a level sensor is illustrated in function form in FIG. 12. In this embodiment, level sensor 87 operates on the theory of time domain reflectometry which uses pulses of electromagnetic energy to measure distances or fluid levels. The level sensor 87 generates an initial pulse 97*a*. When the initial pulse reaches the surface of the blood in reservoir 106, part of the pulse is reflected. The level in the reservoir is determined by the measured differential of the reflected pulse 97*c* and the transmitted pulse 97*b* in a manner known to those of skill in the art. Level sensor 87 is mounted internally to the control unit 10 in a location adjacent to the venous reservoir 106. The level sensor 87 is oriented such that the level sensor is approximately parallel to the vertical wall of the venous reservoir and extends from the lower most portion to the upper most portion of the venous reservoir. In between the level sensor 87 and the venous reservoir 106 is a thin wall, covering or coating that is thin enough and made of a material (e.g. plastic) permitting the transmission of signals into the venous reservoir from the sensor as well as receiving reflected signals from the venous reservoir, in particular reflections from the fluid level in the venous reservoir. The thin wall, covering, or coating would allow positioning the level sensor as close as possible to the external wall of the venous reservoir to aid in signal transmission and reception. The wall could be a part of control unit 10. The level sensor is positioned approximately in a vertical plane such that the transmitting and receiving portions of the sensor would cover the entire height of the venous reservoir to ensure the venous reservoir level could be sensed from a full to empty condition. While a vertical orientation is described, an angled orientation would also functionally work and may add resolution to the level signal.

As previously noted, user interface 50 includes a main display 54, user control knob 52 and backup display 55. The main display 54 and backup display 55 may be provided to display monitored parameters regarding one or more of the fluid circuits discussed hereinabove, to provide alarm indications as noted hereinabove, and to establish predetermined minimum/maximum or control values for monitoring and control purposes. Of particular note, the backup display 55 is located immediately adjacent to control knob 52, wherein when a given parameter is being established via control knob 52, a user may readily observe the backup display 55 as the knob 52 is being manipulated.

Another embodiment of the disposable assembly 100 and component interface of control unit 10 are schematically illustrated in FIG. 3B. As can be seen, the embodiment illustrated in FIG. 3B is similar in many respects to the embodiment illustrated in FIG. 3A. As such, components having common functionality between the two embodiments are labeled with the same reference number and the corresponding description of such components set forth above is applicable. Features unique to the embodiment illustrated in FIG. 3B are described below.

As shown in FIG. 3B, tubing line 116 includes a first spur 116*a* interconnected to an upstream side of an arterial filter 118, and a second tubing spur 116*b* interconnected to a downstream side of arterial filter 118. Second tubing spur 116*b* may be utilized for replacement/bypass of arterial filter 118, while the first tubing spur 116*a* is utilized during oxygenated blood return to a patient during cardiopulmonary bypass procedures. In particular, valve assembly 90 is provided to receive tubing spur 116*a*, and valve assembly 91 is provided to receive tubing spur 116*b*, wherein valve assemblies 90, 91 may be selectively and/or automatically opened/closed together with other valve assemblies, to establish the desired fluid flow (e.g., through tubing spurs 116*b* during filter replacement, and through tubing spur 116*a* during bypass procedures).

Valve assembly 93 is provided to receive tubing line 125 and may be selectively and automatically opened/closed, including, for example, selectively opened for retrograde cerebral perfusion or to quickly reprime the venous tubing line 104 after initial bypass procedure ends in the event the patient needs to go back on bypass.

During bypass procedure control unit 10 may operate to close tubing line 122 and direct blood flow from arterial filter 118 through purge line 119 when bubbles are detected by sensor 114. Further, in the embodiment of FIG. 3B, control unit 10 may operate to close tubing line 122 by closing arterial line valve 92 when gaseous bubbles are detected by sensor 114 and/or sensor 126 thereby causing blood to flow back to the reservoir 106 via tubing line 125. For such purposes, tubing line 125 is interconnected to the venous entry module 108 of the venous circuit as described hereinabove.

During cardioplegia delivery (e.g., when pump 35 is operating and valve 96 is open) and/or during hemoconcentration procedures (e.g., when pumps 37 and 38 are operating to circulate blood through a tubing hemoconcentration assembly 134), the monitored pressure may be compared with a corresponding predetermined minimum value to insure an adequate fluid pressure at cartridge 120 (e.g., so as to reduce any risk of cavitation or air transfer across the membrane of oxygenator 112). In the event the monitored pressure is below the desired level, automated stoppage of pump 35 (e.g., in the case of cardioplegia delivery) and automated stoppage of pumps 37 and 38 and closure of valve 96 (e.g., in the case of hemoconcentration procedures) may be effected and an alarm/indication may be provided at interface 50.

Integral passageway 130 is fluidly interconnected to a tubing loop 132, and may also be fluidly interconnected to a tubing/hemoconcentrator assembly 134. In the later regard, tubing/hemoconcentrator assembly 134 may be optionally interconnected to the disposable assembly 100 when use of a hemoconcentrator 134*a* and waste bag 134*b* is desired.

Pressure sensor 86 may also be provided to sense the pressure within the tubing/hemoconcentrator assembly 134 in the event that a hemoconcentrator is employed. In this regard, the monitored pressure may be compared with a predetermined minimum pressure value necessary to insure flow through the membrane of hemoconcentrator 134*a*, wherein if the pressure falls below the minimum an alarm or other indication may be provided at user interface 50. Further, the monitored pressure in assembly 134 may be compared with a predetermined maximum pressure value. A monitored pressure that exceeds the maximum value may indicate that the outlet of hemoconcentrator 134*a* has become occluded, wherein automated stoppage of pump 37 and pump 38 may be effected and an alarm or other indication may be provided at user interface 50.

In the embodiment of FIG. 3B the downstream end of tubing loop 140 is interconnected with integral passageway 142 having a filter 144 interposed therewithin. Filter 144 serves to filter particulates greater than a predetermined size (e.g., greater than 0.2 microns via a filter screen). Filter 144 may also comprise at least one vent (not shown) having a hydrophobic membrane for venting air bubbles. In this regard, filter 144 may include two hydrophobic vents (not shown), one on each side of a vertical filter screen, for venting air bubbles from a priming solution during priming and for venting air bubbles from solutions passing therethrough (e.g., cardioplegic crystalloid solution during cardioplegia delivery).

Pressure sensor 16 is provided in cartridge interface region 20 for sensing the fluid pressure within integral passageway 142. The monitored pressure may be compared with a predetermined value during cardioplegia delivery (e.g., when pump 36 is operating and valve 96 and one of the valves 99 are open). If the monitored pressure exceeds the predetermined value (e.g., indicating the filter 144 is clogged), then an alarm/indication can be provided at interface 50, and the filter 144 may be automatically or manually bypassed (e.g., via operation of valve 93 so as to open bypass line 143).

For purposes of priming and for filtering in conjunction with priming, valve assemblies 94 and 95, respectively, are provided to receive tubing lines 119 and 166, respectively, for selective and automatic closure/opening.

With further regard to the delivery of the crystalloid solution, valve assembly 93 is provided to receive crystalloid bypass tubing line 143 for selective and automatic opening/closure thereof, including for example opening upon clogging of crystalloid filter 144, as detected by pressure sensor 16. That is, in the event sensor 16 detects a pressure greater than a predetermined value, valve assembly 93 can be automatically and/or selectively opened wherein crystalloid solution will flow through bypass tubing line 143 and back into integral passageway 146.

The downstream ends of tubing loops 178 and 180 are interconnected to integral passageways 182 and 184 of cartridge 120, which passageways 182, 184 are in turn each fluidly interconnected with the integral passageway 164 for the passage of suctioned blood out of cartridge 120 and through tubing line 129 to the filtered inlet of venous reservoir 106 for reuse.

Further, passageway 164 may be interconnected to an outlet (not shown) that may be selectively utilized for passing suctioned blood into a separate reservoir (not shown).

Finally, disposable assembly 100 may also include a transfer bag/tubing assembly 194 (not shown in FIGS. 2A and 2B) that may be utilized for receiving blood from passageway 130 of cartridge 120. The transfer bag/tubing assembly 194 may be employed, for example, to remove excess fluid from the circuit during bypass procedures, to retrieve blood from the circuit post bypass for later reinfusion to the patient or for cell-saving procedures.

Pressure sensor 14 may also be used as a means of checking for proper arterial cannula placement before going on bypass. When arterial patient valve 92 is open during test connection mode as described hereafter, the patient pressure at the cannula can be read at sensor 14.

While FIGS. 3A and 3B correspond with embodiments implementing various aspects of the present invention, other potential embodiments which incorporate one or more of the inventive features of the present invention would be apparent to those skilled in the art.

V. Disposable Cartridge

As illustrated in FIGS. 13-24, the perfusion cartridge 120 can be made of a variety of materials including polymeric materials, metals and composite materials. In a preferred embodiment, the perfusion cartridge 120 of the present invention is formed from polymeric materials which are thermoformed medical grade plastics. Cartridge 120 has a plurality of fluid passageways integrally defined therewithin. By way of example, cartridge 120 may be constructed from a clear, molded front piece (e.g., molded plastic which defines all but a back side of each integral passageway), and an interconnected, pliable back layer (e.g., a vinyl sheet that defines a back side of each integral passageway) attached thereto. In addition to the integral passageways, cartridge 120 may include one or more passive components. Such components may include one or more filters and bubble traps. Various conduits may be formed into the perfusion cartridge 120 during manufacturing such that each of the top and bottom plates or pieces partially define portions of the conduits. Typically, the front portion 802 is translucent to allow for visual inspection of each of the conduits that flow through the cartridge 120. In addition, the integrated fluid conduits are located at various depths and can pass above or below each other.

FIGS. 13-24 are various views of cartridge 120. FIG. 13 is a front perspective view. FIG. 14 is a front plane view. FIGS. 15 and 16 are right and left side views, respectively. FIGS. 17 and 18 are top and bottom views, respectively. FIG. 19A is a back plane view and FIG. 19B is a back perspective view. FIG. 20A is a cross-sectional view along line A-A of FIG. 19A. FIG. 20B is a detail view of a portion of FIG. 20A. FIG. 21 is a cross-sectional view taken along lines B-B of FIG. 19A. FIG. 22 is a back plane view with the flexible back layer removed to better show the various fluid channels and related components within cartridge 120. FIGS. 23A, 23B, 24A, and 24B are partial views of a valve station located in cartridge 120.

In each of these figures, components that have been previously described retain the same reference numerals. This includes the various internal passageways or fluid conduits formed by the cartridge. The various inlet and outlet ports of the cartridge have been labeled with the reference numeral of the external tubing line connected at the port. Those portions of the cartridge which interface with pressure or temperature sensors or with valves comprise sensor or valve stations and are labeled individually with the reference numeral of the sensor or valve with which they interface followed by a small "a". Thus, for example, the sensor station interfacing with cardioplegia line pressure sensor 18 is referenced as 18*a*. Features of cartridge 120 not previously described are discussed below.

Cartridge 120 includes a front substantially rigid portion 802. Front portion 802 defines substantially all of the structure of the various components and passageways of the cartridge. For example, front portion 802 defines the shape and contour of sequestration reservoir 301 except for the back portion thereof. A flexible back layer 804 is connected to the back side of front portion 802. Any flexible, durable, fluid impermeable material which is suitable for contact with a patient's blood may be used. A suitable material is a sheet of vinyl. The sheet can be attached to the front portion by use of medical adhesives or welding techniques known to those of skill in the art. The back layer may be comprised of a flat sheet or, alternatively, can be formed into a contoured shape. Formed elements in the vinyl can assume various formed shapes and can include pressure diaphragms as shown in FIGS. 19A and 19B, valve diaphragms as shown in FIGS. 23A, 24A, 23B, and 24B, fluid passageways matching those on the cartridge as shown in FIGS. 19B and 20B, sequestration reservoir 301 and sequestration reservoir defoamer 790 as shown in FIGS. 15 to 21. The pressure diaphragms isolate the pressure sensor from the cartridge to provide more accurate pressure readings. The valve diaphragms help lower the resistance to valve opening and closing, and can provide a transition zone in the fluid flowing from the passageway through the valve. Fluid passageways can be shaped to smooth fluid flow and/or provide a more consistent cross-sectional fluid volume through passageways particularly where entering or exiting other features such as ports, pressure sensing regions or valve regions. The sequestration reservoir volume may be increased and/or flow enhanced through vinyl forming. In particular, by forming a pocket in the vinyl, the defoamer may be placed into the pocket as best seen in FIG. 20A. A pocket also helps form a sealing interface when positioned against defoamer push bar 790 located in the cartridge interface region 20. Vinyl forming may be accomplished by forming techniques known to those skilled in the art.

As seen in FIGS. 20A and 21, the sequestration reservoir includes a defoamer support element 806. Support element 806 comprises a plurality of struts 806a and 806b which are spaced apart on either side of defoamer 790 and which support defoamer 790 in the sequestration reservoir 301.

As shown in FIGS. 23A, 23B, 24A, and 24B, the valve stations include a valve chamber 808 in the cartridge 120. The valve chamber 808 includes at least first 810 and second 812 passageways. A flexible member 804 is positioned over the valve chamber 808 above first 810 and second 812 passageways.

Typically, first passageway 810 contains a raised lip portion 816 which extends toward flexible back layer 804. A portion of backlayer 804 adjacent raised lip portion 816 is formed as a flexible pleated member 814. A plunger 818 provided in the structural interface is located over the valve chamber 808. To close the valve, plunger 818 is caused to impact and deflect the flexible member 814 to contact the raised lip portion 816 of the first passageway 810. This deflection and contact prevents fluid from flowing out of or into the first conduit 810. To open the valve, the plunger 818 is retracted from the raised lip portion 816 such that fluid pressure displaces the flexible member 814 from the raised lip portion 816 of the fluid conduit 810.

In a further embodiment of the present invention, the cartridge 120 includes a first integral passageway path which occurs in a first plane. The first integral passageway has an entry port and an exit port from the cartridge 120. The first integral passageway, thus, defines first and second areas in cartridge 120, both lying in the first plane and being separated by the first integral passageway. Cartridge 120 also includes a second integral passageway which has an entry port and an exit port from the cartridge. The entry port of the second integral passageway occurs in the first area of the first plane, and the exit port of the second integral passageway occurs in the second area of the first plane. Thus, the first and second conduit paths crossover at a point. At the point of cross-over of the first and second integral passageways, the second integral passageway occurs in a second plane.

In the present invention, as shown in FIGS. 13-24, the perfusion cartridge 120 can be interconnected with a number of fluid circuits. The fluid circuits include a cardiopulmonary circuit which include the venous and arterial circuits, a cardioplegia circuit, a cardiotomy or suction/vent circuit and a fluid management or priming circuit all as previously discussed. The cardiopulmonary circuit is designed to functionally replace and/or supplement the heart and lungs during heart surgery. The cardioplegia circuit delivers cardioplegia to the heart to discontinue beating in a manner that will facilitate operative procedures and minimize damage to the myocardium. The cardiotomy circuit is used to withdraw or suction blood and other fluids from the open heart or chest cavity and deliver it to the cardiopulmonary circuit. The fluid management circuit is used to provide priming fluid, i.e., blood, to the disposable assembly 100 and maintain a proper flow of fluid in the other circuits. In another embodiment, two cartridge assemblies may be interconnected. For example, a first cartridge assembly including the cardioplegia circuit may be connected to a second cartridge assembly including a cardiopulmonary circuit, a cardiotomy circuit and a fluid management circuit can be interconnected.

In the embodiment described herein the cardiopulmonary (arterial and venous) circuit is not interconnected with the disposable cartridge 120 except for air purge and fluid sampling functions. However, it should be appreciated that the cardiopulmonary (arterial and venous) circuit could be included within the cartridge 120.

VI. System Architecture

Control unit 10 includes a plurality of processors which together with system user interface 50, pump user interfaces 31b-36b and pump control knobs 31a-36a operate to control various components of the control unit 10 according to preprogrammed and/or user established instruction sets and user input. In this regard, and referring now to the block diagram of FIG. 25, a control unit 10 comprising processors 300, 306, 304 and 312 is illustrated. Processor 300 is provided to interface with the main display 54 of the user interface 50, and may be a personal computer provided with graphics to facilitate operation of the main display 54. Monitor/control processors 306 are separately provided for automated monitoring and control, respectively, of the various components comprising control unit 10. Backup display 55 may also be provided with redundant monitoring/control processors 304, separate from processors 300 and 306. It is also noted that valves, sensors, flow control components, temperature control components, gas circuit components or other components comprising component interface region 12 may also be separately provided with separate monitoring and control processing chips. Each pump 31-36 also has its own monitor/control processor pairs 312. All of the above-mentioned processors are interconnected through a communications network.

Processors 300, 306, 304, and 312 are interconnected to receive monitoring signals from the various pressure, bubble, temperature, oxygen saturation, hematocrit, level, flow, and other sensors 314 that comprise the control unit 10, and that interface with the disposable assembly 100. In this regard, the monitored signals provide an indication of measured values which may be processed at one or more of the processors in relation to one or more predetermined maximum/minimum values so that one or more of the processors may issue control signals to flow control components 380, temperature control systems 330 or gas circuit components 340 based on preprogrammed instruction sets and/or other indication signals to system user interface 50 and/or pump user interface 31b-36b to prompt a user regarding a monitored condition of potential concern. As will be described, system user interface 50 allows a user to input or modify one or more of the processors parameter settings which one or more of the processors rely upon in issuing instruction signals to flow control components 380, temperature control systems 330 and/or gas circuit components 340 and indication/alarm signals to system user interface 50.

As indicated in FIG. 25, the flow components 380 comprising the control unit 10 include the various pumps and valve assemblies described hereinabove, as well as the venous line clamp 46. Based on signals received from the various pumps or pressure sensors, the processors may be preprogrammed to automatically calculate flow rates in the various fluid circuit lines for monitoring and display at user interface 50. The temperature control systems 330 include controls for establishing the temperature and flow of heating/cooling fluid through the cardioplegia heat exchanger 148 and for controlling the temperature and flow of the heating/cooling fluid circulated through a heat exchanger interconnected to or integrally provided with oxygenator 112. Other features and functions of the system architecture are described in other sections herein.

1. Gas Circuit

Referring now to FIG. 26, a schematic block diagram for the gas circuit 340 referenced in FIG. 25 will be briefly described. The gas circuit 340 may comprise a plurality of external gas sources for air (342a), for $O_2$ (342b) and for an $O_2/CO_2$ mixture (342c), having corresponding in-line filters 344a, 344b and 344c, and pressure regulators 346a, 346b, and 346c, for flowing the respective gases via corresponding check valves 348a, 348b, and 348c into a valve manifold 350. Valve manifold 350 includes valves 352a, 352b and 352c set to establish the desired flow/relative percentage of each gas type. Flow meters 354b and 354c may be provided upstream (as shown) or downstream of valve manifold 350 for the $O_2/CO_2$ source line and $O_2$ source line and/or air source line. As illustrated, the three gas source lines may flow into a common line downstream of the manifold 350. The common line then passes through a total flow meter 356. From flow meter 356 the single stream may be passed through a vaporizer 358 outside of control unit 10 for introduction of an anesthetic agent. A pressure sensor 360 may be provided to monitor the fluid pressure at filter 362. In the event the pressure exceeds a predetermined maximum value (e.g., indicating that filter 362 is clogged), an alarm or other indicator may be provided at user interface 50. Additionally, to insure the desired pressure at oxygenator 112, an additional pressure sensor 364 may be utilized downstream of the filter 362 and upstream of the oxygenator 112. In the event the pressure exceeds a predetermined maximum value, valves 352a, 352b, and 352c may be closed partially or fully to prevent gas bubbles from crossing the oxygenator membrane into the blood. The gas from filter 362 then flows into the oxygenator 112 via inlet port 518a provided in the control unit 10 through the oxygenator 112, and into the control unit 10 via the outlet port 518b (on FIG. 8B). At that point, the gas flow stream will comprise the oxygen-depleted, $CO_2$-containing exhaust from oxygenator 112. Such exhaust may then be passed through a liquid leak detector 366 for monitoring purposes (e.g., to detect any leakage through the oxygenator membrane of blood or priming fluid), and into a scavenge line. An optional gas concentration monitoring system may be included having sampling pumps 368a and 368b to draw gas samples downstream and upstream, respectively, of oxygenator 112. The gas samples may be passed through a dryer 369, analyzed by monitor 370, and returned to the scavenge line. The flow meters 354b, 354c, 356, and monitor 370 may be interconnected to user interface 50 to provide information for display and monitoring for alarm indications. The information provided by the flow meters and concentration sensors, combined with the known blood flow rate, venous saturation, hematocrit and temperature, can be used to estimate arterial blood gas concentrations (e.g., $pO_2$ and $PCO_2$). The gas concentrations measured by the monitor 370 can be compared to the concentrations calculated from the flow rates measured by flow meters 354b, 354c, and 356. If the difference between measured and calculated concentration exceeds a predetermined maximum value, an alarm/indicator may be provided at user interface 50. The arrangement of flow meters and valves allows a comparison of flow meter measurements to verify correct operation of individual flow meters. For example, valves 352c and 352a could be closed, allowing flow only from the $O_2$ source through flow meters 354b and 356. The measured flow rates from meters 354b and 356 should be equal if the flow meters are operating properly. Similar checks/tests could be performed with respect to verifying gas source composition and connection.

VII. System User Interface.

The system user interface 50 includes a control knob 52 and user displays 54 and 55 that provide for the automatic redundant display of alarm indications and certain monitored parameters, and provide for selective user control of various system components. Both main display 54 and backup display 55 may provide a functional user interface (e.g., via touch screen capabilities). Important subsets of the various features described below with respect to main display 54 may also be provided at backup display 55, either all the time or if failure of main display 54 is detected by the system or by the user. In addition to its backup display functions, display 55 serves primarily as a numeric data entry screen, as described below.

Numeric data entry is accomplished by using the control knob 52 and both user displays 54 and 55, as follows. The user contacts a touch screen button on either display 54 or 55 to initiate modification of a particular numeric value represented by that button. The value being modified then appears (usually in a large font) on display 55, as well as appearing within the button originally contacted on display 54 (or its analog on 54, if the original button was on display 55). At this point, the knob 52 may be turned to affect changes in the value displayed in both places. This dual display concept is to provide redundant display of important data parameters as are they are being adjusted, thereby giving an important safety cross-check against incorrect data entry. In most cases, as the number is being adjusted on the screens, it is also taking immediate effect in the system (on-line adjustment). For example, turning the knob to adjust venous line clamp position causes the clamp to move immediately to the value entered. Data entry is terminated by pressing the knob 52 in, or by touching the original touch button or anywhere else on the touch screen. Because of the on-line nature of such adjustments, terminating the data entry is not in anyway "confirming" or "setting" the value entered; that has already happened. Terminating the data entry simply exits the adjustment mode for that particular value. There are many examples of specific data entry actions throughout this section.

FIGS. 27-33 illustrate examples of one embodiment of the system user interface 50, and are presented for illustrative purposes. The arrangement, controls, and information presented on the user interface are not limited to that shown here.

As shown in FIG. 27, processor-driven display 54 is controlled to define three display regions for information presentation and user control. The screen of display 54 comprises a first region 200, a second region 220, and a third region 240. The first region 200 provides for automatic alarm status messages and corresponding user control buttons that are presented when monitored system parameters exceed/fall below predetermined established values (e.g., factory set values or user established values). The second region 220 and third region 240 will be described further hereinbelow.

Alarms:

The first region 200 of display 54 provides alarm and status messages that are presented when certain monitored system parameters exceed/fall below selectable, predetermined established values and/or an otherwise undesired condition is detected. FIGS. 28A-28F illustrate a variety of such messages. In this regard, it should be noted that the messages are presented in relation to their relative degree of importance. That is, in the illustrated embodiment, messages which are of predetermined "critical" nature are displayed against a red box background while messages of a predetermined "warning" nature are displayed against a yellow box background. Further, it should be generally noted that when a condition is detected that would trigger a "critical" message such message will be presented together with a touch screen button that may be immediately contacted by a user to override the alarm. That is, detection of a "critical" condition may result in automatic stoppage of a given system component (e.g., pump 31 or pumps 35 and 36), in which case, the "critical" message may be presented with a touch screen button that may be contacted to restart the stopped component. Alternatively, detection of a "critical" condition may result in display of a button (e.g., with the "critical message") that may be contacted by a user to effect an immediate stoppage of a predetermined component displayed with the message (turn off the override). Additionally, it should be noted that with respect to the "critical" messages, a predetermined hierarchy is preferably established wherein the order of presentation of such "critical" messages will be determined in relation to the hierarchy as preprogrammed at the embedded processor.

The following are examples of "critical" conditions that may trigger an automatic response and a "critical" alarm message. Many other critical alarms may exist in the system:

1. Detection of an air bubble in tubing line 122 or tubing line 156. Such a detected condition may automatically trigger stoppage of pump 31 and/or pumps 35 and 36. Selective, user response buttons may be provided with the corresponding "critical" messages to provide a user with the touch screen capability to restart the stopped pump.
2. Detection of a pressure in line 122 or of a pressure in line 156 that exceeds a corresponding predetermined maximum value. Detection of this condition may trigger an automatic stoppage of pump 31 and/or pumps 35 and 36. Alternatively, the pump may slow until the desired range is re-achieved. Again, button displays may be provided for selective, user restart of the affected pumps.
3. Detection of a volume level in venous reservoir 106 that exceeds or falls below a predetermined level.

Various detected conditions are reflected by FIGS. 28A-28F.

Figures 28A, 28B, 28C:
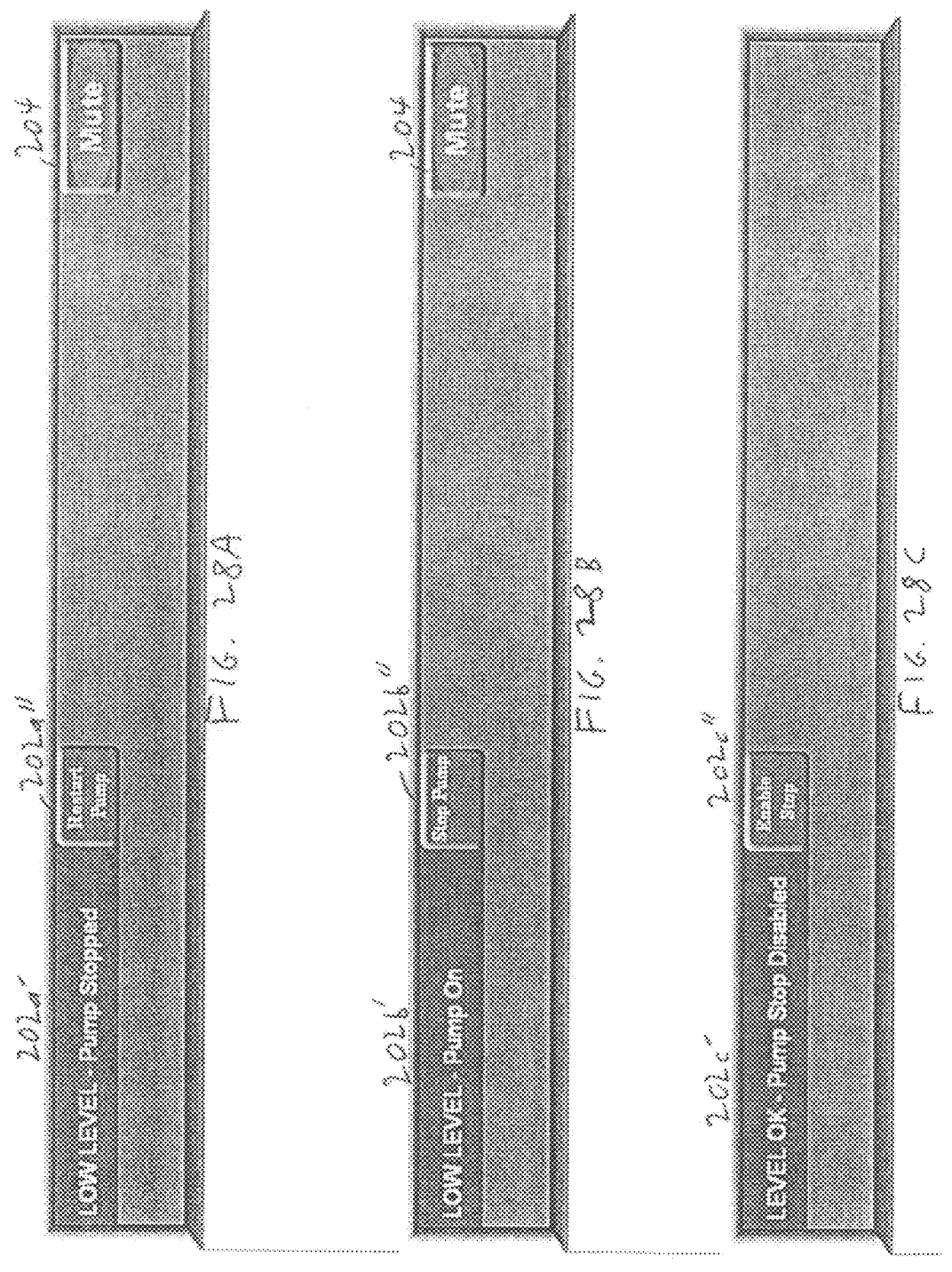

Referring specifically to FIG. 28A, a "critical" alarm box 202*a*' is presented with the message: "LOW LEVEL-Pump Stopped"

This message indicates that the volume in reservoir 106 has been detected to have fallen below a predetermined alarm value. The message also indicates that pump 31 has been automatically stopped. It should also be noted that the message box 202*a*' provides a touch screen button entitled "Restart Pump" 202*a*". Button 202*a*" allows a user to immediately take responsive action, i.e., to contact the "Restart Pump" button 202*a*" so as to start arterial pump 31, by overriding the alarm.

At this point, it should also be noted that in the event of a "critical" message (e.g., the message is displayed against a red background), the control unit 10 may provide for a first audible alarm to a user. Further, in the event of a non-critical message (e.g., a "warning" message displayed against a yellow background), control unit 10 may provide a second audible alarm that is different than the first. Correspondingly, the first region 200 of display 54 may be provided with a touch screen "Mute" button 204 which allows a user to selectively disable the most recent audible alarm. That is, audible alarms may be successively and separately "muted" in relation to each successive triggering-alarm event. The "Mute" button 204 only appears when there is one or more audible alarms currently sounding, and it disappears after being pressed (thereby stopping the audible signal) until the next triggering event occurs causing a new alarm and audible to occur. Thus, the "Mute" button only appears when needed.

FIG. 28B illustrates an alarm box 202*b*' with the message: "LOW LEVEL-Pump On".

This message indicates that the volume in reservoir 106 has been detected to have fallen below a predetermined value and that pump 31 is on (because the alarm is overridden). Block 202*b*' also provides a touch screen button entitled "Stop Pump" 202*b*" to allow a user to immediately stop arterial pump 31 upon contact with button 202*b*".

In FIG. 28C an alarm box 202*c*' is presented with the message: "LEVEL OK-Pump Stop Disabled".

This message indicates that the volume in reservoir 106 is within an acceptable range but that the automatic pump stoppage feature of control unit 10 has been overridden (e.g., the user has contacted the button 202*a*" shown in FIG. 28A). To reactivate the automated pump control feature (turn off the override), a user may contact button 202*c*".

FIG. 28D illustrates a plurality of "critical" alarm boxes corresponding to response buttons 203*a*", 203*b*", and 203*c*" each of which would be illustrated against a red background, and a single "warning" alarm box 206*a*' which would be presented against a yellow background. FIG. 28E illustrates a plurality of "critical" alarm boxes and a plurality of "warning" alarm boxes. The presence of the "MORE button 208*a* indicates that there are more alarms than can be displayed within region 200, which can be selectively cascaded into the second display region 220 via contact with the "MORE" button 208*a*, as shown in FIG. 28F. Pressing the "LESS" button 208*b* in FIG. 28F will collapse the alarms back within region 200, as shown in FIG. 28E.

Dedicated Area:

The second region 220 presents selected, predetermined important information sets to monitor bypass parameters, including values corresponding with selected fluid flow parameters monitored by various components of control unit 10, as well as other parameters monitored by external systems. More particularly, in the screen display embodiment illustrated in FIG. 29, five different information sets are presented in five corresponding sub-regions 222, 224, 226, 228 and 230, having the sub-region headings of "Venous", "Arterial", "Cardioplegia", "Blender" and "Other", respectively. The alphanumeric information in the different sub-regions may be color coded for ready observation (e.g., the alphanumeric information may be blue in "Venous" sub-region 222, red in "Arterial" sub-region 224, yellow in "Cardioplegia" sub-region 226 and white in "Blender" and "Other" sub-regions 228 and 230, respectively).

The information displayed in sub-region 222 under the "Venous" heading pertains to parameters of the venous blood flowing from a patient into venous reservoir 106 of disposable assembly 100 during a bypass procedure. More particularly, the monitored venous blood values include a measure of the venous blood oxygen saturation (i.e., "SAT"), venous blood hematocrit (i.e., "HCT") and venous blood temperature (i.e., "Temp"). Such values are monitored by corresponding oxygen saturation hematocrit and temperature sensors 85 and 81, respectively, in the component interface region 12. Of note, information regarding the volumetric content of venous reservoir 106 is provided both in an animated manner and numerically by the graphic reservoir in sub-region 222. That is, as the level of fluid raises and lowers in venous reservoir 106 during a bypass procedure, a corresponding animated fluid level (e.g., illustrated in red) will be presented in the graphic venous reservoir shown in sub-region 222. Additionally, a numeric representation of the volumetric level within venous reservoir 106 will be increased/decreased. The volumetric level of fluid within reservoir 106 is determined via the level sensor 87 located in component interface region 12.

The "Venous" sub-region 222 further includes object buttons 222a, 222b and 222c having touch screen capabilities to allow a user to selectively control venous line clamp 46 of the component interface region 12 on control unit 10. In particular, the "Full Open" and "Full Close" buttons 222a and 222c, respectively, allow a user to selectively, fully open and fully close venous line clamp 46 upon screen contact. Object button 222b allows a user to select a desired percent of fluid passage through venous tubing line 104 at venous line clamp 46. That is, pursuant to contact with button 222b, a user may then utilize the control knob 52 on system user interface 50 to set a desired percentage for fluid passage through tubing line 104 at venous line clamp 46. The desired percentage is established by dialing/rotating knob 52 until the desired value is displayed by main display 54 and back up display 55. The VLC is moved immediately to the desired position as the knob is moved. A user may then either push the knob 52 or contact button 222b or any other touch screen portion of display 54 to exit the adjustment mode. For example, if venous line clamp 46 is in an open position and a user desires to reduce the flow of venous blood flow into venous reservoir 106 (e.g., due to a detected high level of fluid within venous reservoir 106), a user could contact button 222b and "close" venous line clamp 46 a desired amount via rotation of control knob 52. The set flow percentage will be presented in an illuminated manner within the center of object button 222b and on the back up display 55. The percentage is displayed as a percent of flow expected if the venous line clamp was fully (100%) open.

The information presented within sub-region 224 under the heading "Arterial" pertains to ongoing monitored parameters of the blood passing from venous reservoir 106 through oxygenator 112 for return to a patient. More particularly, the monitored parameters include the pressure of the oxygenated blood in line 122 (i.e., "Pressure"), the flow rate of the blood at pump 31 (i.e., "Flow") and the temperature of the blood in line 122 (i.e., "Temp."). The pressure and temperature values are monitored on an ongoing basis by the pressure sensor 14 and temperature sensor 88 provided in component interface region 12 of control unit 10. The flow rate may be automatically determined by monitoring the RPMs of arterial pump 31 at the pump processor 312 and by using the monitored RPM values with stored stroke volume-values corresponding with pump 31 to calculate flow rate, or to display the flow rate from a flow meter. Such flow rate may be automatically adjusted to compensate for any blood flow downstream of pump 31 that is not directed through arterial tubing line 122. Arterial blood flow may be adjusted to compensate for the flow diverted to the cardioplegia circuit (or other circuits). This is done by monitoring the flow through cardioplegia blood pump 35, and adding that much flow to arterial pump 31 so that the flow to the patient remains the same. Assuming a flow meter is not available, the flow displayed in sub-region 224 will be this calculated patient line flow.

The information set provided under the "Cardioplegia" heading within sub-region 226 includes information corresponding with monitored and preset values corresponding with the cardioplegia mixture flowed through cardioplegia tubing line 156 to a patient. Such parameters include the pressure of the cardioplegia mixture (i.e., "Pressure"), the flow rate of the cardioplegia mixture (i.e., "Flow") and the temperature of the cardioplegia mixture (i.e., "Temp."). Such information is obtained via monitoring signals received from pressure sensor 18, pumps 35 and 36 and temperature sensor 153. Again, the signals from pumps 35 and 36 reflect RPMs which can be employed with stroke volume-related values for pumps 35 and 36 to determine cardioplegia flow rate, or the flow rate from a flow meter may be displayed. Sub-region 226 also provides for the display of information relating to a patient's coronary sinus pressure (i.e., "Coronary Sinus"). Such pressure may be obtained from an auxiliary sensor connected to unit 10 or from a conventional operating room patient monitor interconnected to unit 10. Additionally, sub-region 226 displays values showing a target amount of cardioplegia mixture to be delivered in a given increment (i.e., "Bolus"), the total amount of cardioplegia delivered throughout the case (i.e., "Total"), and the amount of time that has passed between cardioplegia delivery periods (i.e., "Ischemic Time"). The "Ischemic Time" is automatically determined by timing the interval between when pump 35 or 36, or both pumps 35 and 36, stop and subsequently restart.

In the sub-region 228 corresponding with the "Blender" heading, monitored and preset values are presented which pertain to the flow of gas to the oxygenator 112. In particular, in the gas circuit of FIG. 26, the flow rate of the gas supplied to the oxygenator 112 is monitored by flow meter 356. Such amount may be displayed in sub-region 228 (i.e., "Flow"). Further, the desired, preset oxygen percentage for the inspired oxygen supplied to oxygenator 112 is displayed (i.e., "$FiO_2$"), and the desired preset $CO_2$ percentage of the inspired carbon dioxide supplied to oxygenator 112 is displayed (i.e., "$FiCO_2$"). Such percentages may be displayed via signals provided to one or more of the processors of unit 10 from valves 352a-352c in the gas circuit shown in FIG. 26.

The "Other" sub-region 230 is provided to display other monitored values and is re-configurable by a user. In FIG. 29, the "Other" sub-region has been configured to display values corresponding with a patient's arterial blood pressure (i.e., "Patient Arterial") and temperature ("Patient Temp."). Such values may be monitored via an external system (e.g., an operating room monitor) which is interconnected to the embedded processor in control unit 10. Further, the monitored percentage of $CO_2$ in the expired oxygen passing out of oxygenator 112 may be displayed (i.e., "$FeCO_2$"). Such percentage may be provided by monitor 320 in the gas circuit shown in FIG. 26.

Tabbed Area:

The third region 240 of display 54 provides for the selective display of various context-driven, information sets and corresponding context-driven user-control options. During a bypass procedure, such information sets and control options may be navigated via selective contact with a plurality of context-driven touch screen tabs, as will be further described.

Figure 30A:
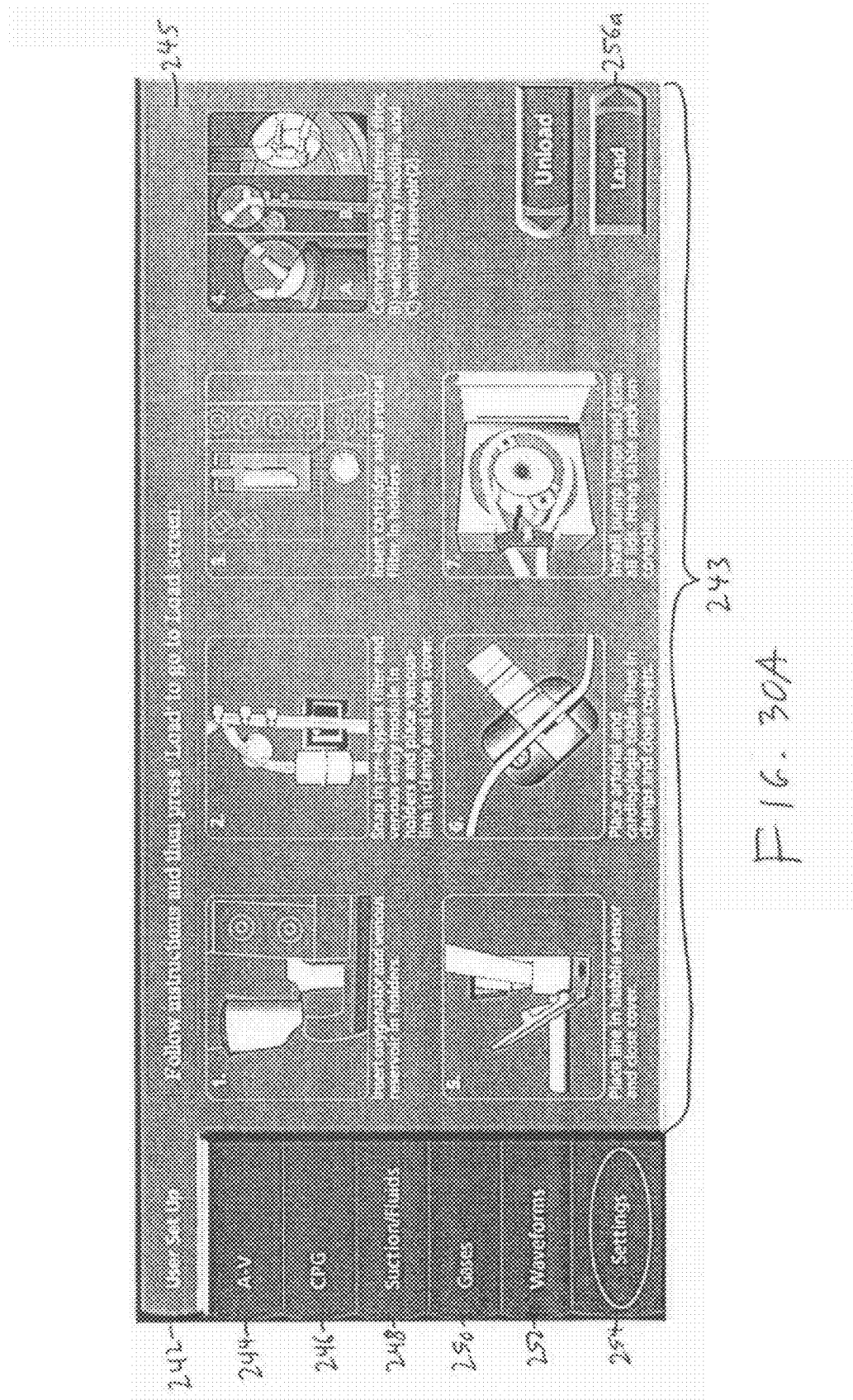

Referring to FIG. 30A, when initiating a procedure, a first tab 242 will present a title that changes in corresponding relation to predetermined, pre-bypass steps to be completed. When these steps are completed as described below, the first tab 242 will present the title "Main" until bypass and post-bypass are complete, when it will present the title "Unload". In addition to tab 242, a plurality of other tabs may be selectively employed to access different screen sets. As will be further described, tabs 244, 246, 248, 250, 252, and 254 are available for selection and use at any time during setup or during bypass procedures and will illuminate upon selection.

"A-V": Tab 244 may be employed to display a pictorial and/or alphanumeric representation of and selectively control certain control unit 10 functions relating to the venous and arterial circuits, collectively, arterial-venous circuit. Additionally, touch key buttons are displayed for immediate user control of selected other functions.

"CPG": Tab 246 may be employed to a display pictorial and/or alphanumeric representation of and selectively control certain control unit 10 functions relating to the cardioplegia circuit, e.g., including settings such as cardioplegia ratios or bolus values. Additionally, touch key buttons are displayed for immediate user control of selected other functions.

"Suction/Fluids": Tab 248 may be employed to display pictorial and/or alphanumeric representations of and selectively control certain control unit 10 functions relating to the suction and left ventricular circuits. Additionally, touch key areas are displayed for immediate user control of selected other functions, including the addition of fluids through the prime lines.

"Gases": Tab 250 may be employed to display pictorial and/or alphanumeric representations of and selectively control certain control unit 10 functions relating to the gas circuit. By way of example, tab 250 may be employed to establish the gas sweep rate and/or defined $FiO_2$ flow for oxygenator 112. Additionally, gas combination ratios, relative concentration values and mass flow rate relative to fluid flow rate may be established for gas circuit 340. For example, the user may establish a desired mixture of $O_2/CO_2$, and air to be established at valves 352c, 352b, and 352a. Additionally, tab 250 may be employed to present various monitored gas pressure readings, including readings taken by pressure sensors 360 and 364 comprising gas circuit 340.

"Waveforms": Tab 252 may be employed to display graphical waveforms and trend settings, and alphanumeric representations, including waveforms corresponding with patient pressure, temperature and ECG signals received by the embedded processor from external or internal systems.

"Settings": Tab 254 may be employed to display a pictorial and/or alphanumeric representation of and selectively control certain control unit 10 functions relating to the various system parameter settings. Additionally, touch key buttons are displayed for immediate user control of other parameter settings.

Main Tab: Tab 242 in region 240 is used to guide the operator through a sequence of steps to setup, load, and prime the tubing set, run the bypass procedure, run post-bypass steps, and, finally, unload the tubing set. In this regard, the title of tab 242 changes to "User Setup", "Load", "Auto-Prime", "Main", and "Unload" as the major steps of the procedure are executed, and where "Main" covers both bypass and post-bypass operations.

Many of the operations encompassed by the Main tab are sequential in nature, meaning that one step must be completed before the next step(s) can be accomplished. Therefore, the screens in tab 242 enforce this sequential nature by both the instructions presented in message block 245, and by not "enabling" touch screen buttons corresponding to later steps until the required prerequisite steps are completed. A button that is not enabled does nothing when touched, and also has a "dimmed out" look, where the text on the button is in a gray color, rather than bright white as exhibited on buttons that are "enabled". The figures discussed below will illustrate this concept many times.

User Setup:

As noted above, upon initiating a procedure the first tab 242 will present a sequence of titles corresponding with certain pre-bypass procedures to be completed. As illustrated in FIG. 30A, the first such title to be presented by tab 242 is "User Set Up". While the "User Set-Up" title is presented, the context-driven portion 243 of the third region 240 presents information in both graphic and narrative form regarding steps to be completed by a user. In particular, in the embodiment shown in FIG. 30A, there are seven set-up steps presented:

1. "Insert oxygenator and venous reservoir in holders." Together with this narrative a graphic depiction is provided corresponding with venous reservoir 106 and oxygenator 112 (with heat exchanger when used) to prompt a user to mount the reservoir 106 in mounting bracket 602 and to interconnect the oxygenator 112 to the bracket 500.
2. "Snap in pre-bypass filter and venous entry module in holders and place venous line in clamp and close cover." Together with this narrative a graphic depiction is presented that corresponds with venous entry module 108 and tubing line 104 positioned within venous line clamp 46, thereby prompting a user to complete the tasks.
3. "Insert cartridge and arterial filter in holders." Together with this narrative instruction a graphic depiction is presented corresponding with cartridge 120 to prompt a user to mount the cartridge 120 in the loading assembly 21 provided in component interface region 12, and prompting a user to place arterial filter 118 in bracket 760 of component interface region 12.
4. "Connect lines to A) arterial filter, B) venous entry module, and C) venous reservoir (2)." Together with this narrative a graphic depiction is presented corresponding with arterial filter 118, venous entry module 108, and venous reservoir 106, prompting the user to connect oxygenator outlet line 116 to arterial filter 118, venous line 104 to venous entry module 108, purge tubing line 119b to venous reservoir 106, and tubing line 129 to filtered input of venous reservoir 106.
5. "Place line in bubble sensor and close cover." Together with this narrative, a graphic depiction is presented corresponding with bubble sensor 114, prompting the user to place tubing line 116 relative to bubble sensor 114.
6. "Place arterial and cardioplegia table lines in clamps and close covers." Together with this narrative, a graphic depiction is presented corresponding with arterial valve block 196 and cardioplegia valve block 195, prompting the user to place arterial patient line 122 relative to arterial valve block 196, and cardioplegia to patient line 156 relative to cardioplegia valve block 195.
7. "Install pump loops and close all lids. Hang table pack on console." Together with this narrative, a graphic depiction is presented that corresponds with a tubing loop (e.g., 110, 178, 190, 180, 132 or 140) positioned within a pump assembly (e.g., 31, 32, 33, 34, 35 or 36), so as to prompt a user to complete all tubing loop/pump installations.

As will be appreciated, the graphic depictions not only prompt a user to complete a given step, but additionally facilitate disposable component recognition and a ready review of the necessary step.

Touch screen buttons found in the lower right corner of the "Main" tab screens being defined here are known as "navigational" buttons, in that they are used to navigate from one "Main" tab screen to the next, or back again. In this regard, it should be noted that the context portion 243 of the "User Set-Up" tab 242 comprises a message block 245 comprising the directive: "Follow instructions and then press 'Load" to go to Load screen." Correspondingly, a navigational touch screen button 256a entitled "Load" is provided that can be contacted by the user so as to proceed from "User Set-Up" procedure step, to an "Auto-Load" procedure step. The "Unload" navigational button may be used to return the Unload screen shown in FIGS. 30K and 30L.

Load:

When the "Load" button 256a is pushed by user, the first tab 242 will present an "Auto-Load" title with the corresponding procedure-related information presented in context portion 243, as illustrated in FIG. 30B. In the context portion 243 of the "Auto-Load" tab screen steps are contemplated, (where only the first button 260b' is enabled initially):

1. "Load Cartridge and oxygenator". Of note, this step is presented in the form of a graphic button 260b' having touch screen capabilities, wherein a user may simply contact the button 260b' so as to cause cartridge 120 to be automatically retracted or loading assembly 21 to be automatically advanced into operative relation with the cartridge interface region 20, and to cause oxygenator 112 to be automatically retracted or moveable carriage member 511 to be automatically advanced into operative relation with the stationary face plate 510. In this regard, the message block 245 comprises the directive "Press 'Load cartridge and oxygenator' to automatically load cartridge and oxygenator into system." While loading is progressing, message block 245 may automatically display a series of messages indicating the automatic configuration steps being completed by control unit 10 (e.g., opening of valves, zeroing pressure sensors, calibrating VLC 46). Block 245 may also include a graphic, percent-of-completion or time-to-completion bar (called a progress bar—see FIG. 30F for an example of one) that automatically fills an outlined region in corresponding relation to the degree of completion of task (e.g., as determined by a comparison of elapsed time to a predetermined or predicted time for completion). When this step is completed, a graphic check-mark will be presented within the "Load Cartridge" button 260b' and the "Pressure sensor zeroed, VLC set" box, so as to indicate to the user that these steps have been successfully completed, and the "Load pump loops" button 260b" is enabled, as shown in FIG. 30C.
2. "Pressure sensor zeroed, VLC set". This narrative, presented with a check mark, indicates that the steps described have been successfully completed automatically upon completion of the cartridge/oxygenator load process.
3. "Check pump loops, close all lids". This narrative corresponds with a tubing loop (e.g., 110, 178, 190, 180, 132 or 140) positioned within a pump assembly (e.g., 31, 32, 33, 34, 35 or 36), so as to prompt a user to check all tubing loop/pump installations.
4. "Load Pump Loops". Of note, this procedural step is presented in the form of a loop touch screen button 260b". In this regard, upon touching the "Load Pump Loops" button 260b" the various tubing loops 110, 178, 190, 180, 132 and 140 will be automatically loaded within the corresponding pumping assemblies 31, 32, 33, 34, 35 and 36, respectively. In this regard, while automatic loading is being completed, message block 245 may include the message "Loading Pump Loops." or other messages indicating the progress of the pump loading and circuit test procedure. Additionally, message block 245 may include a graphic progress bar (as described above and illustrated in FIG. 30F) that automatically fills an outlined region in corresponding relation to the degree of completion of the task. When pump loading is completed, a graphic check-mark will be presented within the Load Pump Loops button 260b", indicating completion of the task, as shown FIG. 30C.
5. "Adjust Arterial pump to fully occluded for Prime." Together with this narrative a pictorial graphic is presented with content that prompts the user to adjust the occlusion setting wheel on the arterial pump rotor to a position that is fully occlusive.

As illustrated in FIGS. 30B-30C, the context portion 243 of the "Auto-Load" screen tab includes a "Set-Up" graphic navigational button 258b and a "Auto-Prime" graphic navigational button 256b having touch screen functionality. The "Set-Up" button 258b is provided to permit a user to return to the previously described "Set-Up" tab screen shown in FIG. 30A. The "Auto-Prime" button 256b allows a user to selectively proceed to the next pre-bypass procedural step, but only after the various loading procedures contemplated by FIGS. 30B-30C have been completed.

Auto-Prime:

As shown in FIG. 30D, the "Auto-Prime" tab screen includes a context portion 243 that identifies the following procedural steps:

1. "Spike prime and cardioplegia bags." Together with this narrative a corresponding graphic depiction is presented to prompt/facilitate a user's interconnection of priming solution bags 162, and crystalloid bags 136 to the corresponding tubing lines interconnected with cartridge 120.
2. "Open water valves." Pressing this button causes the valves connecting the temperature control systems 330 to the oxygenator and cardioplegia heat exchangers to be opened. After a press, the button changes to "Close water valves" (as shown in FIG. 30E) to allow the user to reverse the process.
3. "Check oxygenator and cardioplegia heat exchangers for water leaks." Together with this narrative a pictorial graphic is presented with content that prompts a user to operate the heater/cooler lines connected to oxygenator 112 (e.g., via ports 519a, 519b to insure there are no water leaks across the blood side of oxygenator 112 via the heat exchanger thereof, and similarly for the cardioplegia heat exchanger. The user must press the button labeled "Pass" to confirm that there are no leaks, before the "Start priming" button will be valid.
4. "Start Priming." This procedural step is presented in the form of a graphic touch screen button 260c'. Upon pushing the button 260c', the various fluid circuits of disposable assembly 100 will be automatically primed with priming solution from bags 162 according to a predetermined protocol. Message block 245 may display messages indicating the progress through the automated priming algorithm steps, as seen in FIG. 30F. Additionally, message block 245 may include a graphic progress bar that automatically fills an outlined region in relation to the degree of completion of the priming sequence steps, as seen in FIG. 30F. Upon completion of such priming, a completion check-mark will be presented in the middle of button 260c', as seen in FIG. 30G.
5. "Check occlusion." Pressing this button starts the Arterial pump occlusion setting assist algorithm, including progress messages and progress bar in message block 245, as shown in FIG. 30H.
6. "Pre-Bypass Filter." Of note, this step is presented in the form of a touch screen button 260c" that will be activated and illuminated, or highlighted upon completion of step 4 noted above. Upon pushing the illuminated button 260c" the control unit 10 will automatically initiate pre-bypass filtering of the priming fluid through the pre-bypass filter 168 according to a predetermined protocol. Upon completion of such pre-bypass filtering, a completion check-mark will be presented in button 260c".

Upon completion of step 6, the message block 245 will read: "Pre-Bypass Filter completed, press 'Bypass'." Correspondingly, a user may proceed to bypass operations via pushing a graphic touch screen navigational button 256c entitled "Bypass". Alternatively, a user may go back to the prior step of "Auto-Load", by contacting the graphic navigational button 258c presented. It should be noted that if a user determines it necessary to proceed immediately to bypass during pre-bypass procedures, the user may contact button 256c to interrupt the pre-bypass filtering and initiate bypass.

On Bypass:

Once the "Bypass" button 256c is pressed, the first tab 242 will present the title "Main" as shown in FIG. 30I. Thereafter, the first tab 242 will continue to present the "Main" title in a highlighted manner when selected, until the Unload screen is activated.

As shown in FIG. 30I, "Main" tab 242 selection causes context portion 243 to present narrative instructions in message box 245 and to present graphic touch screen buttons and other information in three rows entitled "System", "User Defined" and "Timers". In particular, the narrative box 245 would normally start with the following instruction: "To begin Bypass, turn on the arterial flow".

At this point, the system is ready for bypass operations and the user may proceed to interconnect the patient with the various cannula assemblies that are interconnected with tubing line 104, arterial patient blood line 122, cardioplegia tubing line 156 and vent tubing line 186. Additionally, prior to or at this time suction tubing lines 170 and 172 will be readied for use. The patient's venous pressure will initiate the flow of venous blood into tubing line 104 wherein the blood is then gravity drained to venous reservoir 106. Alternatively, blood flow may be initiated via the application of vacuum conditions at reservoir 106 or the operation of an optional pump interfacing with venous tubing line 104. To initiate arterial, or oxygenated, blood flow to the patient a user would need to manually start arterial pump 31 on control unit 10 via use of the control knob 31a, or a pre-selected automated start bypass procedure as will be further described.

The user may also select other operations. For example, and as illustrated in FIG. 30I, the "System" row of graphic touch screen buttons provide the following options:

"Pre-Bypass Filter." Of note, this step is presented in the form of a touch screen button 262a. Upon pushing the illuminated button 262a the control unit 10 will automatically initiate pre-bypass filtering of the priming fluid through the pre-bypass filter 168, by a predetermined protocol and the flow set by the user using arterial pump speed knob 31a.

"System Recirc." button 262b: This button provides a user with the ability to cause the recirculation of oxygenated blood within the disposable assembly 100. When the button 262b is activated, pump 31 will operate with valve 92 closed causing oxygenated blood to recirculate in a closed loop through tubing line 119a and 119b (for the FIG. 3A embodiment) reservoir 106, oxygenator 112 and arterial filter 118. Such recirculation will occur when the button 262b is graphically presented in a depressed, or activated state, and will continue until the button 262b is further contacted, whereupon the button will be presented in an non-depressed, or inactive, state. By way of example, this option may be utilized after set-up procedures, but prior to actual cannula placement.

"Test Arterial Connection" button 262c: This button provides the user with the ability to effect an automatic test of the interconnection established between the cannula assembly corresponding with tubing line 122 and a patient. When button 262c is activated, with valve 92 opened and with pump 31 off, pressure sensor 14 will sense a fluid pressure which should correspond with the patient's blood pressure. As such, the user may compare the sensed pressure value with a predetermined or monitored value or range to determine if the patient interconnection is correct. A user may momentarily operate pump 31 at a low rate while monitoring the pressure sensed by sensor 14 to further insure proper interconnection. Valve 92 must not be left open for an extended period of time because there is a danger of draining the patient through the under-occluded arterial pump. Therefore, button 262c should operate as a press-and-hold (meaning valve 92 only stays open while the user is holding button 262c down) and/or logic must be included to automatically shut the valve after a predefined time (e.g., 3-5 seconds).

The "System" row of buttons also includes the following buttons:

"Patient Info." button 262d: This button provides the user with the ability to immediately access a screen comprising specific patient vital information (e.g., height, weight, name, patient ID or social security number, lab data, etc.). In this regard, patient information may be input/modified via touch screen functionalities and/or interconnection of a keyboard to control unit 10.

"Log Event" button 262e: This button provides the user the ability to access a screen for the input/display of specific events which a user may want to keep track of during a procedure (e.g., drug delivery times/amounts). Again, the input of events may be affected with touch screen capabilities and/or a keyboard or other input device interconnected to control unit 10.

The "User Defined" row of graphic touch screen buttons may comprise any of a number of features that may be pre-selected by a user (e.g., via a "Settings" tab as described below). In the embodiment shown in FIG. 30I the touch screen buttons provide a user with the following control options:

"CPG Target" button 264a: This button provides the user with the ability to set the amount of cardioplegia to be dispensed to a patient during any given increment. Upon pushing the button 264a, the button will be presented in a depressed, or activated state, whereupon a user may then utilize control knob 52 to set the desired amount of cardioplegia bolus to be delivered during the given increment. When the desired amount is displayed in the middle to button 264a, the user may again push button 264a or control knob 52 to exit the adjustment mode.

"CPG Delivery" button 264b' with "Reset" button 264b": Button 264b' provides a user with the ability to initiate the delivery of cardioplegia to a patient upon depression of button 264b'. When contacted, button 264b' will be graphically presented in a depressed, or activated, state, and will effect the operation of pump 36 or both pumps 35 and 36, to achieve the desired cardioplegia mixture (i.e., of crystalloid and blood), as may be pre-selected by a user. Additionally, when button 264b' is activated, valve 96 will be opened. Cardioplegia will then flow to a patient through tubing line 156 until the targeted bolus amount set via use of control button 264a has been delivered, whereupon cardioplegia delivery will be automatically stopped. The amount of volume delivered (or yet to be delivered) will be displayed on the control button, and also in the dedicated area. A user may also manually stop cardioplegia delivery at any time by contacting button 264b' or controlling knobs 35a and/or 36a of pumps 35 and 36, respectively. The amount of cardioplegia delivered during a given increment will be displayed on an updated basis in the middle of button 264b'. To reset the volume delivered display to a full bolus amount (e.g., after the dispensation of an incomplete bolus of cardioplegia), a user may push "Reset"

button 264b". As shown in FIG. 30I, an animated light indicator may be provided to indicate when cardioplegia is being delivered (e.g., indicated via green illumination) and when delivery is stopped (e.g., indicated via red illumination).

"Test CPG Connection" button, when depressed, holds cardioplegia patient line valve 96 open, so that distal pressure may be read on cardioplegia pressure sensor 18. Valve 96 must not be left open for an extended period of time because there is a danger of draining the patient through the CPG patient line. Therefore, button "Test CPG Connection" should operate as a press-and-hold (meaning valve 96 only stays open while the user is holding the button down) and/or logic must be included to automatically shut the valve after a predefined time (e.g., 3-5 seconds).

"Cardioplegia Delivery Mode" region with "Antegrade" button 264c' and "Retrograde" buttons 264c": Buttons 264c' and 264c" provide a user with the ability to select different alarm limits for the pressure in tubing line 156 (e.g., via sensing by pressure sensor 18) when cardioplegia is in either antegrade and/or retrograde mode, respectively. In addition, the buttons may tell the system to use a different pressure sensor for alarming and/or limiting cardioplegia flow (e.g., use line pressure for Antegrade, coronary sinus pressure for Retrograde).

The "Timers" row of graphic touch screen buttons can be configured to provide a user with various display options. For example, in the embodiment of FIG. 30I the following features are presented:

"On Bypass" timer 266a': Timer 266a' provides for the automatic display of a timed duration that a patient is on-bypass. Timer 266a' may be automatically started when arterial pump 31 is operated after priming and pre-bypass filtering with valve 92 open. Timer 266a' will automatically stop when arterial pump 31 is stopped, with valve 92 closed, and will automatically start again when pump 31 is restarted with valve 92 open (e.g., with the timer beginning where it left off). The user may also manually start the On-Bypass timer simply by depressing button 266a', whereupon the timer will start. To stop the timer, a user may inactivate button 266a' via contact. To reset the timer, a user may contact button 266a".

"X-Clamp" button 266b' and timer with "reset" button 266b": Button 266b' provides a user with the ability to time the duration the patient has been cross-clamped during a bypass procedure. To do so, a user may simply depress button 266b', whereupon the timer will start. To stop the timer, a user may inactivate button 266b' via contact. To reset the timer, a user may contact button 266b".

"Off-Bypass" timer 266c': Timer 266c' may be provided to provide a user with a timed duration display showing the amount of time that a given patient has been off bypass. Timer 266c' may be automatically started when valve 92 is closed, and may automatically stop when valve 92 is reopened. Timer 266c' will automatically reset when started again. The user may also manually start the Off-Bypass timer simply by depressing button 266c', whereupon the timer will start. To stop the timer, a user may inactivate button 266c' via contact. To reset the timer, a user may contact button 266c".

"Auxiliary" timer 266d' with "reset" button 266d": Button 266d' and reset button 266d" are provided to allow a user to selectively time any given procedure being conducted during a procedure. To initiate the timer, button 266d" may be contacted by a user. To stop the timer, button 266d" may again be contacted so as to deactivate the timer. To reset the time to zero, reset button 266d" may be contacted.

When bypass is complete, the user may press the navigational button "Go to Post Bypass" to move to the Post-Bypass screen described in FIG. 30J.

Post-Bypass:

As shown in FIG. 30J, "Main" tab 242 now shows the Post-Bypass screen, which is similar to the Bypass except for the User Defined row of buttons and the navigational buttons. The User Defined buttons are defined as follows:

"Fill Patient" region with "Bolus" button 264d' and "Deliver" button 264d": Button 264d' provides a user with the ability to set a targeted amount of blood bolus to be dispensed to a patient via tubing line 122. Upon contacting button 264d', a user may utilize control knob 52 to establish the desired amount of bolus to be delivered. The center of button 264d' will present the selected amount. To exit the adjustment mode button 264d' may again be pushed or control knob 52 may be pushed. In order to initiate the delivery of a bolus amount, a user may simply contact button 264d". Button 264d" includes an illuminated display to show the amount of bolus that has been delivered during a bolus delivery period. To stop bolus delivery, a user may contact button 264d" so as to trigger an inactive state. Alternatively, a user may manually stop the delivery of bolus via manual stoppage of pump 31, or just start/stop manually within using the bolus control logic.

"Chase" region operates similarly to Fill Patient, but activates an additional algorithm whereby as fluid is removed from the venous reservoir 108 the prime bag valves are opened to let priming solution in to maintain the initial reservoir level (when Chase was initiated), thereby "chasing" blood out of the reservoir with saline.

"To Bags": This button adds an additional mode to the Fill Patient and Chase modes, whereby instead of "filling" or "chasing" blood down the arterial patient line 122, the arterial line valve stays closed, and the user connects a transfer bag and/or hemoconcentrator to the stopcock provided for such, and then the system is "filling" or "chasing" blood to the bag/hemoconcentrator.

The navigational button "Return to Bypass" will move back to the Bypass screen described in FIG. 30I. The navigational button "Move to Unloading" will move forward to the Unload screen described in FIG. 30K.

Figure 30K:
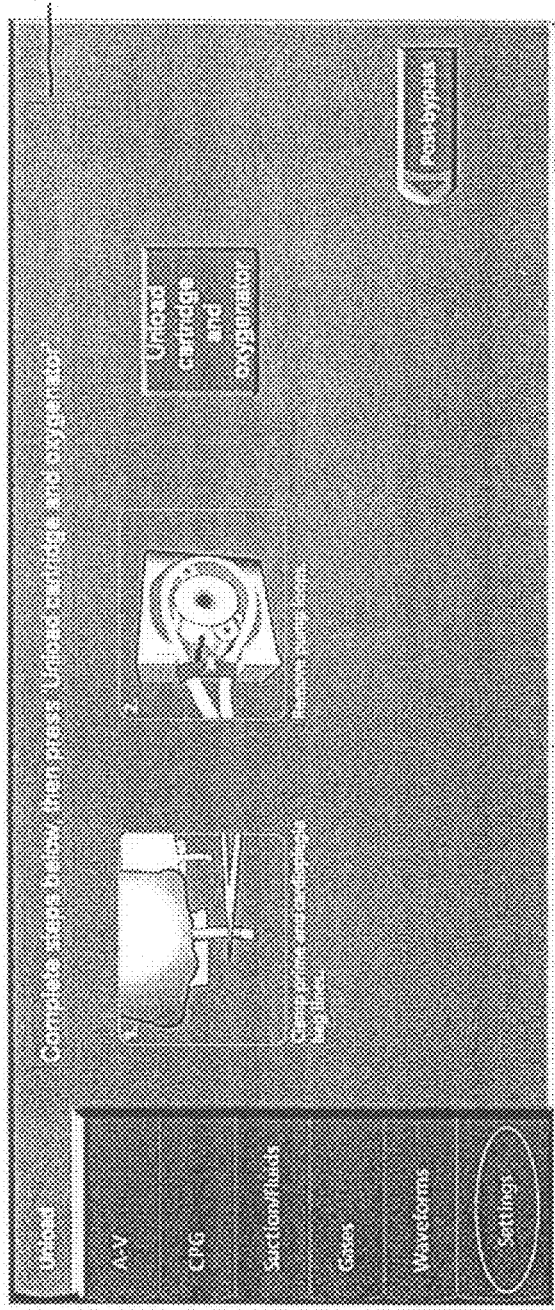
Figure 30L:
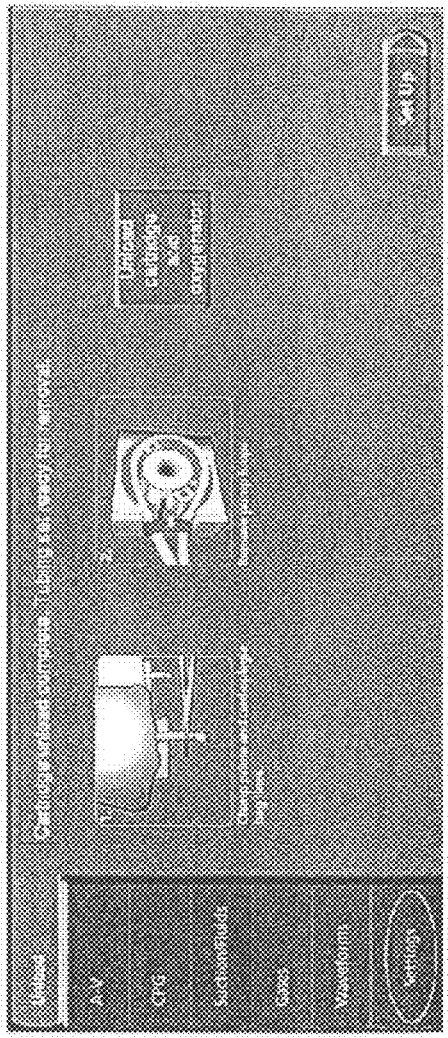

Unload:

When the "Move to Unloading" button is pushed by user, the first tab 242 will present an "Unload" title with the corresponding procedure-related information presented in context portion 243, as illustrated in FIG. 30K-30L.

In the context portion 243 of the "Unload" tab screen steps are included:

"Clamp prime and cardioplegia bag lines." Together with this narrative, a graphic depiction is provided corresponding with crystalloid tubing lines 133 and prime bag lines 160 so as to prompt a user to clamp off the bag lines before the cartridge is disengaged from the platform.

"Remove pump loops." Together with this narrative, a graphic depiction is presented that corresponds with a tubing loop (e.g., 110, 178, 190, 180, 132 or 140) positioned within a pump assembly (e.g., 31, 32, 33, 34, 35 or 36), so as to prompt a user to remove all tubing loops from the pumps.

"Unload cartridge." Of note, this step is presented in the form of a graphic button having touch screen capabilities, wherein a user may simply contact the button so as to cause cartridge 120 to be automatically advanced away from the machine or loading assembly 21 to be automatically retracted away from the cartridge 120, and to cause oxygenator 112 to be automatically advanced away from the machine or moveable carriage member 511 to be automatically retracted away from the stationary face plate 510. In this regard, the message block 245 comprises the directive "Complete steps below, then press 'Unload cartridge and oxygenator.'" While unloading is progressing, message block 245 may automatically display a series of messages indicating the automatic configuration steps being completed by control unit 10. Block 245 may also include a graphic progress bar that automatically fills an outlined region in corresponding relation to the degree of completion of task (e.g., as determined by a comparison of elapsed time to a predetermined or predicted time for completion). When this step is completed, a graphic check-mark will be presented within the "Unload Cartridge and Oxygenator" button, so as to indicate to the user that the step has been successfully completed, as shown in FIG. 30L.

The navigational button "Post-Bypass" in FIG. 30K will be presented before the cartridge is unloaded, to allow the user to move back to the Post-Bypass screen in FIG. 30J. The button will be hidden after the cartridge is unloaded (as shown in FIG. 30L), unless it is reloaded by pressing "Unload cartridge" again.

The navigational button "Set-Up" in FIG. 30L will be presented after the cartridge is unloaded, and allows the user to move back to the beginning screen for a new case (FIG. 30A).

AV Tab:

As previously noted, the "A-V" tab 244 provides for the pictorial depiction of components of the venous and arterial fluid circuits and interfacing flow control and sensor components of component interface region 12, as well as a plurality of touch screen control buttons. As shown in FIG. 31A, the context driven portion 243 of the "A-V" tab 244 comprises a column of touch screen buttons 262a'-262e' in a first sub-region 267, and a fluid circuit illustration in sub-region 268. Buttons 262a'-262e' provide for direct user access to the same functionalities described above in corresponding relation to buttons 262a-262e of FIG. 30I.

With particular reference to the fluid circuit sub-region 268, it can be seen that a number of graphic objects corresponding with components of the arterial-venous circuit defined by disposable assembly 100 are graphically depicted together with graphic objects corresponding with selected flow control and sensing components provided by component interface region 12. The various graphic objects are presented with fluid flow lines therebetween having arrowheads to indicate the direction of fluid flow. The fluid flow lines are color-coded to indicate venous circuit blood flow (e.g., indicated by use of blue fluid flow lines) and arterial circuit blood flow (e.g., indicated by use of red fluid flow lines). As will be further described, certain of the graphic objects have touch screen functionality.

In particular, the objects entitled "Venous Assembly" 270a, "Oxygenator" 270b, "Arterial Filter Assembly" 270c and "Air Shunt" 270d may be contacted by a user to provide additional detail regarding the various corresponding components. More particularly, FIG. 31B illustrates the further componentry that will be visually represented upon contact with each of the three noted objects. Such additional componentry is shown in FIG. 31B corresponding with those described in relation to the disposable assembly 100 and component interface region 12 descriptions hereinabove. Of note, it can be seen that the pictorial representations corresponding with various valve assemblies are illustrated in a manner that indicates whether valve assemblies are in an open or closed state. Further in this regard, it is important to note that the visual depictions of at least some of the valve assemblies are provided with touch screen functionality (e.g., as indicated by a three-dimensional depiction), wherein upon contact with a given one of such graphic representations, the corresponding valve assemblies within the component interface region 20 will automatically change its open or closed state to the opposite state (e.g., if opened upon contact the flow control assembly will close), unless such change of state would present a predetermined undesired condition in which case a change of state would not be effected. In the latter case, a pop-up window may appear describing why the change of state requested would be undesirable, but also allowing the operator to override this constraint and cause the valve to move anyway. Such functionality provides a user with the capability to selectively, manually control the flow of fluids through the system by effectively interfacing only with display 54.

Level Pop-Up:

The venous reservoir object 270e corresponding with venous reservoir 106 is also provided with touch screen functionality. More particularly, FIG. 31C illustrates a pop-up interface window 272 that will be presented upon contact with the venous reservoir object 270e. Such window may be utilized to establish the desired level of fluid to be maintained in venous reservoir. Such pop-up window 272 also allows a user to specify whether the desired level is to be maintained by automatic operation of the arterial pump 31, by the venous line clamp 46 within component interface region 20, or by the vacuum regulator described in FIG. 11.

More particularly, as illustrated in FIG. 31C the pop-up window 272 comprises the following touch screen buttons (one and only one of the four level control buttons 272a, 272b, 272f, and 272g will be presented in a depressed state, to show the current mode of level control):

"Art Pump" button 272a allows a user to readily select the option of having the desired fluid level in venous reservoir 106 established or maintained via automatic operation of arterial pump 31. Upon activation, button 272a will be presented in a depressed state. To deactivate, "Off" button 272g may be contacted so as to turn level control off.

"VLC" button 272b allows a user to readily select the option to have the desired fluid level in venous reservoir 106 established or maintained by the automatic operation of venous line clamp 46. Upon activation, button 272b will be presented in a depressed state. To deactivate, "Off" button 272g may be contacted so as to turn level control off.

"Vacuum" button 272f allows a user to readily select the option to have the desired fluid level in venous reservoir 106 established or maintained by the automatic operation of the vacuum regulator, when Vacuum-Assisted Venous Drainage (VAVD) is being used. Upon activation, button 272f will be presented in a depressed state. To deactivate, "Off" button 272g may be contacted so as to turn level control off.

"Off" button 272g is used to stop level control by any method. When no level control mode is active, button 272g will be presented in a depressed state.

"Level control=reservoir level" button 272c allows a user to automatically set the desired fluid level for reservoir 106 to be whatever the then-current level is within reservoir 106. As such, upon activation of button 272c, level sensor 87 in the component interface region 12 of unit 10 will detect the current fluid level in reservoir 106 and such fluid level will be utilized for purposes of automatic operation of arterial pump 31 or venous line clamp 46.

"Settings" button 272d may be utilized by user as a shortcut to a screen for establishing various sensor settings corresponding with reservoir 106. For example, high level and low level settings may be set by a user and monitored by the system to provide for automated system response and the provision of alarm messages as discussed hereinabove. The establishment of settings will be further described hereinbelow.

Level control button 272e may be utilized by a user to establish the desired fluid level to be maintained in reservoir 106. In particular, the user may activate 272e and then utilize control knob 52 to raise or lower the level control point. As knob 52 is manipulated, the level control button 272e will go up and down relative to reservoir 106 to provide a visual indication of the desired level point. Additionally, the center of level control button 272e will illuminate with the volume setting corresponding with the position of the level control button 272e relative to reservoir 106. Again, to exit adjustment mode, button 272e or control knob 52 may be contacted.

Pressure Pop-Up:

If a pressure sensor is contacted on the graphic depictions in these tabs, an associated pressure sensor pop-up window is displayed. For example, if the arterial pressure sensor on FIG. 31B is touched, the pop-up window shown in FIG. 31D is displayed. This pop-up allows the user to see the pressure limit and control settings, directly turn pressure control on or off for this sensor, or go to the full pressure sensor settings page (FIG. 33D) described hereinbelow by pressing the "Settings" button.

Temperature Pop-Up:

If a temperature sensor is contacted on the graphic depictions in these tabs, an associated temperature sensor pop-up window is displayed. For example, if the venous temperature sensor on FIG. 31B is touched, the pop-up window shown in FIG. 31E is displayed. This pop-up allows the user to see the temperature limit settings, or go to the full temperature sensor settings page (FIG. 33E) described hereinbelow by pressing the "Settings" button.

Sat/Hct Pop-Up:

If the Sat/Hct sensor on FIG. 31B is touched, the pop-up window shown in FIG. 31F is displayed. This pop-up duplicates the front panel of the stand-alone Sat/Hct device, allowing the user to standardize and calibrate the device, or go to the full Sat/Hct sensor settings page (not shown) by pressing the "Settings" button.

CPG Tab:

Referring now to FIG. 32A, CPG tab 246 and its corresponding display are illustrated. As noted above, the CPG tab display provides information relating to the cardioplegia circuit defined by various components of the disposable assembly 100 as well as interfacing components of component interface region 12. The context region 243 of the CPG tab screen comprises a first sub-region 267 that includes various touch screen, graphic buttons and a second region 268 that provides a visual representation of the cardioplegia circuit with objects corresponding with various components of disposable assembly 100 and component interface region 12 graphically represented. In this regard, it can be seen that the circuit illustration region 268 comprises the following graphic objects: "CPG Cardio Outlet Assembly" 274b and "Totals" 274c. Each of these objects may be contacted by a user to access a more detailed illustration of pictorial presentations of corresponding components of the disposable assembly 100 and component interface region 20, as shown in FIG. 32B. The graphic objects noted above are interconnected with fluid flow lines having arrows indicating the direction of fluid flow therebetween. Such fluid flow lines may be color coded in a manner to indicate the type of fluid (e.g., yellow fluid flow line indicates crystalloid and cardioplegia mixture flow and red fluid line indicates arterial blood fluid flow).

As noted the CPG tab 246 shown in FIG. 32A also includes a number of pictorial representations corresponding with various components of the component interface region 20. Such pictorial representations correspond with cardioplegia crystalloid pump 36, cardioplegia blood pump 35, pressure sensor 18 and control valve assembly 96. Valve assembly 96 representation is provided with touch screen capabilities to permit opening and closing of valve 96 upon contact. The CPG tab screen shown in FIG. 32A may include animated representations corresponding with cardioplegia crystalloid bags 136. In this regard, the volume contents within each of the bags 136 may be monitored on an on-going basis via interface of the embedded processor with crystalloid pump 36 wherein volumetric contents may be represented graphically and numerically in the pictorial representations of the crystalloid bags 136.

Referring now to the first sub-region 267 shown in FIG. 32A, it can be seen that a plurality of graphic object buttons are presented. Several of these buttons correspond in type and functionality with the second row of graphic object buttons presented in the "Main" tab screen illustrated in FIG. 30I. Additionally, of importance, a graphic button entitled "Ratio" 276 is presented which indicates the ratio of blood to crystalloid solution to be established for the cardioplegia fluid delivered to a patient utilizing the current settings. In the event that a user would like to selectively change such ratio at any time, the "Ratio" touch screen button 276 may be contacted and the user may then utilize control knob 52 to increase or decrease the ratio to the desired level (as shown in FIG. 32B), which will take effect immediately if a bolus is currently in progress. Pushing in the control knob 52 or pushing or touching another area on the touch screen will exit the adjustment mode. Buttons 464a, 464b' and 464b", and 464c' and 464c", operate in the same functional manner as described above in relation to buttons 264a, 264b' and 264b", 264c' and 264c", respectively. Further, the "Deliver Blood Only" button in FIG. 32A allows the user to deliver cardioplegia blood continuously (non-bolused) through only the cardioplegia blood pump 35, with no crystalloid added (non-ratioed), until the "Deliver Blood Only" button is touched again to terminate the blood only mode.

As noted above, the "CPG Cardio Outlet Assembly" object 274b and "Totals" object 274c of the CPG tab screen shown in FIG. 32A may be contacted by a user. FIG. 32B illustrates the additional information that would be conveyed upon contact with each of the two objects.

Suction/Fluids Tab:

Continuing now to FIG. 32C, the "Suction/Fluids" tab screen and corresponding context driven display region 243 is presented. Region 243 provides graphic representations corresponding with a first suction tubing line 170 and corresponding pump 32, the second suction line 172 and corresponding suction pump 34 and the left ventricle tubing line 186 and corresponding pump 33, along with the three negative pressure sensors associated with these three suction/vent lines. Also depicted are the sequestration reservoir and sequestration drain valve, the two valves that direct the vent pump to either reservoir, and prime bags and associated prime bag valves, and the reservoir filter pressure sensor.

In the alternative circuit embodiment shown in FIG. 3B, a modified user interface could contain the following buttons (not shown):

"Hemoconcentrator to Reservoir" button allows a user to initiate automated hemoconcentration, wherein upon contacting the button pumps 37 and 38 will operate at pre-selected rates to pump the hemoconcentrated blood to reservoir 106.

"Hemoconcentrator to Transfer Bag" button allows a user to initiate automated hemoconcentration, wherein upon contacting the button pumps 37 and 38 will operate at pre-selected rates to pump the hemoconcentrated blood to transfer bag 194.

"Transfer Bag to Reservoir" button allows a user to selectively initiate the flow of fluid from transfer bag 194 to reservoir 106.

"Reservoir to Transfer Bag" button: This button allows a user to selectively effect the transfer of fluid from reservoir 106 to transfer bag 194.

"Off" button allows a user to stop any and all of the functions associated with the four buttons listed above.

Gases Tab:

FIG. 32D illustrates the "Gases" tab 250 and a corresponding context driven region 243. Again, the context driven portion 243 includes a first sub-region 267 with a plurality of touch screen buttons 468a-468c, and a second sub-region 268, which presents a visual representation of a gas circuit servicing oxygenator 112.

Figure 32E:
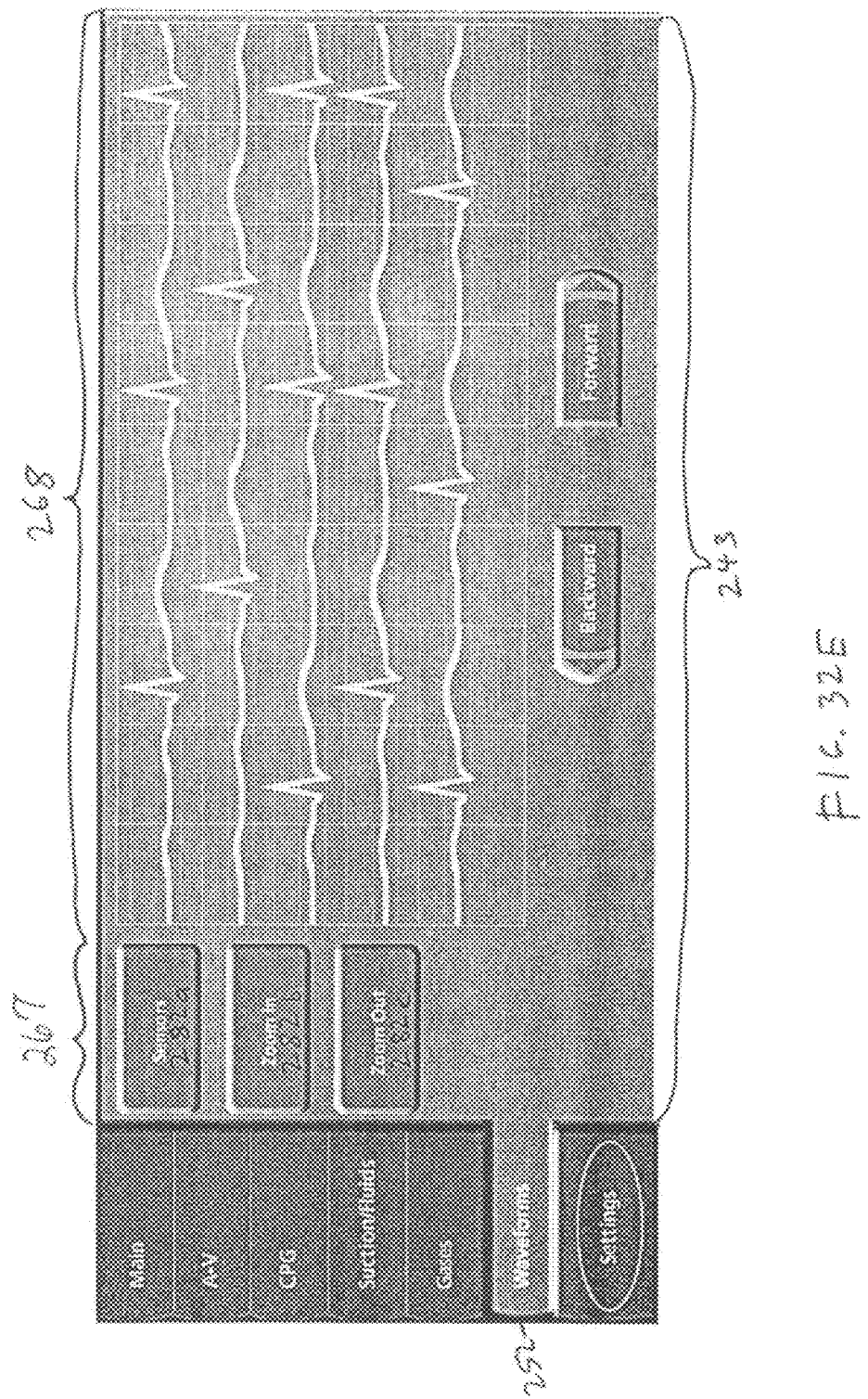

Waveforms Tab:

FIG. 32E illustrates the "Waveforms" tab 252 and corresponding context driven region 243. Again, the context driven portion 243 includes a first sub-region 267 with a plurality of touch screen buttons 282a-282c, and a second sub-region 268 which presents a visual representation of one or more monitored waveforms. More particularly, button 282a may be contacted to access a screen which allows the user to select sensors for which corresponding monitored waveforms are to be presented. The user may select from a plurality of sensors, including for example, sensors to monitor a patient's temperature, blood pressure and ECG readings. Upon selection of a sensed parameter for waveform presentation, the user may utilize buttons 282b and 282c to enlarge and reduce, selectively, a given portion of the presented waveforms.

FIG. 32E also shows a "Backward" button, that, for trending waveforms, allows the user to display waveform activity earlier in time than that currently shown, and a "Forward" button that allows the user to return forward to the waveforms showing data currently being collected.

Settings Tab:

Finally, FIGS. 33A-33F illustrate the "Settings" tab 254 and corresponding context driven region 243 options accessible to a user. In particular, the context-driven portion 243 shown in FIGS. 33A-33F includes a first sub-region 284 comprising a row of touch screen buttons, and a second sub-region 286 which provides a listing of further touch screen options corresponding with the particular button 284a-284f within sub-region 284 that has been contacted by user.

Protocol Settings:

For example, FIG. 33A shows a second sub-region 286 that would be presented upon contact with the "Protocol" button 284a presented in the first sub-region 284. A "Protocol" is a named, stored set of all the parameter settings that may be established by the user through the settings pages described hereinbelow. This includes all sensor limit settings, configuration of user-defined and configurable sections of the screen, and all other settings from these screens. The "Current Protocol" item 286a at the top of sub-region 286 indicates the name of the last protocol that was established for current use ("Loaded"), and will also have a asterisk next to it if any parameters settings have been modified since the last protocol was loaded. Such setting modifications are temporary, and will be overwritten if another (or the same) named protocol is loaded. Such temporary settings may save into a new or existing protocol with the "Save Protocol" control 286e described below.

The touch screen options presented in the second sub-region 286 allow a user to select a protocol set to establish upon power-up of the machine (the "Wake-Up" protocol 286b), establish a different named protocol to be used currently ("Load Protocol" 286c), examine the details of any named protocol ("Display Protocol" 286d), and save the current settings as a new named protocol ("Save Protocol" 286e). Contacting the down arrow (286b', 286c', 286d', 286e') to right of each of these four controls displays what is known as a "pull-down list", which drops down on top of whatever is below, and provides a scrollable list of all currently saved named protocols, including one or more "Factory Default" protocols which are pre-set at the factory, and may not be modified. Selecting a protocol from one of these four lists causes the named protocol to be established as the Wake-Up protocol, loaded as the current protocol, have its parameters displayed, or be overwritten with the current parameter settings, respectively. Additionally, the "Save Protocol" pull-down list will have an item called "New", which, when selected, will allow the user to save a new protocol, and give it a new name using an externally connected or on-screen alphanumeric keyboard.

Figure 33B:
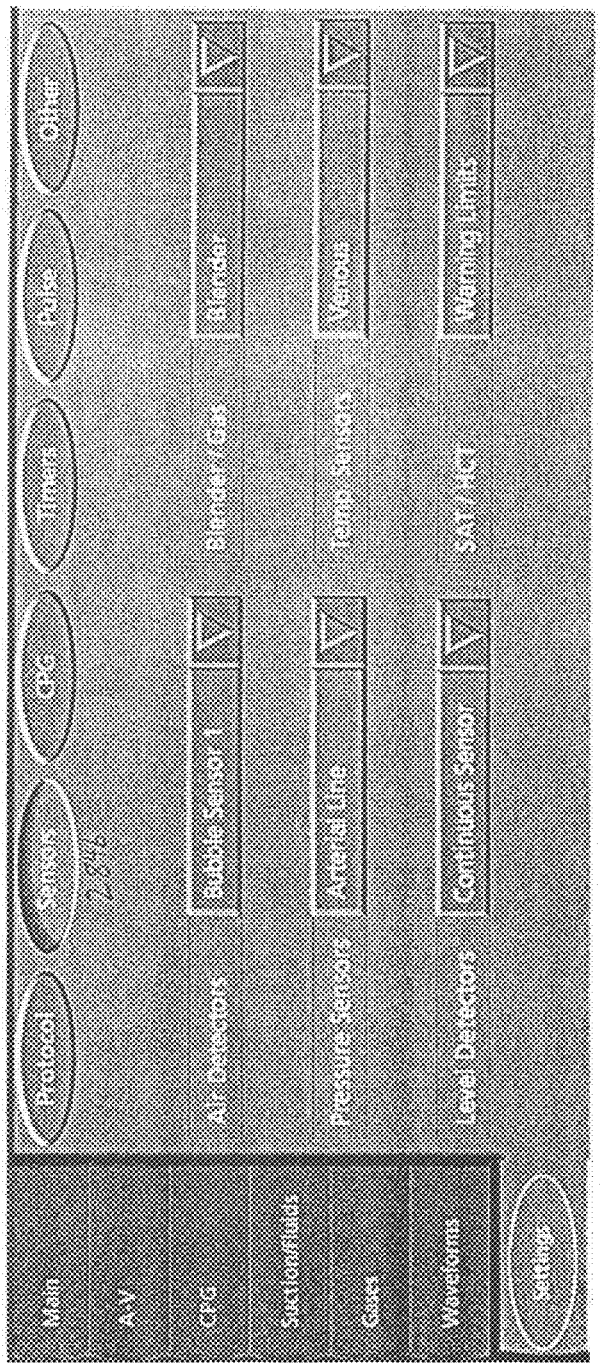
Figure 33C:
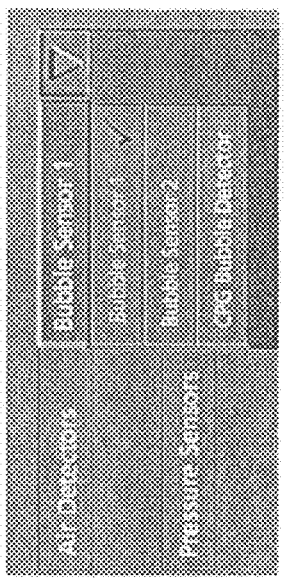

Sensor Settings:

In order to adjust individual component settings, a user may contact one or more of the other buttons of the first sub-region 284. For example, upon contact with the "Sensors" button 284b represented in the first sub-region, the options set forth in FIG. 33B will be presented. In this regard, and as shown in FIG. 33B, the various sensors may be grouped as follows: "air detectors", "pressure sensors", "level detectors", "blender/gas", "temp. sensors" and "SAT/HCT". The various sensors that correspond with each of these categories may be presented via contact with an adjacent down arrow button, wherein a full listing of the various sensors comprising a given group will be listed, each with corresponding buttons. This is demonstrated in FIG. 33C with the air detectors pull-down list. The user may then contact the graphic button corresponding with a given sensor to establish the desired settings. By way of example, FIG. 33D illustrates the display accessible when a user contacts the button for "Arterial Line" pressure sensor, and FIG. 33E illustrates the display accessible when a user contacts the button for "Venous" temperature sensor.

Pressure Sensor Settings:

As shown in FIG. 33D, a number of arterial pressure settings can be established. In particular, the display corresponding with FIG. 33D provides for establishing four different, predetermined pressure settings to be monitored by pressure sensor 14. In order to modify a given setting, a user may simply contact the corresponding set button (e.g., the "low warning") button and then establish the desired setting via control knob 52. As the control knob 52 is adjusted, the corresponding pressure setting button will move along the depicted pressure scale. When the desired pressure setting has been reached, a user may again push the corresponding pressure setting button or control knob 52. In addition to setting the desired pressure levels, a user may further select from a variety of sensor control functions as indicated by the various touch screen buttons.

Temperature Sensor Settings:

As shown in FIG. 33E, a number of venous temperature settings can be established. In particular, the display corresponding with FIG. 33E provides for establishing high and low alarm limit settings to be monitored by the venous temperature sensor in venous entry module 108. Settings methods and options are similar to those described for FIG. 33D.

As will be appreciated, similar screens may be provided for establishing the settings of and control over the operation of the various other types of sensors comprising control unit 10, and generally noted by the groups indicated by FIG. 33B.

Figure 33F:
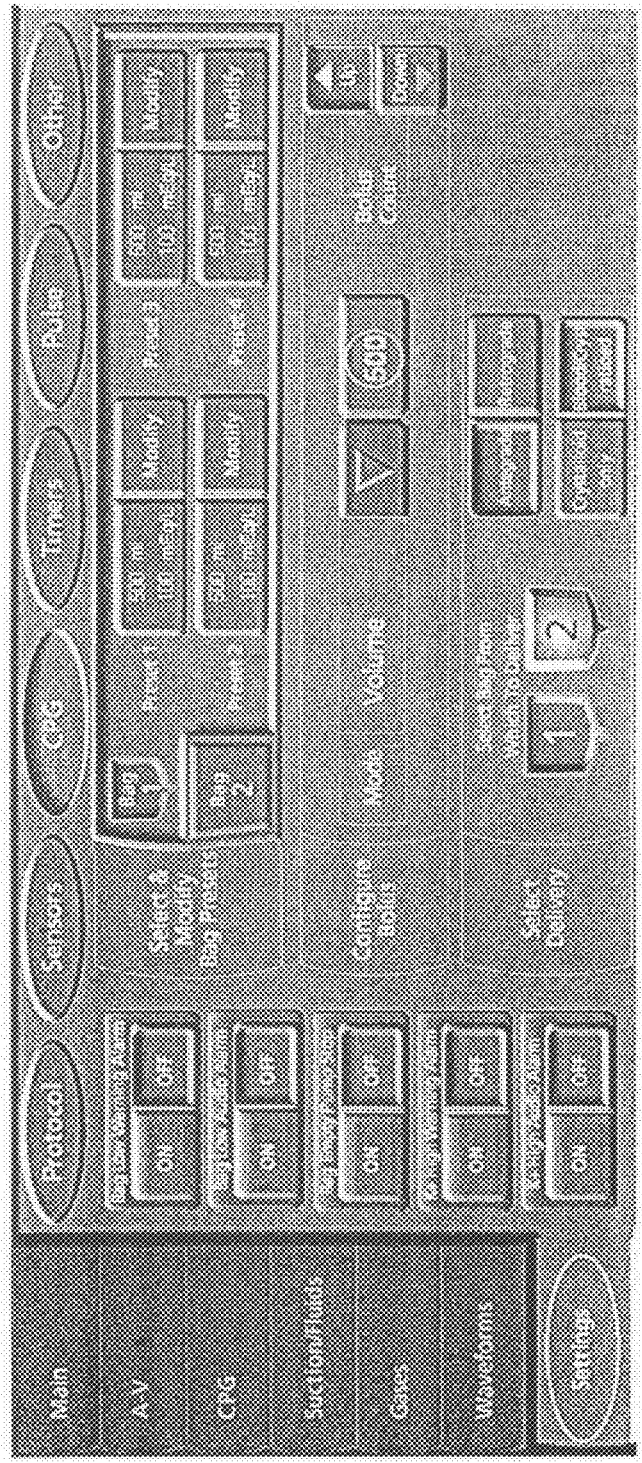

CPG Settings:

FIG. 33F. —CPG Settings (accessed from CPG button 284c on Settings tab FIG. 33A) gives the ability to specify the constituents, starting volume, and default ratio for the crystalloid bags, and change the bolus mode between volume, time or continuous, count up or count down, as well as other settings.

More Settings (not Shown):

Timers button 284d on Settings tab FIG. 33A accesses a Timer Settings screen that gives timer on/off time/date tracking history, and the ability to set timer alarms.

Pulse button 284e on Settings tab FIG. 33A accesses a Pulsatile Flow Settings screen that lets the user set the Pulsatile flow parameters for the arterial pump, such as BPM, duty cycle, and baseline flow.

Other button 284f on the Settings tab FIG. 33A accesses a Miscellaneous Settings screen that lets the user set the system date and time, language to use, and other miscellaneous settings.

VIII. Summary of Control Protocols and Algorithms

The perfusion system uses automated procedures described below.

1. Auto Prime

The "Auto-Prime" procedure, initiated by contacting graphic button 260c' on the "Auto-Prime" tab screen shown in (FIG. 30D) will result in the automatic priming of the venous, arterial and cardioplegia fluid circuits. As will be appreciated, the automatic priming will be controlled in accordance with predetermined protocols stored in memory, and will entail automated steps.

Such steps will include the opening/closing of the priming solution valves 98 so as to cause the priming solution to flow through the integral passageway 164 of cartridge 120 and line 129 into the venous reservoir 106 and fill the venous reservoir 106 to a predetermined volume. Operation of the arterial pump 31 and the opening/closing of the various valve assemblies on control unit 10 will be completed according to the predetermined protocols so as to prime line 110, oxygenator 112, line 116, arterial filter 118, arterial patient line 122, venous patient line 104, venous entry module 108, pre-bypass filter 168, line 166 and the air purge tubing line 119a, integral passageways 309a and 309b of cartridge 120, and line 119b.

In this regard, it should be noted that the disposable assembly 100 will initially provide for a fluid interconnect between arterial patient tubing line 122 and venous tubing line 104, wherein the priming solution may flow through patient tubing line 122, connector 175 and into venous tubing line 104. As will be appreciated, venous line clamp 46 and valve assembly 95 may be employed to direct the priming fluid through tubing lines 166 and 104 for priming purposes. Connector 175 will be disposed for selective removal after priming when patient interconnect for bypass is desired.

The automatic priming protocol will include inverting the arterial filter 118 and reinverting the arterial filter 118 to the up-right position multiple times during the priming sequence to facilitate priming and removing air from the arterial filter.

As priming of the arterial filter 118 is initiated, the filter will be inverted by rotating mounting arm 762 as previously described herein such that the inlet from line 116 and air purge outlet connecting to line 119a of the arterial filter is down, and the outlet connecting to line 122 of the arterial filter is at the top. During the bypass procedure the arterial filter inlet and air purge outlet are located on the top of the arterial filter and the outlet is located at the bottom of the arterial filter. As previously described, initially during the automatic priming procedure the arterial filter is inverted. Flow enters the arterial filter from the inlet and due to the inverted positioning of the arterial filter the flow fills the arterial filter from the bottom up forcing air to naturally rise to the top of the arterial filter and out the outlet of the arterial filter. At some point after the arterial filter has been primed in the described manner the arterial filter is reinverted to the up-right position where air in the arterial filter can rise to the top and be purged out line 119a. The inverting and reinverting to the upright position is repeated multiple times at high and/or low flow rates to ensure the arterial filter is completely primed and air is removed.

Automatic priming will also entail the selective operation of cardioplegia blood pump 35, cardioplegia crystalloid pump 36, arterial pump 31 and the selective opening/closing of appropriate valves comprising control unit 10 so as to direct priming solution from venous reservoir 106 through tubing line 128, and integral passageway 130. Such operation will effect priming of the cardioplegia circuit portion including integral passageways 142, and 150, tubing lines 146, cardioplegia heat exchanger 148, bubble trap 152 as well as tubing loop 132. Similarly, the cardioplegia tubing line 156 will be primed through connector 175 fluidly interconnected with venous line 104 and returning fluid to venous reservoir 106. Similarly, the cardioplegia crystalloid circuit including crystalloid lines 133, integral passageways 138, and 142, and tubing loop 140 will be primed with crystalloid solution.

2. Pre-Bypass Filter

After the "Auto-Prime" procedures, a user may contact the "Pre-Bypass Filter" button 260c" illustrated in (FIG. 30H), thereby causing the priming solution present in the arterial-venous circuit to be filtered via passage through pre-bypass filter 168 for a user selected time at a user selected flow rate by operation of arterial pump 31. In particular, valve 46 will close and valve 95 will open, thereby diverting priming solution which flows into venous entry module to flow through the pre-bypass filter 168 and line 166 into venous reservoir 106. The priming solution may then circulate from venous reservoir 106 through tubing lines 110, 116, and 122, and through the connector 175 that interconnects arterial patient line 122 and venous line 104, through venous entry module 108 and back to pre-bypass filter 168.

Additionally, while pre-bypass filtering described herein above, the cardioplegia blood pump 35 may be operated causing the priming solution in the cardioplegia circuit to flow through pre-bypass filter 168. In particular, cardioplegia blood pump 35 may be operated and valve 96 opened thereby causing the priming solution to be diverted through line 128, integral passageways 130, 142, 150; tubing lines 146, pump tubing loop 132, cardioplegia patient line 156, through connector 175, and into the venous line 104 for return to the pre-bypass filter 168.

3. Start/Stop Bypass

To initiate bypass, the various cannula assemblies provided on cardioplegia tubing line 156, venous tubing line 104 and arterial tubing line 122 may be located as appropriate within the body cavity of the patient.

Thereafter, to initiate actual bypass blood flow, venous line clamp 46 may be manually operated by contacting graphic button 222*a* or button 222*b* and adjusting knob 52 to initiate and sustain the necessary flow of venous blood through tubing line 104 to venous reservoir 106. Arterial pump 31 may also be manually operated by adjusting knob 31*a* and automatically or manually opening valve 92 to initiate and sustain the necessary flow to return blood to the patient through arterial patient line 122.

Additionally, while a user may start or stop a bypass procedure via manual control of venous line clamp 46 and arterial pump 31 and valve 92, a user may initiate an automatic start or stop bypass procedure. The automatic start procedure, initiated and/or enabled by contacting a graphic button (not shown) on user interface 50, will result in the automatic start of the arterial pump 31 and/or the automatic opening of the venous line clamp 46. As will be appreciated, the automatic start procedure will be controlled in accordance with predetermined protocols stored in memory, and will entail automated steps. The control unit 10 may then begin automated start or automated stop of the bypass procedure if the procedure is currently in progress. For example, at the outset of bypass, the starting up of arterial pump 31 is controlled according to a predetermined ramp rate protocol. Such ramp rate, the speed or flow increase per unit time, may be selected by a user by contacting graphic buttons (not shown) and/or adjustment of knob 52 on user interface 50 tab 254. Similarly, at the outset of bypass, the opening of the venous line clamp 46 may occur according to a predetermined ramp rate protocol stored in memory after contacting a graphic button (not shown) on user interface 50. Such ramp rate, the opening rate per unit time, may be selected by a user by contacting graphic buttons (not shown) and/or adjustment of knob 52 on user interface 50.

The automatic/manual operation described herein above of the venous line clamp 46 and arterial pump 31 to start bypass may occur in any combination. More specifically bypass may be initiated by manual operation of both the venous line clamp 46 and arterial pump 31, manual operation of the venous line clamp 46 with automatic operation of the arterial pump 31, automatic operation of the venous line clamp 46 with manual operation of the arterial pump 31, or automatic operation of both the venous line clamp 46 and arterial pump 31.

The manual/automatic methods herein described above to start bypass may be similarly used to stop the bypass procedure. More specifically, the venous line clamp 46 may be manually operated to reduce or terminate the flow of blood from the patient and the arterial pump 31 may be manually operated to reduce or terminate the flow of blood to the patient as necessary to stop bypass. Similarly, the automatic means to start bypass through the automatic operation of the venous line clamp 46 and the arterial pump 31 may be used to stop bypass using the ramp methods described herein above to reduce or terminate the blood flow to or from the patient as necessary to stop bypass. The manual and automatic ramp methods of operating the venous line clamp 46 and arterial pump 31 described herein above to start or initiate bypass may also be used in the same combinations as described herein above to reduce or terminate flow as necessary to stop bypass.

4. Auto Start/Stop Bypass Using Venous Line Clamp to Control Venous Reservoir Level This is a method of either starting or stopping bypass while maintaining the venous reservoir 106 level at a pre-selected value through increasing or decreasing the amount of restriction of the venous line 104 using venous line clamp 46 control. More specifically, prior to initiating bypass, the user would select the desired venous reservoir level to maintain while starting bypass by contacting graphic buttons (not shown) and/or adjusting knob 52 on user interface 50. The pre-selected venous reservoir level could be set to the current reservoir level, or a reservoir level either above or below the current level as desired by the user. The venous line clamp reservoir level control procedure, initiated and/or enabled by contacting a graphic button (not shown) on user interface 50, will result in venous reservoir level control by automatic opening or closing of venous line clamp 46. As will be appreciated, the automatic level control will be controlled in accordance with predetermined protocols stored in memory, and will entail automated steps.

As bypass is started, the user would manually operate the arterial pump 31 to begin bypass flow and slowly or quickly increase flow to the user desired flow rate. While the user started flow by increasing the speed through operation of knob 31*a* on arterial pump 31, the venous line clamp 46 would automatically begin to open to the amount necessary to maintain the venous reservoir 106 level at the pre-selected value. As the venous reservoir level fluctuates either due to adjustment of the arterial pump 31 flow rate or due to other volumetric changes in the patient or bypass circuit, venous line clamp 46 would automatically increase or decrease the amount of restriction in venous line 104 to either increase or decrease the flow into the venous reservoir to maintain the venous reservoir level at the pre-selected value.

Conversely, in order to stop bypass, the venous line clamp reservoir level control procedure, initiated by contacting a graphic button (not shown) on user interface 50, will result in venous reservoir level control by automatic opening or closing of venous line clamp 46. Prior to stopping bypass, the user would select the desired venous reservoir level to maintain while stopping bypass by contacting graphic buttons (not shown) and/or adjusting knob 52 on user interface 50. While the user decreases the flow by reducing the arterial pump flow rate through operation of the knob 31*a* on arterial pump 31, the venous line clamp 46 would automatically begin to close to the restriction necessary to maintain the venous reservoir 106 level at the pre-selected value. As the venous reservoir level fluctuates either due to continued slow down of the arterial pump 31 flow rate or due to other volumetric changes in the patient or bypass circuit, venous line clamp 46 would automatically decrease or increase the amount of restriction in venous line 104 to either increase or decrease the flow into the venous reservoir to maintain the venous reservoir level at the user pre-selected value.

5. Auto Start/Stop Bypass Using Arterial Pump to Control Venous Reservoir Level

This is a method of either starting or stopping bypass while maintaining the venous reservoir 106 level at a pre-selected value through increasing or decreasing the flow into and out of venous reservoir 106 through automatic control of arterial pump 31 flow rate. More specifically, prior to initiating bypass, the user would select the desired venous reservoir level to maintain while starting bypass by contacting graphic buttons (not shown) and/or adjusting knob 52 on user interface 50. The pre-selected venous reservoir level could be set to the current reservoir level, or a reservoir level either above or below the current level as desired by the user. The arterial pump reservoir level control procedure, initiated and/or enabled by contacting a graphic button (not shown) on user interface 50, will result in venous reservoir level control by automatic increasing or decreasing flow of arterial pump 31. As will be appreciated, the automatic level control will be controlled in accordance with predetermined protocols stored in memory, and will entail automated steps.

As bypass is started, the user would manually begin to open venous line clamp 46 to begin bypass flow and slowly or quickly increase venous flow to the user desired flow rate. While the user started flow by decreasing the restriction in venous line 104 through manual operation of venous line clamp 46, the arterial pump 31 would automatically begin to increase flow to the amount necessary to maintain the venous reservoir 106 level at the pre-selected value. As the venous reservoir level fluctuates either due to adjustment of venous line clamp 46 or due to other volumetric changes in the patient or bypass circuit, arterial pump 31 would automatically increase or decrease the amount of flow 104 to either increase or decrease the flow out of the venous reservoir to maintain the venous reservoir level at the pre-selected value.

Conversely, in order to stop bypass, the arterial pump reservoir level control procedure, initiated by contacting a graphic button (not shown) on user interface 50, will result in venous reservoir level control by automatic increasing or decreasing flow by operation of arterial pump 31. Prior to stopping bypass, the user would select the desired venous reservoir level to maintain while stopping bypass by contacting graphic buttons (not shown) and/or adjusting knob 52 on user interface 50. While the user decreases the flow into the venous reservoir 106 by reducing the restriction in venous line 104 through manual operation of the venous line clamp 46, the arterial pump 31 would automatically begin to reduce flow to the amount necessary to maintain the venous reservoir 106 level at the pre-selected value. As the venous reservoir level fluctuates either due to continued restriction of venous line 104 through operation of venous line clamp 46 or due to other volumetric changes in the patient or bypass circuit, arterial pump 31 would automatically decrease or increase the flow exiting venous reservoir 106 to maintain the venous reservoir level at the pre-selected value.

6. Cardioplegia Pressure Protection

The "Cardioplegia Pressure Protection" procedure, initiated and/or enabled by contacting a graphic button (not shown) on user interface 50 will result in the automatic control of cardioplegia pumps 35, 36 to prevent negative pressure occurring on oxygenator 112. As will be appreciated, the automatic cardioplegia pressure protection procedure will be controlled in accordance with predetermined protocols stored in memory, and will entail automated steps.

If enabled, the cardioplegia pressure protection procedure may provide an automated monitoring function, wherein if the pressure in the arterial tubing line 122, as monitored by pressure sensor 14 falls below a predetermined low limit, the cardioplegia blood pump 35 and/or crystalloid pump 36 will automatically slow down while maintaining their respective flow rate ratios such that the flow of the cardioplegia blood pump 35 does not cause the pressure in line 122 as monitored by pressure sensor 14 to fall below a predetermined low pressure limit. Alternatively, if the pressure monitored by pressure sensor 14 falls below a predetermined low limit, the cardioplegia blood pump 35 and/or crystalloid pump 36 will automatically stop. Such automatic control reduces the risk that a negative pressure will act upon the membrane within the oxygenator 112 so as to introduce air into the arterial blood. If the pressure monitored by pressure sensor 14 falls below a predetermined low pressure limit an alarm will occur on user interface 50.

7. Cardioplegia—Arterial Pump Interlock

The "Cardioplegia—Arterial Pump Interlock" procedure, initiated and/or enabled by contacting a graphic button (not shown) on user interface 50 will result in the automatic control of cardioplegia pumps 35, 36 to prevent negative pressure occurring on oxygenator 112. As will be appreciated, the automatic cardioplegia-arterial pump interlock procedure will be controlled in accordance with predetermined protocols stored in memory, and will entail automated steps.

If enabled, the cardioplegia-arterial pump interlock procedure may provide an automated monitoring function, wherein if the arterial pump stops or slows to a flow rate below the flow rate of the cardioplegia blood pump 35, the cardioplegia blood pump 35 and/or the crystalloid pump 36 may stop. Alternatively, if the arterial pump stops or slows to a speed or flow rate below the flow rate of the cardioplegia blood pump 35, the cardioplegia blood pump 35 and/or the crystalloid pump 36 may slow down to a combined flow rate, while maintaining their respective flow rate ratios, such that the cardioplegia blood pump 35 flow rate is less than the arterial pump flow rate 31. Such automatic control reduces the risk that a negative pressure will act upon the membrane within the oxygenator 112 so as to introduce air into the arterial blood.

8. Post Bypass Fluid Recovery

Upon completion of a bypass procedure, additional automated operations may be completed. For example, specific protocols may be followed to recover as much usable blood as possible from the fluid circuits. Such procedures may include the drainage of blood from a sequestration reservoir 301 into venous reservoir 106 via selective control over valve 401 by contacting a graphic button (not shown) on user interface 50. Additionally, a user may drain blood from the venous tubing line 104 into the venous reservoir 106 by opening venous line clamp 46 by contacting graphic buttons (not shown) and/or adjusting knob 52 on user interface 50. Cardioplegia blood pump 35 and arterial pump 31 may also be selectively operated in reverse by contacting graphic buttons (not shown) on user interface 50 resulting in the automatic operation of cardioplegia blood pump 35 and arterial pump 31 and cardioplegia patient line valve 96. As will be appreciated, the procedure will be controlled in accordance with predetermined protocols stored in memory, and will entail automated steps by contacting graphic buttons (not shown) on user interface 50 as to empty the cardioplegia circuit blood through integral passageway 130 to tubing line 128, arterial filter 118, tubing lines 116 and 118, and back into the venous reservoir 106. The collected body fluid may then be diverted to a transfer bag through valve 311 or through line 122 or through connection directly to an autologous blood salvage device for subsequent washing for later return to the patient.

9. Sequestration Level Sensing

The "Sequestration Level Sensing" procedure, initiated and/or enabled by contacting a graphic button (not shown) on user interface 50, will result in the automatic control of suction and vent pumps 32, 33, and 34 and/or sequestration drain valve 401 to prevent overfilling of the sequestration reservoir. As will be appreciated, the automatic sequestration level sensing procedure will be controlled in accordance with predetermined protocols stored in memory, and will entail automated steps.

If enabled, the sequestration level sensing procedure may provide an automated function. If the lower level sensor 322 detects fluid an advisory alarm occurs to alert the user that the level in sequestration reservoir 301 is rising. The user may then open drain valve 401 and empty the contents through integral passageway 305 and tubing line 129 into the venous reservoir 106 or drain off contents to a transfer bag or cell washing device through manual valve 303.

If the higher level sensor 320 detects fluid an advisory alarm occurs at user interface 50 indicating that sequestration reservoir 301 is full. The sequestration drain valve 401 automatically opens causing the contents of sequestration reservoir 301 to flow into venous reservoir 106 until the fluid level drops below the lower level sensor 322 or until all suction pumps are stopped. Alternatively, if the operator prefers that the sequestered blood not be automatically added to the venous reservoir, the suction pumps 32 and 43 could be selectively stopped automatically. The vent pump 33 could also be automatically stopped or the fluid re-routed to the venous reservoir 106 through integral passageway 192*b* and line 129 by opening valve 403 and closing valve 402.

The user options described herein above could be selected by contacting graphic buttons (not shown) on user interface 50 to enable the desired options.

10. Automatic Air Shunt

The "Automatic Air Shunt" procedure will result in the automatic shunting of air through automatic control of arterial pump 31 and valves 405 and 406 to remove air from the circuit and prevent air from entering the patient. As will be appreciated, the automatic air shunt procedure will be controlled in accordance with predetermined protocols stored in memory, and will entail automated steps.

When a predetermined small amount of air (i.e., small amount of air is a given volume of air in a given amount of time where most of the air would flow through the air shunt circuit line 119*a*, integral passageways 309*a* and optionally 309*b* and line 119*b* without a significant amount of air entering the arterial filter then transiting the arterial filter medium and exiting the arterial filter), is detected at oxygenator bubble sensor 114 the high flow arterial filter purge valve 406 and optionally the low flow arterial filter purge valve 405 opens and the air/fluid is routed through line 116, arterial filter 118, line 119*a*, integral passageways 309*a* and/or 309*b*, line 119*b* to venous reservoir 106. An alarm condition will be generated and displayed on user interface 50. Valve 406 and optionally valve 405 remain open until a predetermined amount of time after no air is present at the bubble sensor 114 to ensure that all air is removed from the circuit.

When a predetermined large amount of air (i.e., large amount of air is a given volume of air in a given amount of time that would exceed the amount of air that could flow through the air shunt circuit line 119*a*, integral passageways 309*a* and optionally 309*b* and line 119*b* resulting in a significant amount of air entering the arterial filter and transiting the arterial filter medium then exiting the arterial filter and potentially into the arterial patient line 122), or a continuous amount of small air is detected at oxygenator bubble sensor 114 the high flow arterial filter purge valve 406 and optionally low flow arterial filter purge valve 405 opens and the air/fluid is routed through line 116, arterial filter 118, line 119*a*, integral passageways 309*a* and/or 309*b*, line 119*b* to venous reservoir 106. Additionally, arterial pump 31 slows to a flow that will not generate a pressure that exceeds a predetermined value as seen at pressure sensor 114 and valve 92 is closed. An alarm condition will be generated and displayed on user interface 50. After a predetermined amount of time after no air is present at bubble sensor 114 valves 406 and optionally valve 405 close. After the air condition has cleared, valve 92 is opened and arterial pump speed returns to the pre-air flow rate either automatically or manually by the user. Alternatively, instead of slowing down arterial pump 31, arterial pump 31 may be stopped and valve 92 closed.

In each case where the arterial pump 31 is slowed or stopped and valves 405 and 406 opened or closed, the user can override the automated procedure by contacting graphic buttons (not shown) on user interface 50 which returns the arterial pump and/or valves to their pre-automatic air shunt condition settings.

If the arterial line pressure as measured at pressure sensor 14 is not sufficiently high enough to prevent retrograde flow of air through purge valves 405 and 406, valves 405 and 406 could be closed if the arterial line pressure falls below a predetermined value.

In addition, when air is detected at bubble sensor 114 blood cardioplegia delivery is automatically interrupted to prevent air from reaching the cardioplegia system if the amount of air exceeds a predetermined amount that could transition the arterial filter and potentially enter the cardioplegia blood supply line 128.

11. Automatic Fill Patient

The "Automatic Fill Patient" procedure, initiated and/or enabled by contacting graphic button 264*d*" on user interface 50 will result in the automatic control of arterial pump 31 and arterial patient line valve 92 to deliver preselect volume to the patient. As will be appreciated, the automatic fill patient procedure will be controlled in accordance with predetermined protocols stored in memory, and will entail automated steps. The user would select the desired volume to transfer to the patient by contacting graphic buttons (not shown) and/or adjusting knob 52 on user interface 50.

If enabled, this protocol automatically returns fluid to the patient at a user-selected bolus volume and flow rate at the end of the procedure. The user initiates the autofill procedure by touching the 264*d*" button at the user interface 50. This automatically causes arterial line valve 92 in arterial patient line 122 to open and arterial pump 31 to run at the user-selected flow rate set at control knob 31*a*. After the selected bolus volume is delivered, the arterial pump 31 stops and valve 92 is closed. As the bolus is delivered, the current, and/or accumulated amount can be displayed on user interface 50.

12. Positive and Negative Pressure Control

The "Pressure Control" procedures, initiated and/or enabled by contacting a graphic button (not shown) on user interface 50 will result in the automatic control of any pump to control the pressures in the respective pump circuits. As will be appreciated, the pressure control procedures will be controlled in accordance with predetermined protocols stored in memory, and will entail automated steps. The user would select the desired pressure control settings by contacting graphic buttons (not shown) and/or adjusting knob 52 on user interface 50.

This control protocol is useful to control pressure in various circuits in the perfusion system by controlling pump speed. This control algorithm may be used in any pump circuit. This is more desirable than stopping the pumps on an overpressure condition since a complete stop of the pump results in completely stopping fluid flow in the circuit and potentially creating vastly fluctuating pressures.

This control protocol allows the pump to be controlled to a speed lower than its user-set speed in order to control to a programmable set point pressure. This pressure set point may be either positive (for arterial or cardioplegia pumps) or negative (for suction or vent pumps). The maximum pump speed is the user-set speed at pump knobs 31*a*-36*a*. The pump will run at this speed unless the measured pressure increases over the set point pressure (or decreases below the set point for negative pressure control). When measured pressure exceeds set point pressure a pressure control loop is enabled. Use of this control algorithm requires a pressure transducer calibrated in appropriate units, having an appropriate sample rate (i.e., 40 Hz).

The monitored pressure is used as a feedback control parameter to automatically adjust pump speed to maintain pressure at the control point. In the event the monitored pressure falls outside of user set limits an alarm/indication may be provided at interface 50 and/or the speed of one or more (e.g., both cardioplegia pumps simultaneously) is either increased or decreased in order to maintain the desired pressure. For example, the user may set at the user interface a high pressure limit of 150 mmHg, a low pressure limit of 20 mmHg and a control point of 100 mmHg. By utilizing the monitored pressure as a feedback control parameter the system will automatically adjust the speed of the pumps to maintain pressure at the control point. If the pressure exceeds for any reason the upper or lower limit an alarm is activated at the user interface.

13. Venous Reservoir Level Control by Arterial Pump

The venous reservoir level control by arterial pump procedure, initiated and/or enabled by contacting a graphic button (not shown) on user interface 50 will result in the automatic control of arterial pump 31 to maintain the desired level or volume in the venous reservoir. As will be appreciated, the level control procedure will be controlled in accordance with predetermined protocols stored in memory, and will entail automated steps. The user would select the desired venous reservoir level to maintain by contacting graphic buttons (not shown) and/or adjusting knob 52 on user interface 50.

This control protocol maintains the level in the venous reservoir 106 at a pre-selected value by controlling the speed of arterial pump 31. The continuous level control is an operational mode by which the level of the reservoir is not allowed to increase above or decrease below the pre-selected value which can be adjusted by the user. Use of this mode requires that a continuous level sensor such as that described with respect to FIG. 12 is present on the system to provide feedback of the current level of fluid in the reservoir. The pump's maximum flow rate is set by the user at pump knob 31*a*. As the level increases above or decreases below the pre-selected value, a software and/or hardware implemented PID (Proportional, Integral, Differential) servo slows the pump down or speeds up the pump and adjusts the pump speed to maintain the pre-selected reservoir level resulting in the flow rate out of the reservoir closely matching the flow into the reservoir. If the flow into the reservoir increases substantially, then the level may rise above the set point because the pump flow rate is limited by the setting of the pump knob 31*a*.

The advantage of this method of level control is that the level in the reservoir can be controlled to any level. The level can also be changed at any time and there will be a smooth transition between the old and new levels. Use of the pump continuous level control system also increases patient safety because it will prevent emptying of the venous reservoir 106 in case of temporary user inattention.

14. Venous Reservoir Level Control by Venous Line Clamp

The venous reservoir level control by venous line clamp procedure, initiated and/or enabled by contacting a graphic button (not shown) on user interface 50 will result in the automatic control of venous line clamp 46 to maintain the desired level or volume in the venous reservoir. As will be appreciated, the level control procedure will be controlled in accordance with predetermined protocols stored in memory, and will entail automated steps. The user would select the desired venous reservoir level to maintain by contacting graphic buttons (not shown) and/or adjusting knob 52 on user interface 50.

This control protocol maintains the level in the venous reservoir 106 at a pre-selected value by controlling the venous line clamp 46. The continuous level control is an operational mode by which the level of the reservoir is not allowed to decrease below or increase above some pre-selected value which can be adjusted by the user. Use of this mode requires that a continuous level sensor such as that described with respect to FIG. 12 is present on the system to provide feedback of the current level of fluid in the reservoir. As the level increases above or decreases below the pre-selected value, a software and/or hardware implemented PID (Proportional, Integral, Differential) servo partially or completely opens or closes venous line clamp 46 to maintain the preselected reservoir level resulting in the flow rate into the reservoir closely matching the flow out of the reservoir.

The advantage of this method of level control is that the level in the reservoir can be controlled to any level. The level can also be changed at any time and there will be a smooth transition between the old and new levels. Use of the venous line clamp continuous level control system also increases patient safety because it will prevent emptying of the venous reservoir 106 in case of temporary user inattention.

15. Venous Reservoir Level Control by Venous Reservoir Vacuum

The venous reservoir level control by venous reservoir vacuum procedure, initiated and/or enabled by contacting a graphic button (not shown) on user interface 50 will result in the automatic control of venous reservoir vacuum to maintain the desired level or volume in the venous reservoir. As will be appreciated, the level control procedure will be controlled in accordance with predetermined protocols stored in memory, and will entail automated steps. The user would select the desired venous reservoir level to maintain by contacting graphic buttons (not shown) and/or adjusting knob 52 on user interface 50.

This control protocol maintains the level in the venous reservoir 106 at a pre-selected value by controlling the level of vacuum in the venous reservoir. Typically, vacuum level control would most likely be used when vacuum is already in use for vacuum assisted venous drainage procedures in order for vacuum to have an effect on increasing or lowering level. The continuous level control is an operational mode by which the level of the reservoir is not allowed to decrease below or increase above some pre-selected value that can be adjusted by the user. Use of this mode requires that a continuous level sensor such as that described with respect to FIG. 12 is present on the system to provide feedback of the current level of fluid in the reservoir. As the level increases above or decreases below the pre-selected value, a software and/or hardware implemented PID (Proportional, Integral, Differential) servo increases or decreases the vacuum in the venous reservoir to maintain the preselected reservoir level resulting in the flow rate into the reservoir closely matching the flow out of the reservoir. If vacuum is not currently in use in the venous reservoir, the ability to reduce vacuum to lower the reservoir level would not exist. In this case vacuum reservoir level control would only be one sided whereby vacuum could only be added and used to increase the level in the reservoir level.

The advantage of this method of level control is that the level in the reservoir can be controlled to any level. The level can also be changed at any time and there will be a smooth transition between the old and new levels. Use of the venous reservoir vacuum continuous level control system also increases patient safety because it will prevent emptying of the venous reservoir 106 in case of temporary user inattention.

16. Automatic Fluid Shuttling

The automatic fluid shuttling procedure, initiated and/or enabled by contacting a graphic button (not shown) on user interface 50 will result in the automatic control of venous line clamp 46 to transfer a preselected volume of fluid to or from the bypass circuit to the patient during bypass. As will be appreciated, the automatic fluid shuttling procedure will be controlled in accordance with predetermined protocols stored in memory, and will entail automated steps. The user would select the desired volume to transfer by contacting graphic buttons (not shown) and/or adjusting knob 52 on user interface 50.

To transfer fluid to the patient, the system control automatically senses the current level in the venous reservoir 106 and causes the venous line clamp 46 to reduce flow by restricting the venous line and/or the arterial pump to increase flow by increasing the pump speed until the selected volume has been transferred to the patient. Either the venous line clamp 46 setting or the arterial pump 31 flow setting mode is selectable by the user by contacting graphic buttons (not shown) and/or adjusting knob 52 on user interface 50. At completion of the volume transfer the venous line clamp and/or the arterial pump will return to their previous settings. To transfer fluid from the patient, the system control automatically senses the current level in the venous reservoir and causes the venous line clamp 46 to increase flow and/or the arterial pump 31 to decrease flow until the selected volume has been transferred from the patient. The venous line clamp 46 setting or the arterial pump 31 flow setting, whichever mode was used, will return to the previous settings after completing the volume transfer.

17. Variable Minimum Reservoir Level

The variable minimum reservoir level control procedure, initiated and/or enabled by contacting a graphic button (not shown) on user interface 50 will result in the automatic control of arterial pump 31 to a safe flow rate to prevent emptying the venous reservoir and ensure that air is not introduced into the venous reservoir outlet line. As will be appreciated, the variable minimum reservoir level procedure will be controlled in accordance with predetermined protocols stored in memory, and will entail automated steps.

To ensure the venous reservoir 106 is not emptied when operating at lower levels in the venous reservoir and to ensure that air is not introduced into the venous reservoir outlet line 110 due to high flow rates causing air generation from vortexing or entrained air to enter the venous reservoir outlet, the arterial pump 31 flow is automatically reduced as the venous reservoir level decreases. Typically, the automatic slow down of arterial pump 31 occurs at levels below 200 ml to 500 ml. For example, as the venous reservoir level decreases below 200 ml, the arterial pump would begin to reduce flow to a safe flow rate. As the level in the reservoir continues to decrease, the arterial pump flow would also continue to decrease flow until the safe flow rate for that level in the reservoir is reached. The safe flow rate for the arterial pump 31 at a given venous reservoir level is based on determining the current volume in venous reservoir 106, and determining the time it would take to safely stop the arterial pump (i.e., how fast the arterial pump 31 can be stopped without emptying the venous reservoir) and determining the maximum operable flow rate where air would be prevented from entering the venous reservoir outlet tubing 110 due to vortexing or air entrainment. From the venous reservoir level, the time required to safely stop the arterial pump, and the maximum operable flow rate for a given level, the safe arterial pump flow rate for a given venous reservoir level can be determined.

The advantage of using this low level slow down technique is that the arterial pump flow rate is reduced depending upon the reservoir level and there are no abrupt stops and starts of the arterial pump. This smoother control helps improve safety with less chance of entraining air into the venous reservoir outlet tubing 110.

Existing systems that do not have an available continuous level sensor cannot provide an equivalent form of pump slow down at low reservoir levels. A discreet single level sensor, used on some perfusion systems, can only provide a pump shut down at that level, with the possibility of reverting to some sort of oscillation of the pump around that level.

Alternatively, a system using two discreet level sensors could be used to provide a form of level control to maintain level between the locations of these two sensors. The control point is then fixed and no advanced slow down of the pump is possible using this configuration as described above but the arterial pump flow could be increased or reduced to keep the venous reservoir level essentially between the two discrete level sensors.

18. Auto Arterial Line Clamp with Arterial Pump Stop

The automatic arterial line clamp with arterial pump stop procedure, initiated and/or enabled by contacting a graphic button (not shown) on user interface 50 will result in the automatic open or close arterial line clamp 92 if arterial pump 31 is started or stopped. As will be appreciated, the automatic line clamp procedure will be controlled in accordance with predetermined protocols stored in memory, and will entail automated steps.

This protocol may automatically close the arterial line clamp 92 in arterial line 122 when arterial pump 31 is stopped. This prevents draining the patient through the under occluded pump or possibly drawing air through the cannula purse strings if arterial pump 31 is stopped. Conversely, arterial line clamp 92 in arterial line 122 may open when arterial pump 31 is started.

19. Auto Venous Line Clamp with Arterial Pump Stop

The automatic venous line clamp with arterial pump stop procedure, initiated and/or enabled by contacting a graphic button (not shown) on user interface 50 will result in the automatic open or close of venous line clamp 46 if arterial pump 31 is started or stopped. As will be appreciated, the automatic venous line clamp procedure will be controlled in accordance with predetermined protocols stored in memory, and will entail automated steps.

This protocol may automatically close venous line clamp 46 in venous line 104 when arterial pump 31 is stopped. This prevents exsanguination of the patient or overflowing the venous reservoir 106 if arterial pump 31 was stopped and venous line clamp 46 was left open. Conversely, venous line clamp 46 in venous line 104 may open when arterial pump 31 is started.

20. Automatic Cardioplegia Delivery

The automatic cardioplegia delivery procedures herein described below, initiated and/or enabled by contacting graphic buttons (not shown) on user interface 50 will result in the automatic control of cardioplegia circuit pumps and valves to facilitate delivery of cardioplegia delivery solutions. As will be appreciated, the automatic cardioplegia delivery procedures will be controlled in accordance with predetermined protocols stored in memory, and will entail automated steps. The user would select the cardioplegia delivery parameters by contacting graphic buttons (not shown) and/or adjusting knob 52 on user interface 50.

In one automatic cardioplegia delivery procedure, the cardioplegia patient valve 96 and pre-selected crystalloid solution valve 99 can be automatically opened when delivery begins (i.e., when cardioplegia pumps 35 and/or 36 are operated) and both the cardioplegia patient valve 96 and the pre-selected crystalloid solution valve 99 can be automatically closed when delivery stops (i.e., when cardioplegia pumps 35 and 36 are stopped).

In another cardioplegia automated feature, the user can pre-select different ratios for each of the cardioplegia crystalloid bags 136. During cardioplegia delivery, control unit 10 will automatically invoke the pre-selected ratio for the respective crystalloid bag 136 selected for delivery to the patient.

Additionally, cardioplegia may be automatically delivered to the patient by either volume delivery (i.e., where a pre-selected bolus volume is delivered to the patient and when the pre-selected volume is delivered, cardioplegia delivery is terminated) or time delivery (i.e., where a cardioplegia bolus is delivered for a pre-selected amount of time and at the end of the pre-selected time, cardioplegia delivery is terminated) or cardioplegia may be delivered manually where the user manually starts cardioplegia until a volume or time has expired and whereby the user manually terminates cardioplegia delivery.

Additionally, cardioplegia crystalloid valves 99 can be alternately opened and closed while operating crystalloid pump 36 to allow variable concentration, fixed dilution delivery. The first crystalloid valve 99 is opened to draw in a specific volume of crystalloid solution containing a first set of constituent ingredients. Then, the second valve 99 is opened to draw in a second specific volume of crystalloid solution second set of constituent ingredients. Typically, the two crystalloid solutions contain one or more different constituent ingredients whereby the mixing of the two crystalloid solutions at the pre-selected proportions will yield the desired concentrations for cardioplegia delivery. The proportion of the volumes drawn from each crystalloid bag 136 determines the resultant crystalloid constituent concentration(s).

21. Vacuum Assisted Venous Drainage (VAVD) Feedback/Control

During vacuum assisted venous drainage the vacuum is used to augment the venous return from the patient to ensure there is adequate flow from the patient to maintain the patient on bypass. When flow rates are reduced during the procedure while moving or filling the heart, at the end of the procedure, or any other reason, the vacuum may not be necessary to maintain flow and may create unsafe vacuum levels on circuit components which may cause air to enter the patient circuits.

The automatic vacuum assisted venous drainage (VAVD) feedback/control procedure, initiated and/or enabled by contacting a graphic button (not shown) on user interface 50 will result in the automatic control of the venous reservoir vacuum pump or pressure regulator to prevent adverse effects of vacuum on various circuit components. As will be appreciated, the automatic vacuum assisted venous drainage (VAVD) feedback/control procedure will be controlled in accordance with predetermined protocols stored in memory, and will entail automated steps.

To prevent the possibility of negative effects from the vacuum, such as creating a negative pressure acting on the oxygenator membrane and drawing air across membrane into the blood lines, the vacuum can be reduced or stopped through control of a vacuum regulator (not shown) or vacuum pump (not shown) as the arterial pump 31 flow is reduced. Once the system detects the arterial pump 31 is slowing down, the vacuum can be reduced to maintain the level in the reservoir. This control method is similar to venous reservoir level control with vacuum as previously described herein.

Additionally, if arterial pump 31 is stopped the venous reservoir vacuum can be turned off to ensure negative pressure is not applied to the oxygenator or other circuit elements that may not operate properly under negative pressure. In addition to turning the vacuum off control unit 10 can also vent the venous reservoir to atmosphere to quickly relieve the vacuum in the venous reservoir through the operation of a vacuum regulator or valve (not shown).

Additionally, if positive pressure is created in the venous reservoir for example due to a malfunction of a passive pressure relief valve, the positive pressure can be automatically released by the vacuum regulator or valve (not shown) to prevent pressure build up inside the venous reservoir as the pressure exceeds a predetermined value.

22. Automatic Hemoconcentration

The automatic hemconcentration procedures herein described below, initiated and/or enabled by contacting graphic buttons (not shown) on user interface 50 will result in the automatic control of hemoconcentrator pumps and valves to facilitate hemoconcentration. As will be appreciated, the automatic hemoconcentration delivery procedures will be controlled in accordance with predetermined protocols stored in memory, and will entail automated steps.

The user would select the hemoconcentration parameters by contacting graphic buttons (not shown) and/or adjusting knob 52 on user interface 50.

A two pump hemoconcentration system as described previously with respect to FIG. 3B uses a blood inflow pump 37 to the hemoconcentrator and a blood outflow pump 38 from the hemoconcentrator. It has a pressure monitor 86 on the hemoconcentrator blood inlet. The pressure sensor monitors the inlet pressure to ensure the pressure does not exceed a predetermined value where an alarm would occur on user interface 50 and/or both the inflow and outflow pumps could be slowed or stopped. There is also a valve 39 on the waste line which is closed during a portion of the priming sequence to prevent the prime solution from being passed through the hemoconcentrator and later opened to allow priming across the hemoconcentrator membrane or the valve could be used to provide a restriction on the hemoconcentrator effluent line to reduce effluent flow. Effluent rate and volume could be precisely controlled and determined by controlling the inflow and outflow pump flow rates. The inflow pump flow rate would be greater than the outflow pump flow rate to ensure air is not drawn into the hemoconcentrator circuit across the hemoconcentrator membrane. The effluent rate or ultrafiltrate rate equals the difference between inflow and outflow blood pump rates. The control unit 10 could automatically operate both pumps at respective flow rates to deliver a user selected effluent rate or a user selected effluent volume in a user selected period of time. A scale could be added on the ultrafiltrate waste bag to weigh the effluent to determine the effluent volume.

Alternatively, the outflow pump could be replaced with a variable restrictor valve (not shown) on the blood outflow line from the hemoconcentrator to change the transmembrane pressure (TMP) which is the driving force of the effluent across the hemoconcentrator membrane. Restricting the valve would increase TMP, subsequently increasing effluent rate and opening the valve would decrease TMP, subsequently decreasing effluent rate.

Additionally, a hematocrit sensor (not shown) could be added in the circuit to measure the hematocrit at the outlet of the hemoconcentrator. The control unit 10 could use the outlet hematocrit information and the inlet hematocrit information as measured at hematocrit sensor 85 or only the hemoconcentrator outlet hematocrit to feedback to and automatically adjust the hemoconcentrator inlet and outlet flow rate to yield a user selected hematocrit of the blood exiting the hemoconcentrator.

23. Correct Pump Load and Circuit Test

This is a series of automatic tests performed by control unit 10 in conjunction with disposable assembly 100 to determine if the pump headers are loaded properly, if the suction, vent and cardioplegia pumps are fully occluded, and if the arterial pump is overoccluded or underoccluded.

The automatic pump load and circuit test procedures herein described below, may be automatically initiated during or after disposable load and/or priming will result in the automatic operation of any pump or valve to test the disposable assembly for proper loading and or function. As will be appreciated, the automatic pump load and circuit test procedures will be controlled in accordance with predetermined protocols stored in memory, and will entail automated steps. The user would select the user settable pump load and circuit test parameters by contacting graphic buttons (not shown) and/or adjusting knob 52 on user interface 50.

After loading disposable assembly 100 on control unit 10 the suction and vent pumps can be automatically operated to test for correct loading or for leaks in their respective circuits. The patient lines 170, 172 and 186 of these circuits are sealed by connection to plugs or some other connector or connectors that seal the ends of lines 170, 172, and 186. The sealing may occur during assembly of disposable assembly 100 or the lines could be clamped by the user during the test. The test is performed by operating the two suction pumps and vent pump at a predetermined or user selected speed or flow rate over a predetermined or user selected time period. As the pumps are operated, a vacuum is generated in the suction and vent circuits and measured at pressure sensors 40, 42, and 44 until a predetermined pressure is reached where the respective pumps are stopped. If a positive pressure is generated, this indicates the pump tubing lines 178, 180, and 190 are probably loaded incorrectly (i.e., reversed) and an alarm occurs advising the user of the condition and any appropriate checks or corrective actions that should occur. If the predetermined pressure cannot be reached during the predetermined test time period, this indicates a leak exists in the circuit and an alarm occurs advising the user of the test failure which may include advisory messages in checking for the leak or resolution of the problem. If the predetermined pressure is reached, the pumps are stopped and a pressure decay test is performed which monitors the pressure at sensors 40, 42, and 44 and if a predetermined pressure loss over a predetermined time occurs, a leak may exist in the circuit and an alarm occurs advising the user of the test failure and any appropriate checks or corrective actions that should occur. If the pressure at sensors 40, 42, and 44 reach the predetermined pressure limit and no significant pressure decay occurs, the circuit is not leaking, the pump tubing has been loaded correctly, and the pump is fully occlusive on the pump tubing.

A similar test is performed on the cardioplegia circuit. For the cardioplegia circuit the cardioplegia patient valve 96 is closed and the pumps (35, 36) are operated at a predetermined flow one pump at a time which creates a positive pressure in the circuit to a predetermined pressure as measured at pressure sensor 18. If the predetermined pressure cannot be reached during the predetermined test time period, this indicates a leak exists in the circuit and an alarm occurs advising the user of the test failure which may include advisory messages in checking for the leak or resolution of the problem. If the predetermined pressure is reached, the pumps are stopped, and a pressure decay test is performed which monitors the pressure at sensor 18, and if a predetermined pressure loss over a predetermined time occurs, a leak may exist in the circuit and an alarm occurs advising the user of the test failure and any appropriate checks or corrective actions that should occur. If the pressure at 18 reaches the predetermined pressure limit and no significant pressure decay occurs, the circuit is not leaking, the pump tubing has been loaded correctly and the pump is fully occlusive on the pump tubing. This test is repeated for the second cardioplegia pump. The test is performed one cardioplegia pump at a time because the two pumps share the same outlet connection which if the two pumps are operated simultaneously they may mask a small leak.

The arterial-venous circuit (A-V circuit) could be checked in a similar manner as herein described once the arterial circuit has been primed. The circuit requires priming because air alone would not hold pressure since the pressure would leak across the oxygenator membrane. The test would be conducted in a similar manner as described herein with similar alarm messages.

Alternatively, a pressure sensor (not shown) could be added to the A-V circuit on the outlet of the arterial pump 31 between the arterial pump and the oxygenator 112 and a valve (not shown) could be added and positioned downstream of the pressure sensor just described. Using this pressure sensor and valve, a similar circuit pressure test as previously described herein for the cardioplegia pumps could be performed to check for circuit leaks, correct loading of the tubing line and pump occlusion in the A-V circuit.

After auto prime, the system may be checked for leaks by closing various valves, and operating various pumps in various combinations and monitoring respective pressures and pressure decay rates and providing alarms advising the user of circuit or equipment problems if the predetermined pressure limits are not reached or the pressure decay rates exceeded.

Additionally, by pressurizing the priming solution in the oxygenator to a predetermined value, leaks in the membrane can be detected with the liquid leak detector 366 shown on FIG. 26 as fluid would transverse a leaky oxygenator membrane at a predetermined pressure.

24. Arterial Pump Occlusion Setting Assist

The automatic pump occlusion setting assist procedures herein described below, initiated and/or enabled by contacting the graphic "check occlusion" button on user interface 50 will result in the automatic control of arterial pump 31 and valves 92, 405 and 406 while monitoring pressure at pressure sensor 14 to aid in setting the arterial pump occlusion. As will be appreciated, the automatic pump occlusion setting assist procedures will be controlled in accordance with predetermined protocols stored in memory, and will entail automated steps. The user would select the user settable parameters by contacting graphic buttons (not shown) and/or adjusting knob 52 on user interface 50. The occlusion check normally occurs after priming but could occur after loading disposable assembly 100 and before prime.

After initiation of the automatic pump occlusion setting assist, arterial patient line valve 92, and purge valves 405, 406 are closed and arterial pump 31 is operated at a predetermined speed for a predetermine time. If the arterial pump outlet pressure as measured at pressure sensor 14 exceeds a predetermined pressure value, the pump is stopped and purge valves 405 and/or 406 are opened to release the pressure and the occlusion is determined to be overoccluded. The user is advised through user interface 50 of the overoccluded condition and the user is instructed to reduce the occlusion by a predetermined amount and to repeat the test by contacting the check occlusion button (#) on user interface 50. If the predetermined pressure value is not reached, the average pressure is calculated. If the average pressure is greater than a second predetermined pressure value, the user is instructed to reduce the occlusion by a predetermined amount and to repeat the test by contacting the check occlusion button on user interface 50. If the average pressure is less than a third predetermined pressure value, the user is instructed to increase the occlusion by a predetermined amount. If the average pressure is between the second and third pressure values, the occlusion setting is determined to be acceptable and the user is advised of that on user interface 50. The occlusion test is repeated until the pressure is in the predetermined acceptable range or the user ends the test.

A polynomial is used to determine the occlusion adjustment amount for both reducing or increasing occlusion for an over pressure condition or under pressure condition, respectively.

Alternatively, a method of measuring occlusion is to close the arterial line valve 92 and the purge valves 405 and 406, then operate arterial pump 31 until a predetermined pressure has been reached. The arterial pump is then stopped and the pressure decay (i.e., pressure drop over a period of time) is determined by recording the measured pressure at pressure sensor 14 at predetermined time intervals. A decay rate of a predetermined range of values would result in an acceptable occlusion. A decay rate exceeding the predetermined decay rate range of values would indicate an underocclusion setting and the user would be instructed to increase occlusion as described herein above. A decay rate less than the predetermined decay rate range of values would indicate an over occlusion setting and the user would be instructed to decrease occlusion as described herein above.

25. Arterial Pump Occlusion Setting Methods Using the Cardioplegia Blood Pump.

The automatic pump occlusion setting assist procedures herein described below, initiated and/or enabled by contacting a graphic "check occlusion" button on user interface 50 will result in the automatic control of cardioplegia blood pump 34 and valves 92, 405 and 406 while monitoring pressure at pressure sensor 14 to aid in setting the arterial pump occlusion. As will be appreciated, the automatic pump occlusion setting assist procedures will be controlled in accordance with predetermined protocols stored in memory, and will entail automated steps. The user would select the user settable parameters by contacting graphic buttons (not shown) and/or adjusting knob 52 on user interface 50. The occlusion check normally occurs after priming but could occur after loading disposable assembly 100 and before prime.

The cardioplegia blood pump 34 can be operated in reverse, pumping fluid backwards through the underoccluded arterial pump, while monitoring the arterial line pressure as measured at pressure sensor 14 and with arterial patient valve 92, purge valves 405 and 406 all closed. The flow rate and pressure generated would indicate the occlusion as in a similar manner as previously described herein.

Alternatively, the cardioplegia blood pump can be operated in the forward direction, with the arterial pump pumping at a predetermined RPM and the arterial outlet line clamped. The speed of the cardioplegia blood pump can be varied to maintain a constant pressure in the arterial line as measured at pressure sensor 14. The difference between the predicted arterial pump flow at full occlusion and the cardioplegia pump flow rate would be the leakage rate due to underocclusion. (A positive pressure must be maintained to prevent air passing across the oxygenator membrane.)

The description provided above is strictly for exemplary purposes. Numerous modifications, extensions and adaptations of the present invention will be apparent to those skilled in the art upon consideration, and are intended to be within the scope of the present invention.

We claim:

1. An extracorporeal blood perfusion system for receiving venous blood from a patient and for returning oxygenated blood to the patient in a cardiopulmonary bypass procedure, comprising:

a disposable assembly including a cartridge and a plurality of interconnected tubing lines, the cartridge having one or more sensor stations and a plurality of internal fluid passageways, wherein a first of the tubing lines is fluidly interconnected with at least one of the plurality of fluid passageways, wherein the disposable assembly comprises an oxygenator connected in a blood circuit, wherein the disposable assembly defines the blood circuit for receiving venous blood from the patient and transferring oxygenated blood to the patient in a cardiopulmonary bypass procedure, and wherein the disposable assembly further comprises a reservoir having an inlet connected to receive venous blood from the patient through a second of the positioned tubing lines; and a control unit having a component interface region, the component interface region including a cartridge interface region that includes one or more sensors, wherein the cartridge interface region receives the cartridge and aligns the one or more sensors of the cartridge interface region with the one or more sensor stations on the cartridge, a first pump for operatively interfacing with the blood circuit, wherein the venous blood is pumped through the blood circuit by the first pump, a flow control clamp for controlling the flow of venous blood through the second tubing line to the reservoir, and at least one blood flow sensor for monitoring the flow of venous blood and that is capable of sending a control signal to trigger the flow control clamp.

2. The extracorporeal blood perfusion system of claim 1, wherein the flow control clamp is controllable to maintain at least one of a predetermined relative flow percentage through the second tubing lines to the reservoir and a predetermined fluid volume within the reservoir.

3. The extracorporeal blood perfusion system of claim 1, wherein the oxygenator is connected in the blood circuit downstream from the reservoir, and wherein the first pump is configured to pump accumulated venous blood from the reservoir through the oxygenator to provide for the transfer of the oxygenated blood to the patient.

4. The extracorporeal blood perfusion system of claim 1, the component interface region further comprises a sensor for detecting the presence of gaseous bubbles within the oxygenated blood and at least one valve assembly configured for diverting the flow of the oxygenated blood to the reservoir upon detection of gaseous bubbles in the oxygenated blood by the sensor.

5. The extracorporeal blood perfusion system of claim 1, wherein the disposable assembly further defines a cardioplegia circuit for supplying a cardioplegia solution to the patient, the cardioplegia circuit including a fluid interconnected with the blood circuit for flowing at least a portion of the oxygenated blood to one of the plurality of fluid passageways for mixture with a cardioplegia solution.

6. The extracorporeal blood perfusion system of claim 1, wherein the component interface region further comprises a plurality of sensors positioned for monitoring an oxygen saturation, hematocrit and temperature of the venous blood received in the blood circuit.

7. The extracorporeal blood perfusion system of claim 1, wherein the component interface region further comprises a pressure sensor positioned for monitoring a fluid pressure of the oxygenated blood in the blood circuit.

8. The extracorporeal blood perfusion system of claim 7, wherein the control unit is operable to automatically suspend operation of the first pump when the pressure sensor detects a fluid pressure greater than a predetermined level.

9. The extracorporeal blood perfusion system of claim 1, wherein the cartridge comprises a housing including a first rigid potion connected to a second flexible portion.

10. The extracorporeal blood perfusion system of claim 9, wherein the cartridge interface region further includes a pressure sensor configured to sense fluid pressure in an internal passageway of the cartridge through the second flexible portion of the housing.

11. The extracorporeal blood perfusion system of claim 1, wherein the cartridge interface region further includes a valve actuator and the cartridge further includes a valve station, the valve station being in fluid communication with an internal passageway, the valve station having a flexible member configured to be moveable from a first position allowing fluid flow between the internal passageway and a second position preventing fluid flow between the internal passageways, the valve actuator being configured to interface with the flexible member to cause movement of the flexible member between the first and second positions.

12. The extracorporeal perfusion system of claim 1, further comprising a display, wherein the display is integrated with a processor that allows modification of various settings for monitoring and controlling various parameters of the system.

13. An extracorporeal blood perfusion system for receiving venous blood from a patient and for returning oxygenated blood to the patient, comprising:

a disposable oxygenator assembly including:
   a reservoir having an inlet for receiving venous blood from the patient and an outlet for returning oxygenated blood to the patient;
   a cartridge having a housing, at least one sensor station, and a plurality of internal fluid passageways; and
   a plurality of interconnected tubing lines, wherein a first of the tubing lines is fluidly interconnected with at least one of the plurality of internal fluid passageways, and a second of the tubing lines is fluidly interconnected with the inlet; and
a control unit having a component interface region, the component interface region including a cartridge interface region having one or more sensors, wherein the cartridge interface region receives the cartridge and aligns the one or more sensors of the cartridge interface region with the one or more sensor stations on the cartridge;
a first pump for operatively interfacing with the blood circuit and for pumping venous blood through the blood circuit;
a flow control clamp for controlling the flow of venous blood through the second tubing line to the reservoir, and at least one blood flow sensor for monitoring the flow of venous blood, wherein the blood flow sensor is capable of generating a control signal for triggering the flow control clamp.

* * * * *